US012690910B2

(12) United States Patent
Weber et al.

(10) Patent No.: US 12,690,910 B2
(45) Date of Patent: Jul. 28, 2026

(54) DETACHABLE SURGICAL TOOL CONFIGURED AS A FINITE STATE MACHINE

(71) Applicant: LivsMed, Inc., Seongnam-si (KR)

(72) Inventors: Matthew P. Weber, Brighton, MI (US); Deepak Sharma, Ann Arbor, MI (US); Zachary Zimmerman, Northville, MI (US); Shorya Awtar, Ann Arbor, MI (US); James Duncan Geiger, Ottawa Hills, OH (US); James Michael Licht, Boyne Falls, MI (US); Srinivas Bidare, Novi, MI (US); Pradeep Akkineni, Farmington Hills, MI (US)

(73) Assignee: LivsMed, Inc., Seongnam-si (KR)

( * ) Notice: Subject to any disclaimer, the term of this patent is extended or adjusted under 35 U.S.C. 154(b) by 407 days.

(21) Appl. No.: 17/477,872

(22) Filed: Sep. 17, 2021

(65) Prior Publication Data

US 2022/0175441 A1     Jun. 9, 2022

Related U.S. Application Data

(60) Provisional application No. 63/079,550, filed on Sep. 17, 2020.

(51) Int. Cl.
*A61B 18/14*          (2006.01)
*A61B 17/00*          (2006.01)
*A61B 18/00*          (2006.01)

(52) U.S. Cl.
CPC .. *A61B 18/1445* (2013.01); *A61B 2017/0046* (2013.01); *A61B 2018/00172* (2013.01);
(Continued)

(58) Field of Classification Search
CPC ........ A61B 18/1445; A61B 2017/0046; A61B 2018/00172; A61B 2018/00595;
(Continued)

(56) References Cited

U.S. PATENT DOCUMENTS

|  |  |  |  |
|---|---|---|---|
| 331,598 | A | 12/1885 | White |
| 3,028,126 | A | 4/1962 | Holleman |

(Continued)

FOREIGN PATENT DOCUMENTS

| CN | 211325282 | U | 8/2020 |
|---|---|---|---|
| CN | 111789662 | A | 10/2020 |

(Continued)

OTHER PUBLICATIONS

International Preliminary Report on Patentability for International Application No. PCT/US2021/035469 dated Dec. 6, 2022 (8 pages).
(Continued)

*Primary Examiner* — Adam Z Minchella
*Assistant Examiner* — Ashleigh Lauren Kern
(74) *Attorney, Agent, or Firm* — REISING ETHINGTON, P.C.

(57)          ABSTRACT

Many embodiments of a surgical tool are set forth herein that can be employed for use in minimally invasive surgical procedures and in remote access surgical procedures. The surgical tool has multiple bodies with one or more detachable structural interfaces that can be established between one or more pairs of the bodies. Certain locks, interlocks, and/or joints can be present in the surgical tool and among the bodies in various embodiments in order to provide certain functionalities during use.

12 Claims, 168 Drawing Sheets

(52) U.S. Cl.
CPC .............. *A61B 2018/00595* (2013.01); *A61B 2018/0091* (2013.01)

(58) Field of Classification Search
CPC ...... A61B 17/2909; A61B 2017/00314; A61B 2017/00327; A61B 2017/00424; A61B 2017/00442; A61B 2017/00477; A61B 2017/291; A61B 17/29
See application file for complete search history.

(56) References Cited

U.S. PATENT DOCUMENTS

| | | | |
|---|---|---|---|
| 3,350,956 A | 11/1967 | Monge | |
| 3,497,083 A | 2/1970 | Anderson et al. | |
| 4,328,839 A | 5/1982 | Lyons et al. | |
| 4,466,649 A | 8/1984 | Ozawa | |
| 4,491,325 A | 1/1985 | Bersheim | |
| 4,568,311 A | 2/1986 | Miyake | |
| 4,712,545 A | 12/1987 | Honkanen | |
| 4,740,126 A | 4/1988 | Richter | |
| 4,750,475 A | 6/1988 | Yoshihashi | |
| 4,754,909 A | 7/1988 | Barker et al. | |
| 4,950,273 A | 8/1990 | Briggs | |
| 5,021,969 A | 6/1991 | Okamura et al. | |
| 5,069,596 A | 12/1991 | Mueller et al. | |
| 5,147,357 A | 9/1992 | Rose et al. | |
| 5,209,747 A | 5/1993 | Knoepfler | |
| 5,297,443 A | 3/1994 | Wentz | |
| 5,317,952 A | 6/1994 | Immega | |
| 5,323,570 A | 6/1994 | Kuhlman et al. | |
| 5,330,502 A | 7/1994 | Hassler et al. | |
| 5,350,391 A | 9/1994 | Iacovelli | |
| 5,368,600 A | 11/1994 | Failla et al. | |
| 5,374,277 A | 12/1994 | Hassler | |
| 5,379,663 A | 1/1995 | Hara | |
| 5,379,758 A | 1/1995 | Snyder | |
| 5,454,827 A | 10/1995 | Aust et al. | |
| 5,456,695 A | 10/1995 | Herve Dallemagne | |
| 5,549,637 A | 8/1996 | Crainich | |
| 5,599,151 A | 2/1997 | Daum et al. | |
| 5,620,415 A | 4/1997 | Lucey et al. | |
| 5,626,608 A | 5/1997 | Cuny et al. | |
| 5,683,412 A | 11/1997 | Scarfone | |
| 5,713,505 A | 2/1998 | Huitema | |
| 5,716,352 A | 2/1998 | Viola et al. | |
| 5,735,874 A | 4/1998 | Measamer et al. | |
| 5,782,748 A | 7/1998 | Palmer et al. | |
| 5,807,376 A | 9/1998 | Viola et al. | |
| 5,810,880 A | 9/1998 | Jensen et al. | |
| 5,813,813 A | 9/1998 | Daum et al. | |
| 5,816,770 A | 10/1998 | Itagaki | |
| 5,817,084 A | 10/1998 | Jensen | |
| 5,820,009 A | 10/1998 | Melling et al. | |
| 5,853,412 A | 12/1998 | Mayenberger | |
| 5,860,995 A | 1/1999 | Berkelaar | |
| 5,908,436 A | 6/1999 | Cuschieri et al. | |
| 6,042,555 A | 3/2000 | Kramer et al. | |
| 6,088,020 A | 7/2000 | Mor | |
| 6,104,379 A | 8/2000 | Petrich et al. | |
| 6,270,453 B1 | 8/2001 | Sakai | |
| 6,309,403 B1 | 10/2001 | Minor et al. | |
| 6,312,435 B1 | 11/2001 | Wallace et al. | |
| 6,330,837 B1 | 12/2001 | Charles et al. | |
| 6,413,229 B1 | 7/2002 | Kramer et al. | |
| 6,607,475 B2 | 8/2003 | Doyle et al. | |
| 6,707,447 B1 | 3/2004 | Goranowski | |
| 6,714,839 B2 | 3/2004 | Salisbury, Jr. et al. | |
| 6,746,443 B1 | 6/2004 | Morley et al. | |
| 6,853,879 B2 | 2/2005 | Sunaoshi | |
| 6,858,005 B2 | 2/2005 | Ohline et al. | |
| 6,889,116 B2 | 5/2005 | Jinno | |
| 6,994,716 B2 | 2/2006 | Jinno et al. | |
| 7,101,363 B2 | 9/2006 | Nishizawa et al. | |
| 7,147,650 B2 | 12/2006 | Lee | |
| 7,338,513 B2 | 3/2008 | Lee et al. | |
| 7,410,338 B2 | 8/2008 | Schiele et al. | |
| 7,470,268 B2 | 12/2008 | Doyle et al. | |
| 7,553,275 B2 | 6/2009 | Padget et al. | |
| 7,608,083 B2 | 10/2009 | Lee et al. | |
| 7,708,756 B2 | 5/2010 | Nobis et al. | |
| 7,736,254 B2 | 6/2010 | Schena | |
| 7,862,554 B2 | 1/2011 | Hegeman et al. | |
| 7,866,527 B2 | 1/2011 | Hall et al. | |
| 7,947,035 B2 | 5/2011 | Miyamoto et al. | |
| 7,963,913 B2 | 6/2011 | Devengenzo et al. | |
| 8,029,531 B2 | 10/2011 | Lee et al. | |
| 8,057,487 B2 | 11/2011 | Chu et al. | |
| 8,105,319 B2 | 1/2012 | Doyle et al. | |
| 8,105,350 B2 | 1/2012 | Lee et al. | |
| 8,365,633 B2 | 2/2013 | Simaan et al. | |
| 8,398,587 B2 | 3/2013 | Dewaele et al. | |
| 8,425,408 B2 | 4/2013 | Boulais et al. | |
| 8,465,475 B2 | 6/2013 | Isbell, Jr. | |
| 8,528,440 B2 | 9/2013 | Morley et al. | |
| 8,540,748 B2 | 9/2013 | Murphy et al. | |
| 8,551,076 B2 | 10/2013 | Duval et al. | |
| 8,603,135 B2 | 12/2013 | Mueller | |
| 8,668,702 B2 | 3/2014 | Awtar et al. | |
| 8,672,206 B2 | 3/2014 | Aranyi et al. | |
| 8,734,312 B2 | 5/2014 | Conner et al. | |
| 8,764,448 B2 | 7/2014 | Yang et al. | |
| 8,777,898 B2 | 7/2014 | Suon et al. | |
| 8,821,512 B2 | 9/2014 | Barrier et al. | |
| 8,828,046 B2 | 9/2014 | Stefanchik et al. | |
| 8,870,867 B2 | 10/2014 | Walberg et al. | |
| 8,881,616 B2 | 11/2014 | Dize et al. | |
| 8,968,355 B2 | 3/2015 | Malkowski et al. | |
| 8,992,422 B2 | 3/2015 | Spivey et al. | |
| 9,050,121 B2 | 6/2015 | Doyle | |
| 9,060,796 B2 | 6/2015 | Seo | |
| 9,084,621 B2 | 7/2015 | Weitzner et al. | |
| 9,161,771 B2 | 10/2015 | Steger | |
| 9,220,398 B2 | 12/2015 | Woodley et al. | |
| 9,522,014 B2 | 12/2016 | Nishizawa et al. | |
| 9,532,839 B2 | 1/2017 | Seo | |
| 9,575,504 B2 | 2/2017 | Dize et al. | |
| 9,579,013 B2 | 2/2017 | Dewaele et al. | |
| 9,622,729 B2 | 4/2017 | Dewaele et al. | |
| 9,629,682 B2 | 4/2017 | Wallace et al. | |
| 9,629,689 B2 | 4/2017 | Bowles et al. | |
| 9,649,096 B2 | 5/2017 | Sholev | |
| 9,675,370 B2 | 6/2017 | Awtar et al. | |
| 9,695,916 B2 | 7/2017 | Lee | |
| 9,696,700 B2 | 7/2017 | Beira et al. | |
| 9,770,300 B2 | 9/2017 | Kwon et al. | |
| 9,814,451 B2 * | 11/2017 | Sharma ................. A61B 17/00 | |
| 9,869,339 B2 | 1/2018 | Zimmerman et al. | |
| 9,889,874 B1 | 2/2018 | Clause | |
| 9,901,412 B2 | 2/2018 | Lathrop et al. | |
| 9,955,988 B2 | 5/2018 | Stefanchik et al. | |
| 10,005,181 B2 | 6/2018 | Hasegawa et al. | |
| 10,085,624 B2 | 10/2018 | Isoda et al. | |
| 10,198,086 B2 | 2/2019 | Parazynski et al. | |
| 10,265,129 B2 | 4/2019 | Beira | |
| 10,271,913 B2 | 4/2019 | Yoshii et al. | |
| 10,325,072 B2 | 6/2019 | Beira et al. | |
| 10,363,055 B2 | 7/2019 | Beira et al. | |
| 10,426,471 B2 * | 10/2019 | Shelton, IV ..... A61B 17/07207 | |
| 10,449,010 B2 | 10/2019 | Dewaele et al. | |
| 10,617,413 B2 | 4/2020 | Shelton, IV et al. | |
| 10,660,719 B2 | 5/2020 | De Mathelin et al. | |
| 10,660,721 B2 | 5/2020 | Bonny et al. | |
| 10,664,002 B2 | 5/2020 | Parazynski et al. | |
| 10,695,141 B2 | 6/2020 | Lee | |
| 10,709,467 B2 | 7/2020 | Lee et al. | |
| 10,722,315 B2 | 7/2020 | Lee et al. | |
| 10,758,230 B2 | 9/2020 | Shelton, IV et al. | |
| 11,241,247 B2 | 2/2022 | Yuan et al. | |
| 11,344,381 B2 | 5/2022 | Lee et al. | |
| 11,490,980 B2 | 11/2022 | Lee et al. | |
| 11,510,746 B2 | 11/2022 | Lee et al. | |
| 11,523,840 B2 | 12/2022 | Yuan et al. | |
| 2001/0031983 A1 | 10/2001 | Brock et al. | |
| 2003/0036748 A1 | 2/2003 | Cooper et al. | |

(56) References Cited

U.S. PATENT DOCUMENTS

| | | |
|---|---|---|
| 2003/0083673 A1 | 5/2003 | Tierney et al. |
| 2003/0135203 A1 | 7/2003 | Wang et al. |
| 2003/0135204 A1 | 7/2003 | Lee et al. |
| 2003/0153902 A1 | 8/2003 | Doyle et al. |
| 2003/0176880 A1 | 9/2003 | Long et al. |
| 2003/0176948 A1 | 9/2003 | Green |
| 2004/0023616 A1 | 2/2004 | Straub et al. |
| 2004/0049205 A1 | 3/2004 | Lee et al. |
| 2004/0138700 A1 | 7/2004 | Cooper et al. |
| 2004/0236316 A1 | 11/2004 | Danitz et al. |
| 2004/0253079 A1 | 12/2004 | Sanchez |
| 2005/0004431 A1 | 1/2005 | Kogasaka et al. |
| 2005/0038469 A1 | 2/2005 | Lang |
| 2005/0090811 A1 | 4/2005 | Doyle et al. |
| 2005/0107667 A1 | 5/2005 | Danitz et al. |
| 2006/0074415 A1 | 4/2006 | Scott et al. |
| 2006/0111210 A1 | 5/2006 | Hinman |
| 2006/0111616 A1 | 5/2006 | Danitz |
| 2006/0156848 A1 | 7/2006 | Gosselin et al. |
| 2006/0199999 A1 | 9/2006 | Ikeda et al. |
| 2006/0259073 A1 | 11/2006 | Miyamoto et al. |
| 2006/0282063 A1 | 12/2006 | Gotani |
| 2007/0021738 A1 | 1/2007 | Hasser et al. |
| 2007/0072466 A1 | 3/2007 | Miyamoto et al. |
| 2007/0078565 A1 | 4/2007 | Ghodoussi et al. |
| 2007/0093790 A1 | 4/2007 | Downey et al. |
| 2008/0004493 A1 | 1/2008 | Schiemann |
| 2008/0039256 A1 | 2/2008 | Jinno et al. |
| 2008/0065098 A1 | 3/2008 | Larkin |
| 2008/0177285 A1 | 7/2008 | Brock et al. |
| 2008/0193260 A1 | 8/2008 | Yokokohji et al. |
| 2008/0243176 A1 | 10/2008 | Weitzner et al. |
| 2009/0118044 A1 | 5/2009 | Kuo et al. |
| 2009/0171147 A1 | 7/2009 | Lee et al. |
| 2009/0192511 A1 | 7/2009 | Haffenreffer |
| 2010/0004606 A1 | 1/2010 | Hansen et al. |
| 2010/0016853 A1 | 1/2010 | Burbank |
| 2010/0030018 A1 | 2/2010 | Fortier et al. |
| 2010/0056863 A1 | 3/2010 | Dejima et al. |
| 2010/0111645 A1 | 5/2010 | Al-Mouhamed et al. |
| 2010/0234831 A1 | 9/2010 | Hinman et al. |
| 2010/0249497 A1 | 9/2010 | Peine et al. |
| 2011/0024145 A1 | 2/2011 | Click et al. |
| 2011/0106145 A1 | 5/2011 | Jeong |
| 2011/0118707 A1 | 5/2011 | Burbank |
| 2011/0152881 A1 | 6/2011 | Conner et al. |
| 2011/0152922 A1 | 6/2011 | Jeong |
| 2011/0178531 A1 | 7/2011 | Caputo et al. |
| 2011/0319911 A1 | 12/2011 | Conner et al. |
| 2012/0083799 A1 | 4/2012 | Chen et al. |
| 2012/0095298 A1 | 4/2012 | Stefanchik et al. |
| 2012/0118097 A1 | 5/2012 | Ilch |
| 2012/0186383 A1 | 7/2012 | Schvalb et al. |
| 2012/0271283 A1 | 10/2012 | Doyle |
| 2012/0277762 A1 | 11/2012 | Lathrop et al. |
| 2012/0289973 A1 | 11/2012 | Prisco et al. |
| 2012/0303006 A1 | 11/2012 | Lee et al. |
| 2013/0012958 A1 | 1/2013 | Marczyk et al. |
| 2013/0023868 A1 | 1/2013 | Worrell et al. |
| 2013/0023974 A1 | 1/2013 | Amrani |
| 2013/0066334 A1 | 3/2013 | Schoepp |
| 2013/0172860 A1 | 7/2013 | Szewczyk et al. |
| 2013/0224710 A1 | 8/2013 | Yang et al. |
| 2013/0239734 A1 | 9/2013 | Hinman |
| 2014/0135805 A1 | 5/2014 | Windgassen et al. |
| 2014/0142595 A1 | 5/2014 | Awtar et al. |
| 2014/0197060 A1 | 7/2014 | Witt et al. |
| 2014/0246471 A1 | 9/2014 | Jaworek et al. |
| 2014/0263541 A1* | 9/2014 | Leimbach .......... A61B 17/0686 |
| | | 227/175.2 |
| 2014/0331798 A1 | 11/2014 | Shim et al. |
| 2014/0371532 A1 | 12/2014 | Trovato |
| 2015/0021068 A1 | 1/2015 | Bernhardt et al. |
| 2015/0053455 A1 | 2/2015 | Hagi |
| 2015/0164601 A1 | 6/2015 | Sholev |
| 2015/0230697 A1 | 8/2015 | Phee et al. |
| 2016/0135830 A1 | 5/2016 | Volkmer et al. |
| 2016/0256161 A1* | 9/2016 | Overmyer ............ A61B 17/072 |
| 2016/0256232 A1 | 9/2016 | Awtar et al. |
| 2016/0291383 A1 | 10/2016 | Han et al. |
| 2016/0303734 A1 | 10/2016 | Bowles et al. |
| 2017/0095922 A1 | 4/2017 | Licht et al. |
| 2017/0202570 A1 | 7/2017 | Shelton, IV et al. |
| 2017/0245954 A1 | 8/2017 | Beira |
| 2017/0360522 A1 | 12/2017 | Beira |
| 2018/0000318 A9 | 1/2018 | Rogers et al. |
| 2018/0049842 A1 | 2/2018 | Bowles et al. |
| 2018/0085117 A1* | 3/2018 | Shelton, IV ......... A61B 17/068 |
| 2018/0125519 A1 | 5/2018 | Beira et al. |
| 2018/0125592 A1 | 5/2018 | Beira |
| 2018/0221045 A1 | 8/2018 | Zimmerman et al. |
| 2018/0289384 A1 | 10/2018 | Bowles et al. |
| 2018/0368839 A1 | 12/2018 | Shelton, IV et al. |
| 2019/0133698 A1 | 5/2019 | Beira et al. |
| 2019/0151035 A1 | 5/2019 | Chaplin et al. |
| 2019/0167365 A1 | 6/2019 | Chaplin et al. |
| 2019/0336230 A1 | 11/2019 | Awtar et al. |
| 2020/0121406 A1 | 4/2020 | Lee |
| 2020/0146766 A1 | 5/2020 | Lee |
| 2020/0222137 A1 | 7/2020 | Lee et al. |
| 2020/0229835 A1 | 7/2020 | Lee et al. |
| 2020/0237466 A1 | 7/2020 | Lee et al. |
| 2020/0289141 A1 | 9/2020 | Yuan et al. |
| 2021/0045825 A1 | 2/2021 | Lee et al. |
| 2021/0145470 A1 | 5/2021 | Holsten |
| 2021/0282797 A1 | 9/2021 | Bhowmick et al. |
| 2021/0386428 A1 | 12/2021 | Larsen et al. |
| 2022/0079611 A1 | 3/2022 | Lee et al. |
| 2022/0273381 A1 | 9/2022 | Lee et al. |
| 2023/0034145 A1 | 2/2023 | Awtar et al. |

FOREIGN PATENT DOCUMENTS

| | | |
|---|---|---|
| CN | 113925569 A | 1/2022 |
| EP | 3232951 A2 | 10/2017 |
| EP | 3232952 A1 | 10/2017 |
| EP | 3232973 A1 | 10/2017 |
| EP | 3232974 A2 | 10/2017 |
| EP | 3232977 A1 | 10/2017 |
| EP | 3340897 A1 | 7/2018 |
| EP | 3476306 A2 | 5/2019 |
| EP | 3566664 B1 | 3/2022 |
| GB | 937587 A | 9/1963 |
| GB | 973587 A | 10/1964 |
| GB | 2513326 A | 10/2014 |
| GB | 2552540 A | 1/2018 |
| GB | 2552541 A | 1/2018 |
| JP | H0884702 A | 4/1996 |
| JP | H0996146 A | 4/1997 |
| JP | 2002102248 A | 4/2002 |
| JP | 3292879 B2 | 6/2002 |
| JP | 2003061969 A | 3/2003 |
| JP | 2007130485 A | 5/2007 |
| JP | 2009127289 A | 6/2009 |
| JP | 6220085 B2 | 10/2017 |
| WO | WO2006036067 A2 | 4/2006 |
| WO | WO2007137304 A2 | 11/2007 |
| WO | WO2007146894 A2 | 12/2007 |
| WO | WO2008020964 A2 | 2/2008 |
| WO | WO2013027203 A1 | 2/2013 |
| WO | WO2014033717 A1 | 3/2014 |
| WO | WO2015125140 A1 | 8/2015 |
| WO | WO2016063213 A1 | 4/2016 |
| WO | WO2016161449 A1 | 10/2016 |
| WO | WO2020141702 A1 | 7/2020 |

OTHER PUBLICATIONS

Ikuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.

(56)        References Cited

OTHER PUBLICATIONS

Clement et al.; Design of a Snake-Like Manipulator; Robotics and Autonomous Systems; 6(3); pp. 265-282; Jul. 1990.

Jug et al.; The JPL Sepentine Robot: a 12 DOF System for Inspection (Conference Paper); Proceedings—IEEE International Conference on Robotics and Automation 3: 5 pgs.; Jun. 1995.

Walker et al.; Novel 'Elephant's Trunk' Robot; IEEE/ASME International Conference on Advanced Intelligent Mechatronics, AIM; Piscataway, NJ, United States; pp. 410-415; Sep. 19-23, 1999.

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Awtar et al.; A minimally invasive surgical tool with enhanced dexterity and intuitive actuation; J. Med. Devices; 4(3); 8 pages; (Author's Draft; 12 pages); Sep. 10, 2010.

Do et al.; Adaptive control of position compensation for cable-conduit mechanisms used in flexible surgical robots; Proceedings of the 11th International Conference on Informatics in Control, Automation and Robotics (ICINCO-2014); IEEE; pp. 110-117; Sep. 1, 2014.

Licht et al.; U.S. Appl. No. 15/286,489 entitled "Medical devices having smoothly articulating multi-cluster joints," filed Oct. 5, 2016.

Zimmerman et al.; U.S. Appl. No. 15/286,547 entitled "End-effector jaw closure transmission system for remote access tools," filed Oct. 5, 2016.

Wikipedia; Constant Velocity Joint; 6 pgs.; retrieved from the Internet (https://en.wikipedia.org/wiki/Constant-velocity_joint) on Dec. 22, 2016.

Awtar; U.S. Appl. No. 15/564,112 entitled "Tension management apparatus for cable-driven transmission," filed Oct. 3, 2017.

Zimmerman et al.; U.S. Appl. No. 15/946,612 entitled "End-effector jaw closure transmission systems for remote access tools," filed Apr. 5, 2018.

Wikipedia; Six-bar linkage; 2 pages; retrieved from the internet (https://en.wikipedia.org/w/index.php?title=Six-bar_linkage&oldid=670945266) on Apr. 26, 2019.

International Preliminary Report on Patentability for International Application No. PCT/US2021/050843 dated Mar. 21, 2023 (6 pages).

International Search Report and Written Opinion for International Application No. PCT/US2021/050843 dated Dec. 28, 2021 (11 pages).

Supplementary European Search Report for European Patent Application No. EP21870281.9 dated Sep. 2, 2024 (7 pages).

Israeli Office Action for Israeli Application No. 301013 dated Jul. 24, 2025 (5 pages).

Japanese Office Action for Japanese Patent Application No. 2023-517758 dated Apr. 15, 2025 (15 pages).

* cited by examiner

34

48, 52

46, 50

Rotates with Dial

Does not rotate with Dial

Rotates with Dial

Does not rotate with Dial

PART OF MI
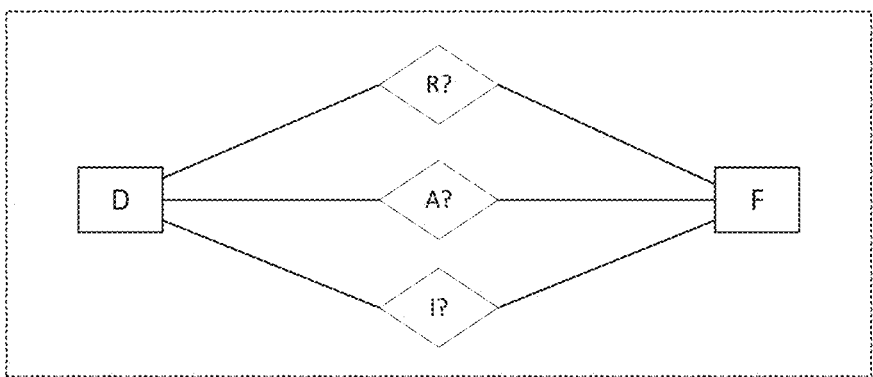
PART OF DI
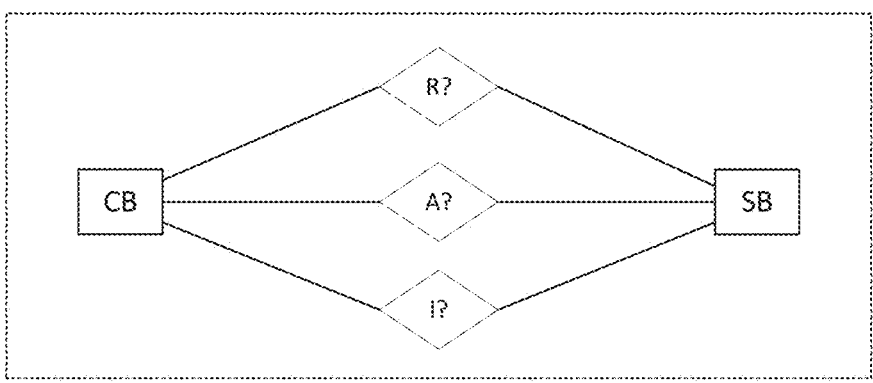
STORAGE STATE
(STATE 1)
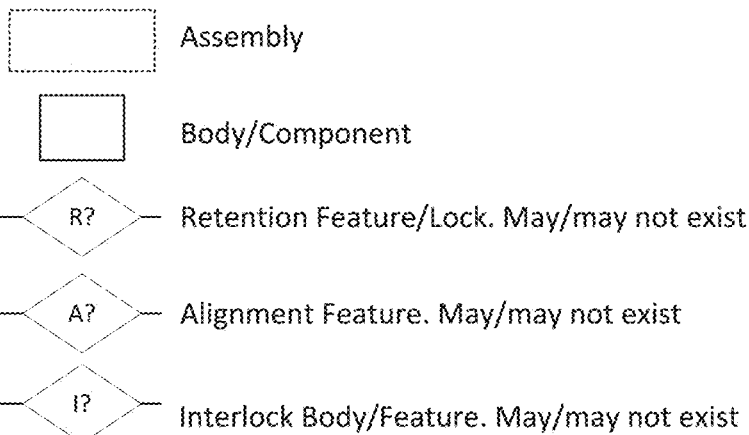
Fig. 13A

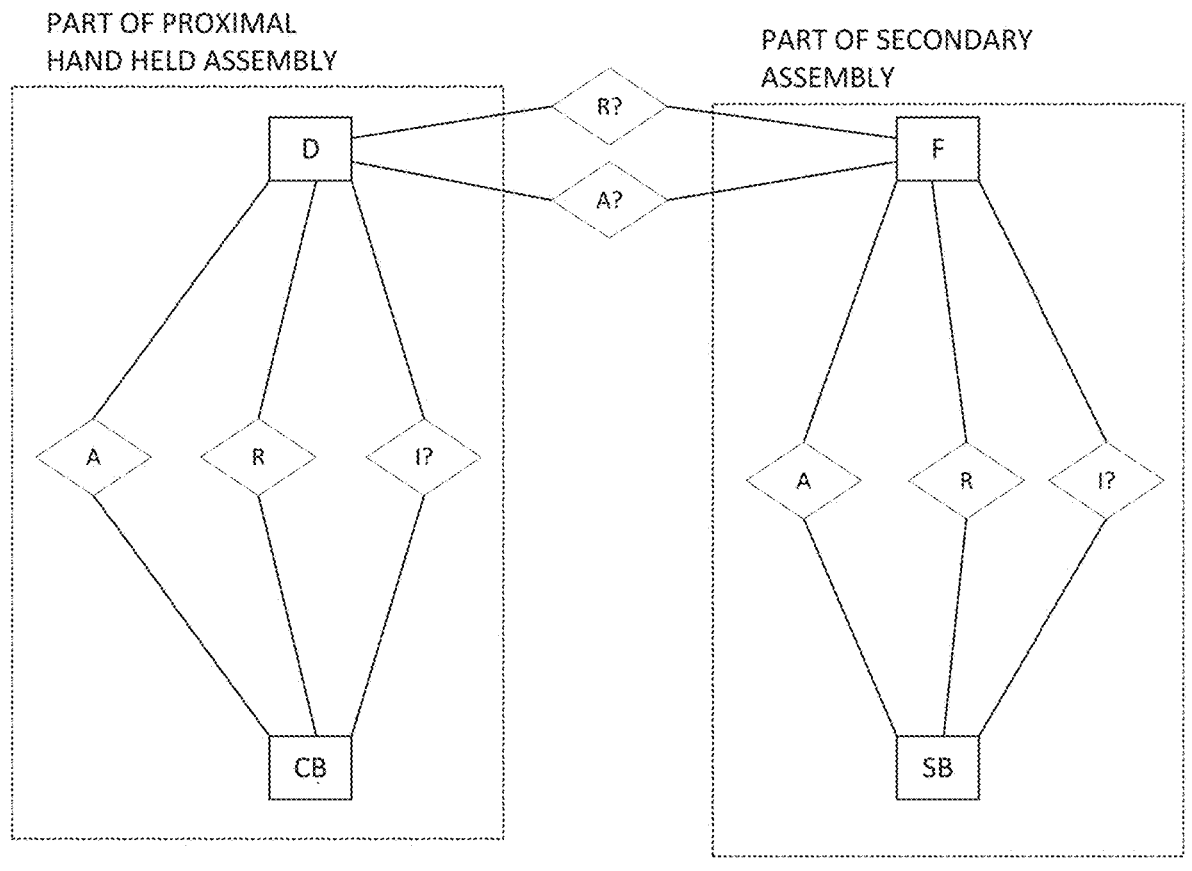
PART OF PROXIMAL
HAND HELD ASSEMBLY
PART OF SECONDARY
ASSEMBLY
USE STATE
(STATE 3)
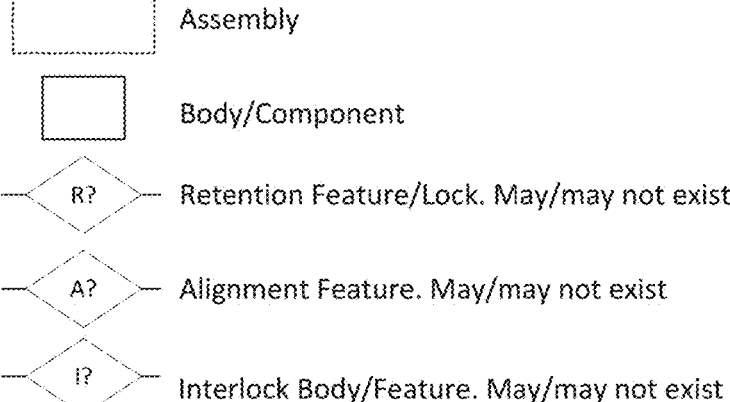
Assembly
Body/Component
Retention Feature/Lock. May/may not exist
Alignment Feature. May/may not exist
Interlock Body/Feature. May/may not exist
Fig. 13B

PART OF PROXIMAL
HAND HELD ASSEMBLY

PART OF SECONDARY
ASSEMBLY

ASSEMBLED STATE
(STATE 2)

Assembly

Body/Component

R? — Retention Feature/Lock. May/may not exist

A? — Alignment Feature. May/may not exist

I? — Interlock Body/Feature. May/may not exist

PART OF VCU (MI)
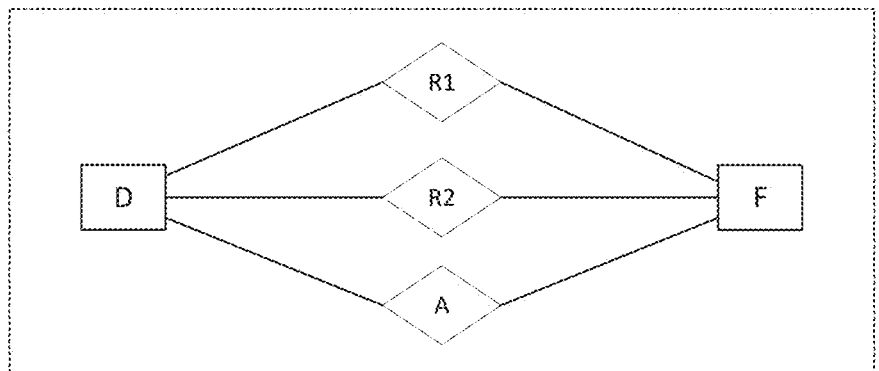
PART OF DI
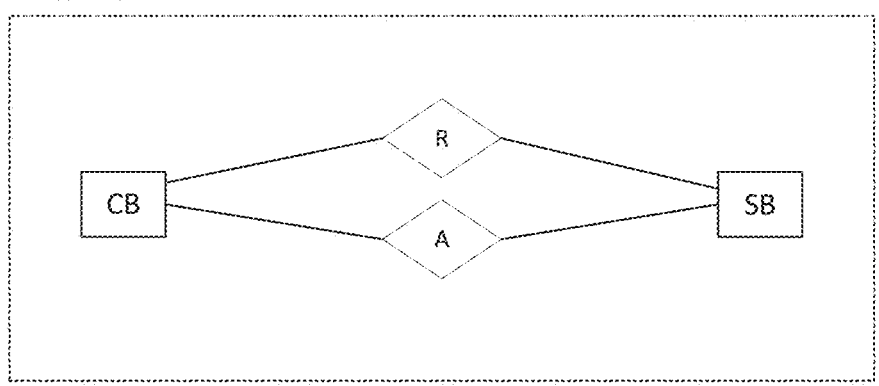
STORAGE STATE
(STATE 1)
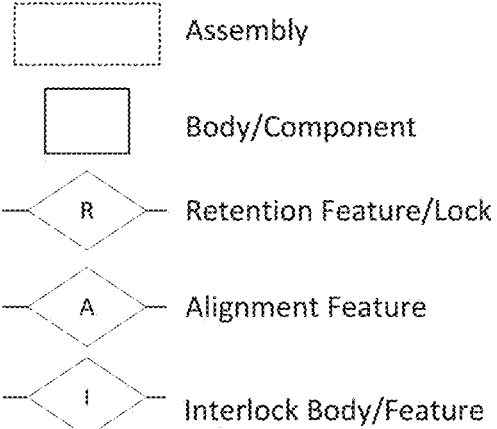
Fig. 15A PART OF PROXIMAL
HAND HELD ASSEMBLY
PART OF SECONDARY
ASSEMBLY
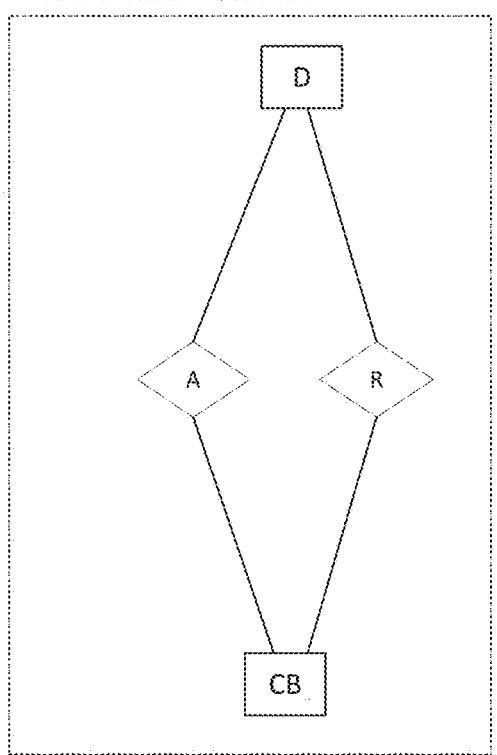
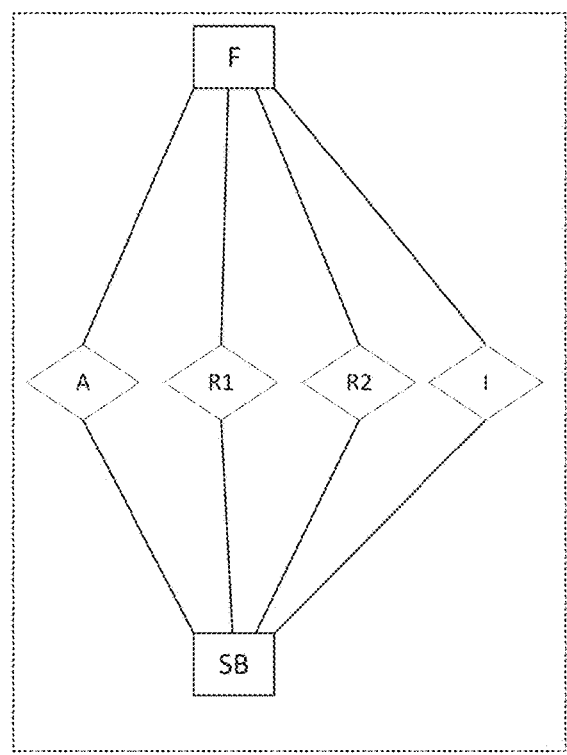
USE STATE
(STATE 3)
Assembly
Body/Component
Retention Feature/Lock
Alignment Feature
Interlock Body/Feature
Fig. 15B

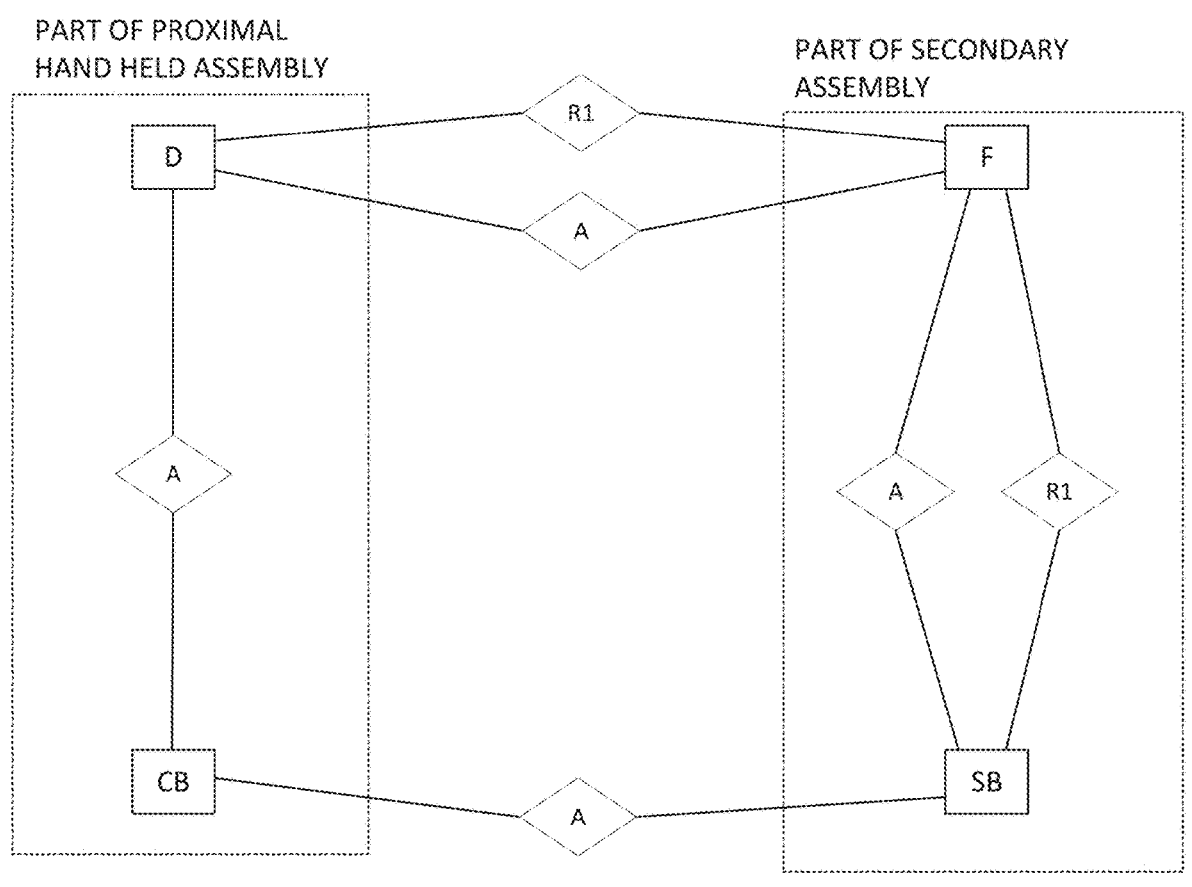
PART OF PROXIMAL
HAND HELD ASSEMBLY
PART OF SECONDARY
ASSEMBLY
ASSEMBLED STATE
(STATE 2)
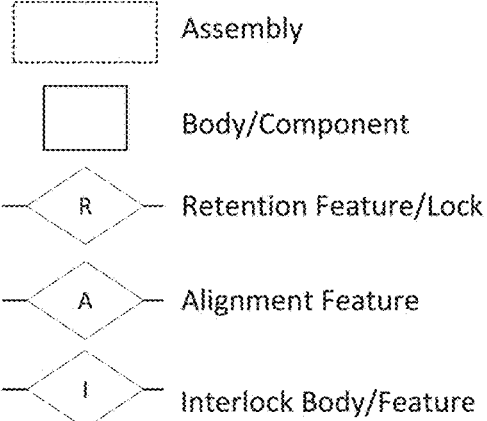
Assembly
Body/Component
Retention Feature/Lock
Alignment Feature
Interlock Body/Feature
Fig. 15C

16

116

126

112

113

112

119

115

76

83

79

81

76

107

90

131

88

94

Offset in axes
rotation

152

154

FRAME-SB STRUCTURAL DI: STATE 1

FRAME-SB STRUCTURAL DI: STATE 2

Jaw Closure
Transmisson Path

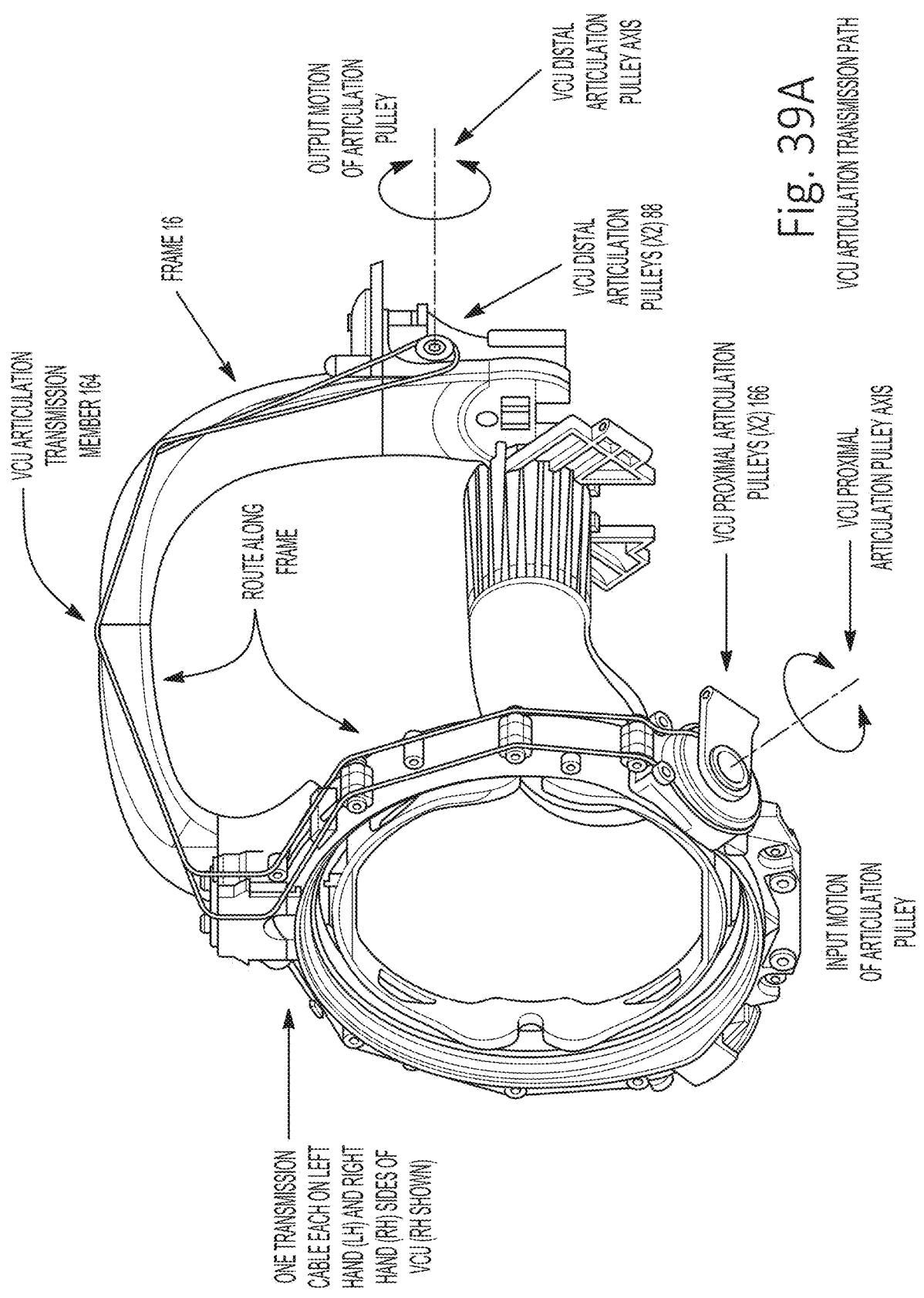

OUTPUT MOTION OF ARTICULATION PULLEY

VCU DISTAL ARTICULATION PULLEY AXIS

FRAME 16

VCU DISTAL ARTICULATION PULLEYS (X2) 88

VCU ARTICULATION TRANSMISSION MEMBER 164

ROUTE ALONG FRAME

VCU PROXIMAL ARTICULATION PULLEYS (X2) 166

VCU PROXIMAL ARTICULATION PULLEY AXIS

INPUT MOTION OF ARTICULATION PULLEY

ONE TRANSMISSION CABLE EACH ON LEFT HAND (LH) AND RIGHT HAND (RH) SIDES OF VCU (RH SHOWN)

Fig. 39A
VCU ARTICULATION TRANSMISSION PATH

VCU DISTAL
ARTICULATION PULLEY
(88) TRANSMISSION
INTERFACES

VCU ARTICULATION TRANSMISSION PATH
ROUTED AROUND VCU ARTICULATION PULLEYS

SHAFT BOX
ARTICULATION
TRANSMISSION
MEMBER 168

ROUTE THROUGH
SHAFT BOX LH AND
RH INTO SHAFT

SHAFT BOX ARTICULATION TRANSMISSION PATH
(SIDE VIEW)

145

94

Axis 1

20

24

16

30

| Initial State | Transition | Final State | Action applied | L1 (76) | L2 (74) | L3 (90) | L4 (72) | L5 (92) | L6 (112) | L7 (118) | I1 (72) | I2 (73) |
|---|---|---|---|---|---|---|---|---|---|---|---|---|
| S1 | - | S1 | - | 1 | 1 | 0 | 0 | 1 | 0 | 1 | 0 | 0 |
| S1 | T1 | S2 | A1 | 0 | 1 | 1 | 0 | 0 | 0 | 0 | 0 | 0 |
| S2 | T2 | S3 | A2 | 0 | 0 | 1 | 1 | 0 | 1 | 0 | 1 | 1 |
| S1 | T3 | S4 | A3 | 0 | 0 | 0 | 0 | 0 | 0 | 1 | 0 | 0 |

Fig. 56B

| States | Install | Uninstall | Un-home | Home |
|--------|---------|-----------|---------|------|
| STATE 1 | ✓ | n/a | X | n/a |
| STATE 2 | n/a | ✓ | ✓ | n/a |
| STATE 3 | n/a | X | n/a | ✓ |

Fig. 57

CLEARANCE B/W GUIDE CHANNEL
ON LEFT .58 TO DF BOTTOM GUIDE
X_DIRECTION

CLEARANCE B/W GUIDE CHANNEL
ON LEFT .58 TO DF BOTTOM GUIDE
X_DIRECTION

CLEARANCE B/W GUIDE CHANNEL
ON RIGHT .58 TO DF BOTTOM GUIDE
X_DIRECTION

CLEARANCE B/W GUIDE CHANNEL
ON RIGHT .58 TO DF BOTTOM GUIDE
X_DIRECTION

Frame Top Pin

SB Top Pin Channel

CB Guide Channel

Dial Guide

X-Axis dial
interface
(alignment)

X-Axis dial
interface
(alignment)

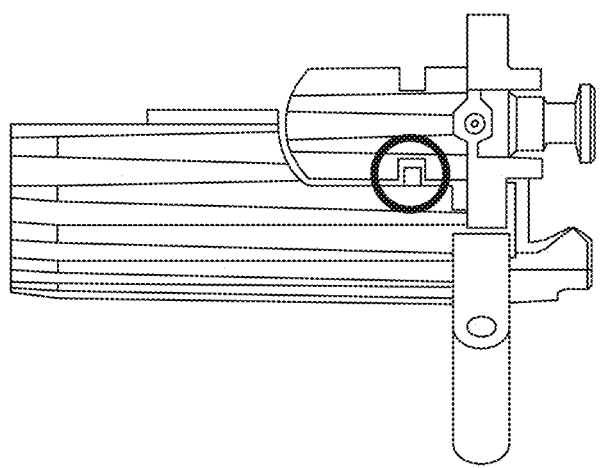
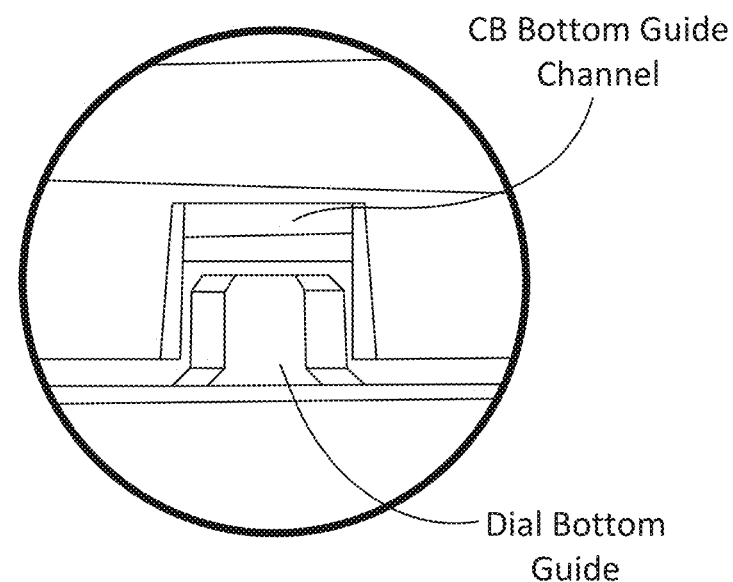
CB Bottom Guide
Channel
Dial Bottom
Guide
Fig. 70

90

Locking profile of Button has same center point as the pivot point. Any reaction force on the locking surface will intersect the pivot axis of the Button.

116

120

28

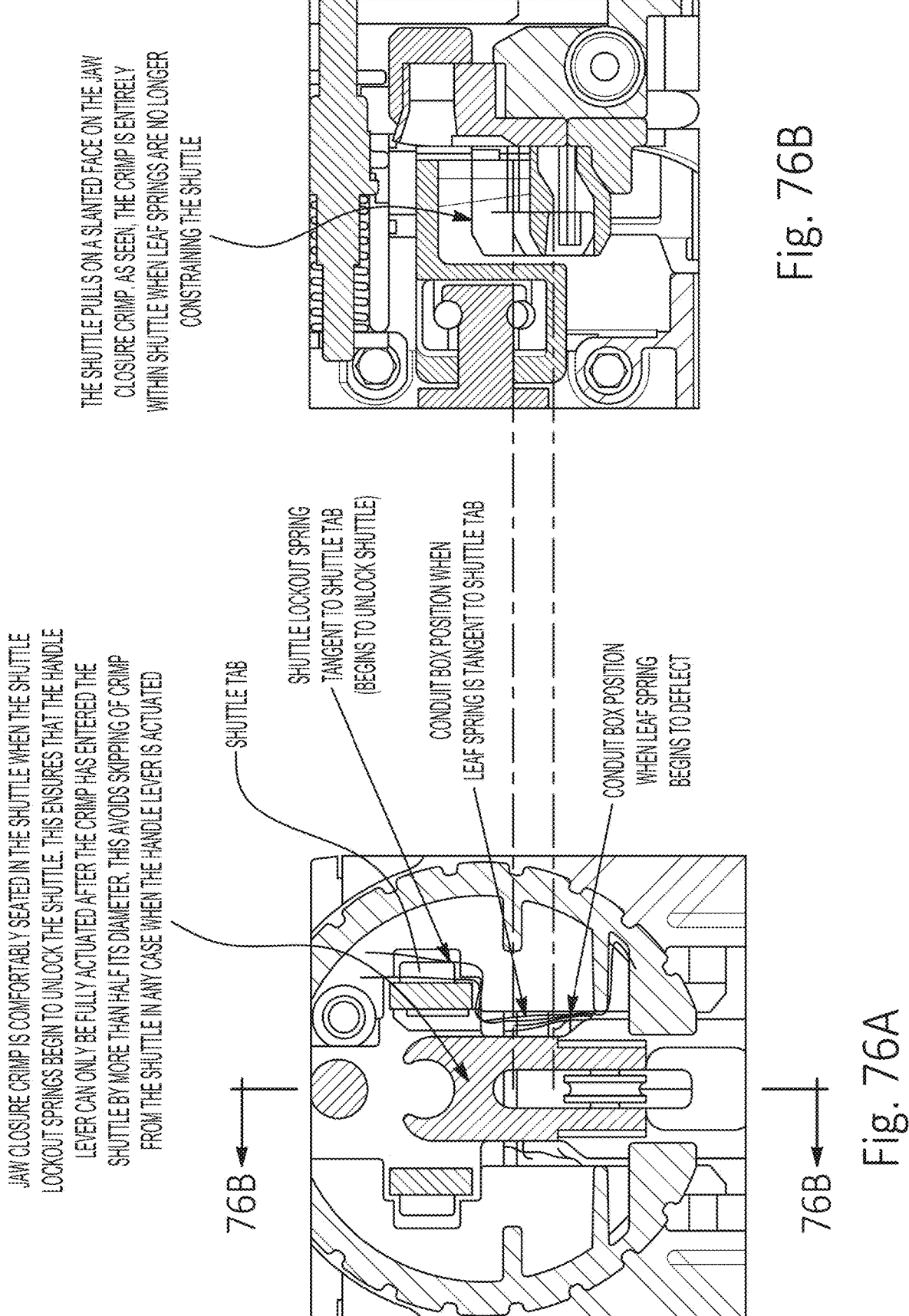

THE SHUTTLE PULLS ON A SLANTED FACE ON THE JAW CLOSURE CRIMP. AS SEEN, THE CRIMP IS ENTIRELY WITHIN SHUTTLE WHEN LEAF SPRINGS ARE NO LONGER CONSTRAINING THE SHUTTLE

Fig. 76B

JAW CLOSURE CRIMP IS COMFORTABLY SEATED IN THE SHUTTLE WHEN THE SHUTTLE LOCKOUT SPRINGS BEGIN TO UNLOCK THE SHUTTLE. THIS ENSURES THAT THE HANDLE LEVER CAN ONLY BE FULLY ACTUATED AFTER THE CRIMP HAS ENTERED THE SHUTTLE BY MORE THAN HALF ITS DIAMETER. THIS AVOIDS SKIPPING OF CRIMP FROM THE SHUTTLE IN ANY CASE WHEN THE HANDLE LEVER IS ACTUATED

SHUTTLE TAB

SHUTTLE LOCKOUT SPRING TANGENT TO SHUTTLE TAB (BEGINS TO UNLOCK SHUTTLE)

CONDUIT BOX POSITION WHEN LEAF SPRING IS TANGENT TO SHUTTLE TAB

CONDUIT BOX POSITION WHEN LEAF SPRING BEGINS TO DEFLECT

Button seated
onto Frame and
locking SB w.r.t.
Frame

Conduit Box
aligned w.r.t.
Dial

CBLP unlocks the CB w.r.t.
SB (clearance exists
between CB and CBLP)

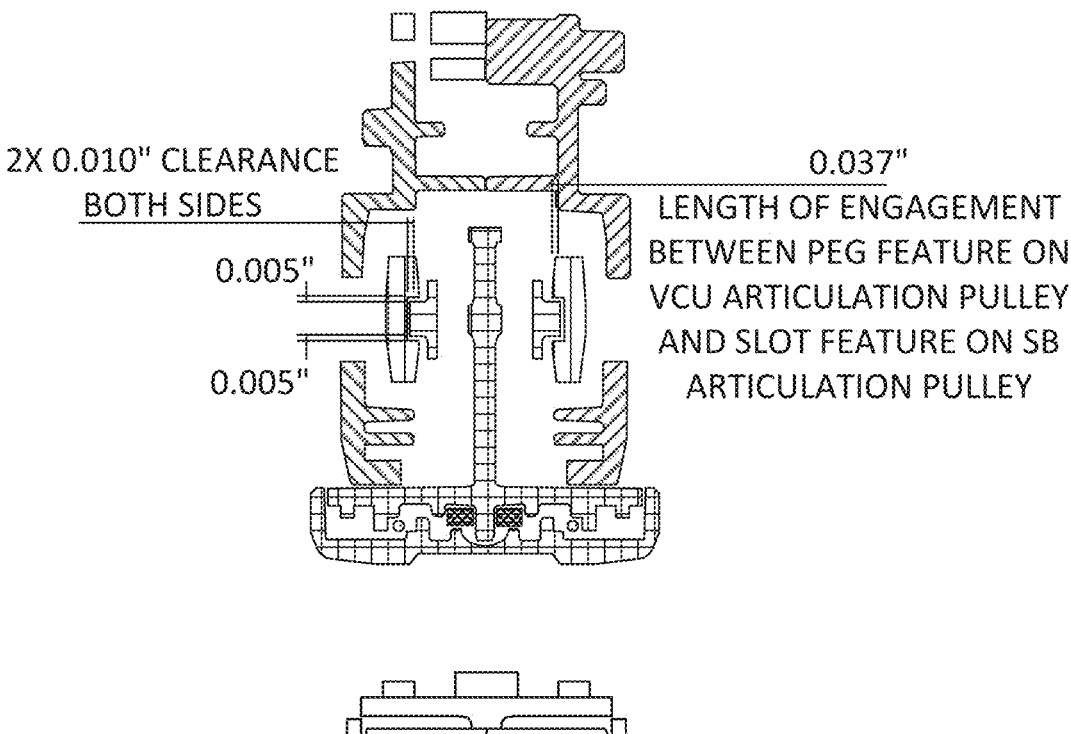
2X 0.010" CLEARANCE BOTH SIDES
0.005"
0.005"
0.037" LENGTH OF ENGAGEMENT BETWEEN PEG FEATURE ON VCU ARTICULATION PULLEY AND SLOT FEATURE ON SB ARTICULATION PULLEY
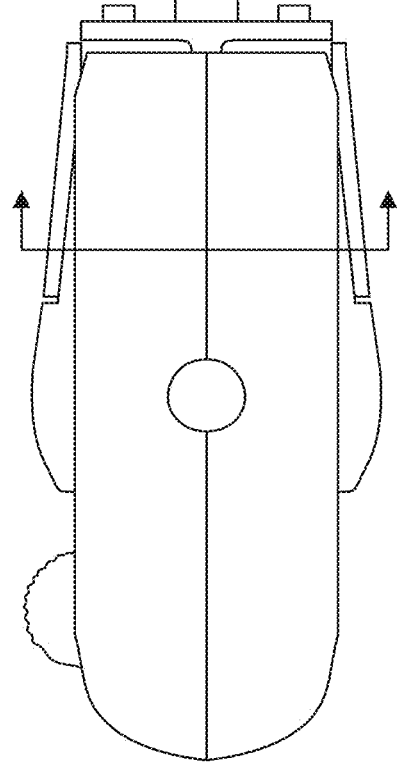
Fig. 79

Transition 1: State 1 to State 2

| # | Transition Description | Timeline ➡ | |
|---|---|---|---|
| | | $t_0$                    $t_f$ | |
| T1.1 | Shaft Box alignment to Frame | | T1.1 |
| T1.2 | Conduit Box alignment to Dial | | T1.2 |
| T1.3 | Shaft Box retention to Frame | | T1.3 |
| T1.4 | Alignment and retention of Crimp Housing w.r.t. Shuttle | | T1.4 |
| T1.5 | Shuttle getting unlocked w.r.t. Dial | | T1.5 |
| T1.6 | Dial unlocking w.r.t. Frame | | T1.6 |
| T1.7 | Conduit Box unlocking w.r.t. Shaft Box | | T1.7 |
| T1.8 | Articulation Pulleys (Frame and SB) Interface | | T1.8 |

Fig. 80

POSITIVE ENGAGEMENT FEATURES ON CB

CONDUIT BOX
LOCKOUT SHAFT 112

CONDUIT BOX 28

SHUTTLE INTERFACE WITH VCU LEVER
PRODUCES CCW ROTATION OF VCU LEVER
TO BUILD CLEARANCE BETWEEN VCU LEVER
AND BUTTON

VCU LEVER 72

BUTTON'S
ROTATION
BLOCKED BY
VCU LEVER

BUTTON 90

Transition 2: State 2 to State 3

| # | Transition Description | Timeline ➡ | |
|---|---|---|---|
| | | $t_0$             $t_f$ | |
| T2.1 | Dial un-homed w.r.t. Frame | | T2.1 |
| T2.2 | Conduit Box locked w.r.t. Dial | | T2.2 |
| T2.3 | Button blocked by VCU Lever | | T2.3 |
| T2.4 | Shaft Box locked by VCU Lever | | T2.4 |

Fig. 88

Magnets x2

Ramp
surface

DI Locked

DI Unlocked

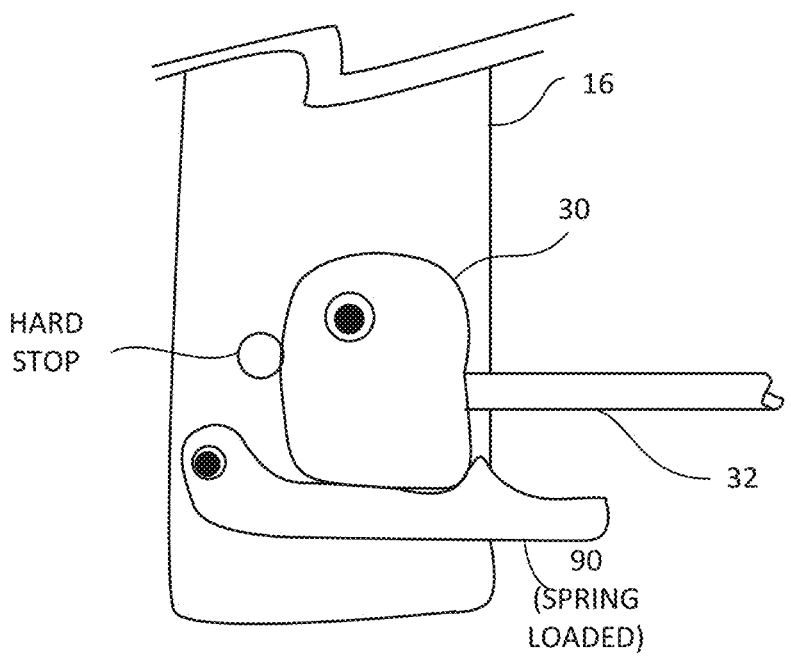
HARD STOP
16
30
32
90
(SPRING
LOADED)
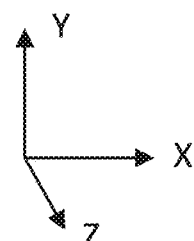
Y
X
Z
Fig. 100B

DETACHABLE SURGICAL TOOL CONFIGURED AS A FINITE STATE MACHINE

CROSS-REFERENCE TO RELATED APPLICATION

This application claims the benefit of U.S. Provisional Patent Application No. 63/079,550, filed on Sep. 17, 2020.

INTRODUCTION

This application relates generally to surgical tools that can be employed for use in minimally invasive surgical procedures and remote access surgical procedures and, more particularly, to surgical tools with multiple bodies.

SUMMARY

In an embodiment, a surgical tool may include a first body, a second body, and a third body. The surgical tool may further include a detachable structural interface, a first lock, a second lock, and an interlock. The detachable structural interface can be established between the first body and the second body. The first lock can be established between the first body and the second body. When established, the first lock maintains establishment of the detachable structural interface. The second lock can be established between the first body and the third body. When established, the second lock retains the first body and the third body together. The interlock can be established at the first lock. When established, the interlock precludes disestablishment of the first lock. Further, the action of disestablishing the second lock prompts the establishment of the interlock.

In another embodiment, a surgical tool may include a first body, a second body, and a third body. The surgical tool may further include a detachable structural interface, a joint, a first lock, and a second lock. The detachable structural interface can be established between the first body and the second body. The joint resides between the first body and the third body, and has two or more degrees of freedom. The first lock can be established between the first body and the second body. When established, the first lock maintains establishment of the detachable structural interface. The second lock can be established between the first body and the third body. In a first state of the surgical tool, the detachable structural interface lacks establishment, the first lock lacks establishment, and the second lock is established. In the first state, the second lock disenables the two or more degrees of freedom. In a second state of the surgical tool, the detachable structural interface is established, the first lock is established, the action of establishing the detachable structural interface prompts the ability to disestablish the second lock. When the second lock is disestablished, the two or more degrees of freedom of the joint between the first body and the third body is enabled.

In yet another embodiment, a surgical tool may include a first body, a second body, a third body, and a fourth body. The surgical tool may further include a first detachable structural interface, a first assembly, a second detachable structural interface, and a second assembly. The first detachable structural interface can be established between the first body and the second body. The first assembly is constituted by the first body and the second body when the first detachable structural interface is established. The second detachable structural interface can be established between the third body and the fourth body. The second assembly is constituted by the third body and the fourth body when the second detachable structural interface is established. The first detachable structural interface and the second detachable structural interface provide independent mechanical energy transmission paths. The first body or the second body of the first assembly is directly coupled to the third body or the fourth body of the second assembly by way of a joint. The joint has one or more degrees of freedom.

BRIEF DESCRIPTION OF THE DRAWINGS

Embodiments of the disclosure are described with reference to the appended drawings, in which:

FIGS. 13A-C are schematic representations of various forms of FSM possible in states 1 through 3;

FIGS. 15A-C are schematic representations of the form in which FSM exists and its various states 1-3;

3

Figure 28A:
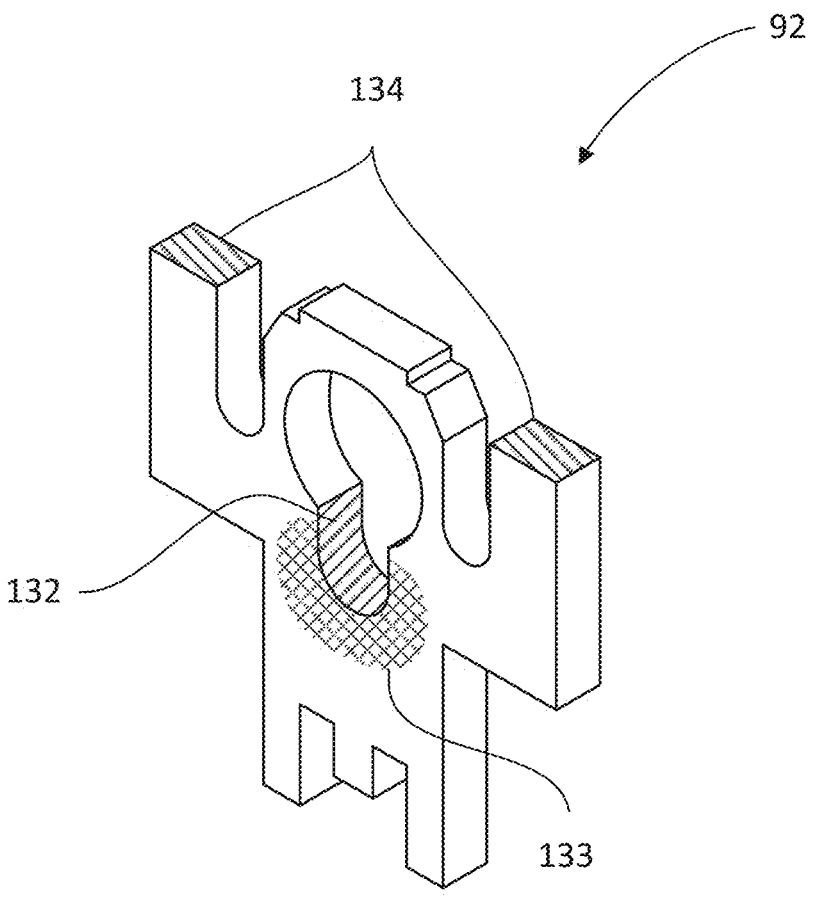
Figure 28B:
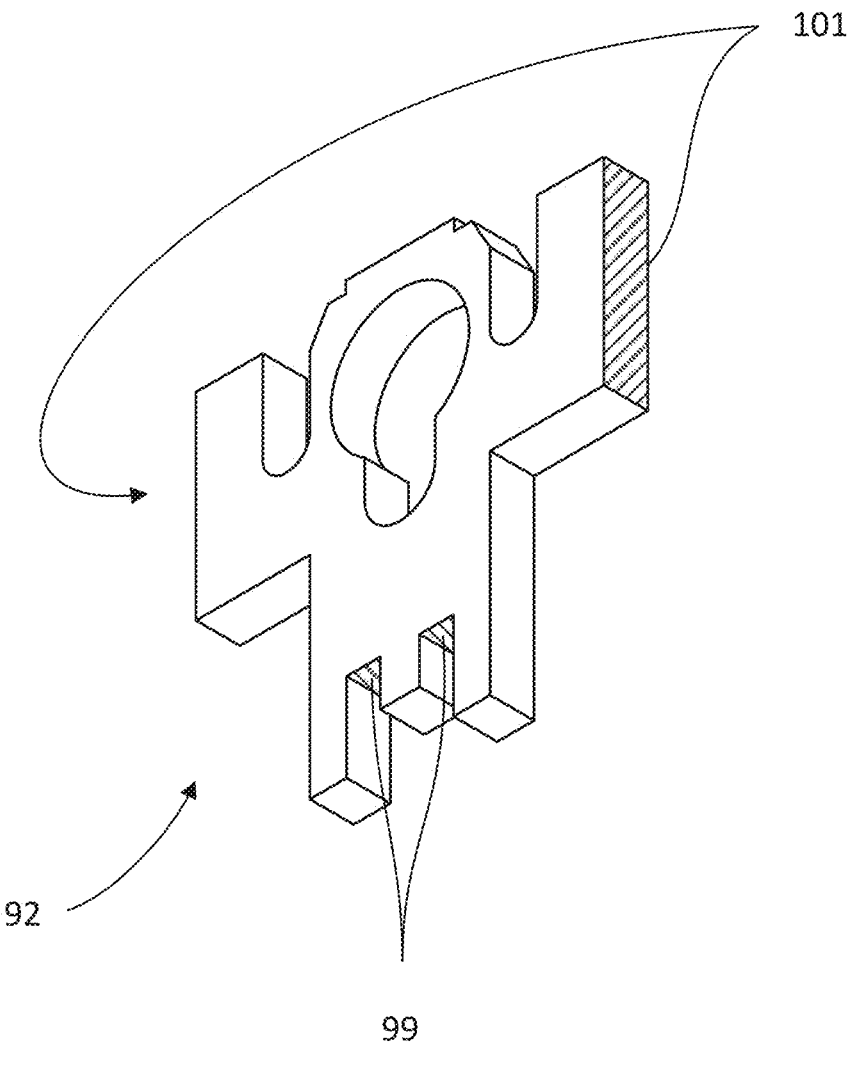
Figure 28C:
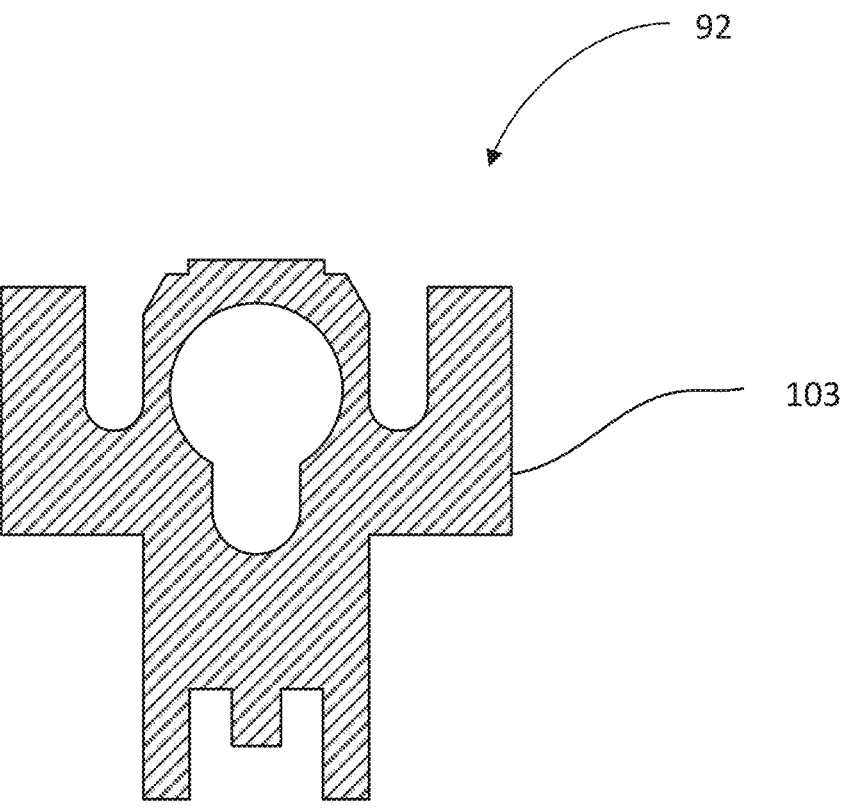
Figure 29A:
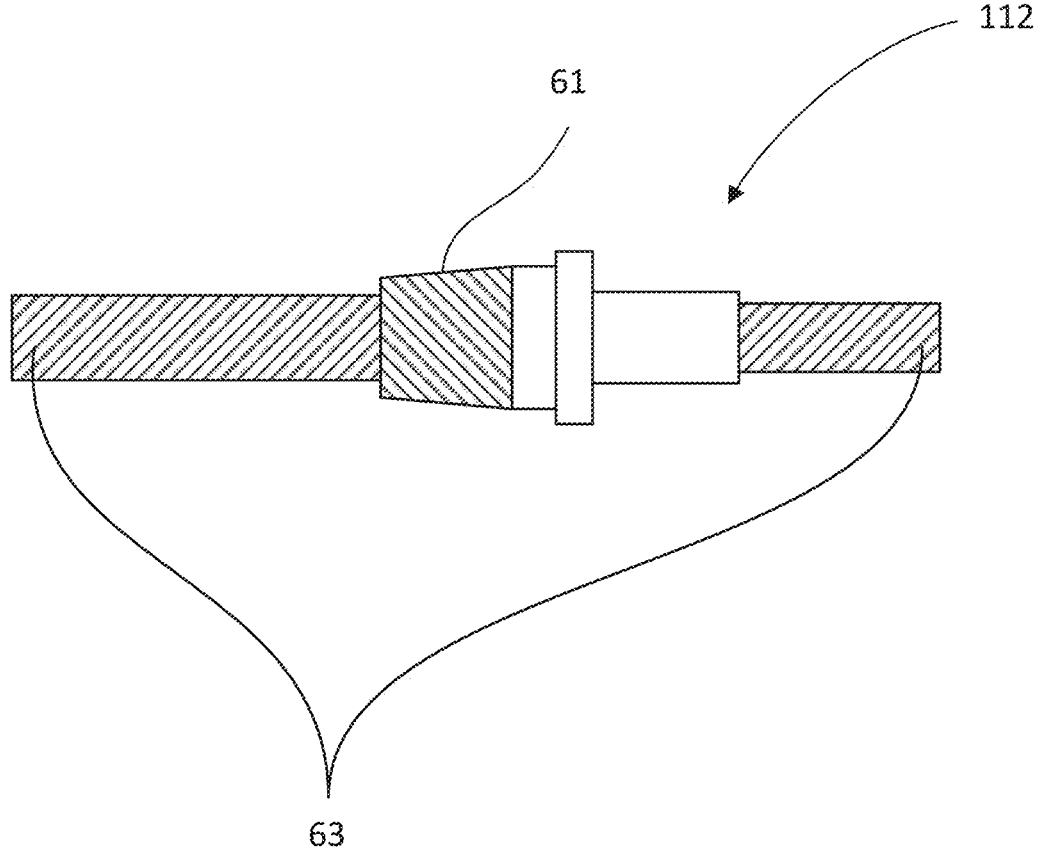
Figure 29B:
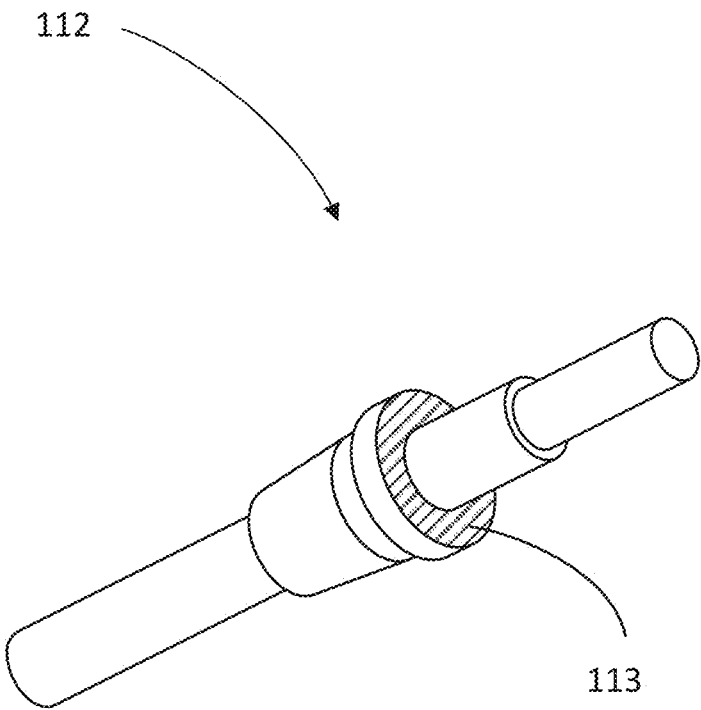
Figure 29C:
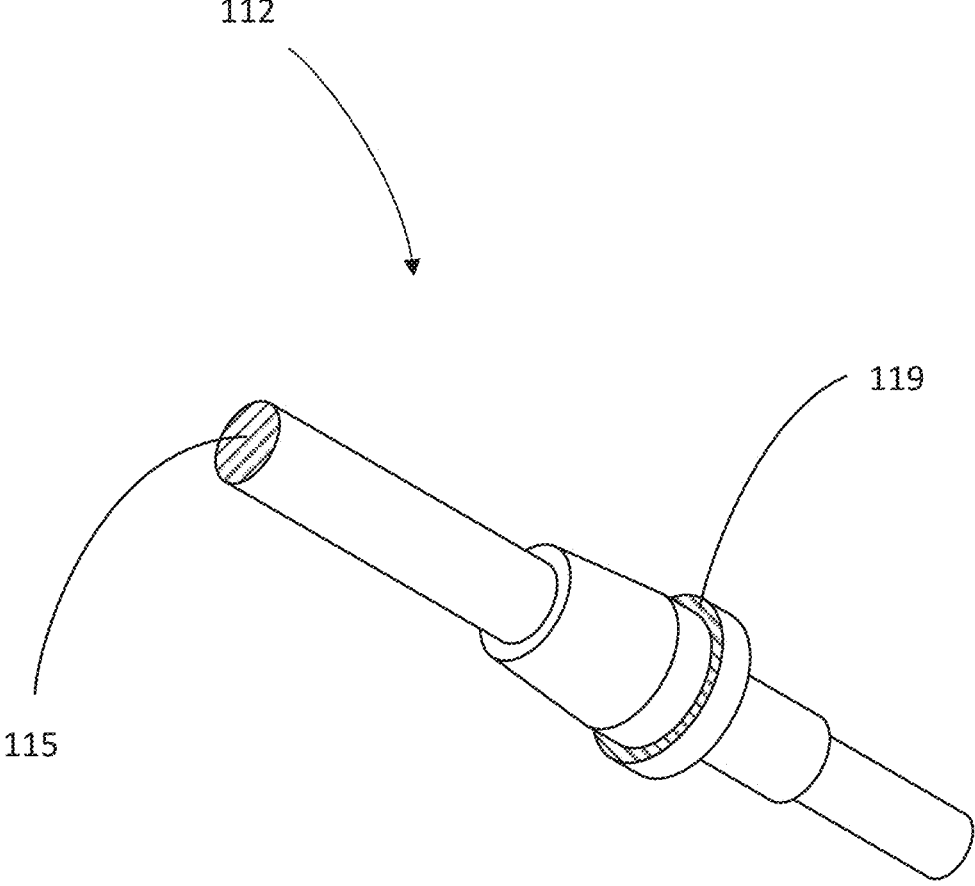
Figure 30A:
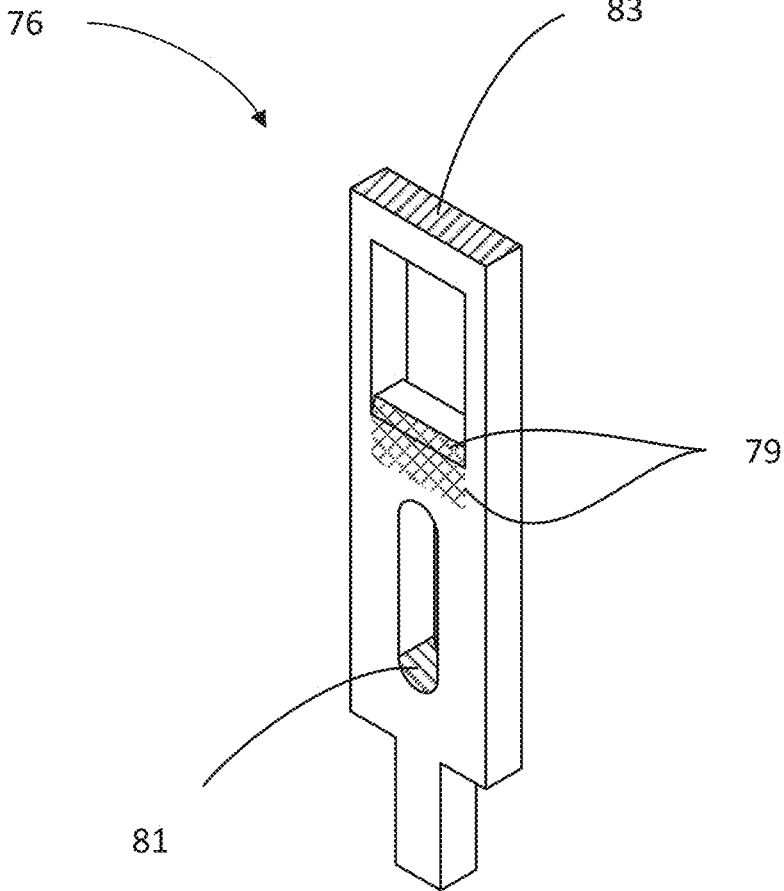
Figure 30B:
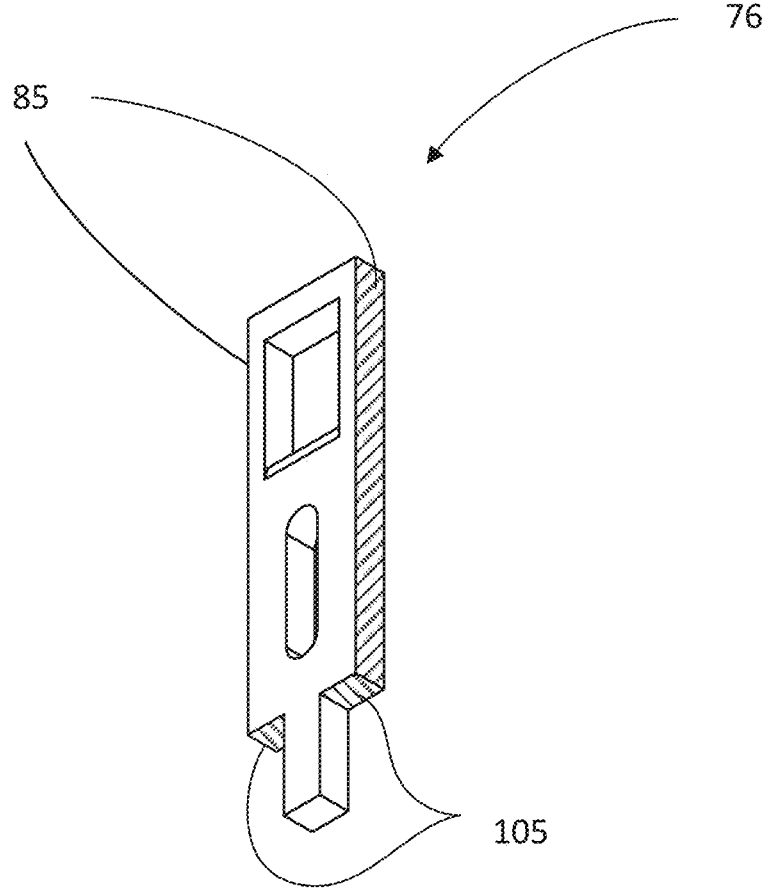
Figure 30C:
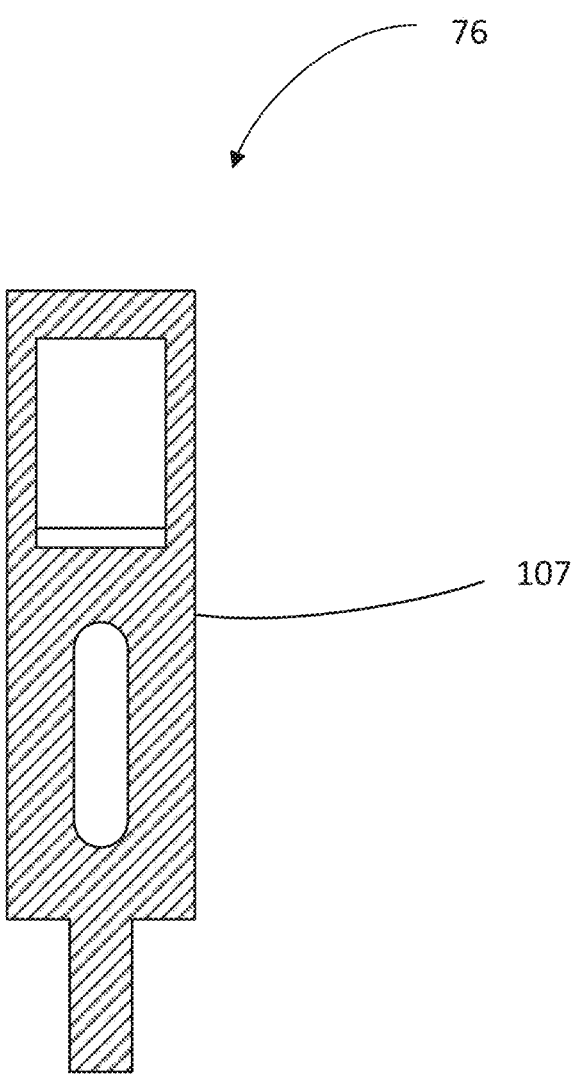
Figure 31A:
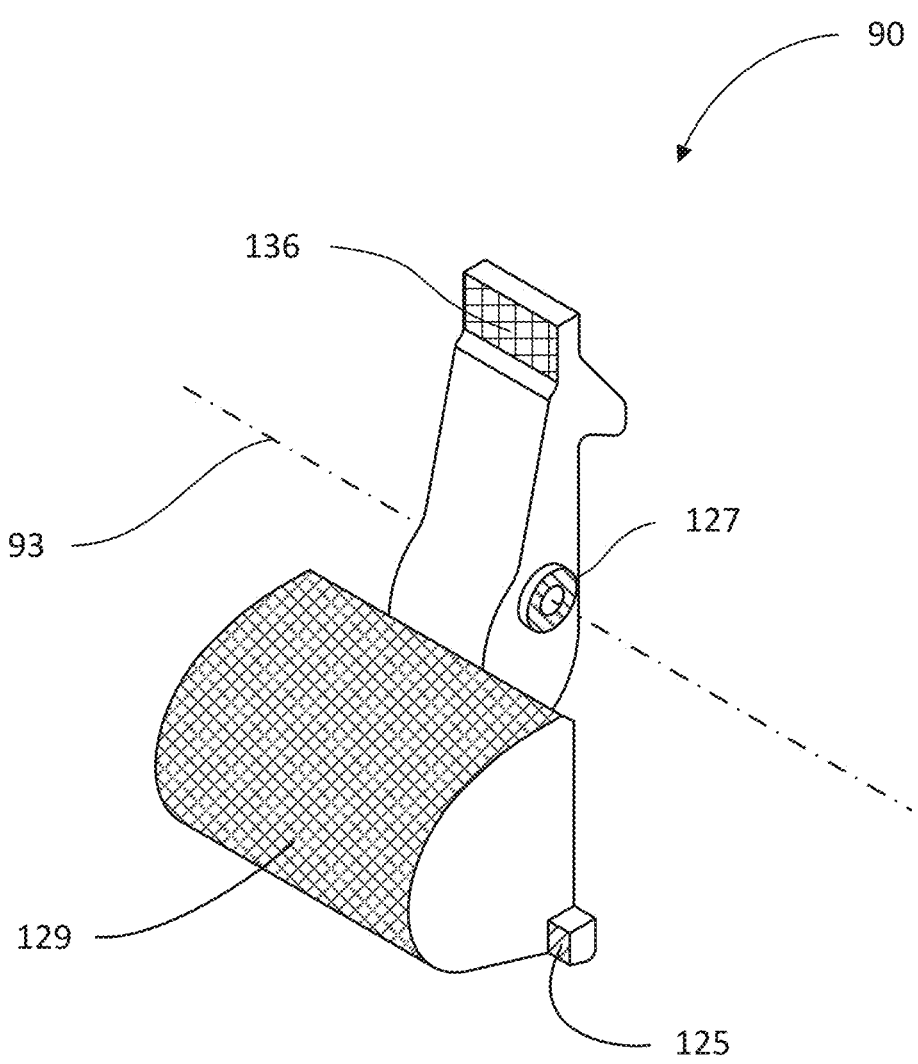
Figure 31B:
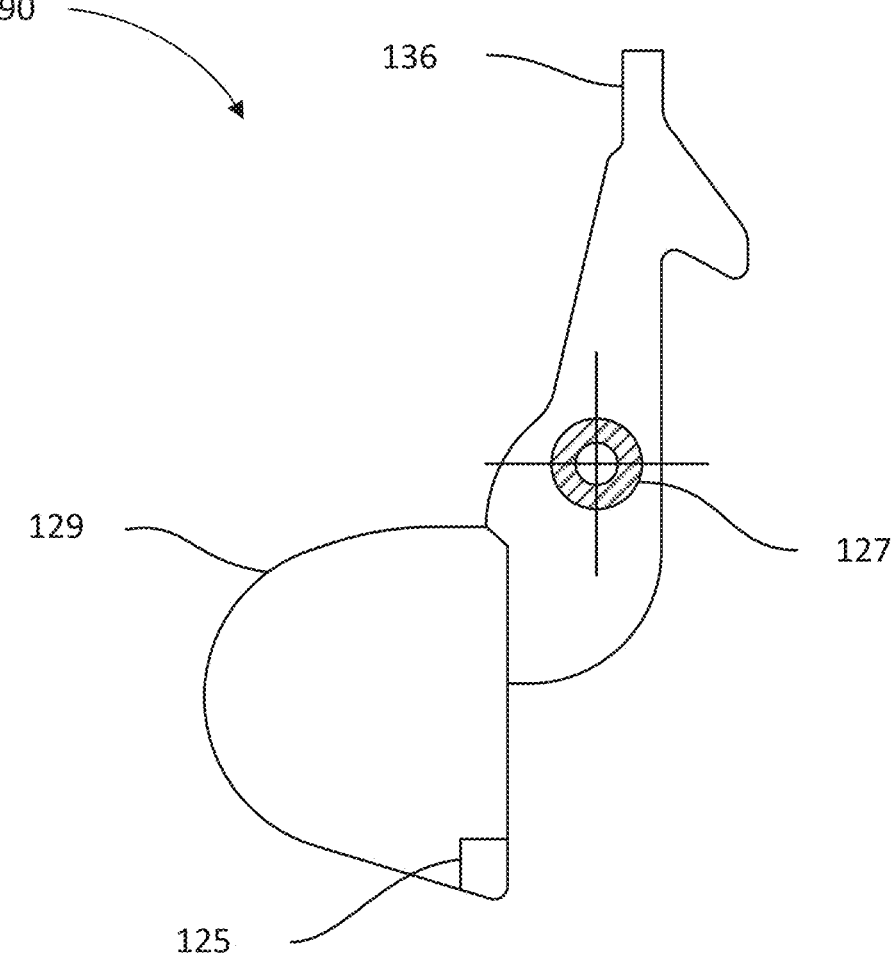
Figure 31C:
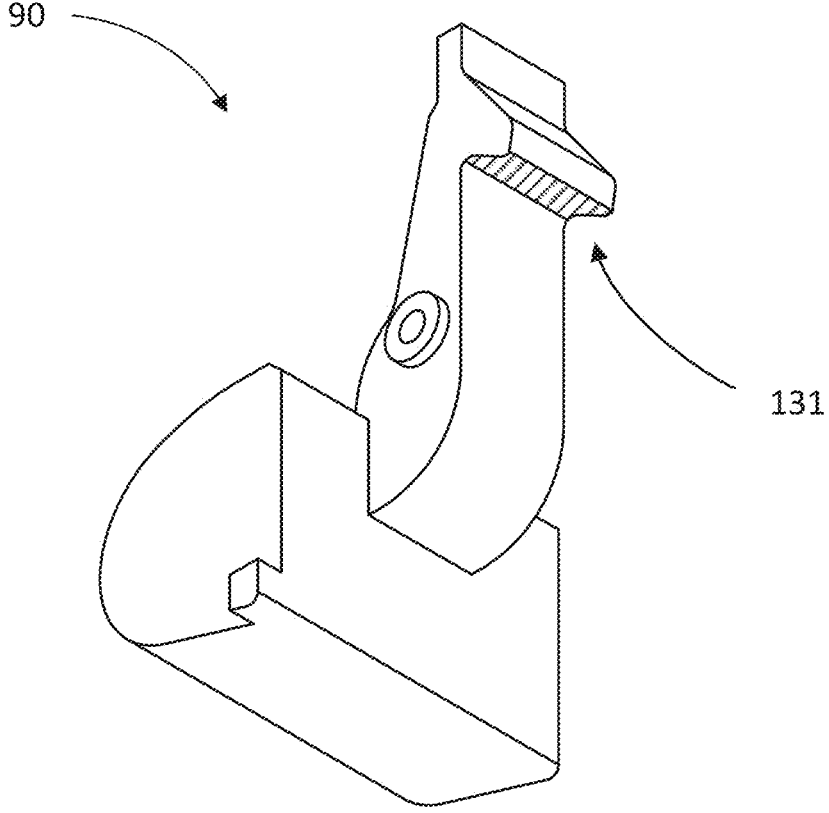
Figure 32A:
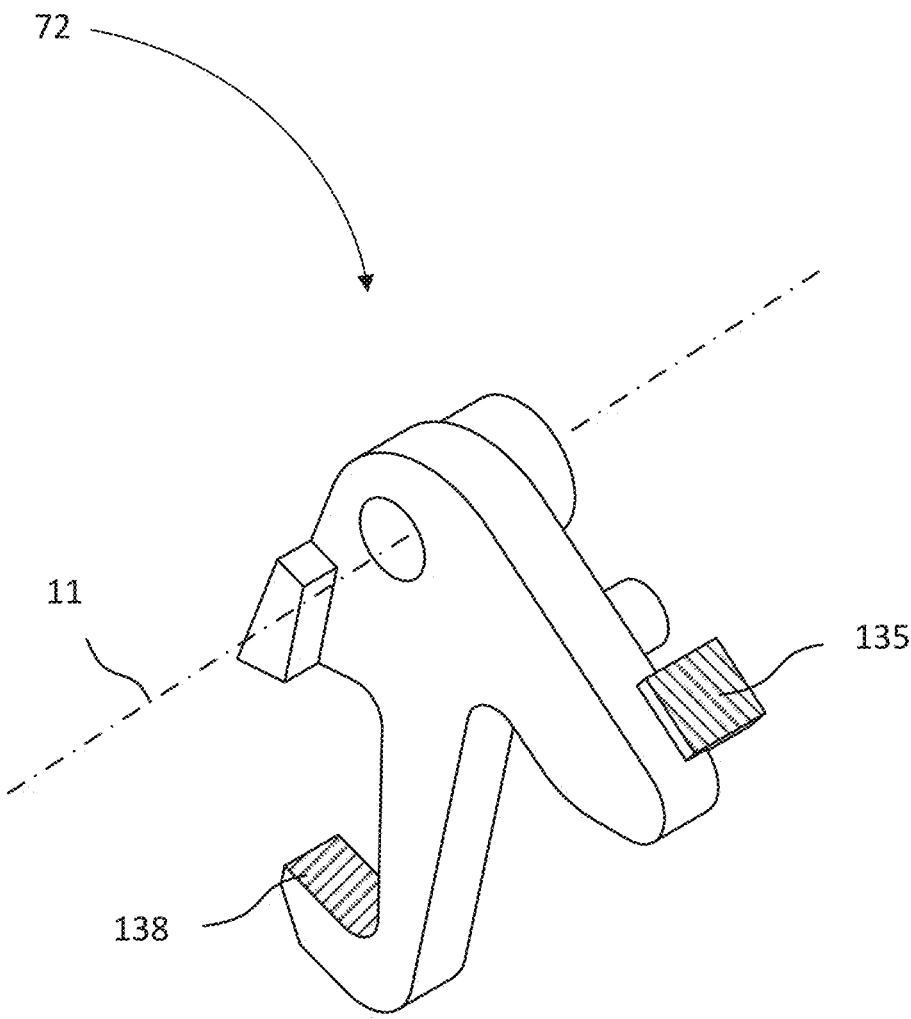
Figure 32B:
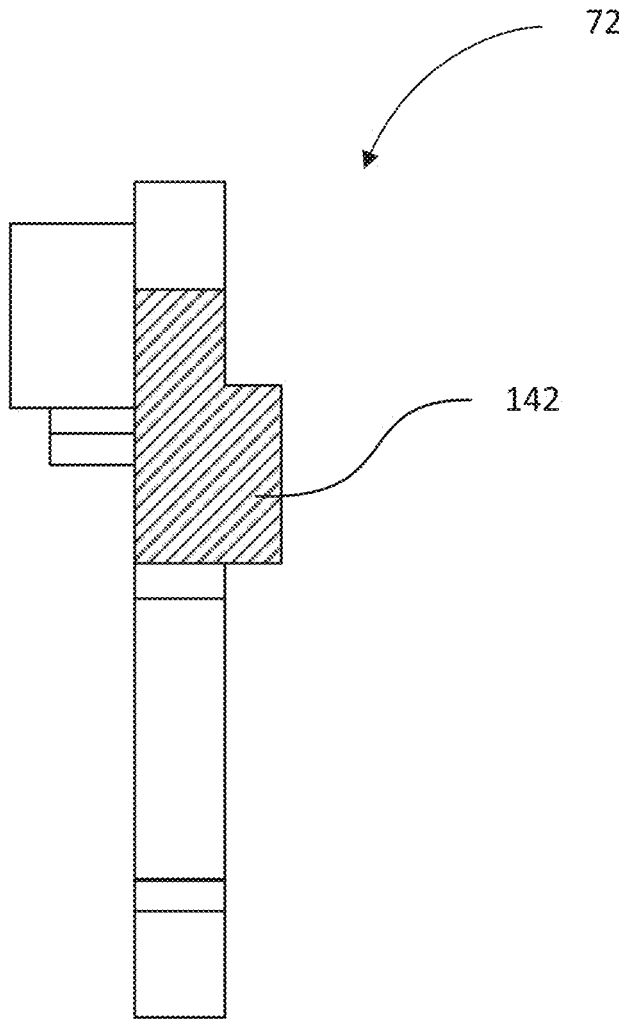
Figure 32C:
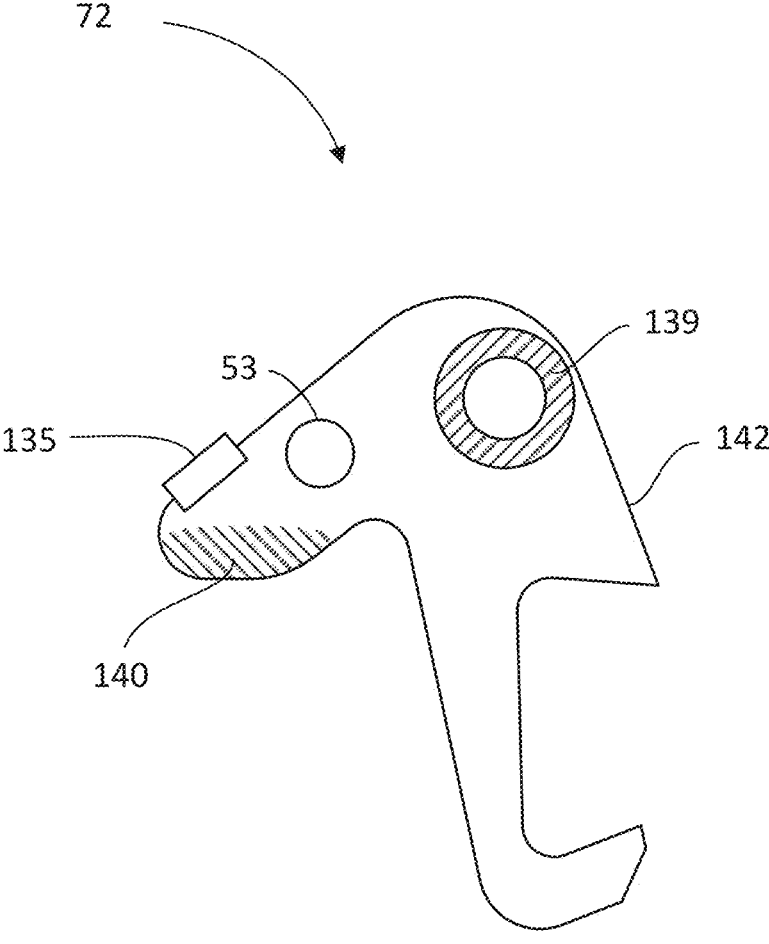
Figure 33A:
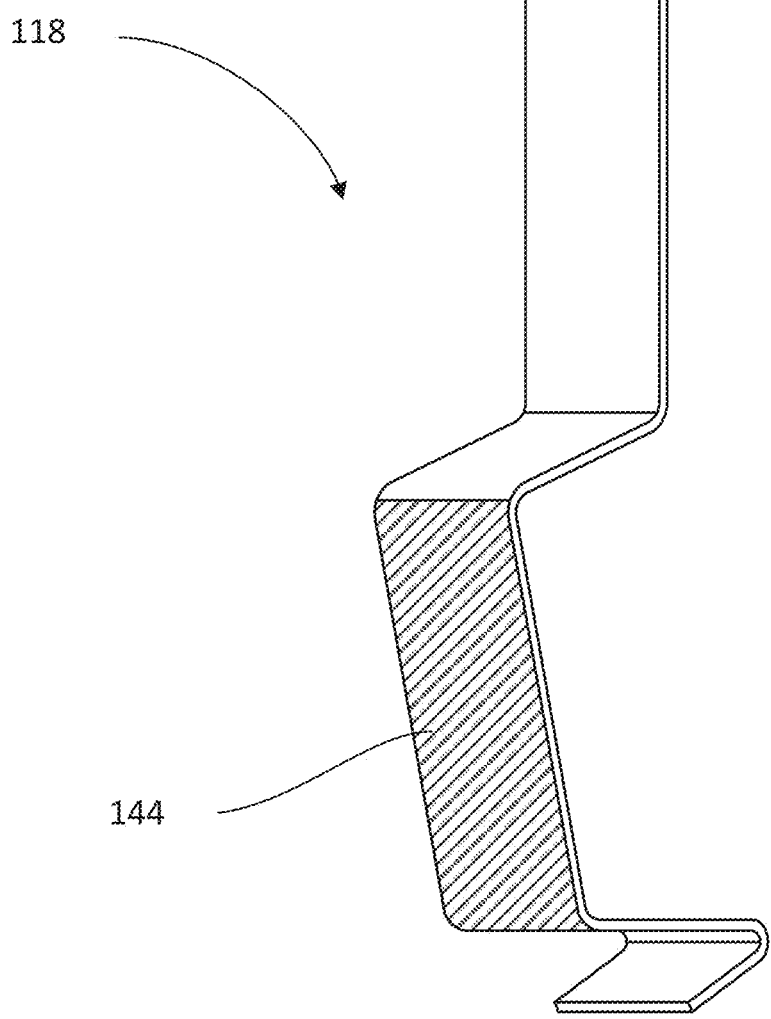
Figure 33B:
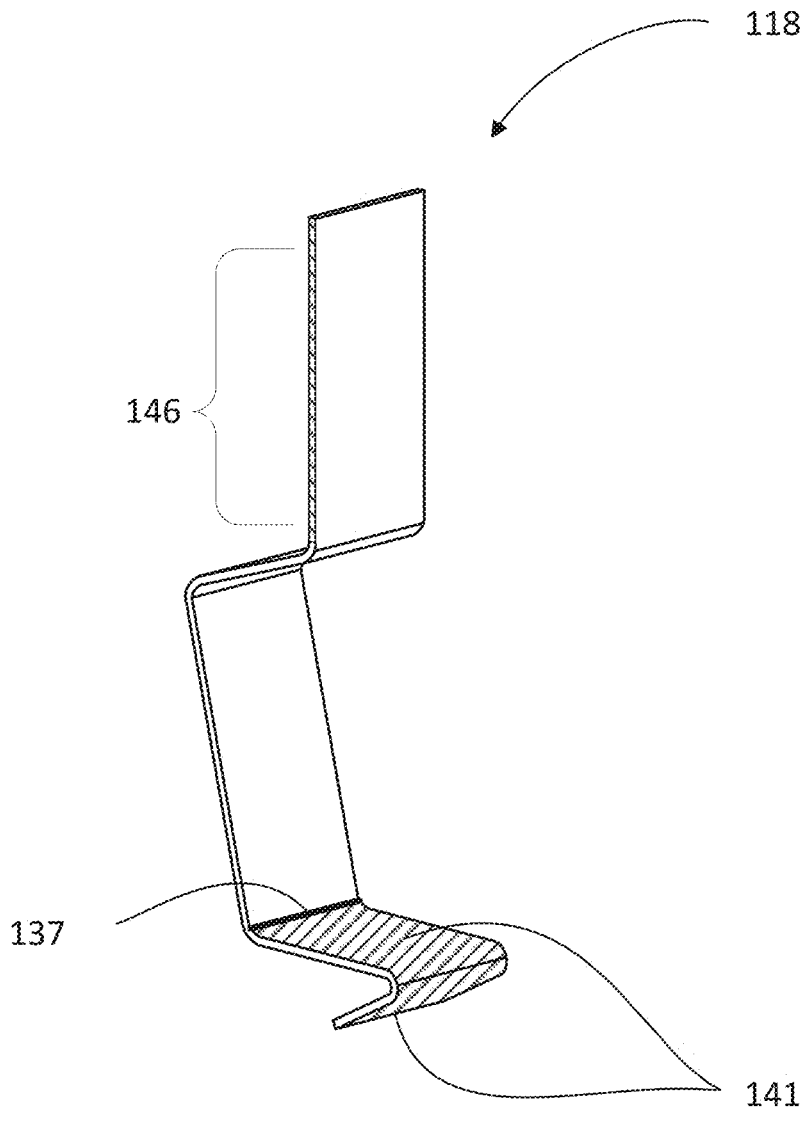
Figure 34:
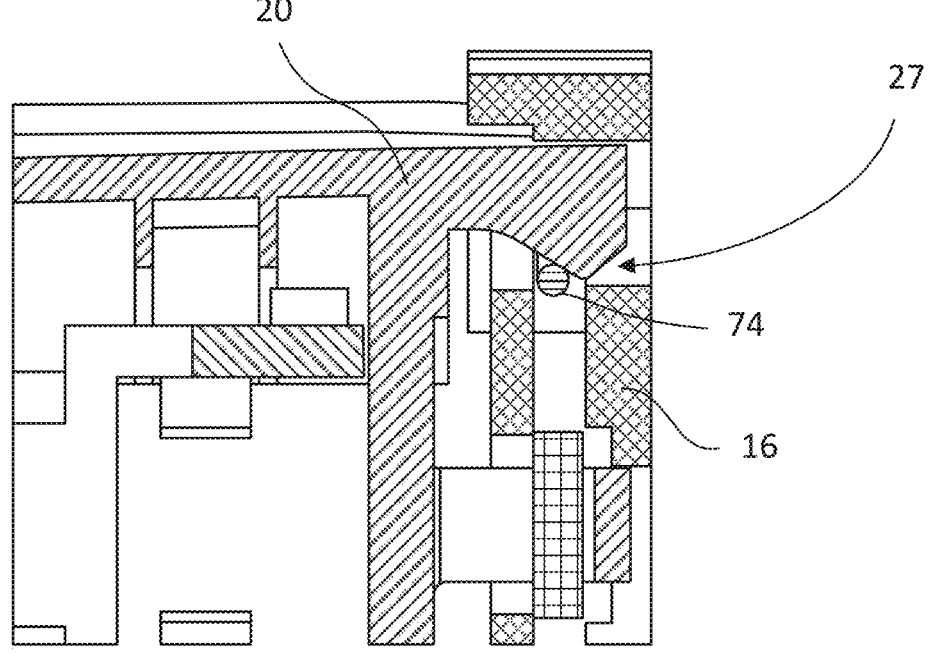
Figure 35A:
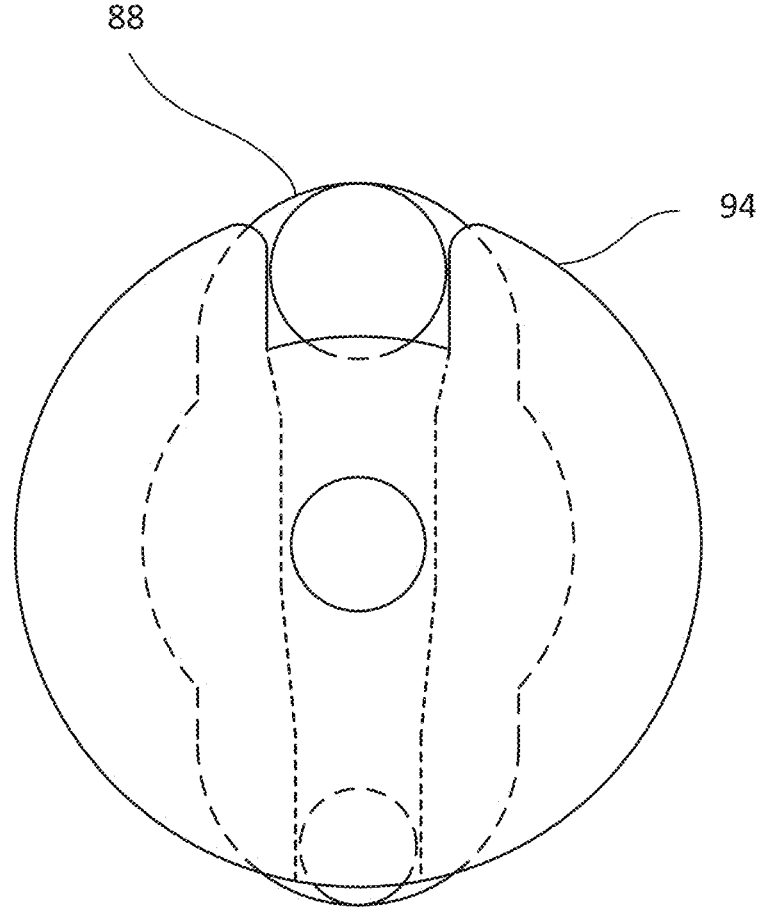
Figure 35B:
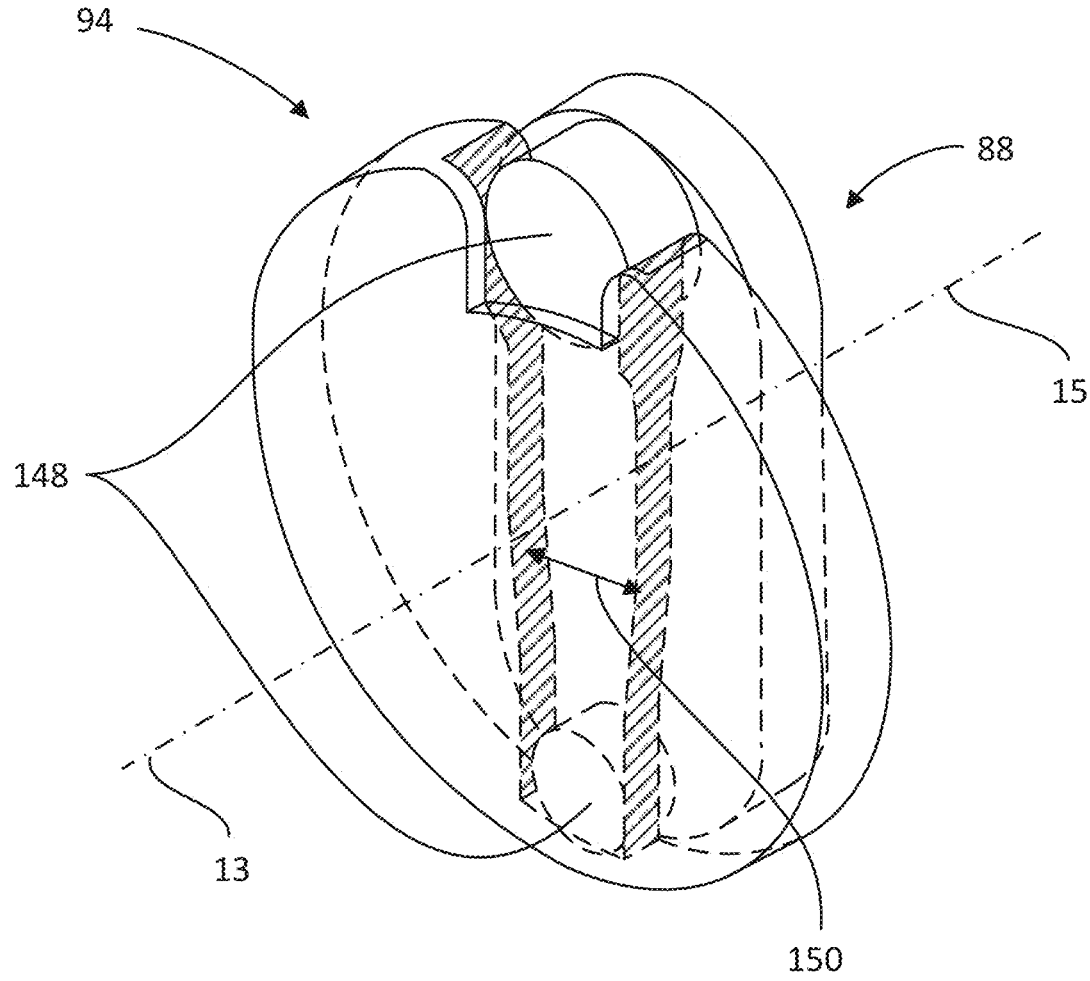
Figure 36:
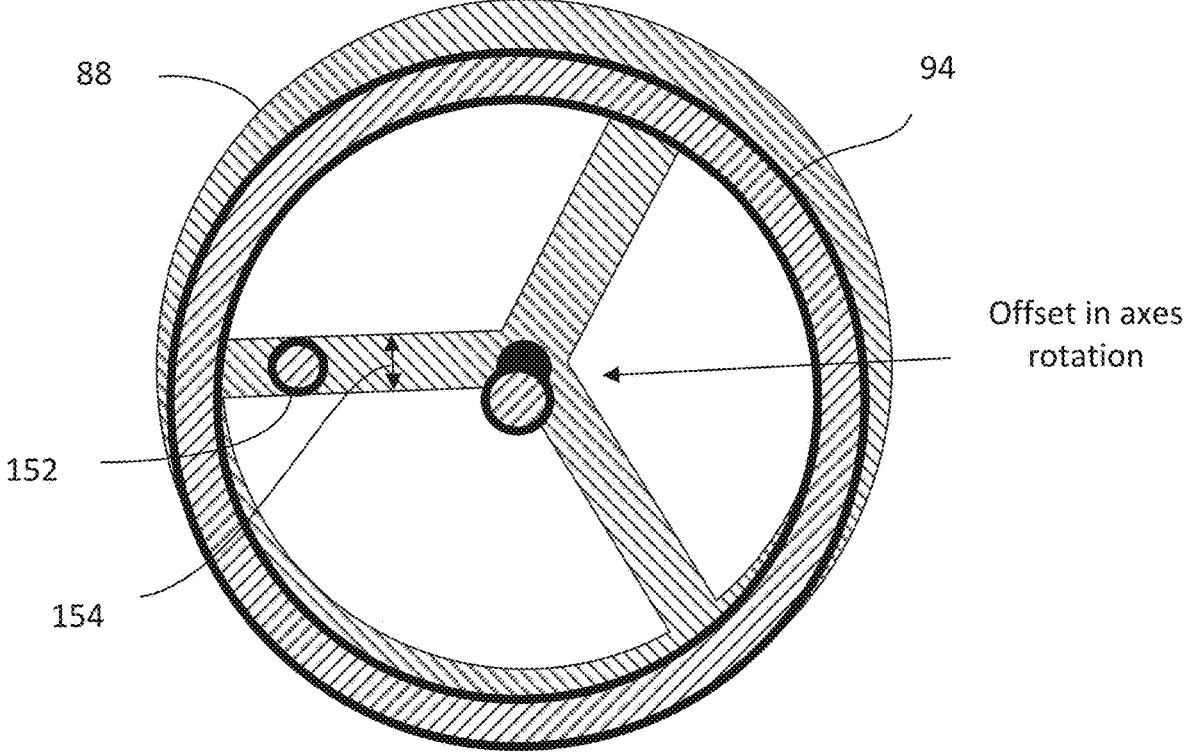
Figure 37A:
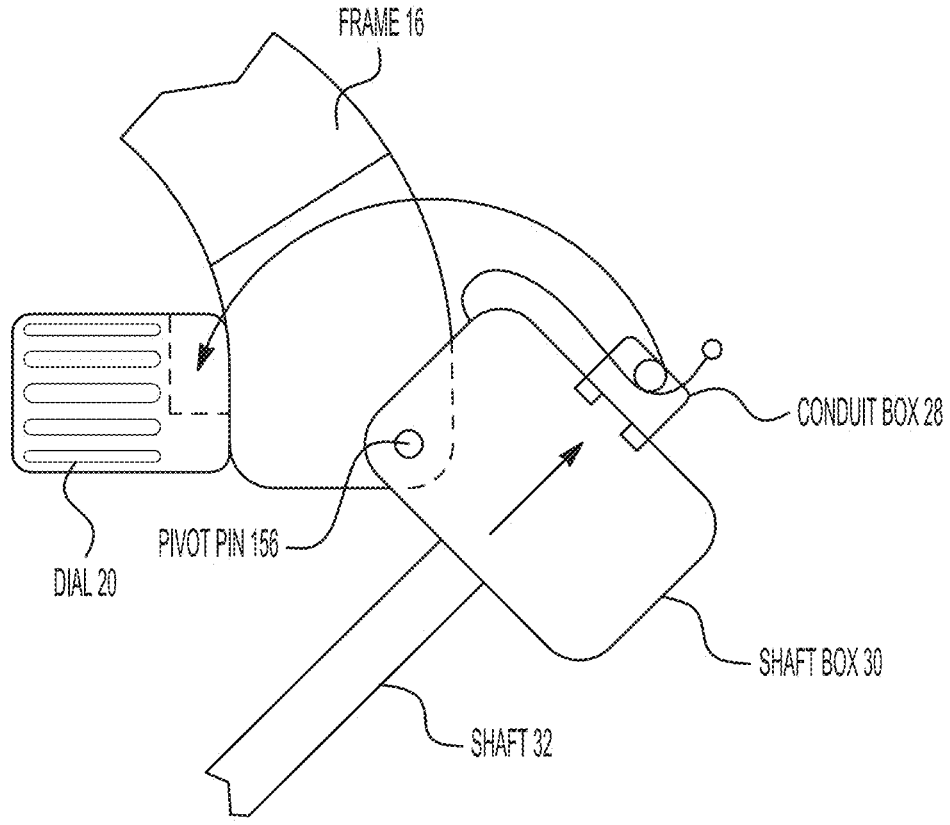
Figure 37B:
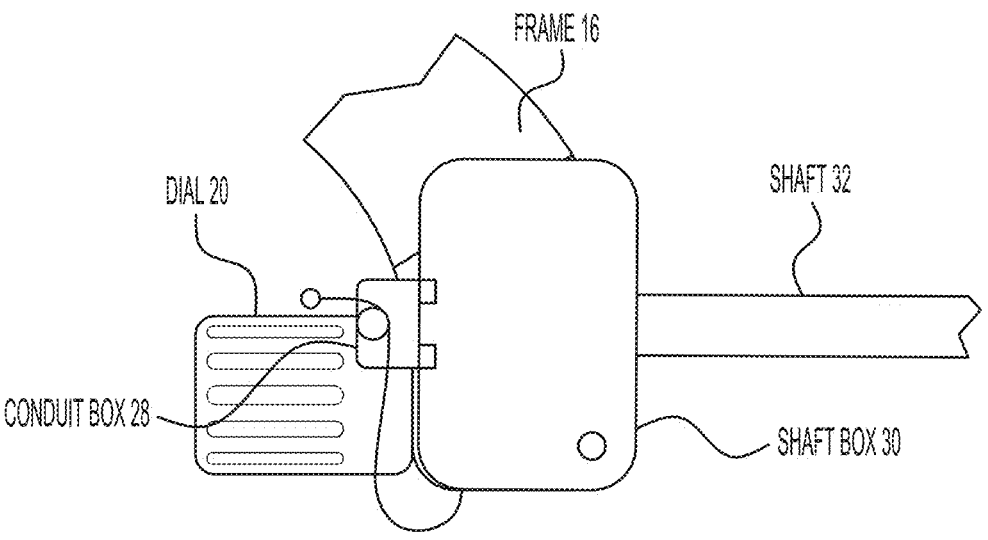
Figure 38A:
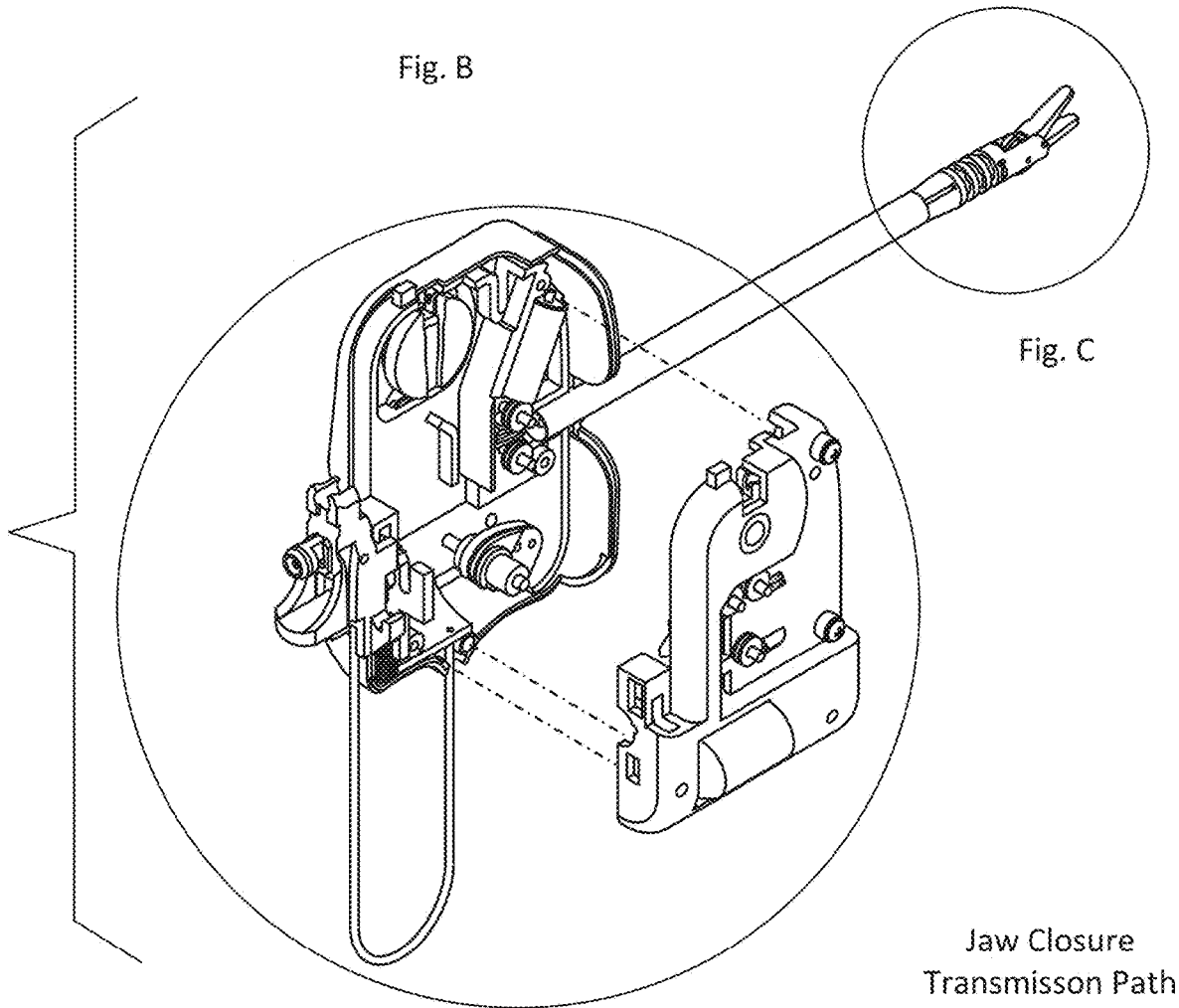
Figure 38B:
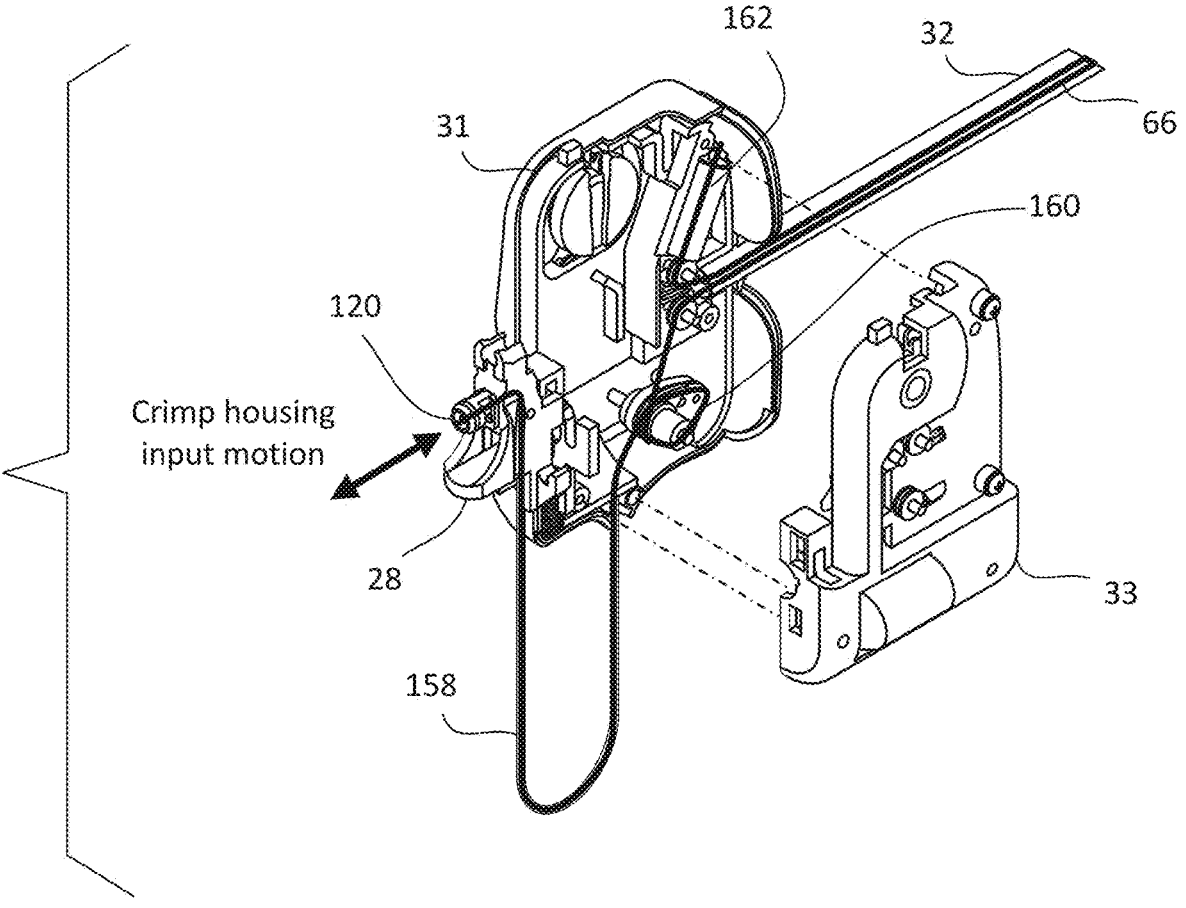
Figure 38C:
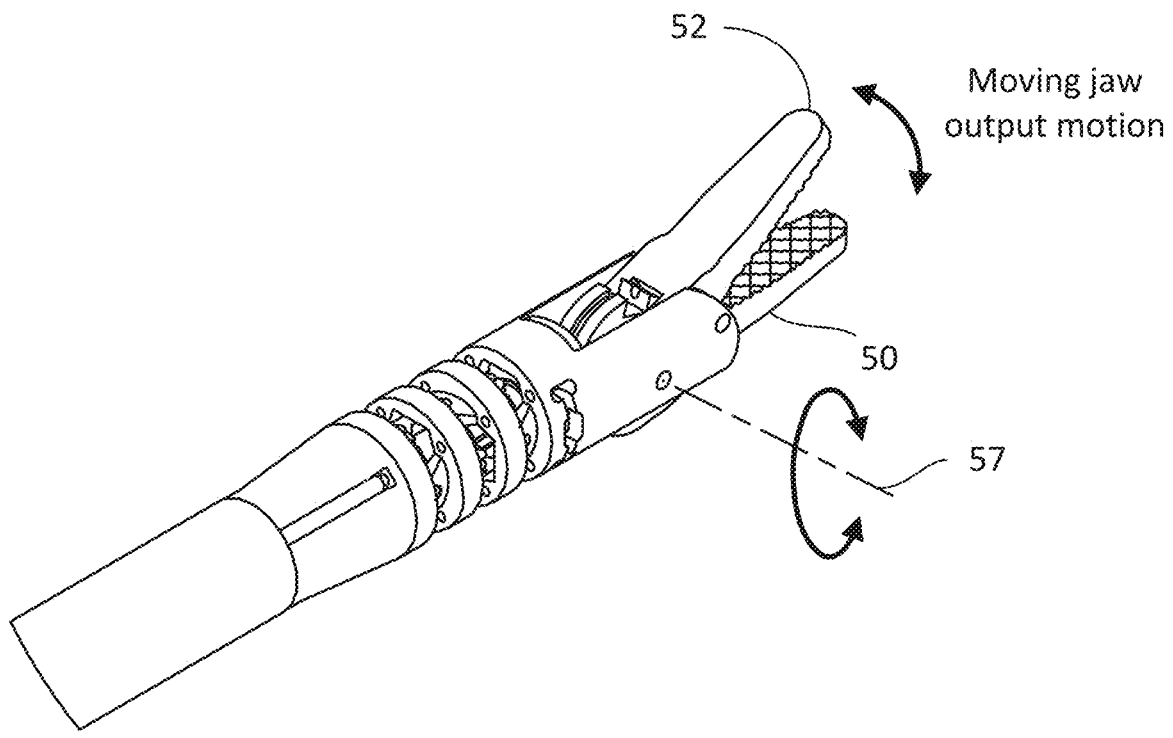
Figure 39B:
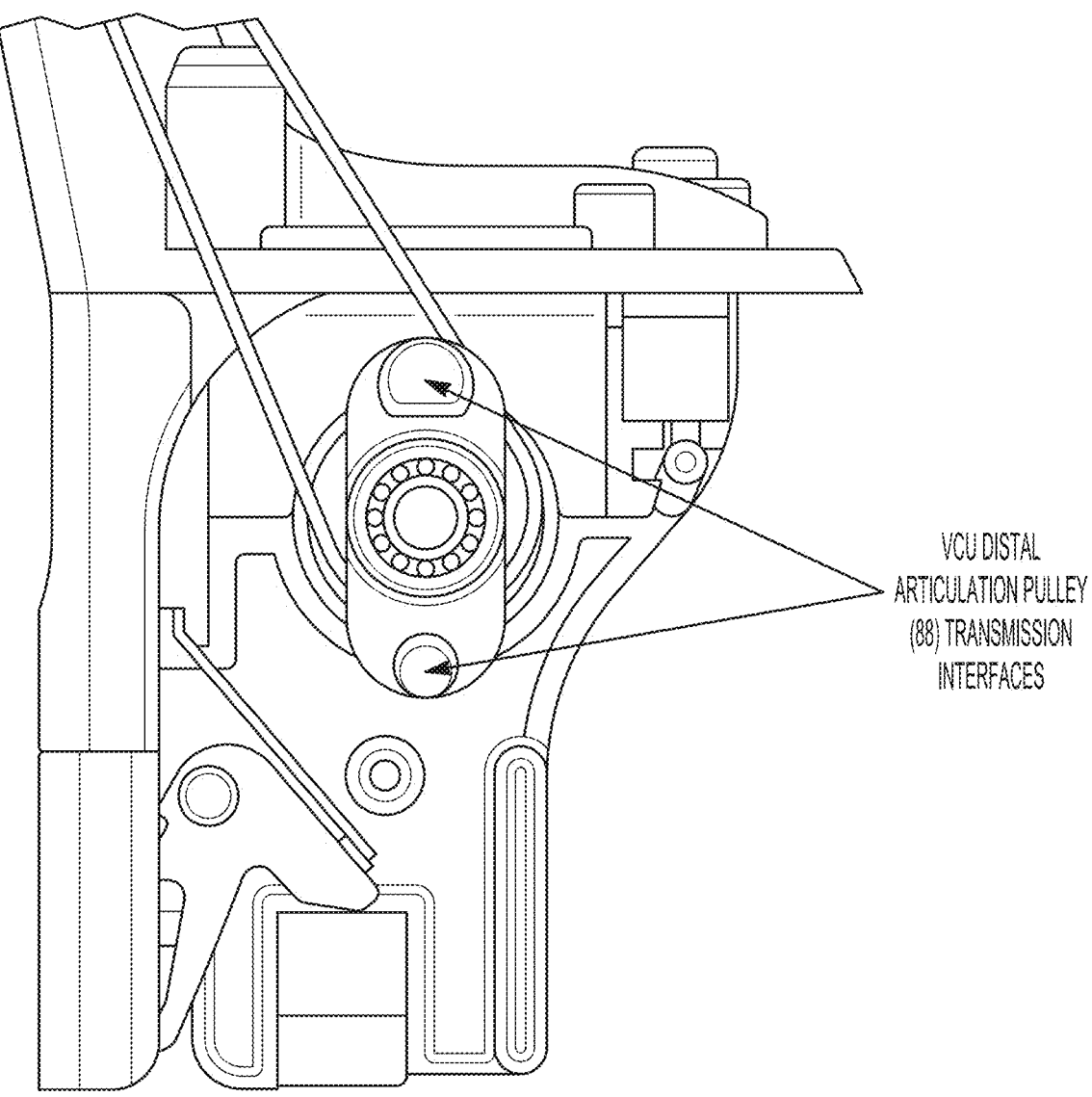
Figure 41A:
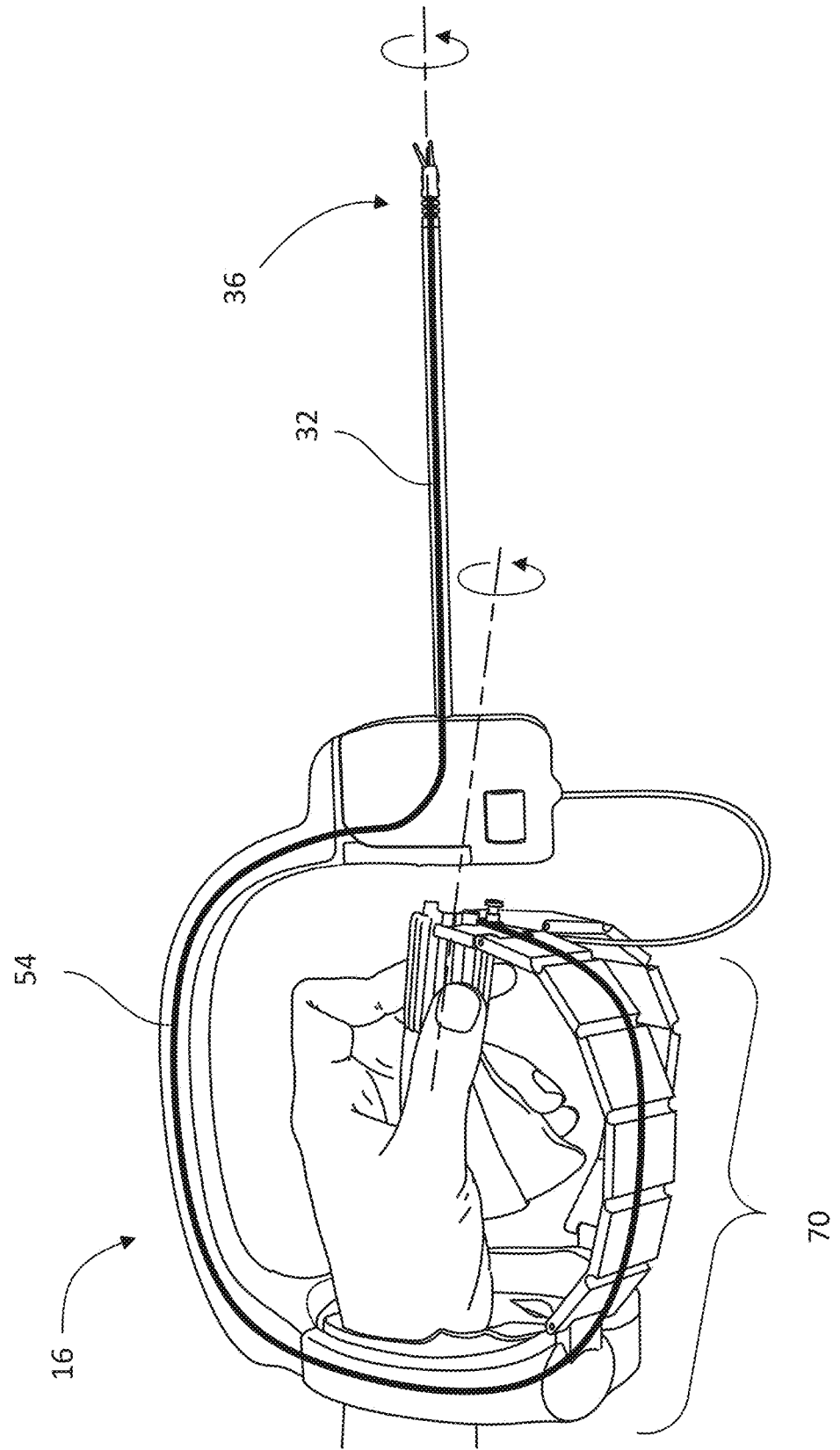
Figure 41B:
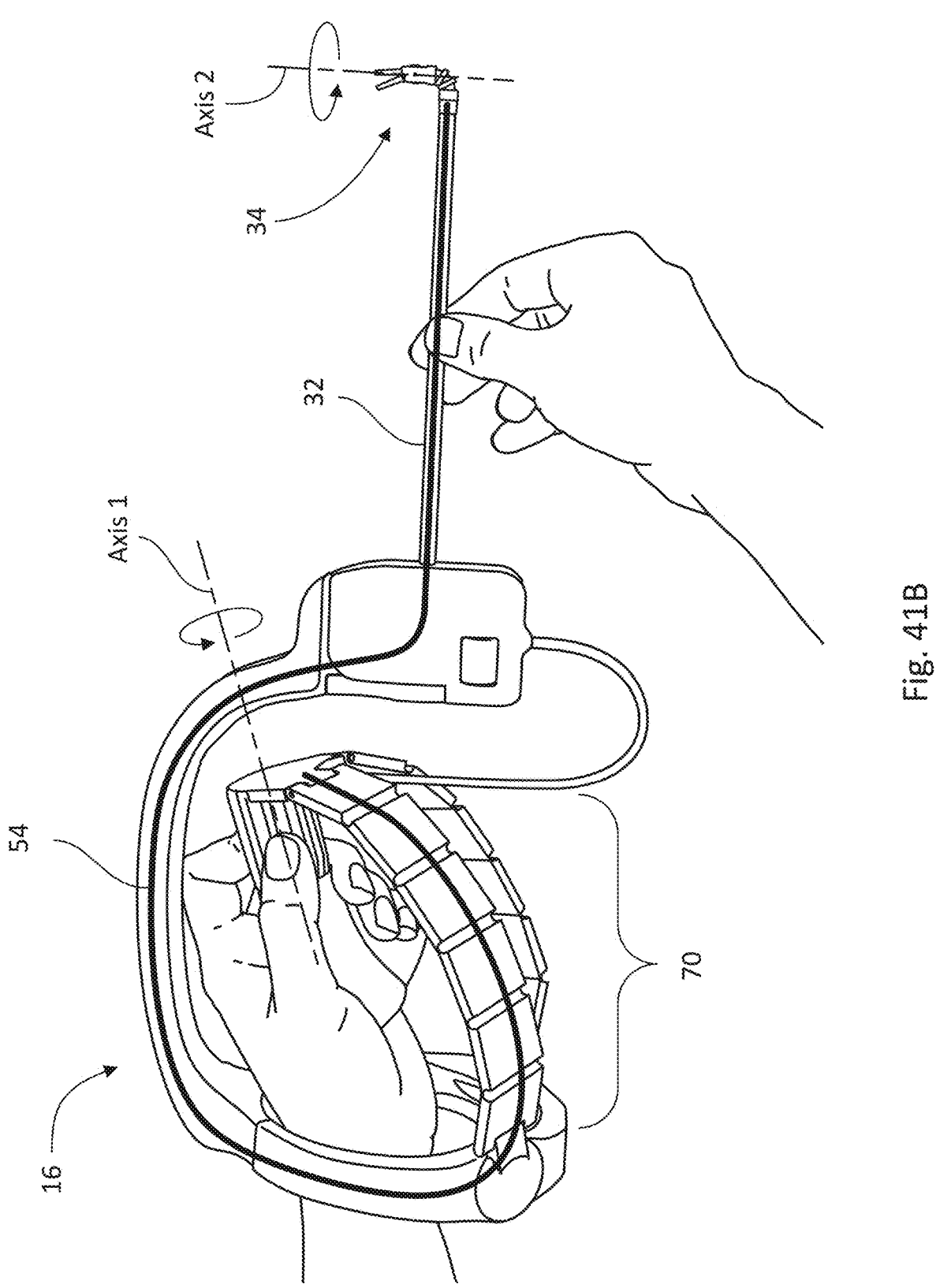
Figure 42:
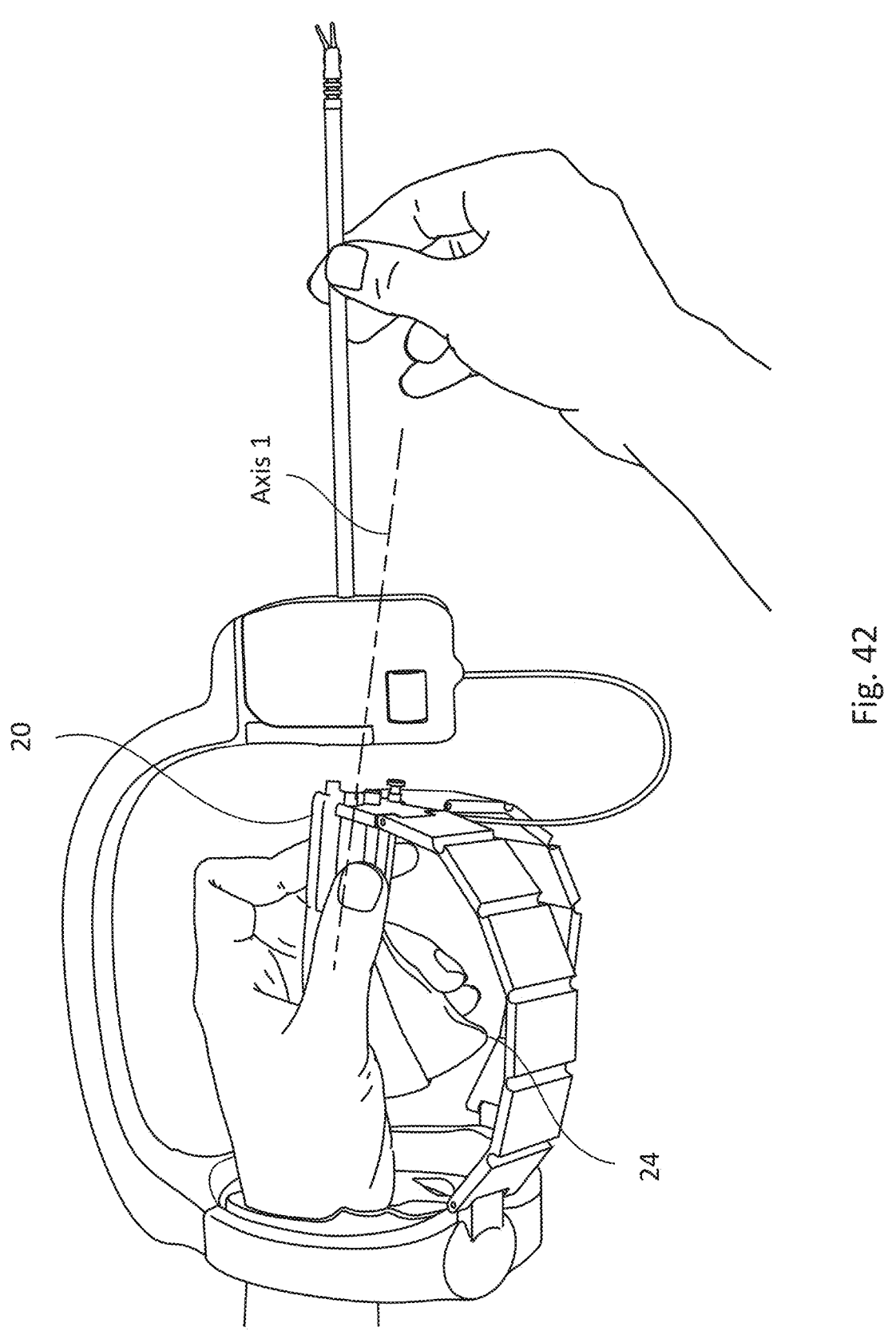
Figure 43:
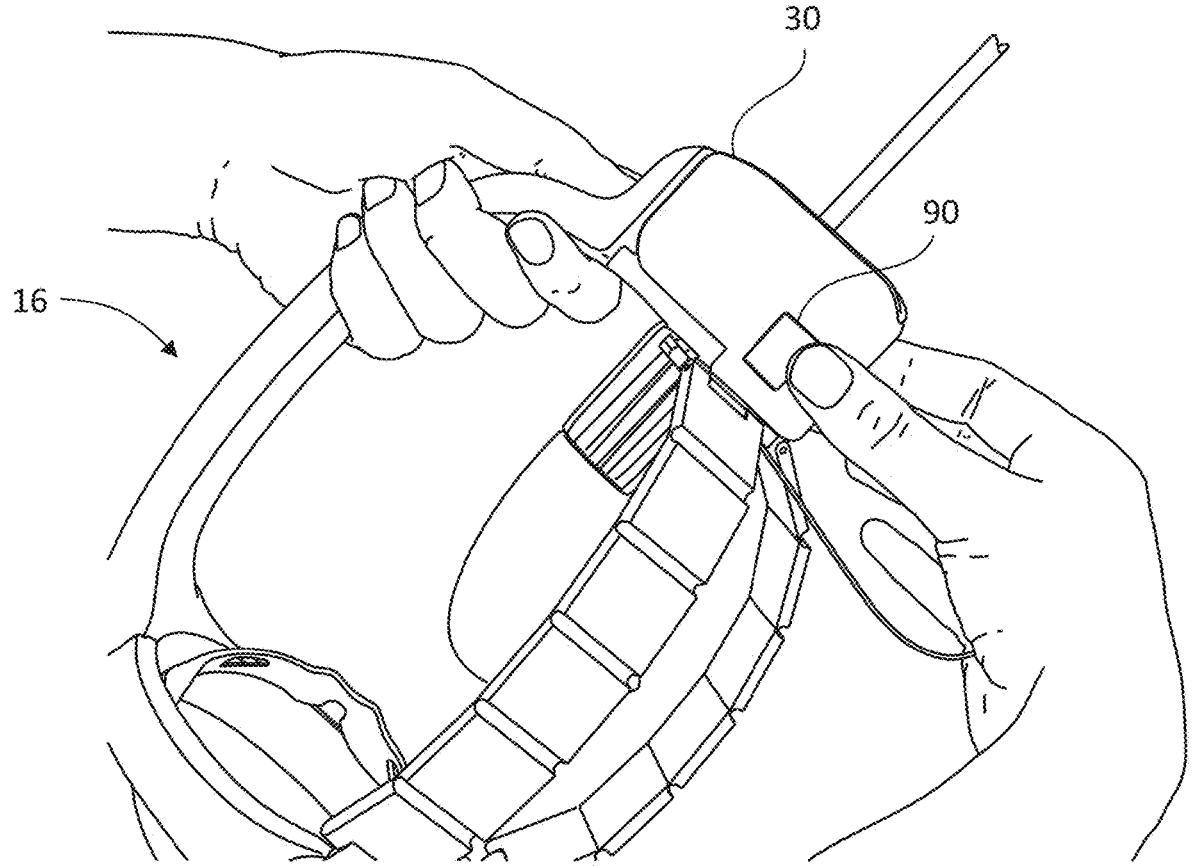
Figure 44A:
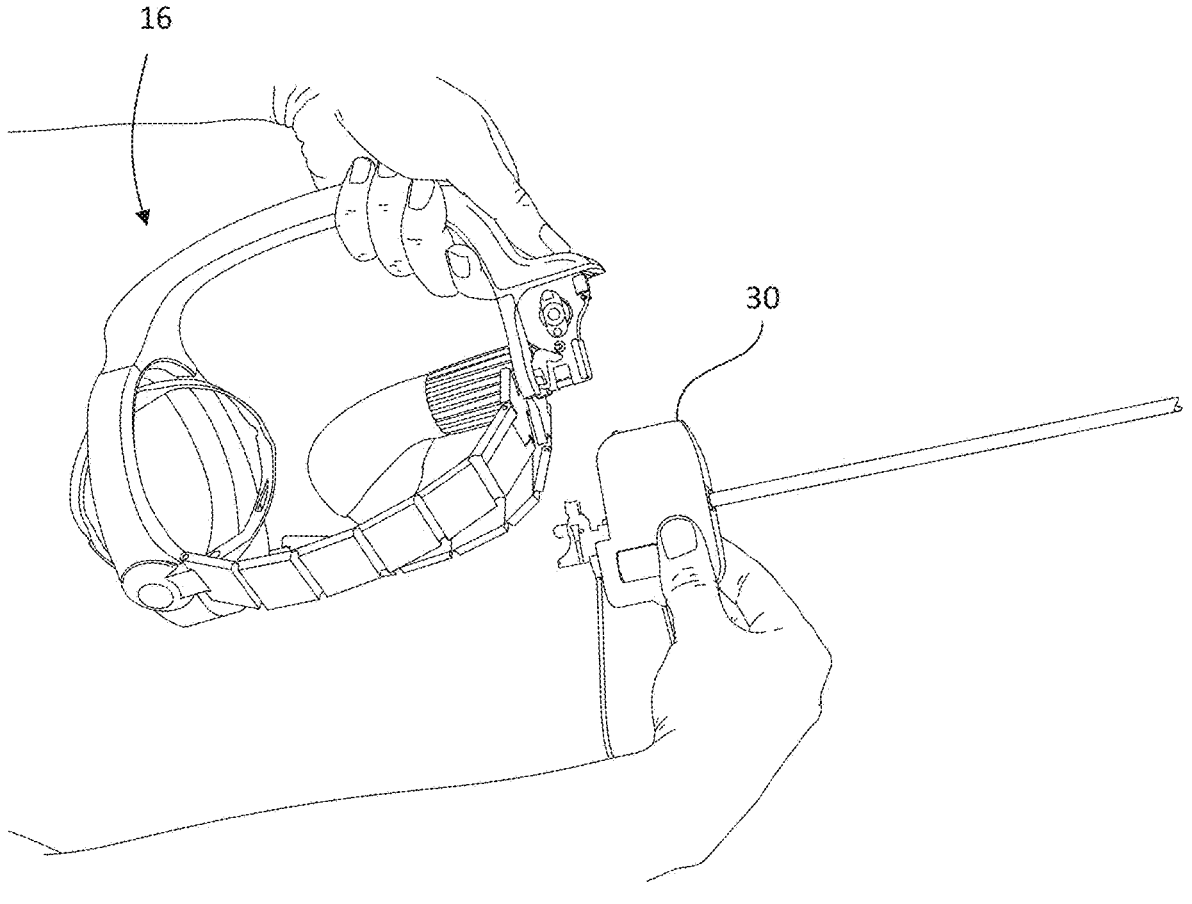
Figure 44B:
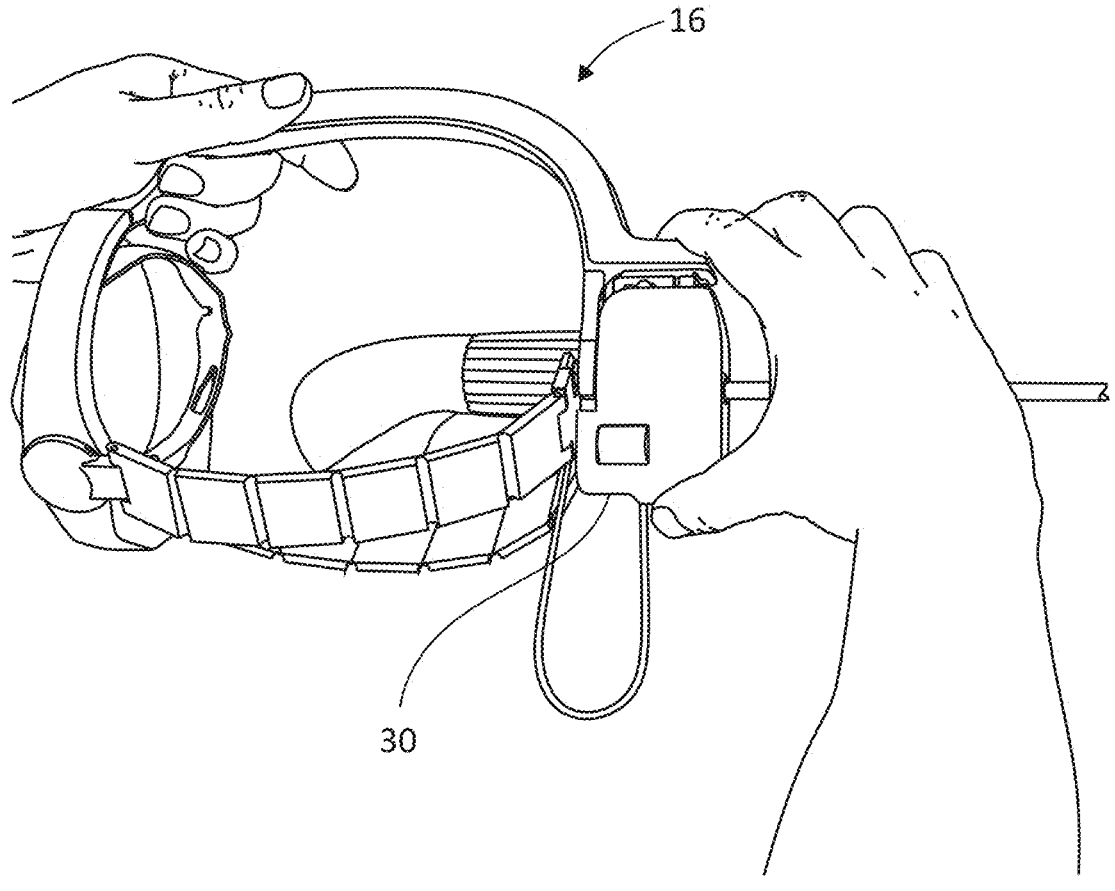
Figure 45A:
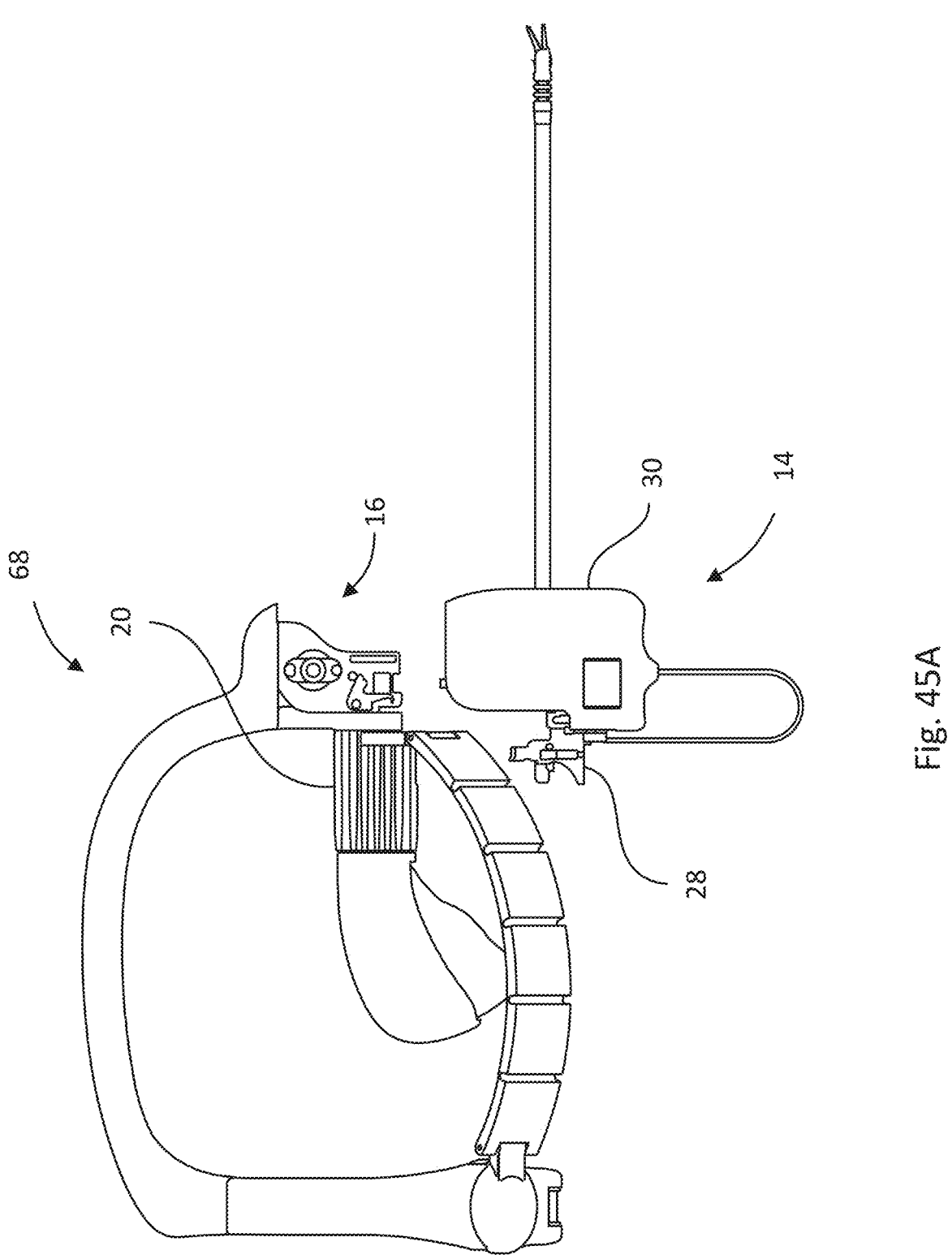
Figure 45B:
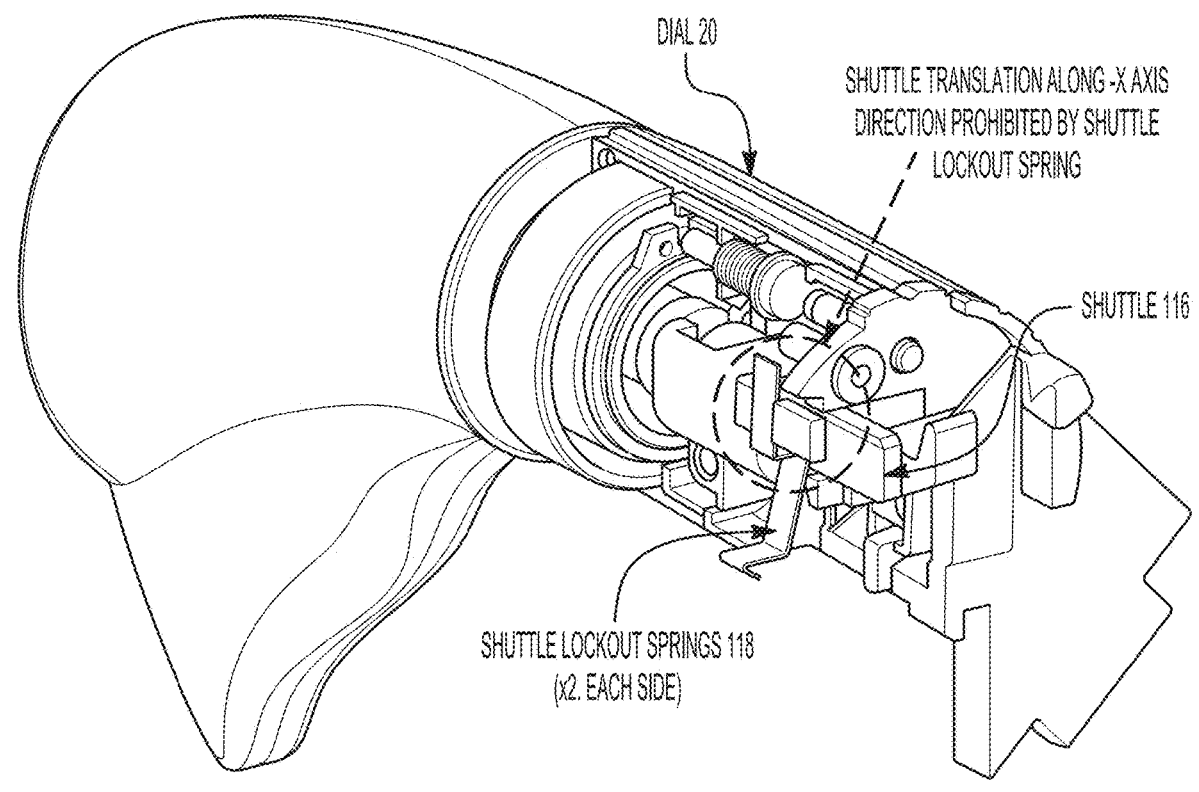
Figure 46A:
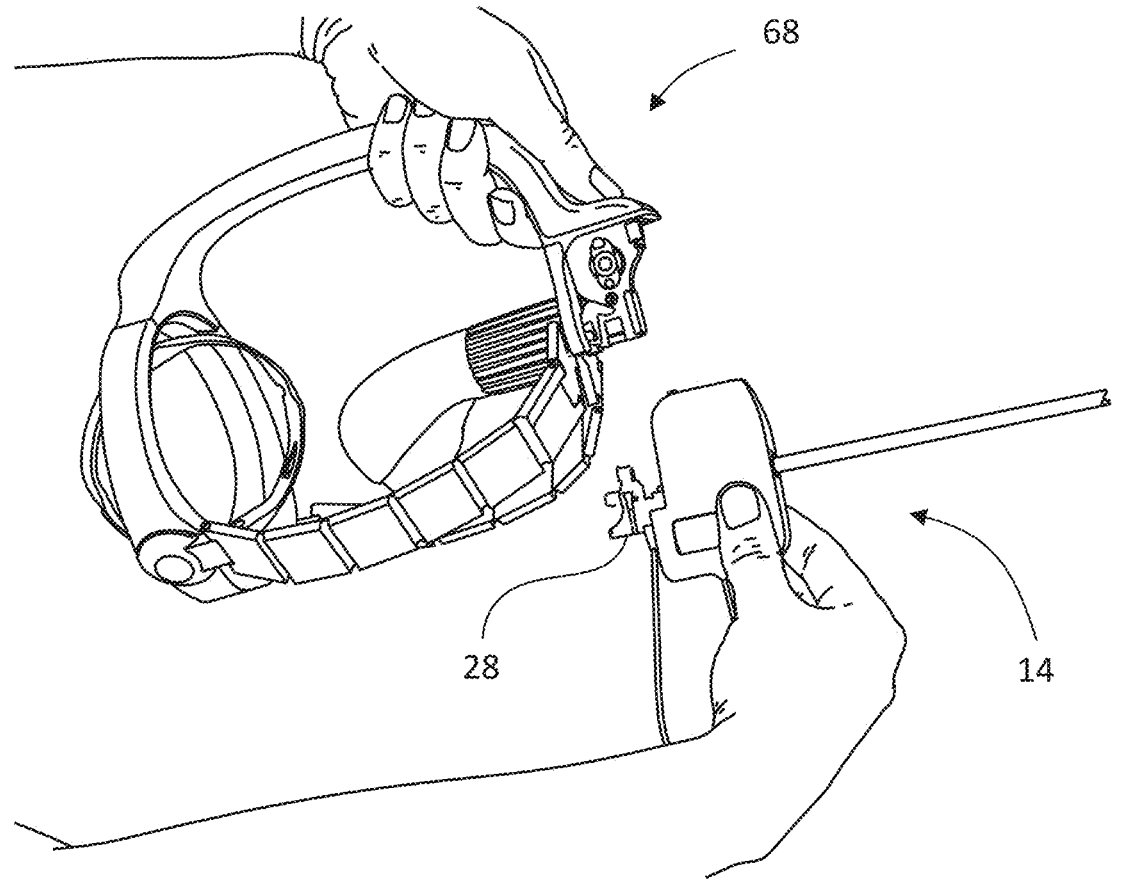
Figure 46B:
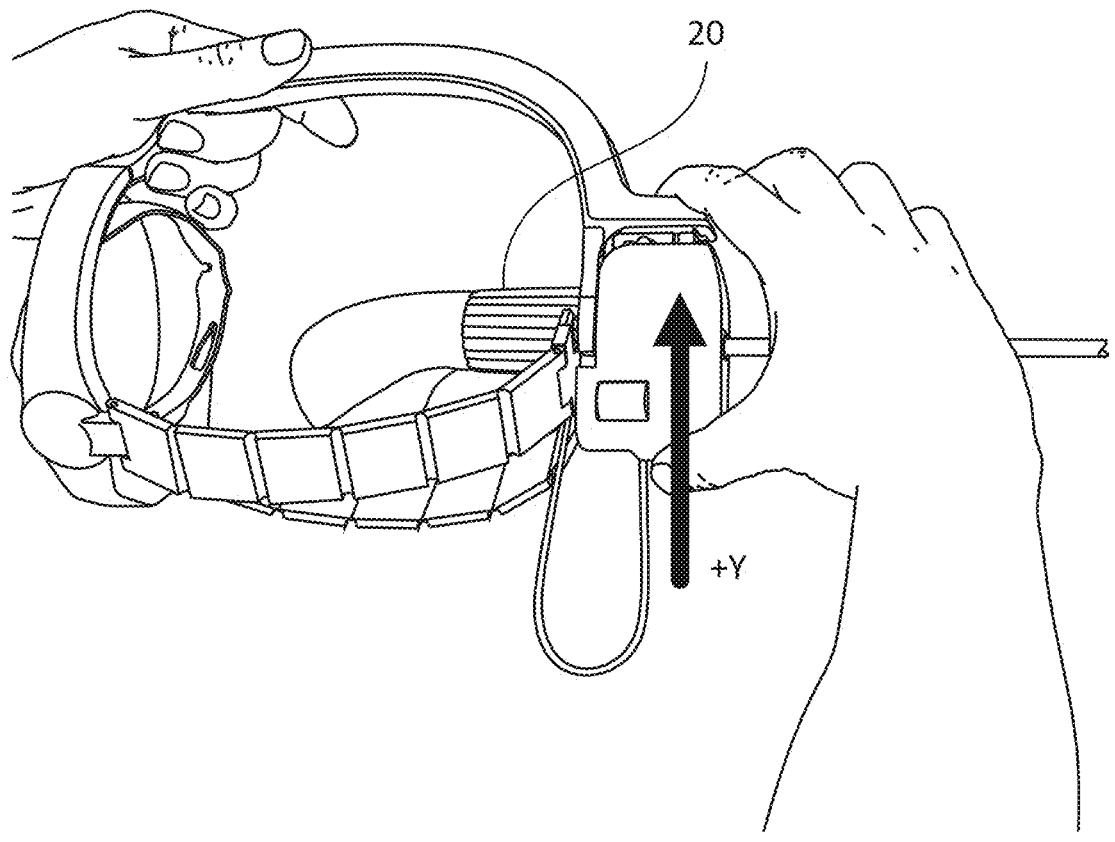
Figure 46C:
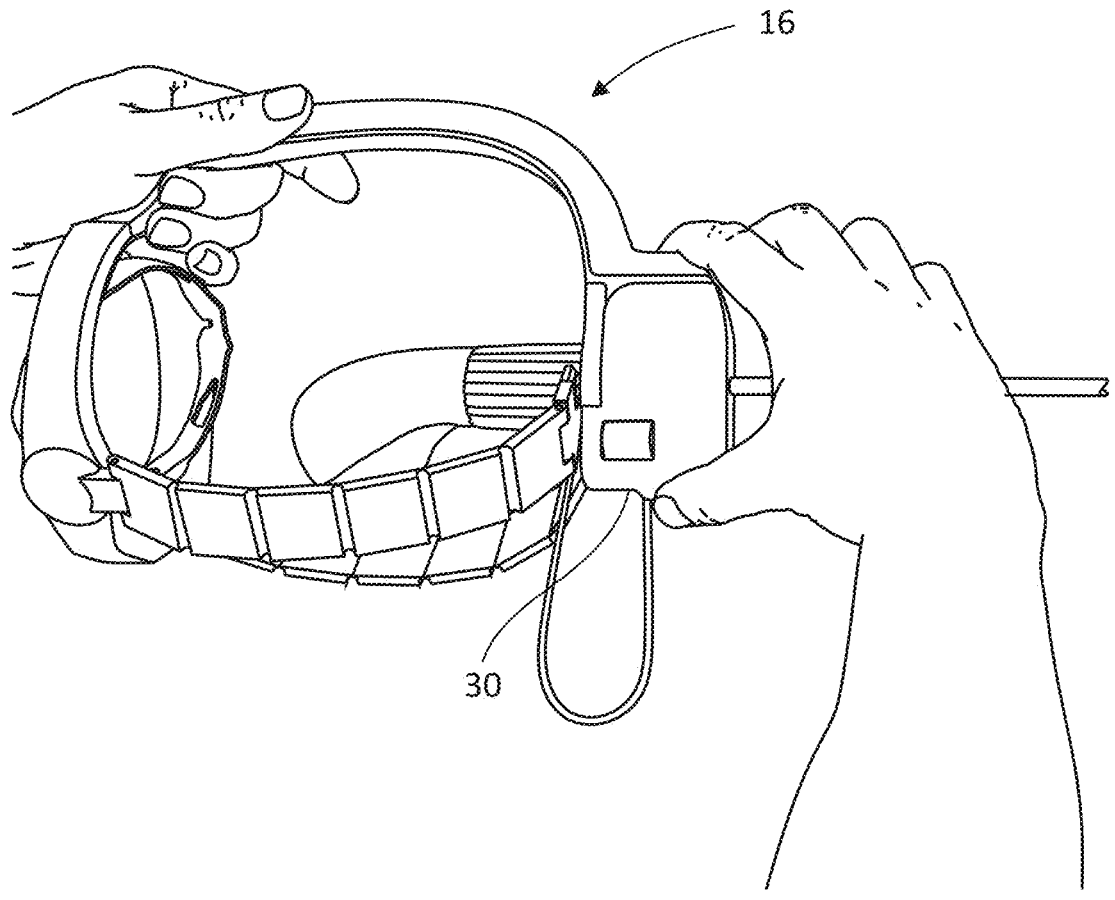
Figure 47A:
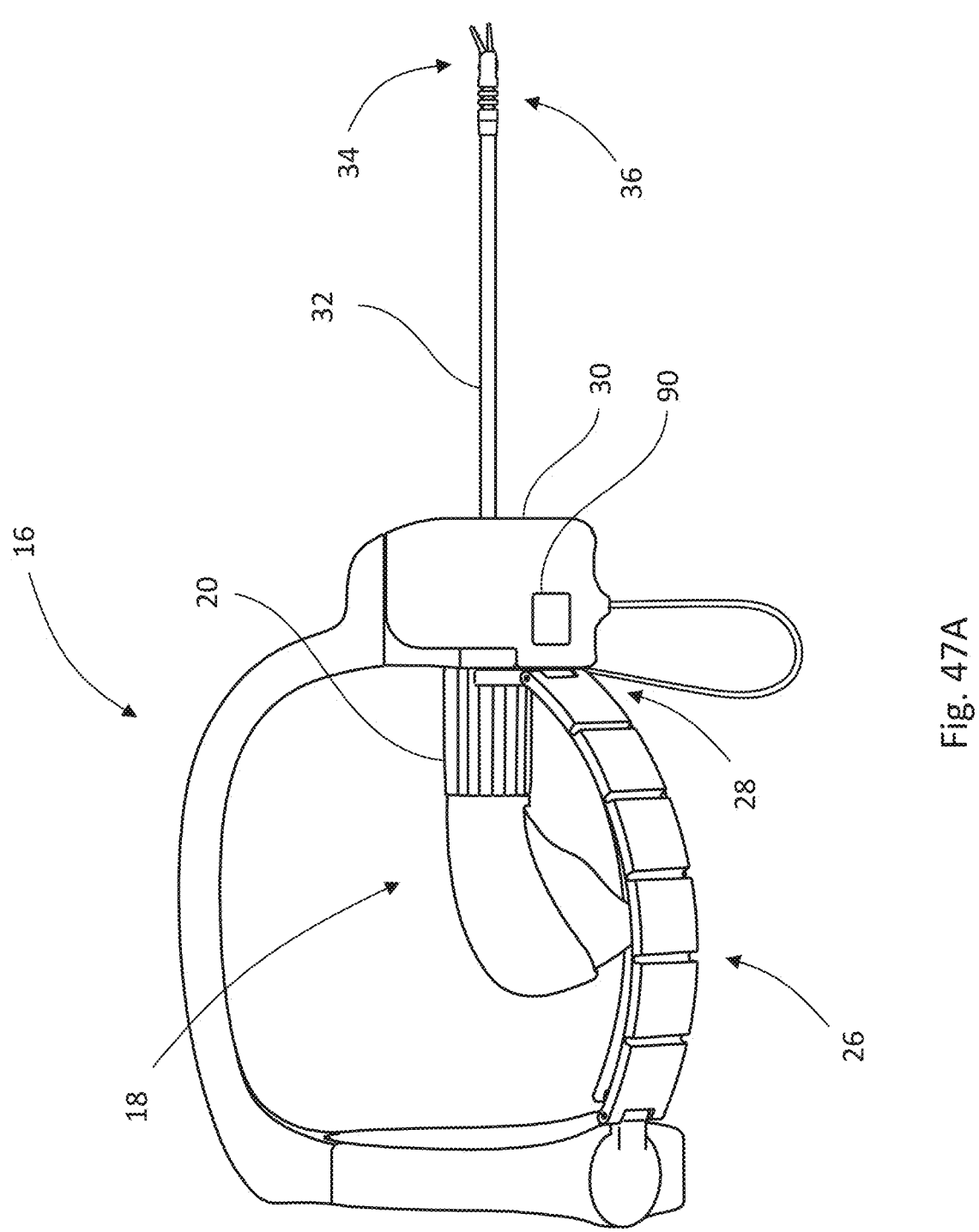
Figure 47B:
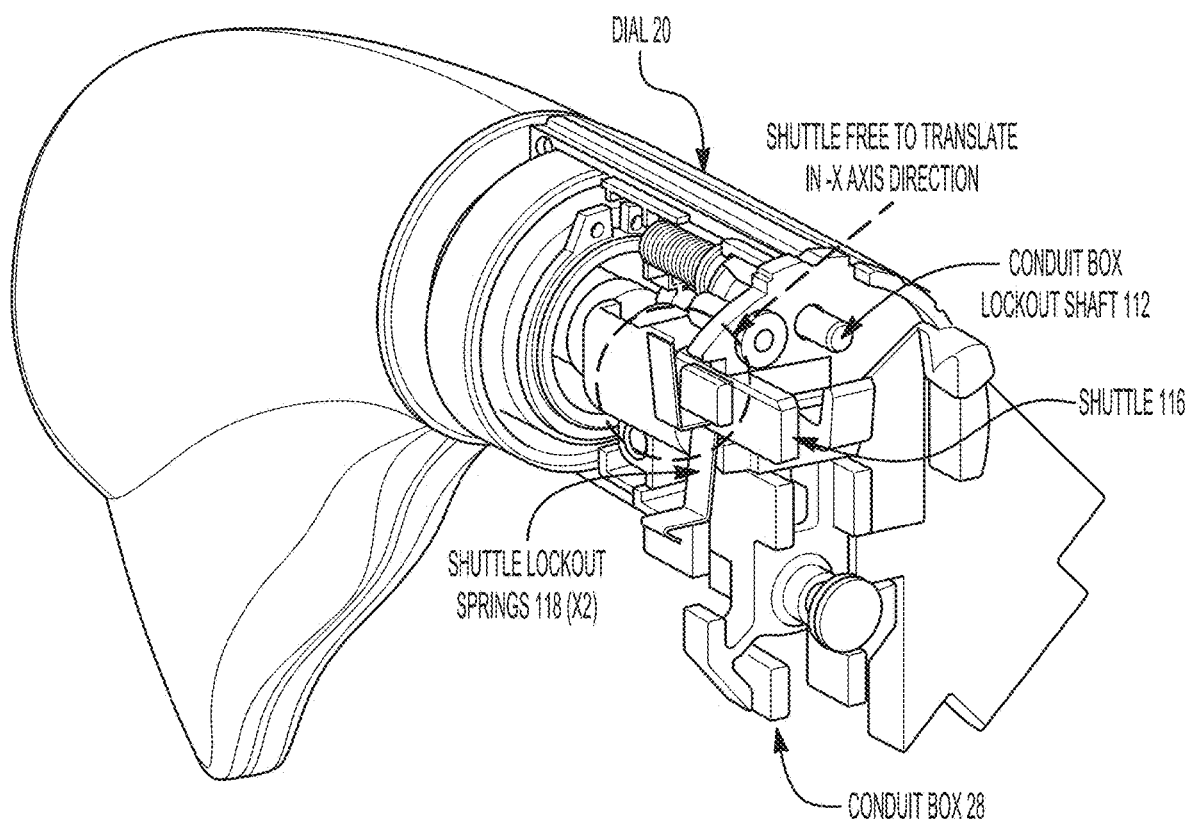
Figure 47C:
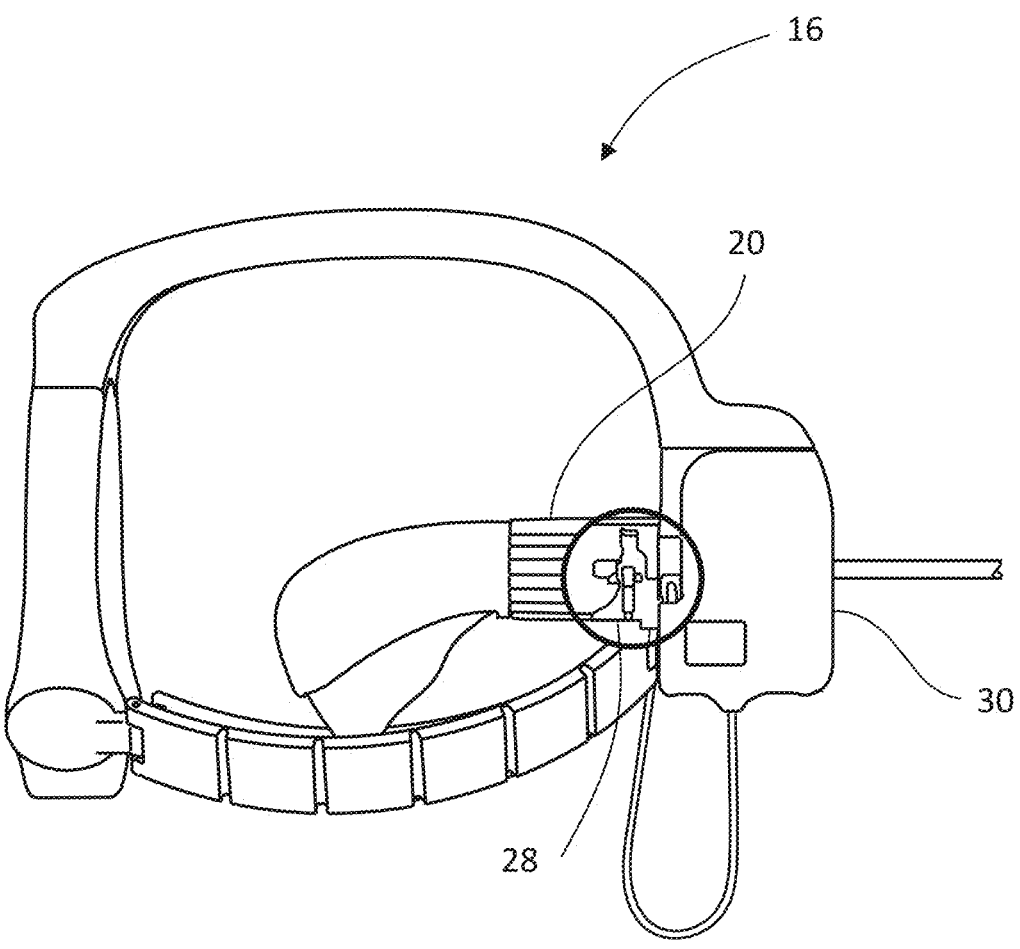
Figure 48:
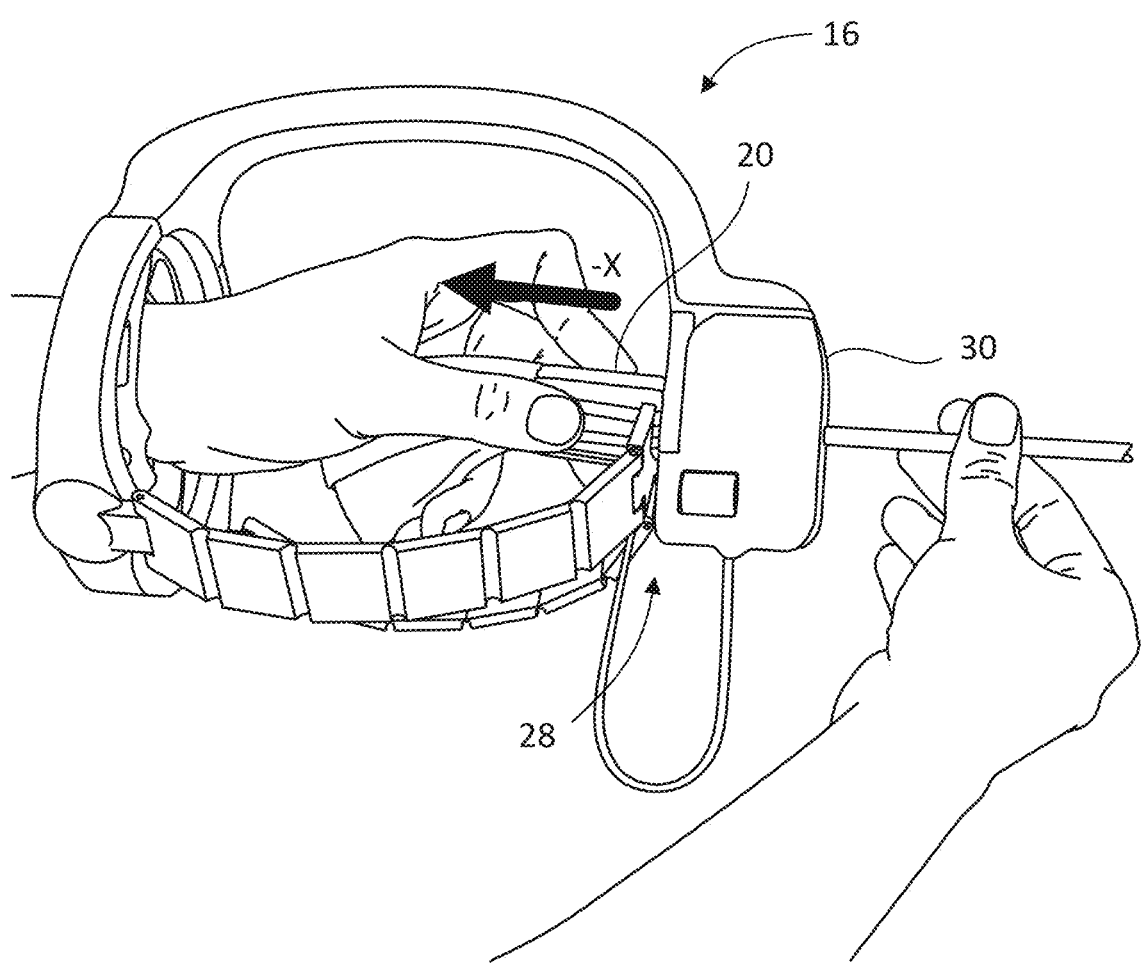
Figure 49A:
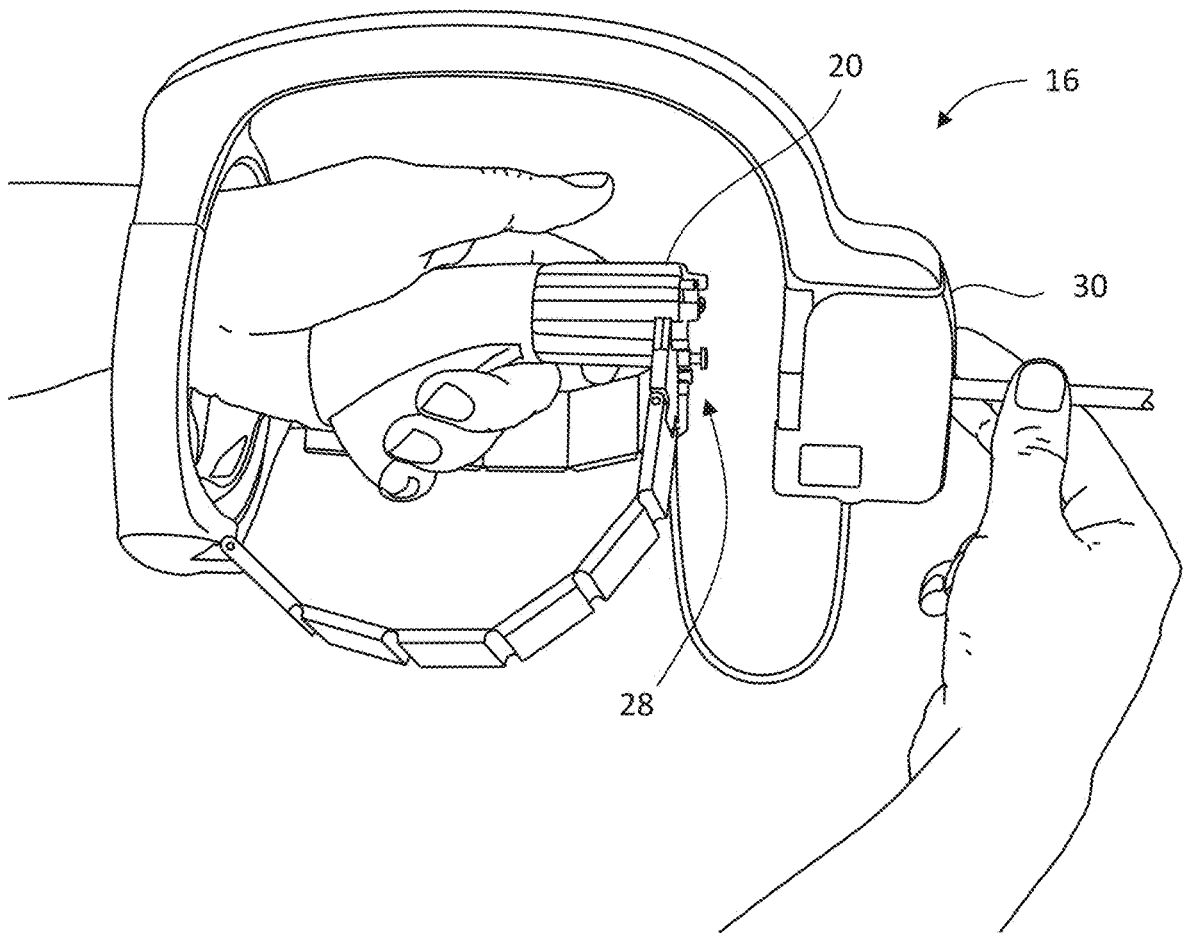
Figure 49B:
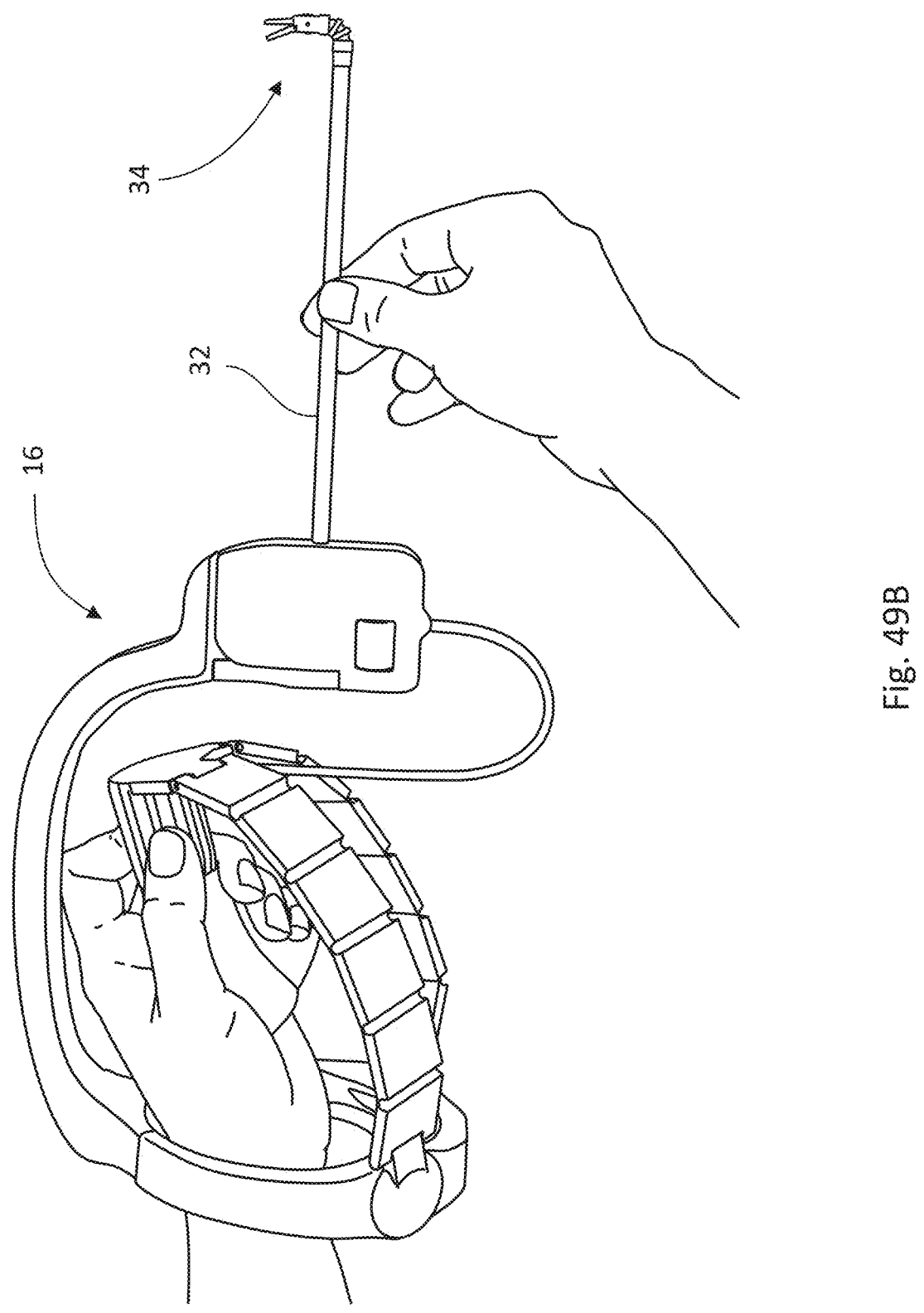
Figure 49C:
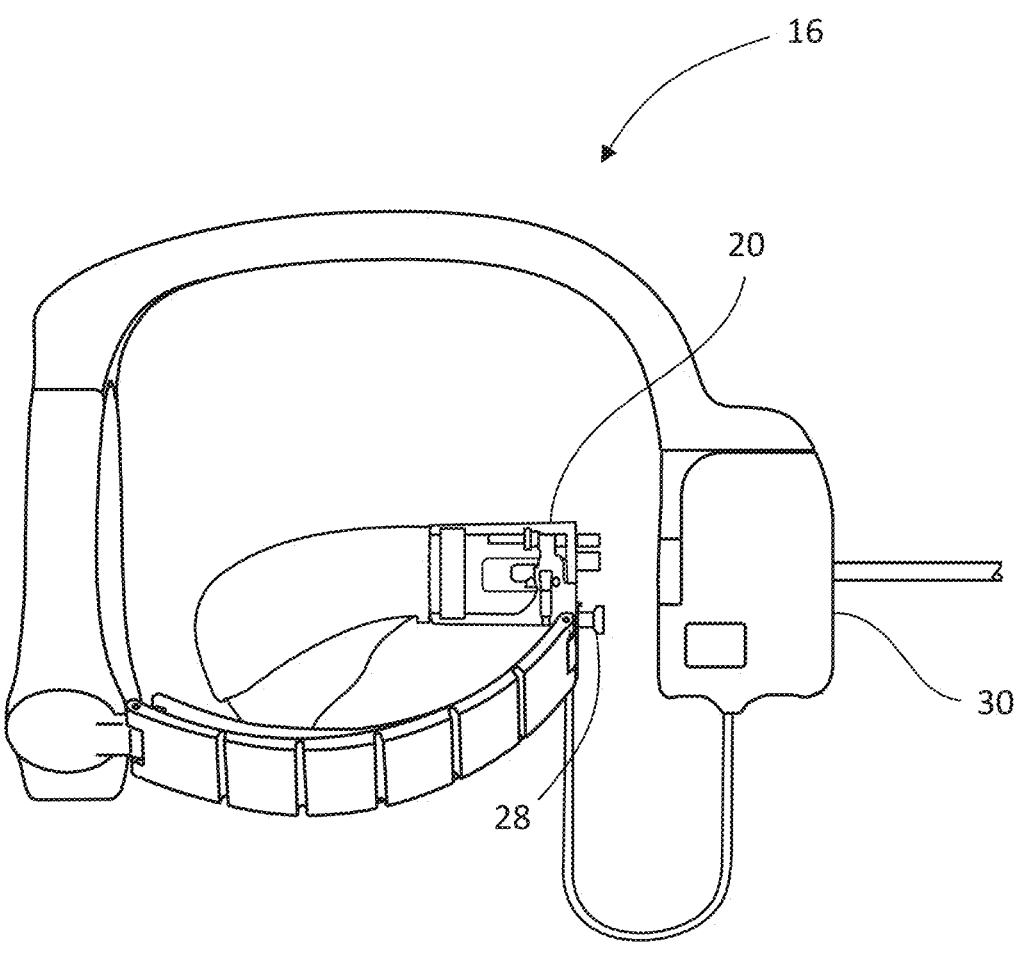
Figure 50:
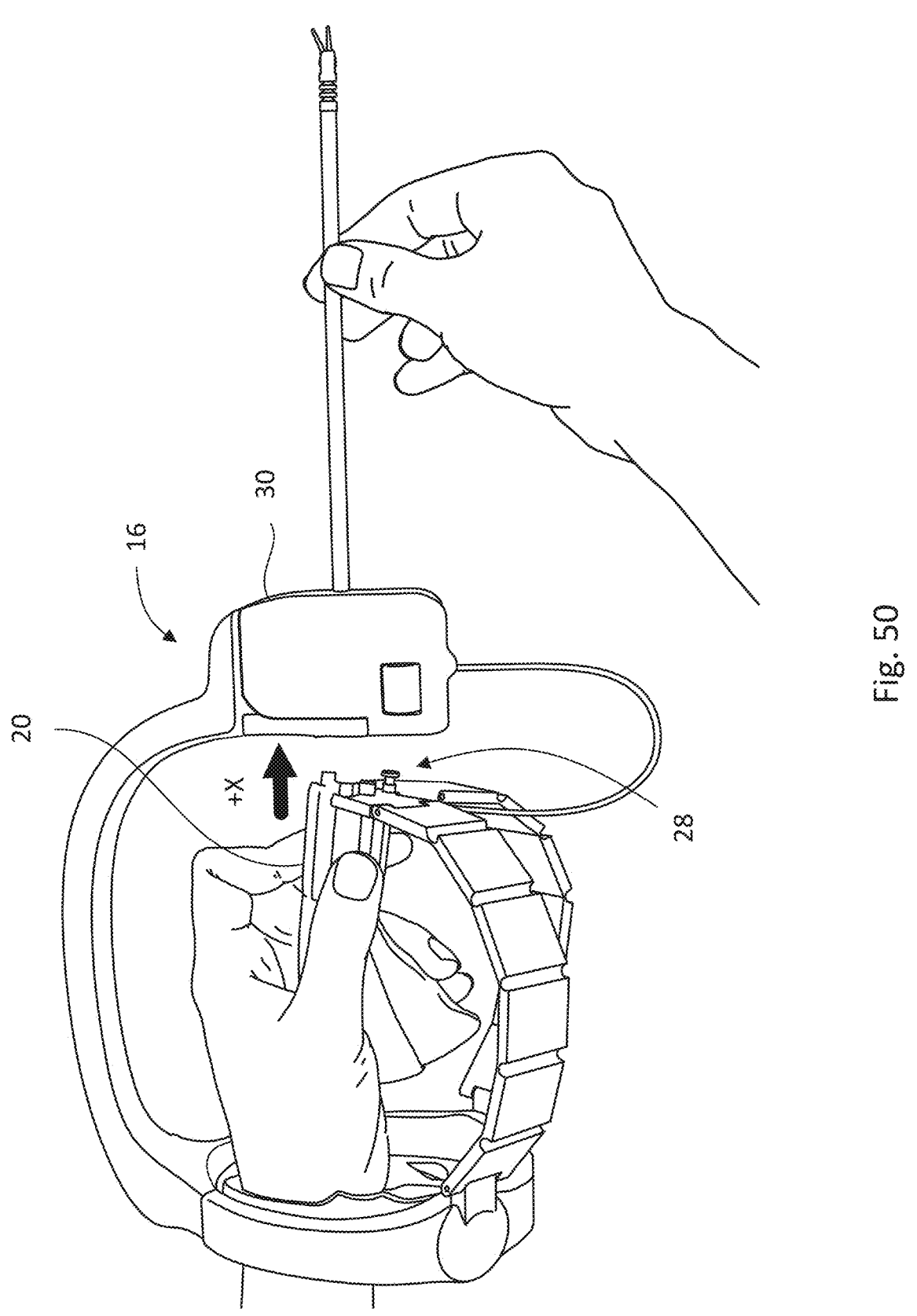
Figure 51A:
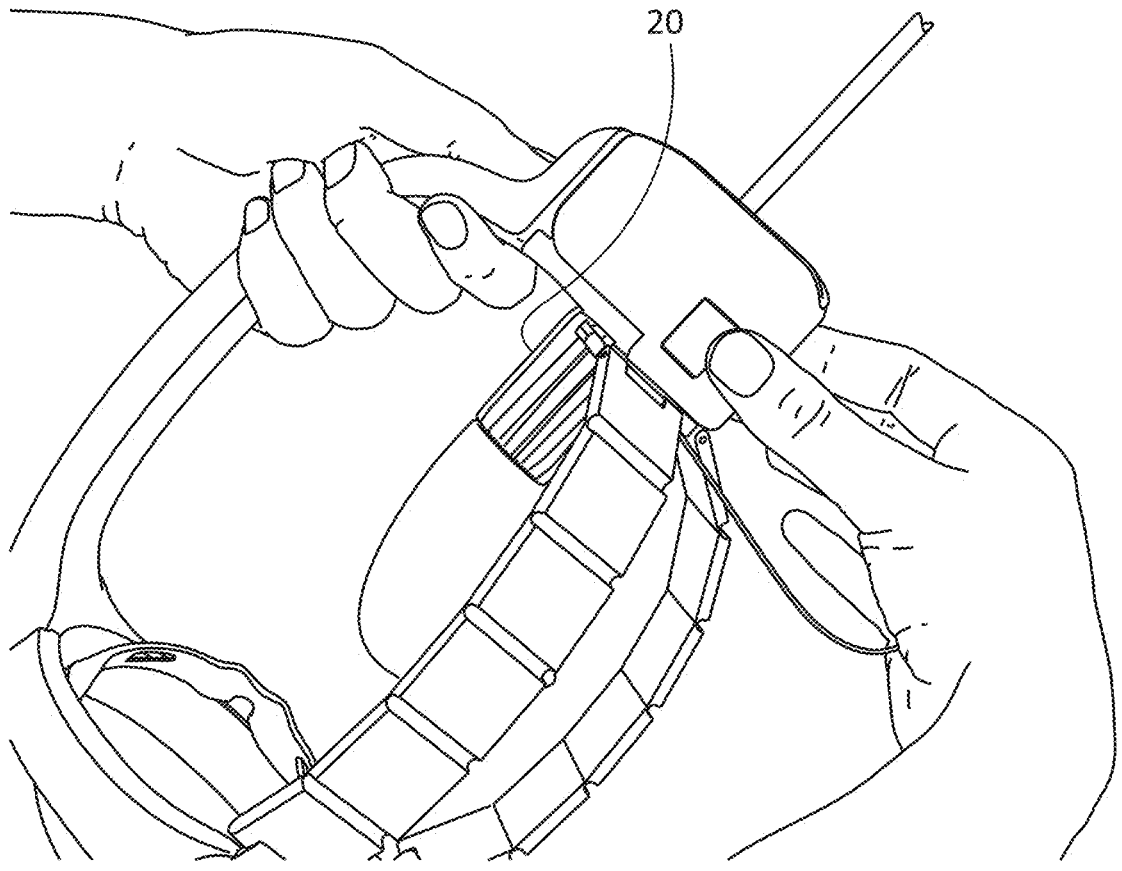
Figure 51B:
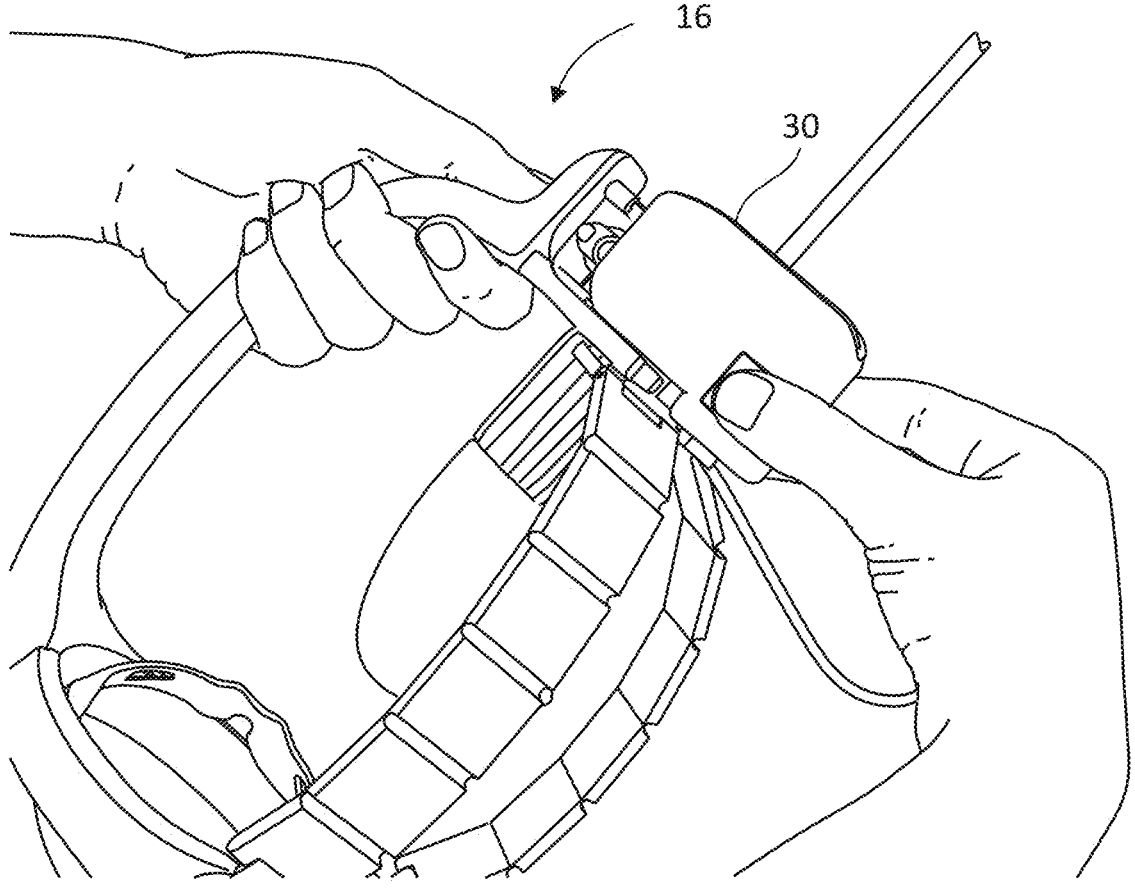
Figure 51C:
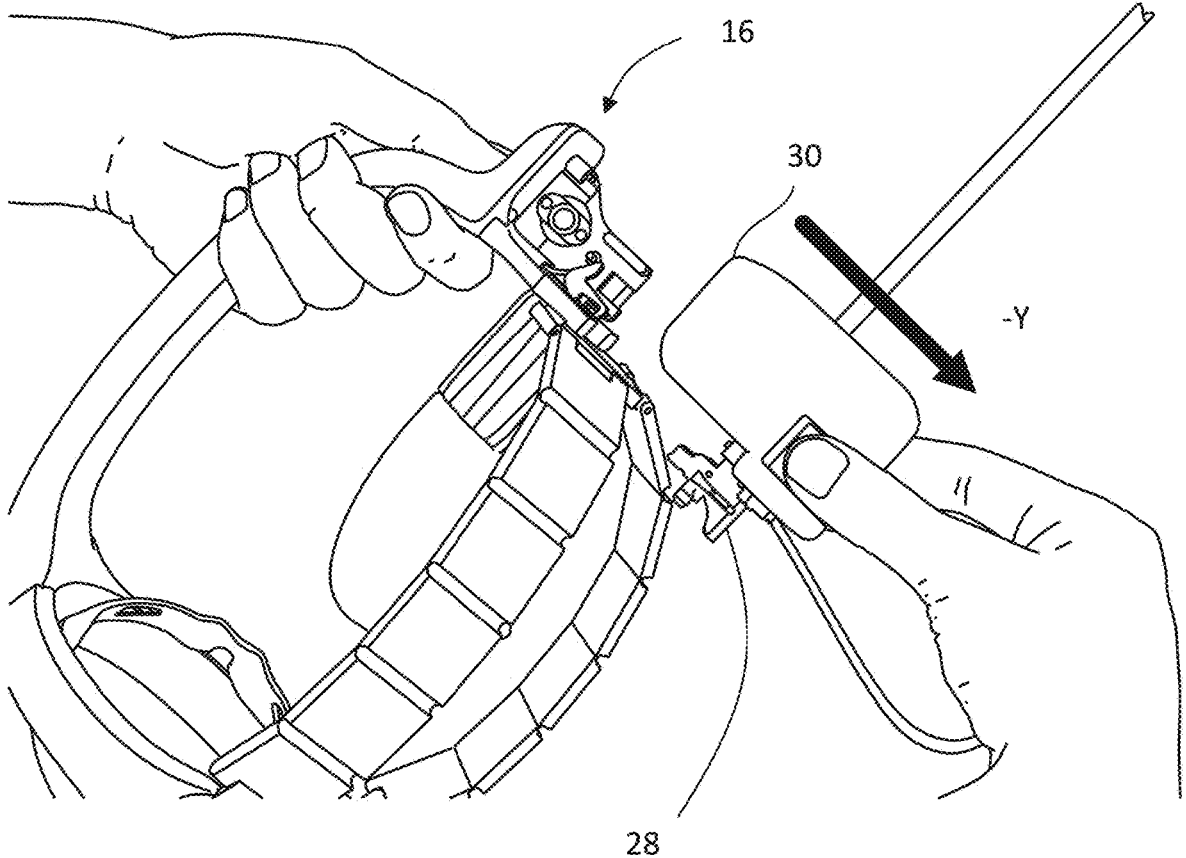
Figure 52A:
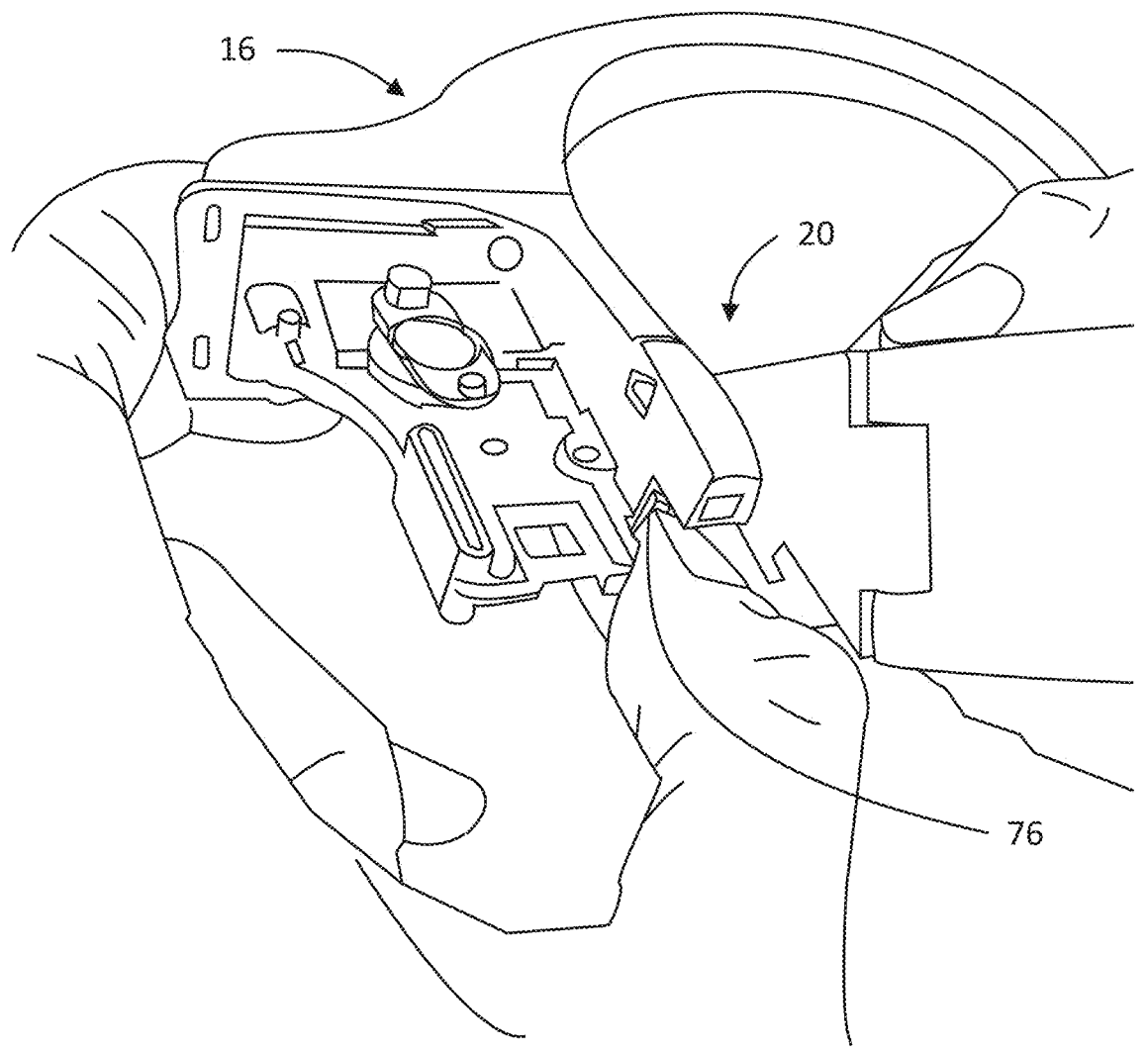
Figure 52B:
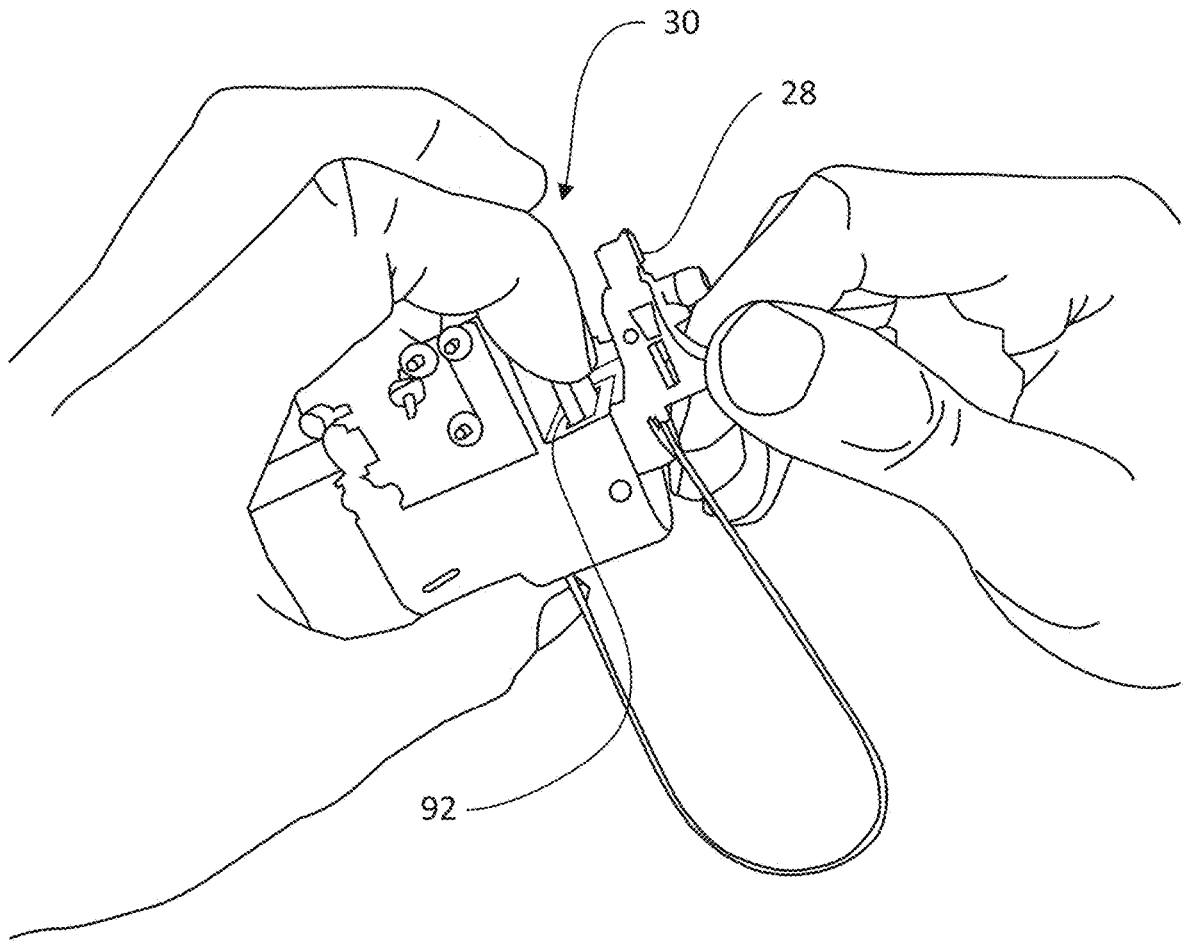
Figure 53A:
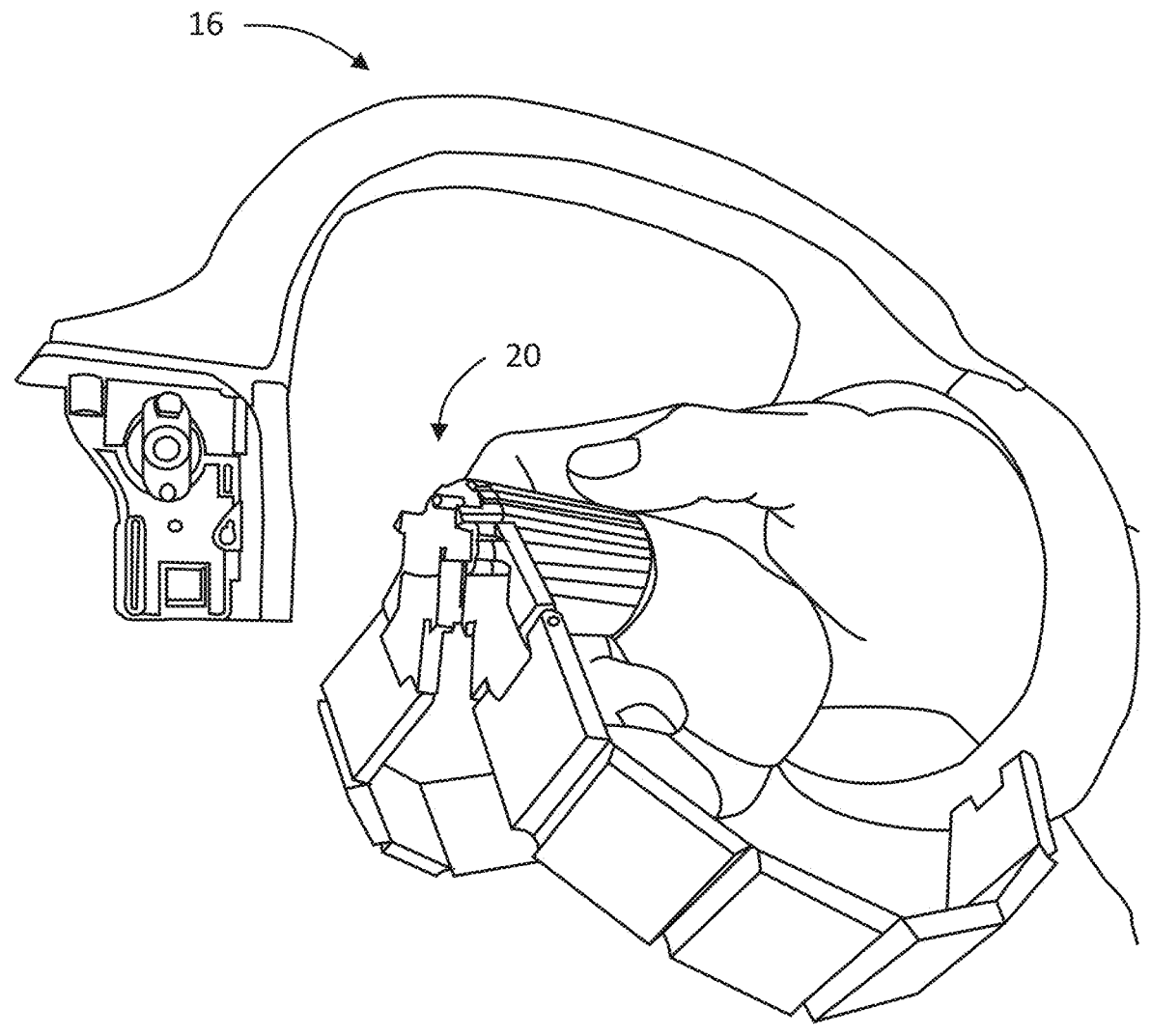
Figure 53B:
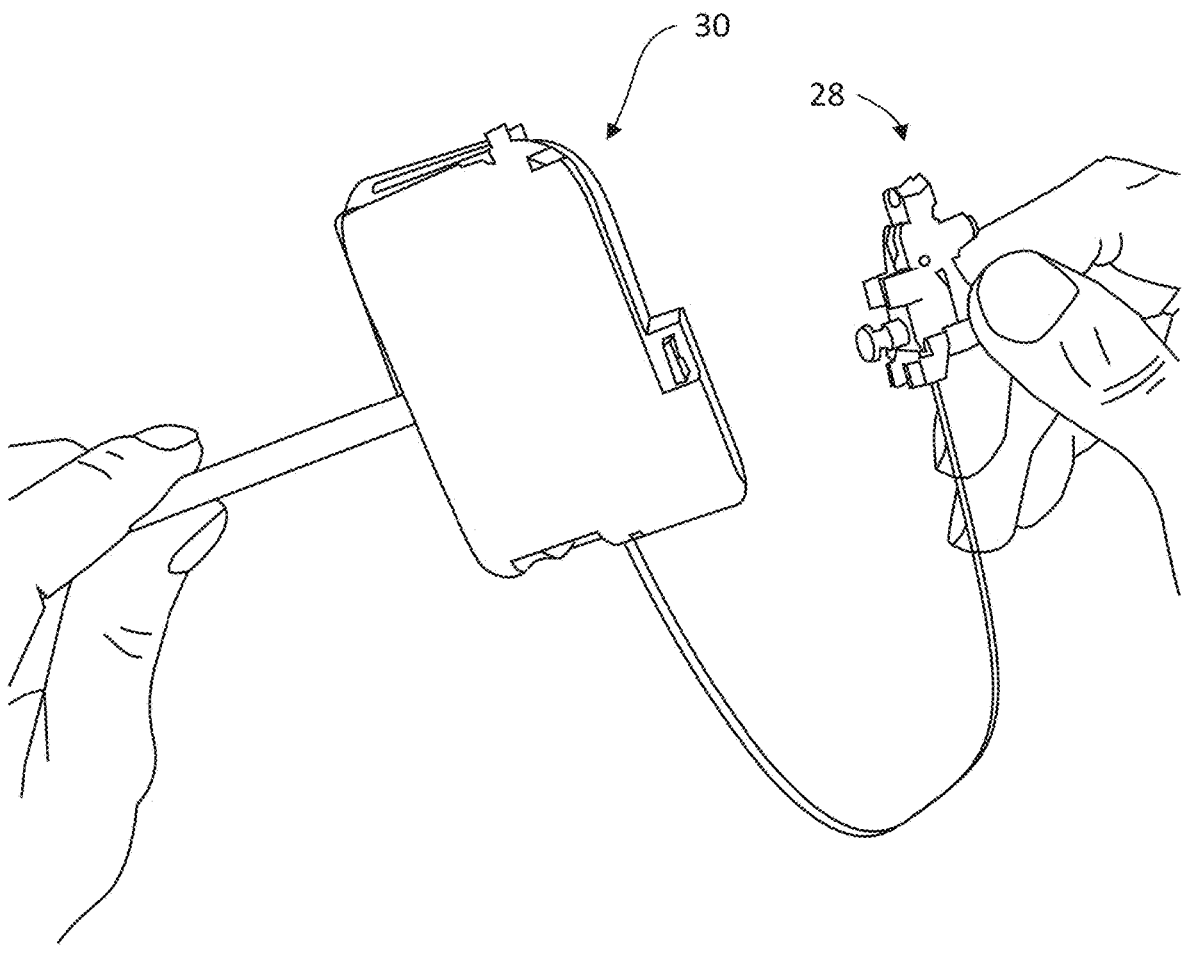
Figure 54:
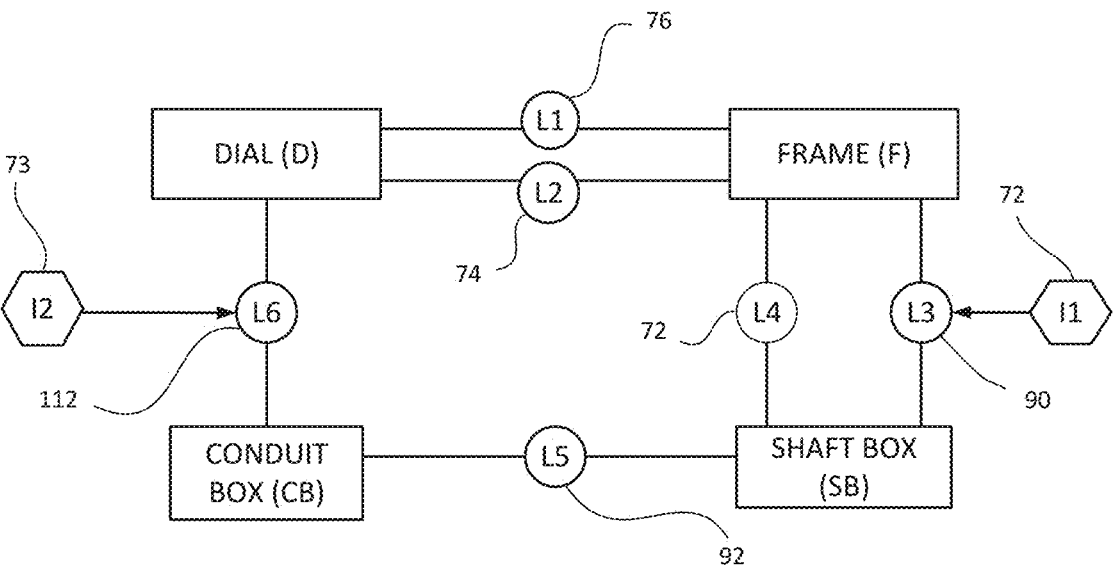
Figure 55A:
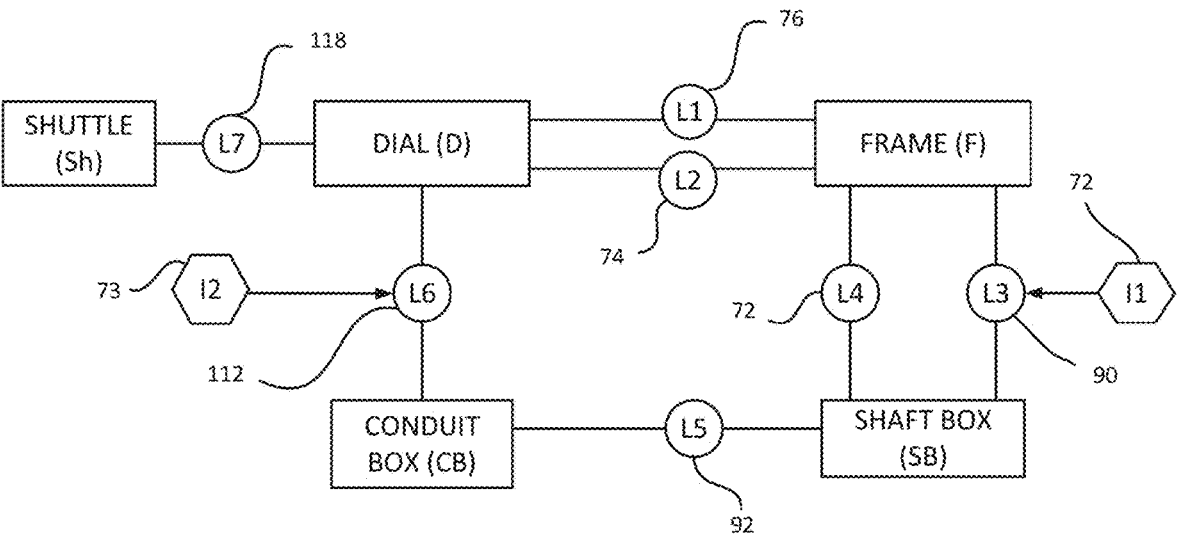
Figure 55B:
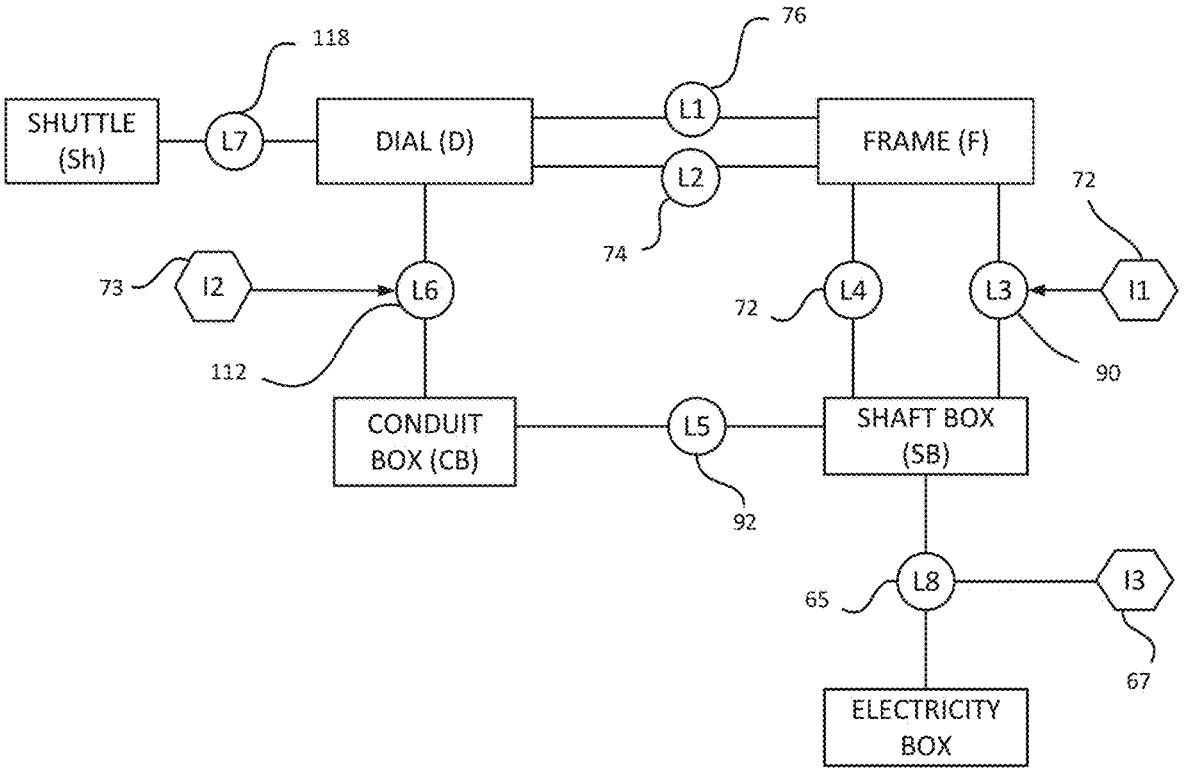
Figure 56A:
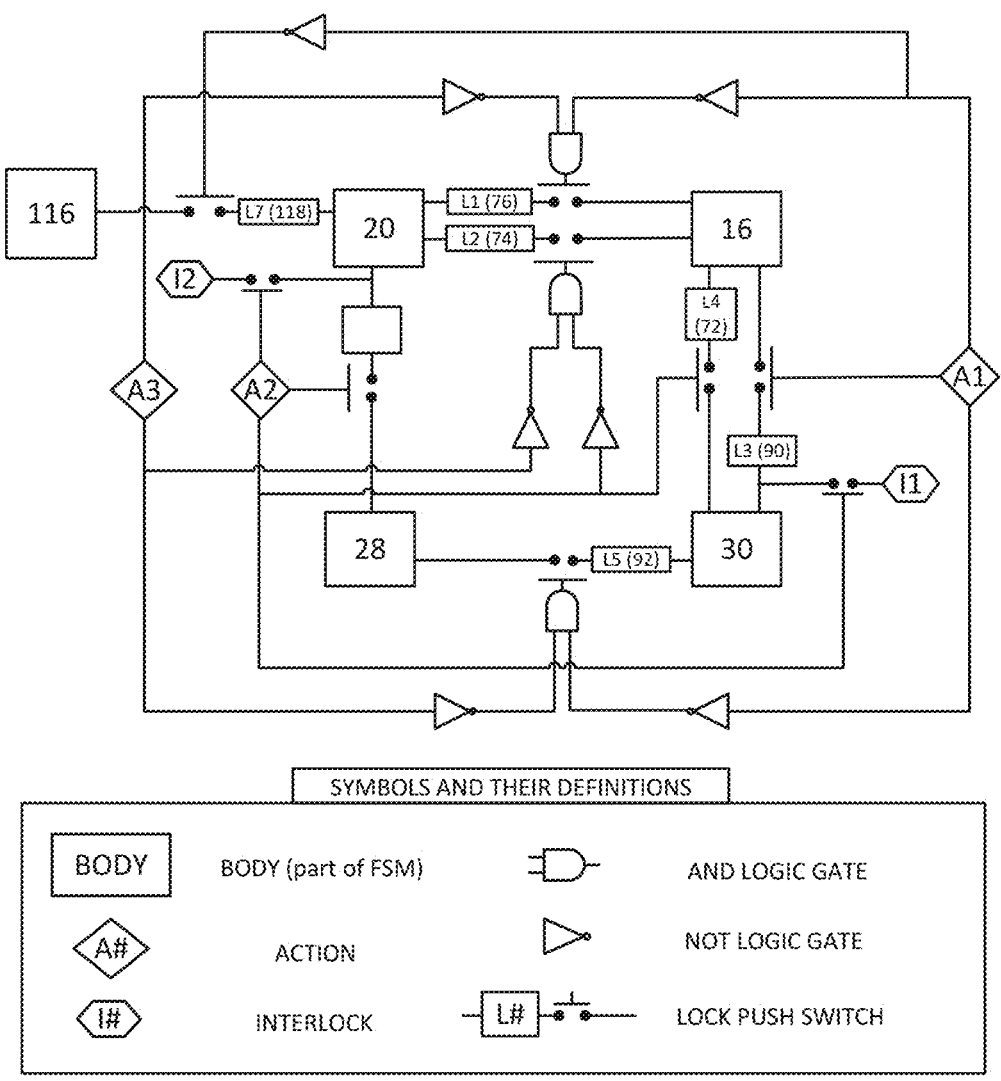
Figure 58A:
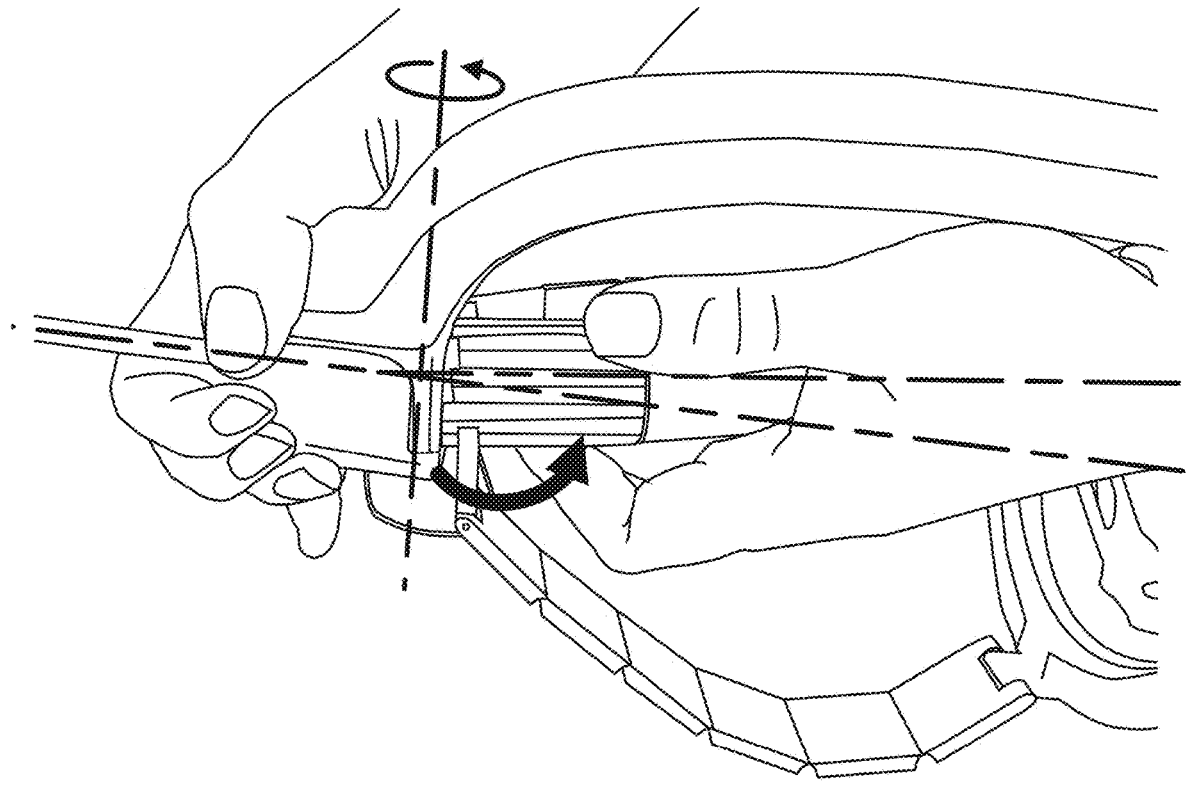
Figure 58B:
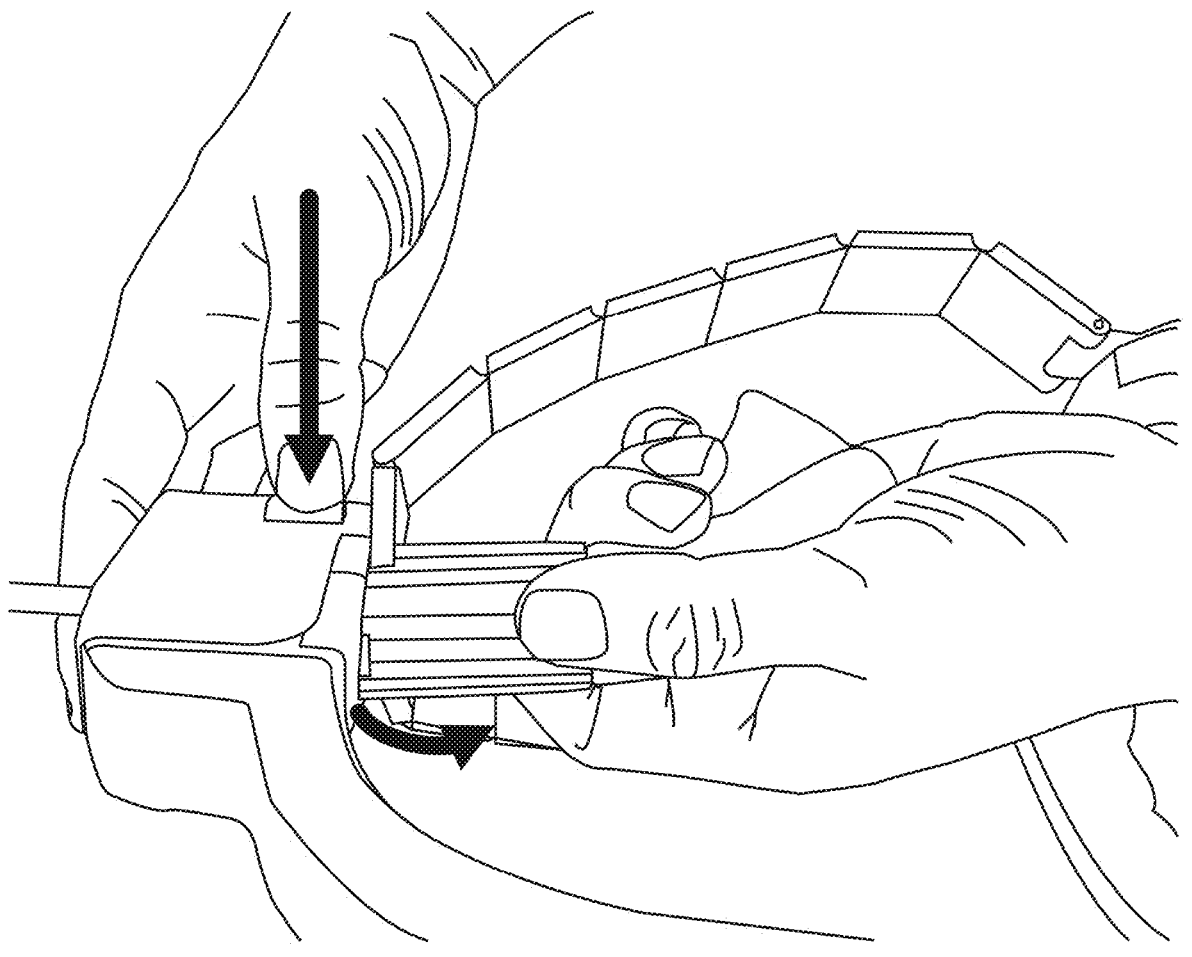
Figure 59:
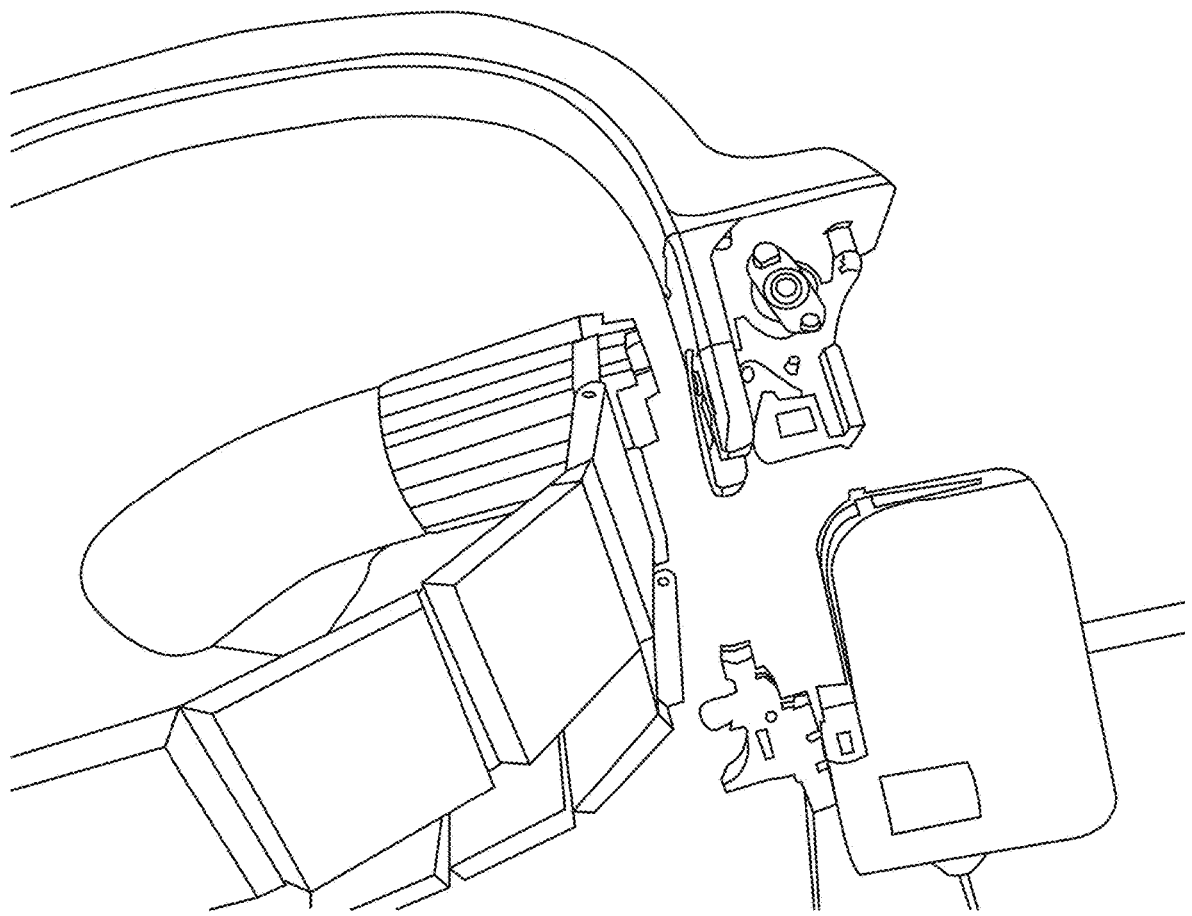
Figure 60:
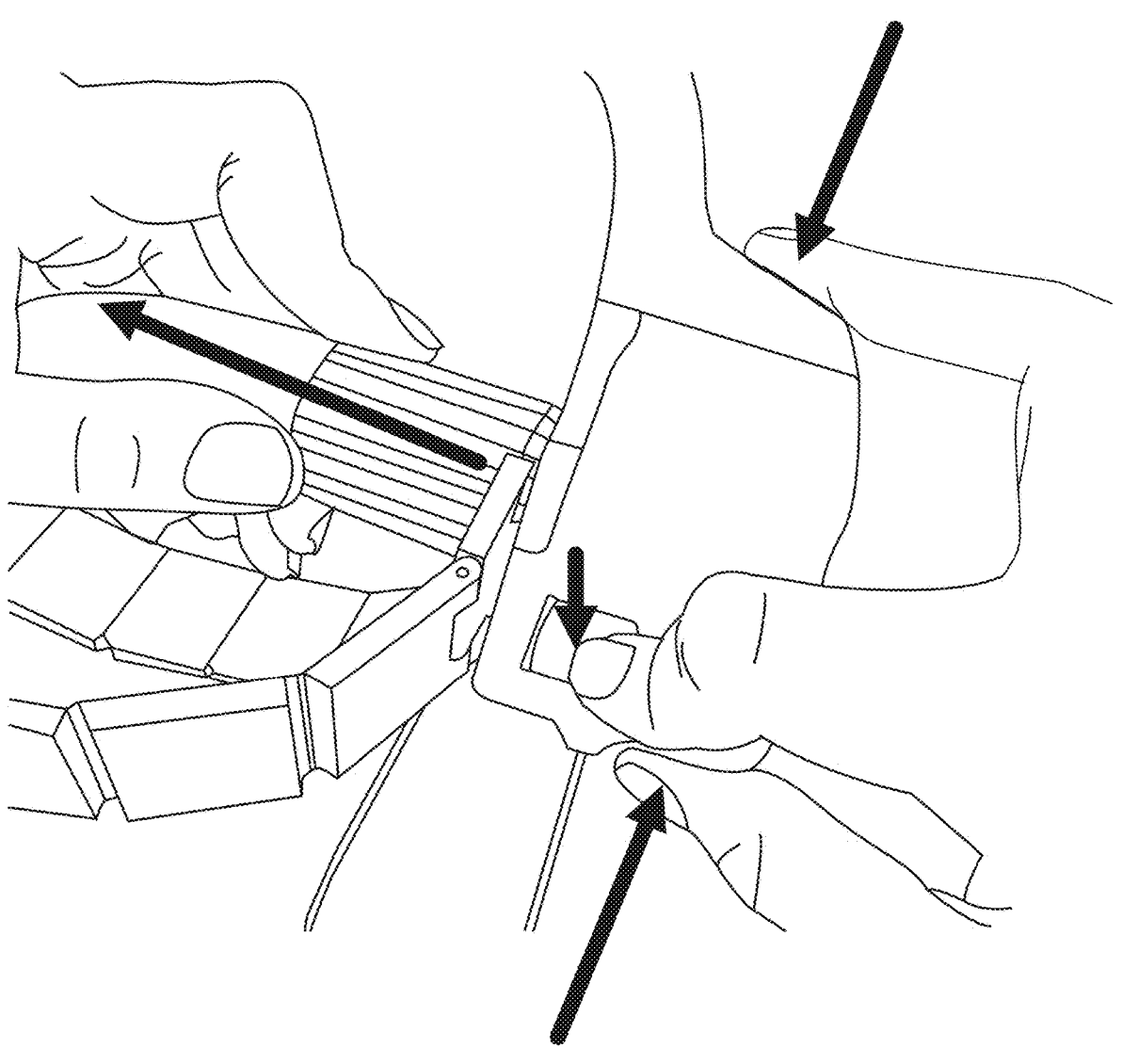
Figure 61:
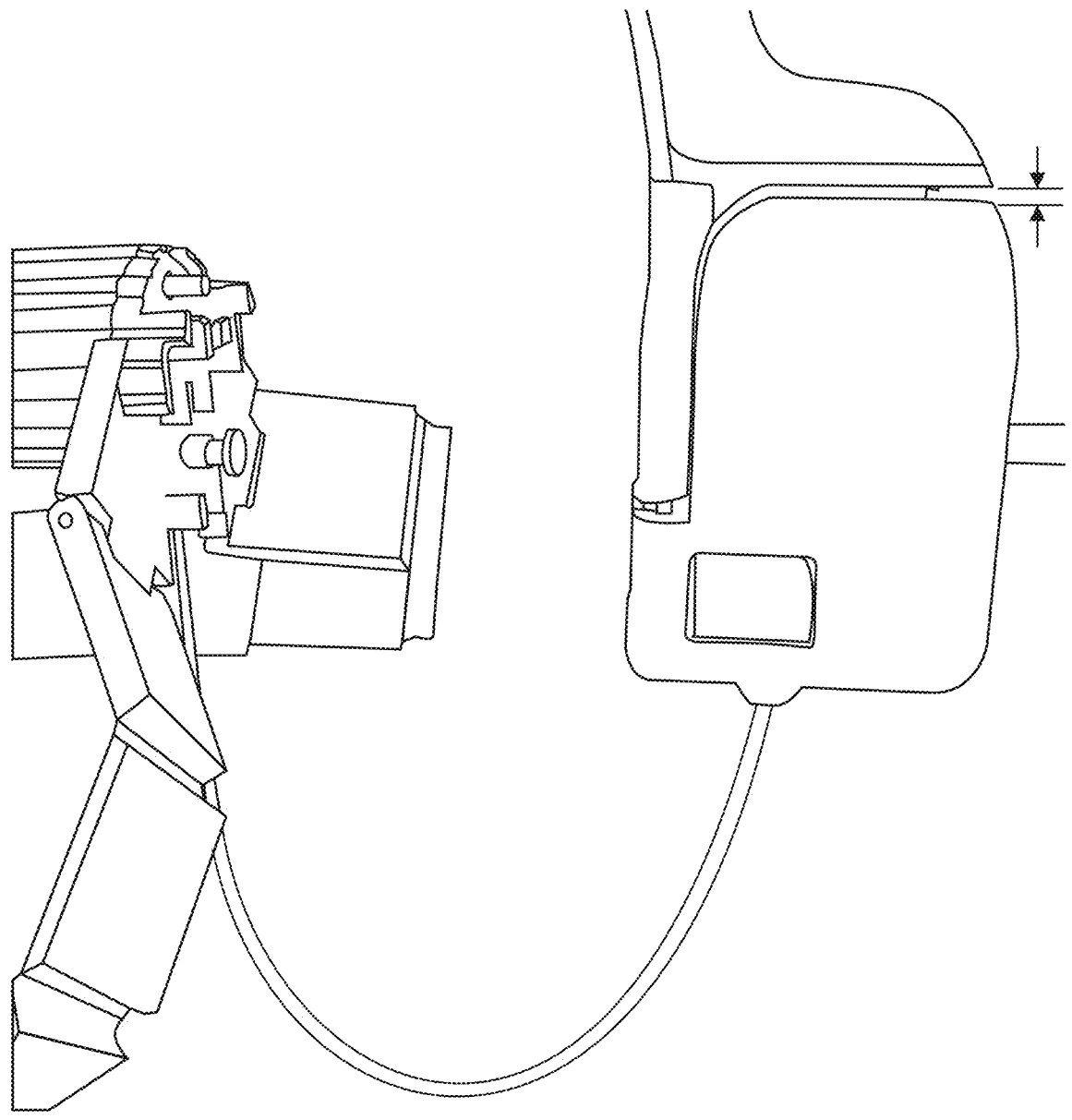
Figure 62:
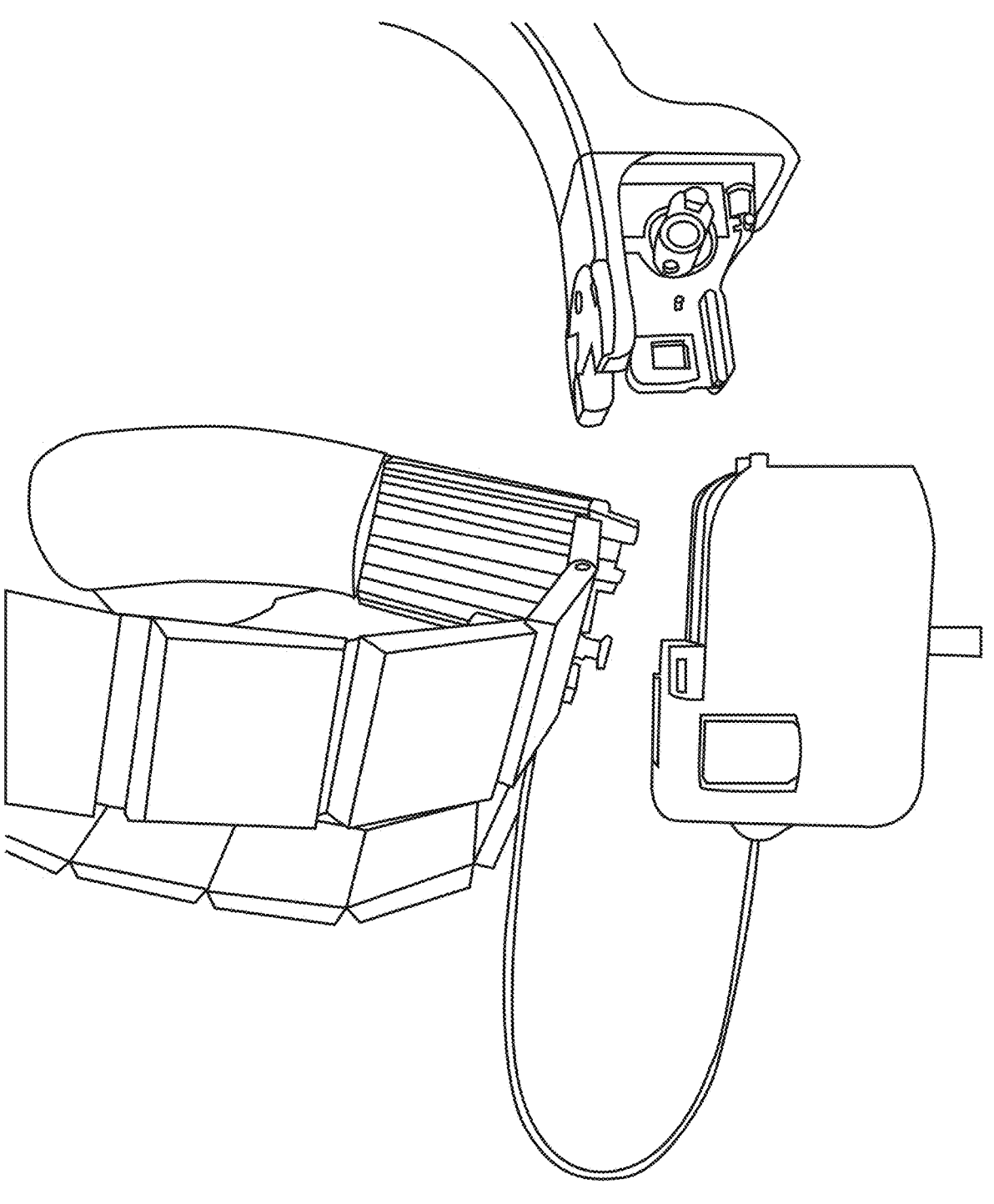
Figure 63:
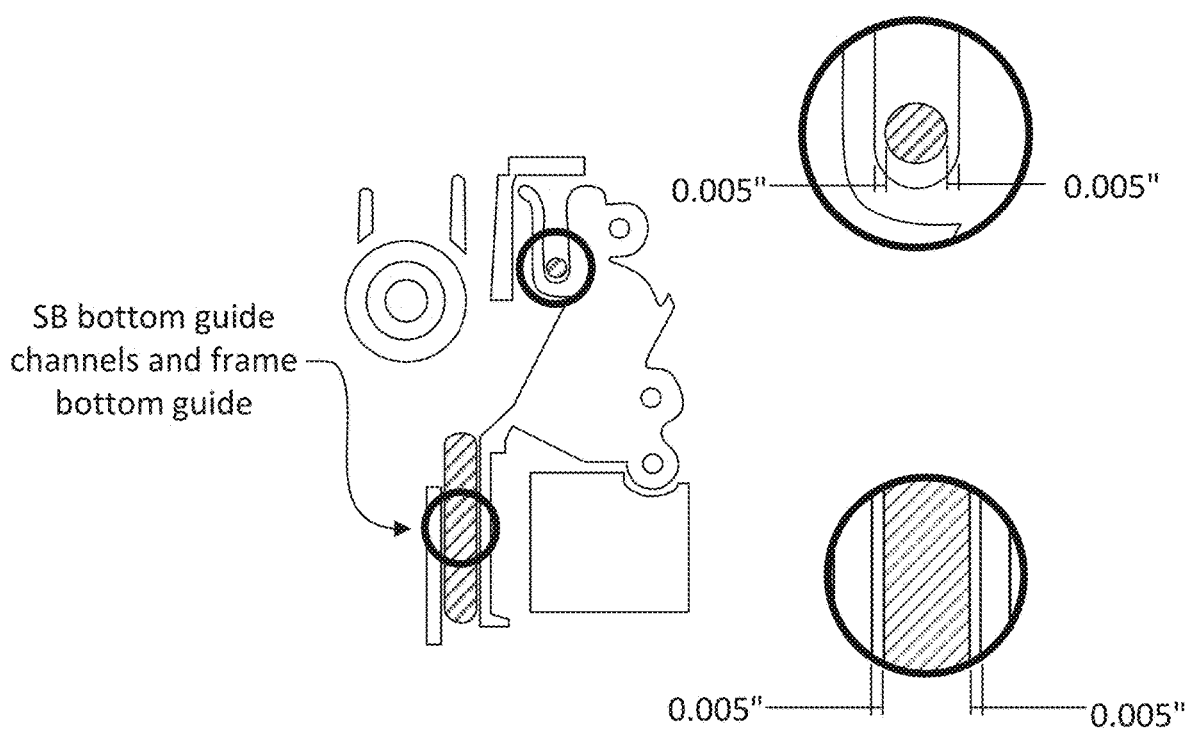
Figure 64A:
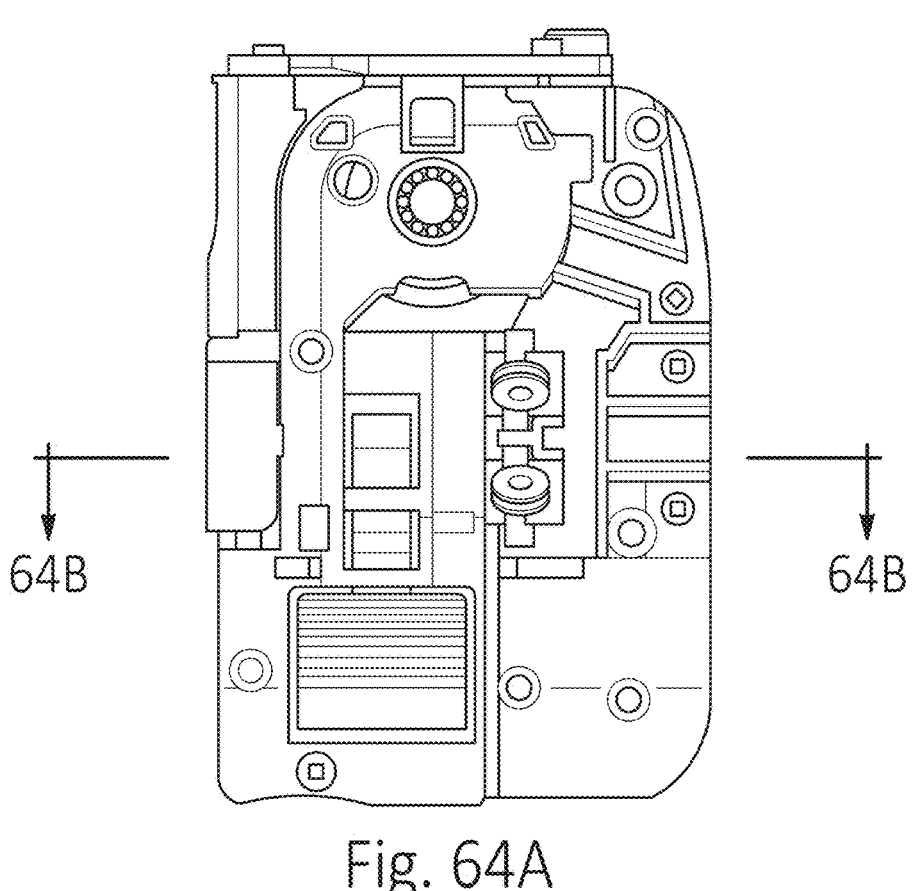
Figure 64B:
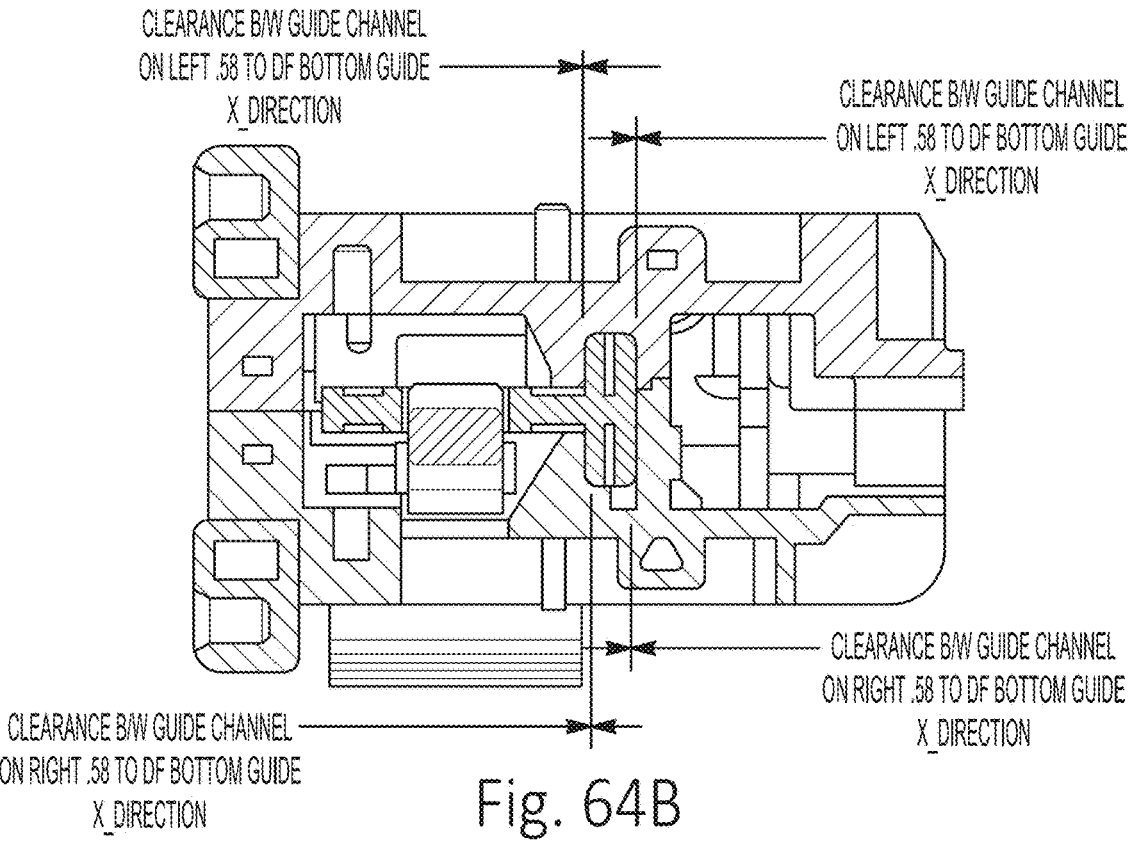
Figure 65:
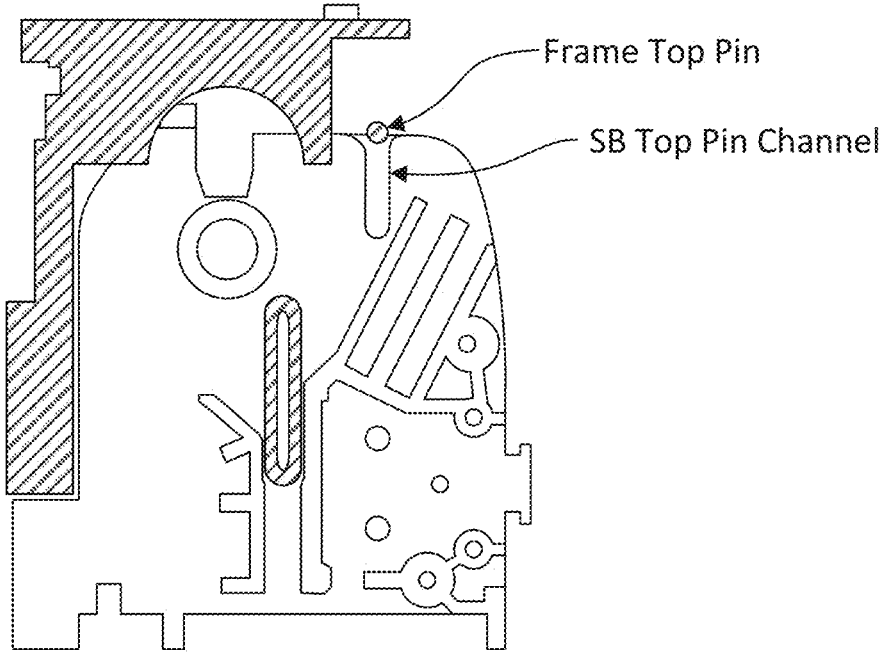
Figure 66A:
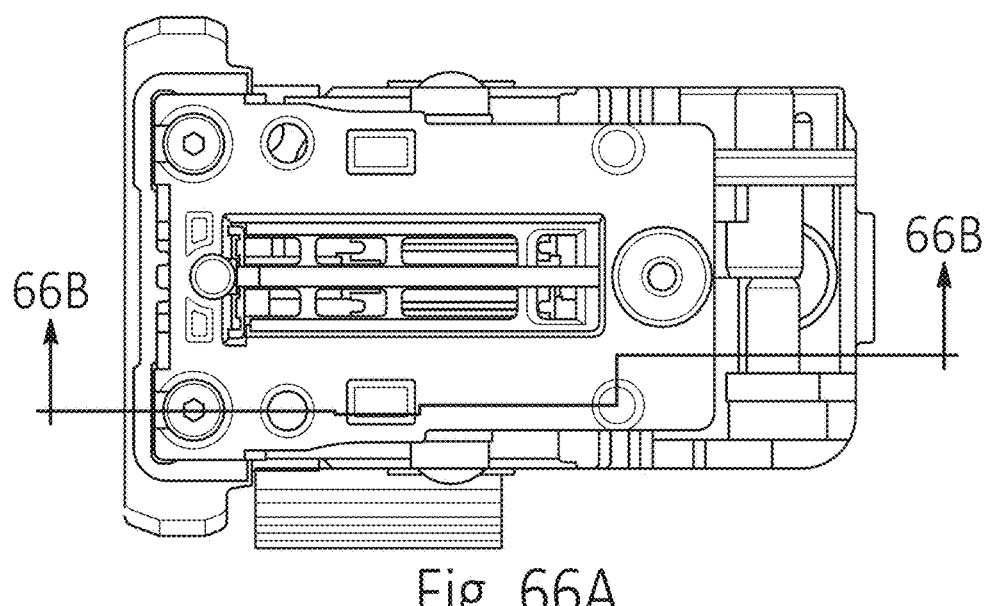
Figure 66B:
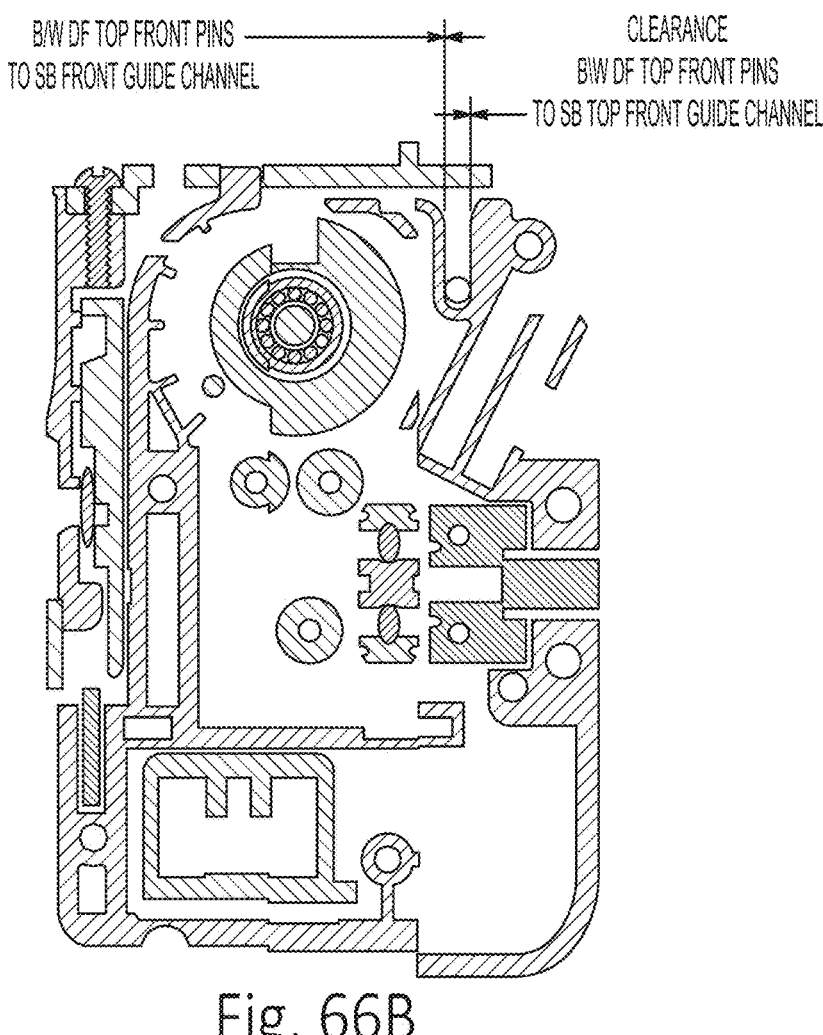
Figure 67:
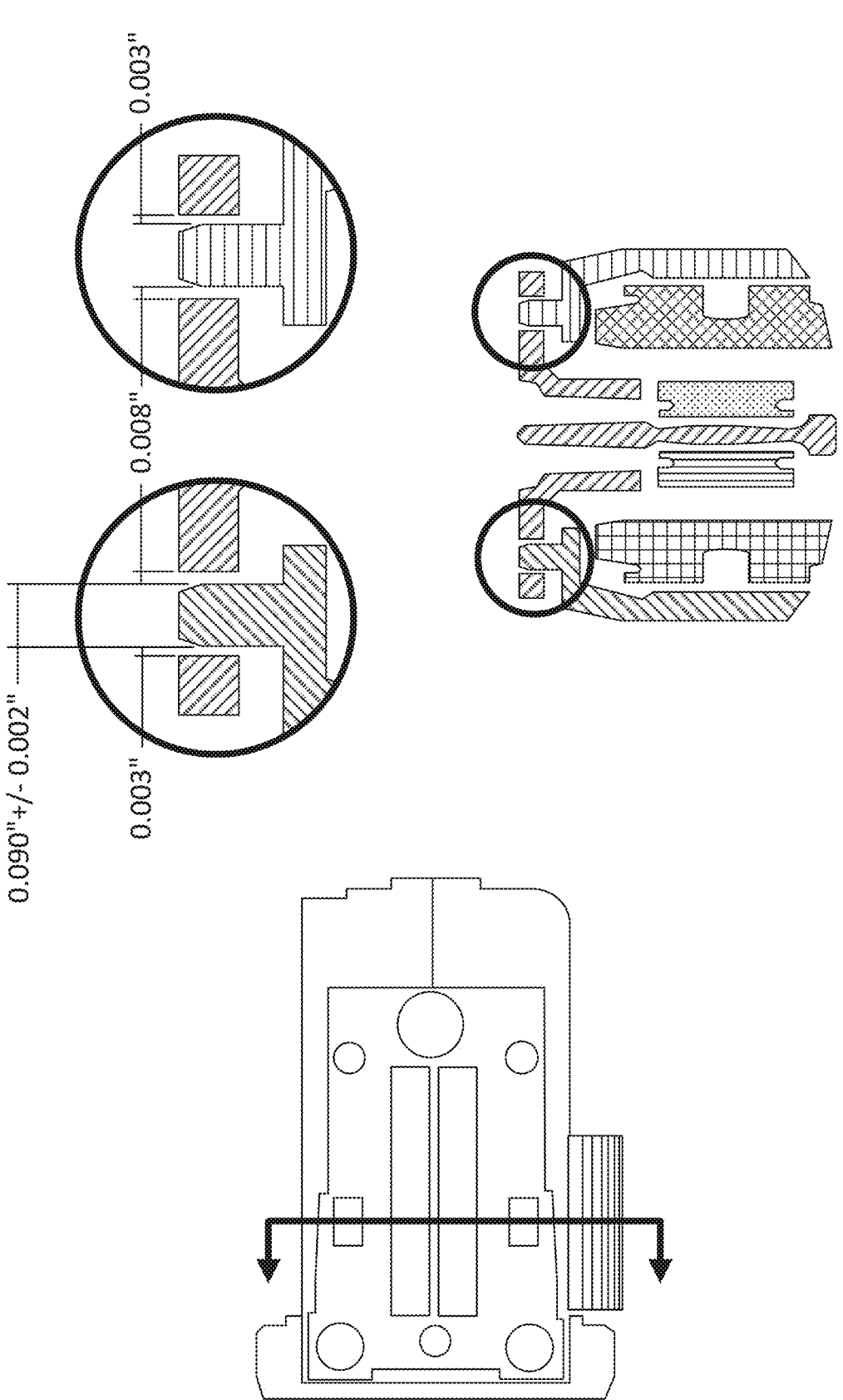
Figure 68:
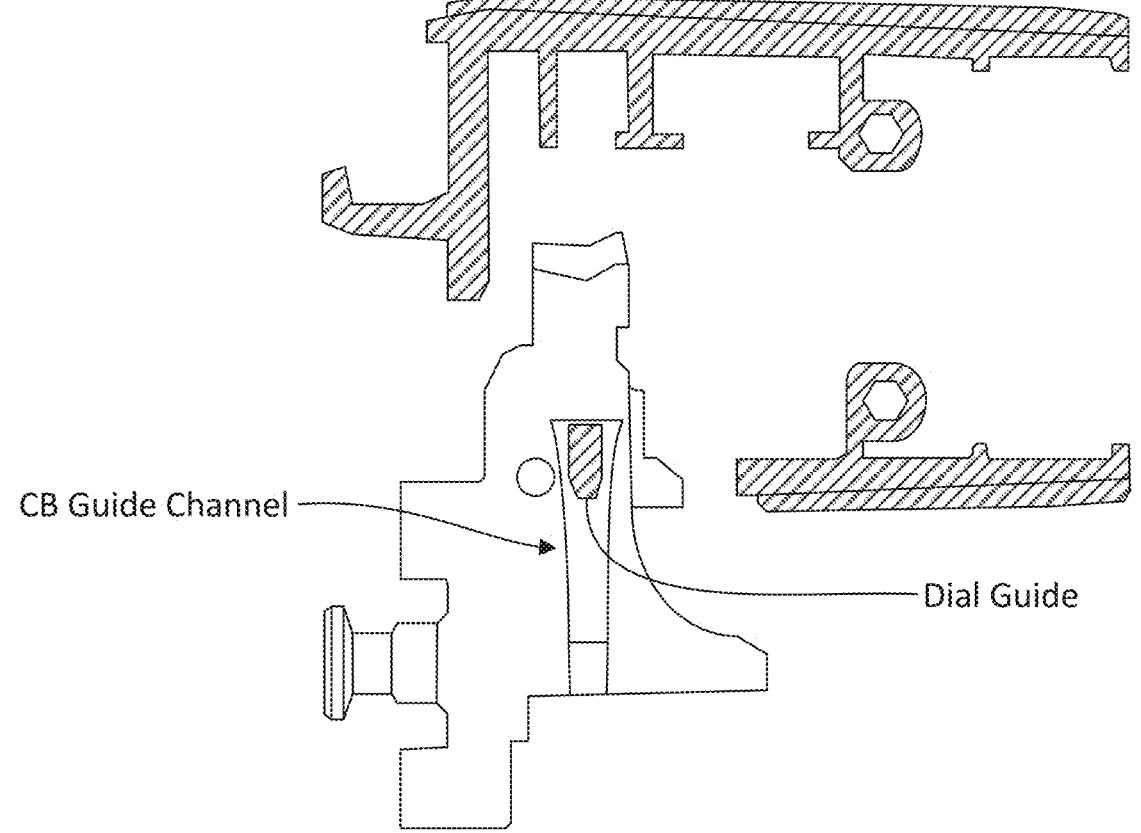
Figure 69:
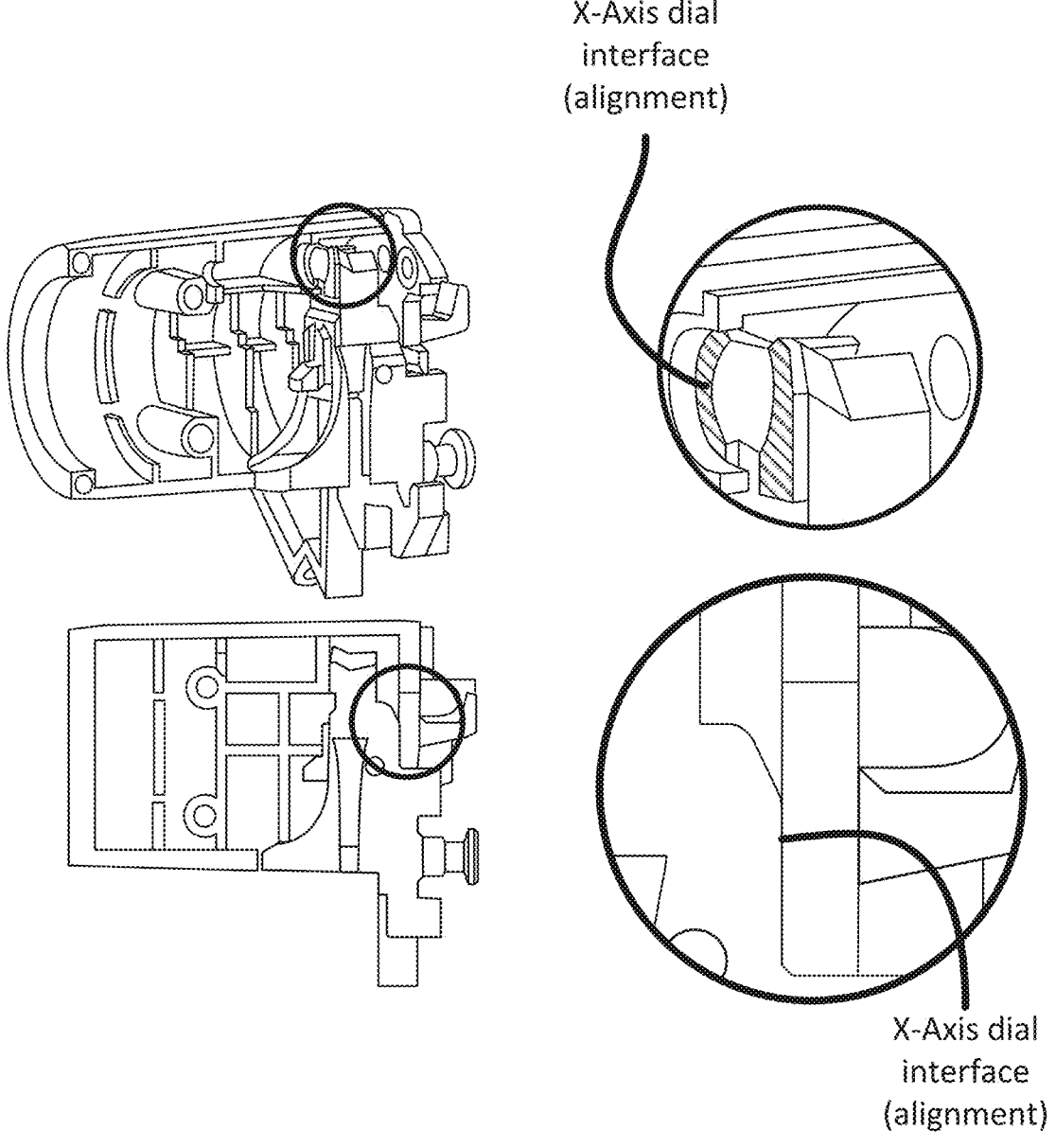

FIGS. 28A-C depict a conduit box lockout plate (CBLP) and certain interaction elements;

FIGS. 29A-C depict a conduit box lockout shaft (CBLS) and certain interaction elements;

FIGS. 30A-C depict a dial lockout plate (DLP) and certain interaction elements;

FIGS. 31A-C depict a button and certain interaction elements;

FIGS. 32A-C depict VCU lever and certain interaction elements;

FIGS. 33A-B depict shuttle lockout spring (SLS) and certain interaction elements;

FIG. 34 shows cross-section of a dial detent spring (DDS)-dial interface while dial is locked;

FIGS. 35A-B show different views of an embodiment of an articulation transmission interface;

FIG. 36 shows an embodiment of an articulation transmission interface;

FIGS. 37A-B show another embodiment of means to produce VCU-DI interface;

FIGS. 38A-C depict jaw closure transmission path and transmission member (TM);

FIGS. 39A-B depict frame articulation transmission path and TM;

FIGS. 40A-D depict SB articulation transmission path and TM;

FIGS. 41A-B depict roll transmission path in case of beta configuration with and without articulation function in use;

FIG. 42 depicts User Interface-Dial and Closure input;

FIG. 43 depicts User Interface-Button;

FIGS. 44A-B depict User Interface-Shaft Box and Frame;

FIGS. 45A-B depict tool apparatus—Storage State;

FIGS. 46A-C depict Transition 1—State 1 to State 2;

FIGS. 47A-C depict tool apparatus—Assembled State;

FIG. 48 depicts Transition 2—State 2 to State 3;

FIGS. 49A-C depict tool apparatus—Use State;

FIG. 50 depicts Transition 2'—State 3 to State 2;

FIGS. 51A-C depicts Transition 1'—State 2 to State 1;

FIGS. 52A-B depict Transition 3—State 1 to State 4;

FIGS. 53A-B depict tool apparatus—Service State;

FIG. 54 is a schematic diagram of 4-body FSM;

FIGS. 55A-B are schematic diagrams of 5-body and 6-body FSM;

FIGS. 56A-B depict Lock Status diagram for 5 body FSM;

FIG. 57 depicts relationship between key actions and states;

FIGS. 58A-B depict Transition 4—State 2 to Misuse 1 state (M1);

FIG. 59 depicts Misuse 1 State (M1);

FIG. 60 depicts Transition 5'—State 2 to Misuse 2 state (M2);

FIG. 61 depicts Misuse State 2.1 (M2.1);

FIG. 62 depicts Misuse State 2.2 (M2.2);

FIG. 63 depicts SB bottom guide channels and frame button guide;

FIG. 64A-B depict clearance between frame bottom guide and SB bottom guide channel;

FIG. 65 depicts Frame top pin and SB top pin channel;

FIG. 66A-B depict completely aligned frame top pin and SB top pin channel;

FIG. 67 depicts third set of alignment features between frame and shaft box;

FIG. 68 depicts Dial guide and CB guide channel at start of alignment;

FIG. 69 depicts Dial guide and CB guide X axis direction alignment features;

4

Figure 71:
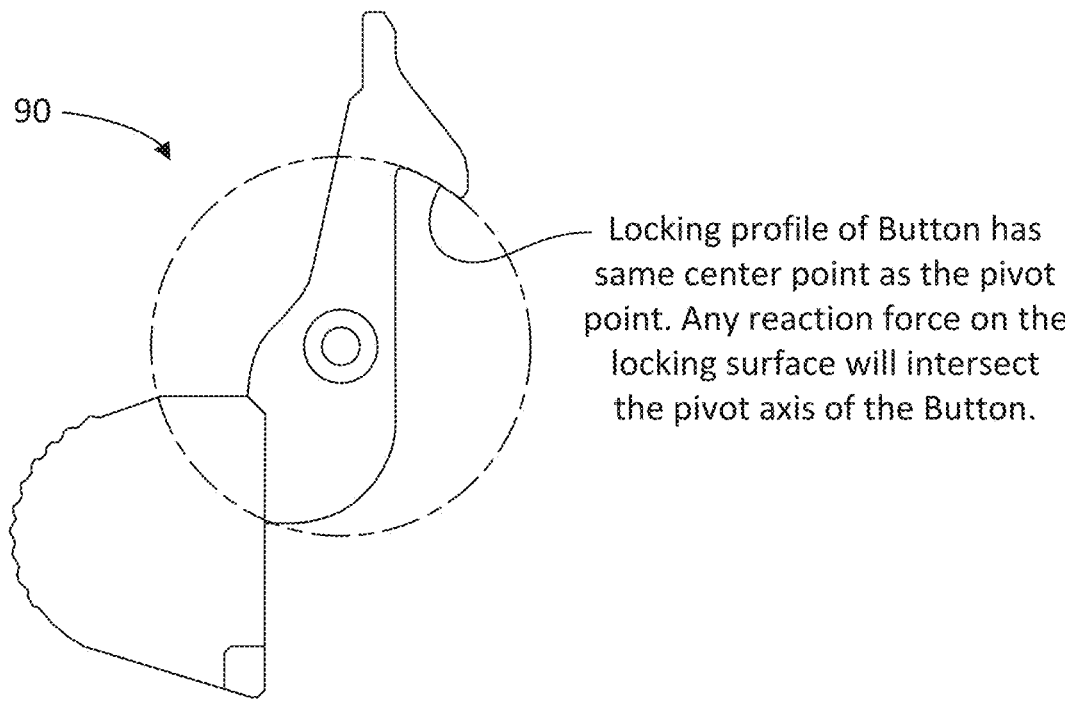
Figure 72:
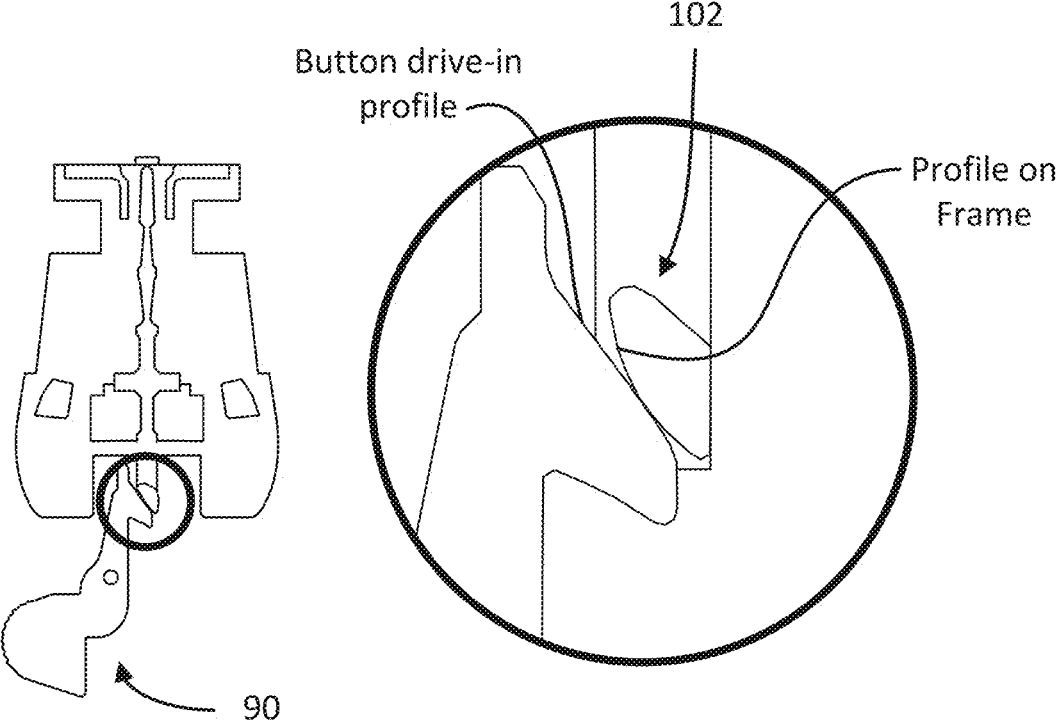
Figure 73:
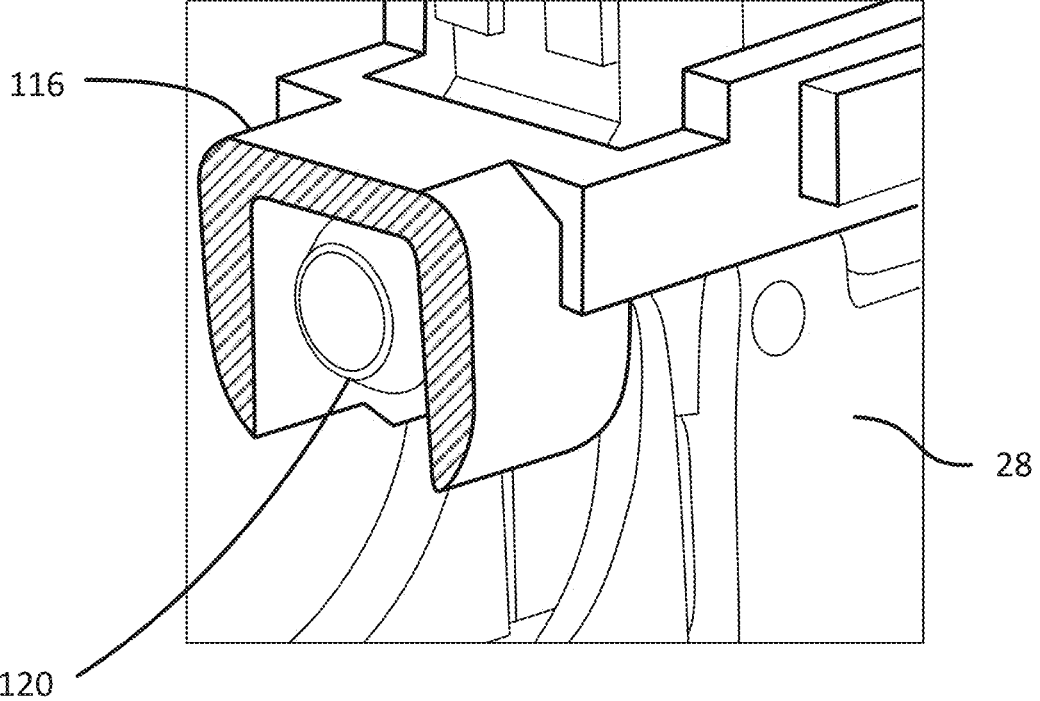
Figure 74A:
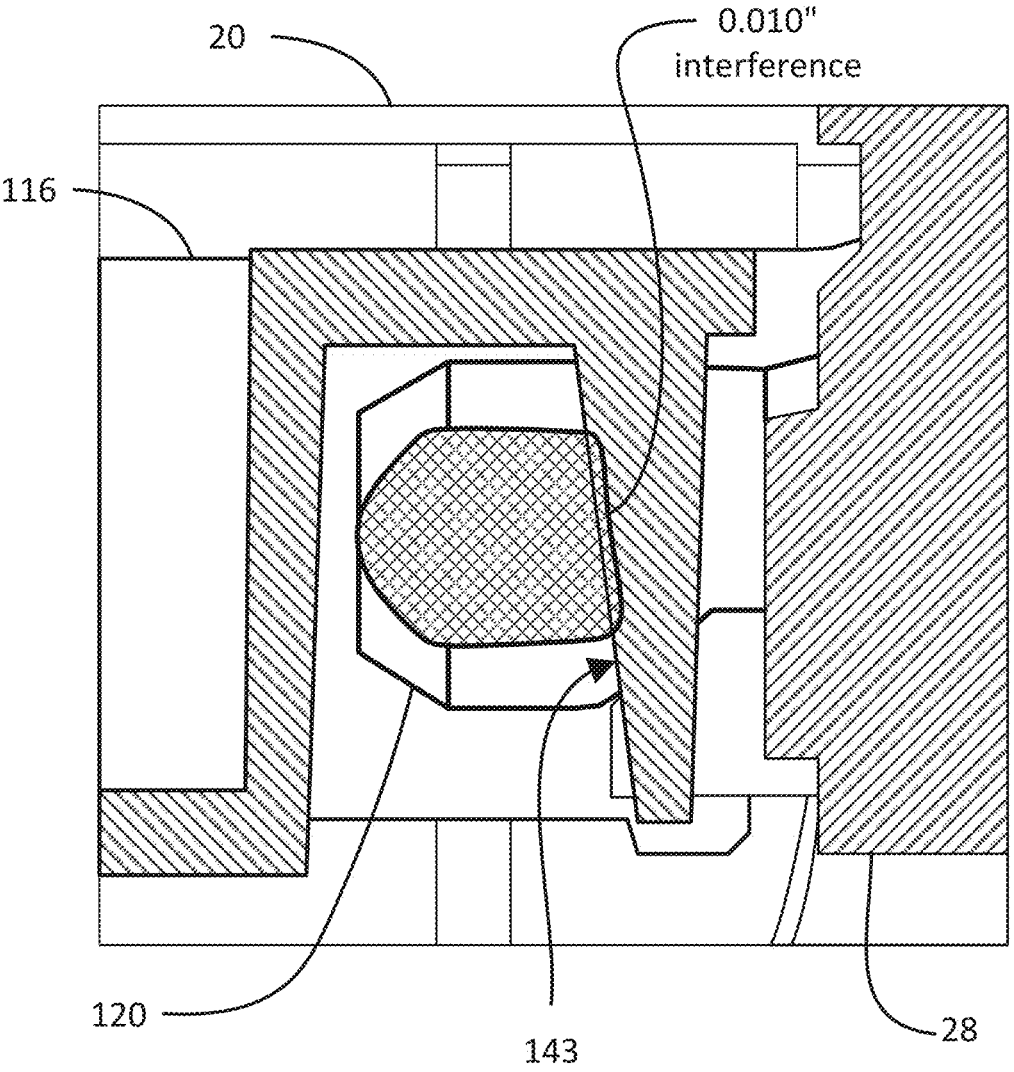
Figure 74B:
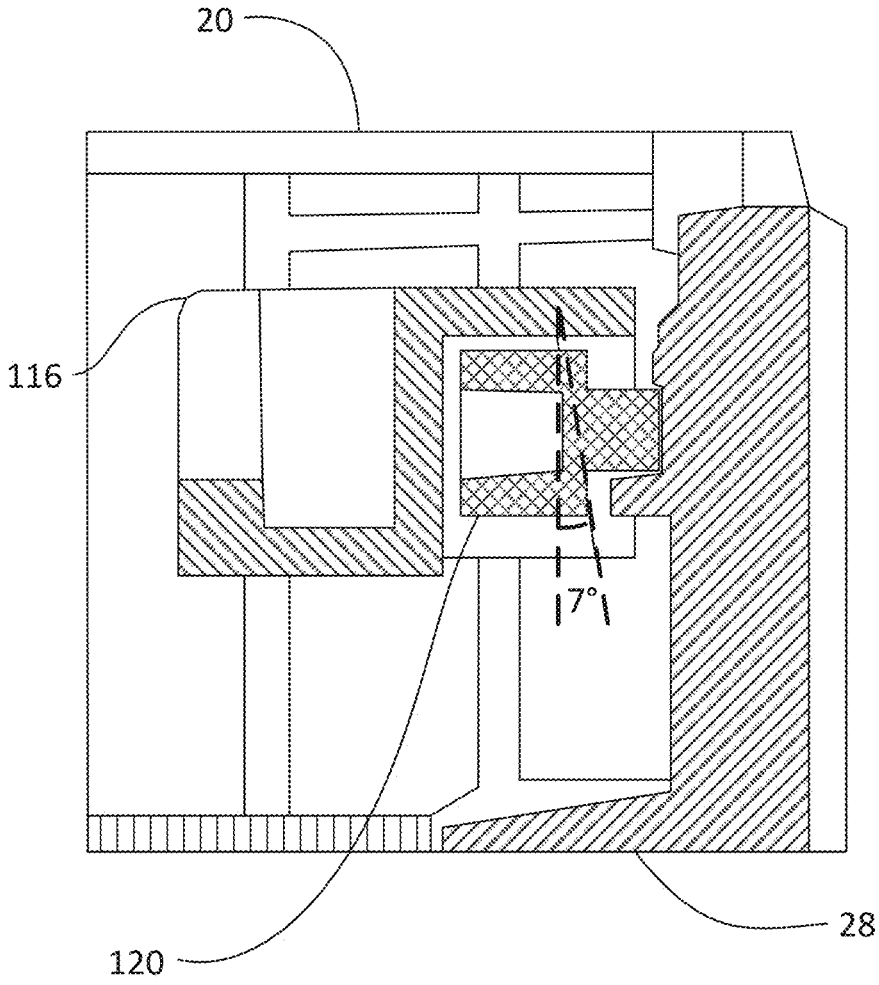
Figure 75:
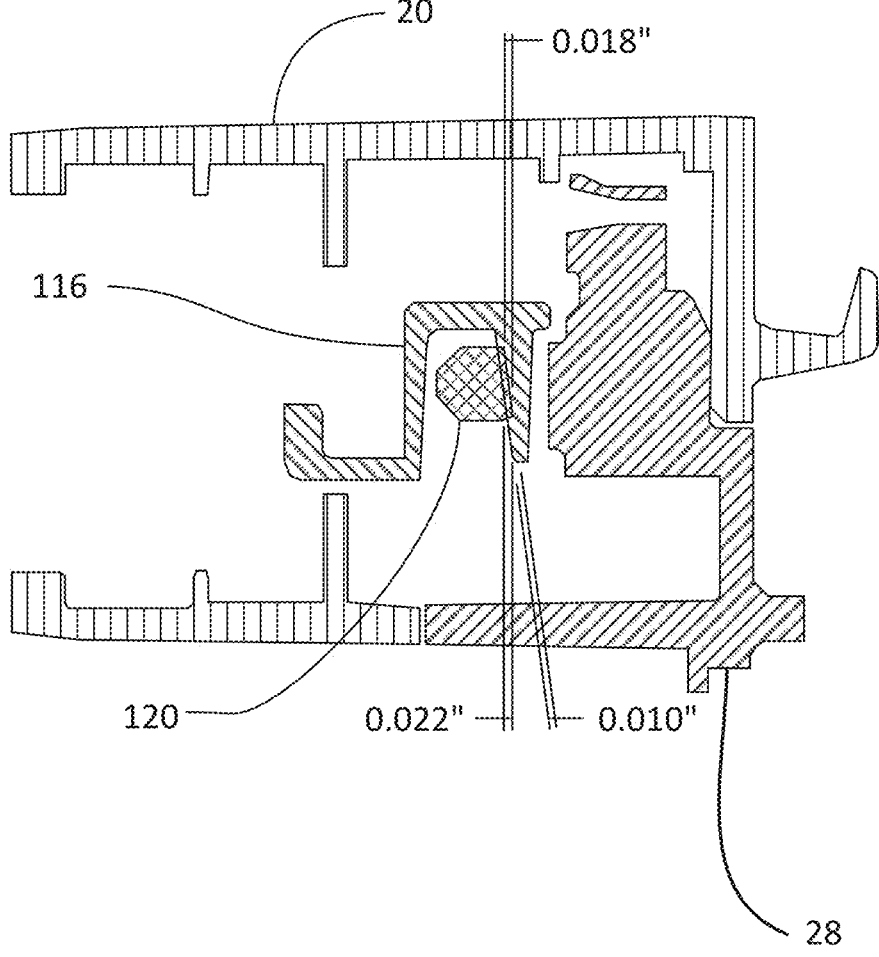
Figure 77:
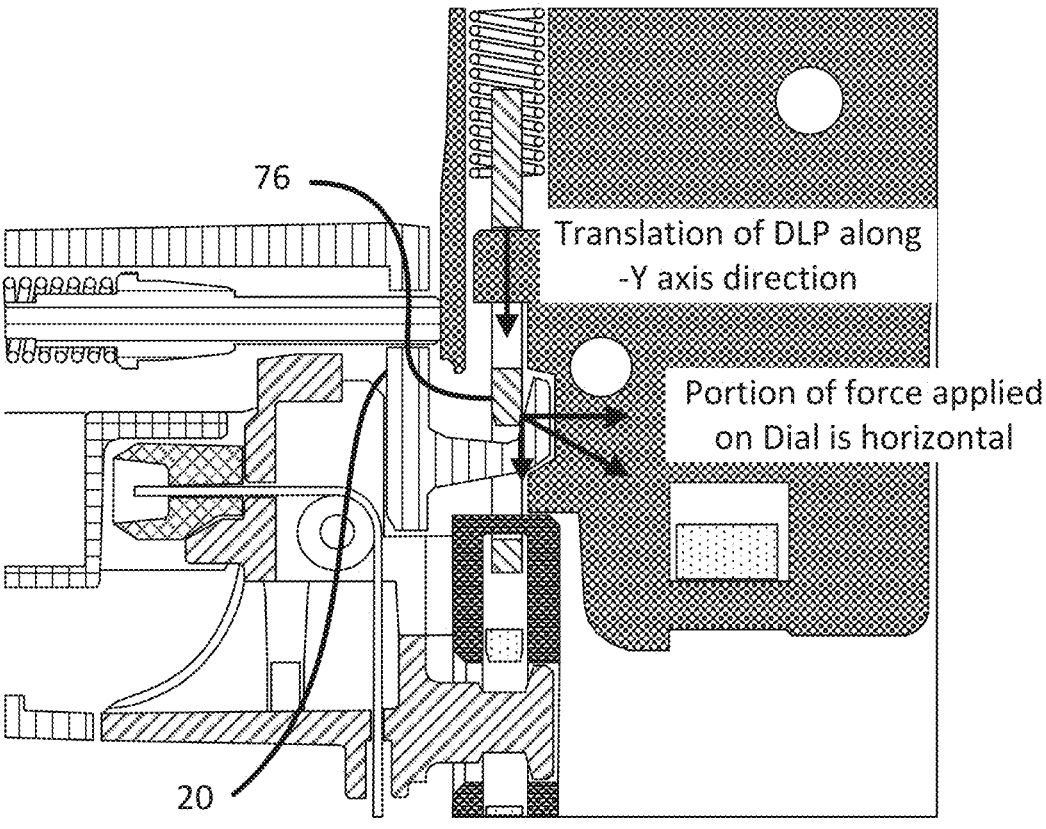
Figure 78:
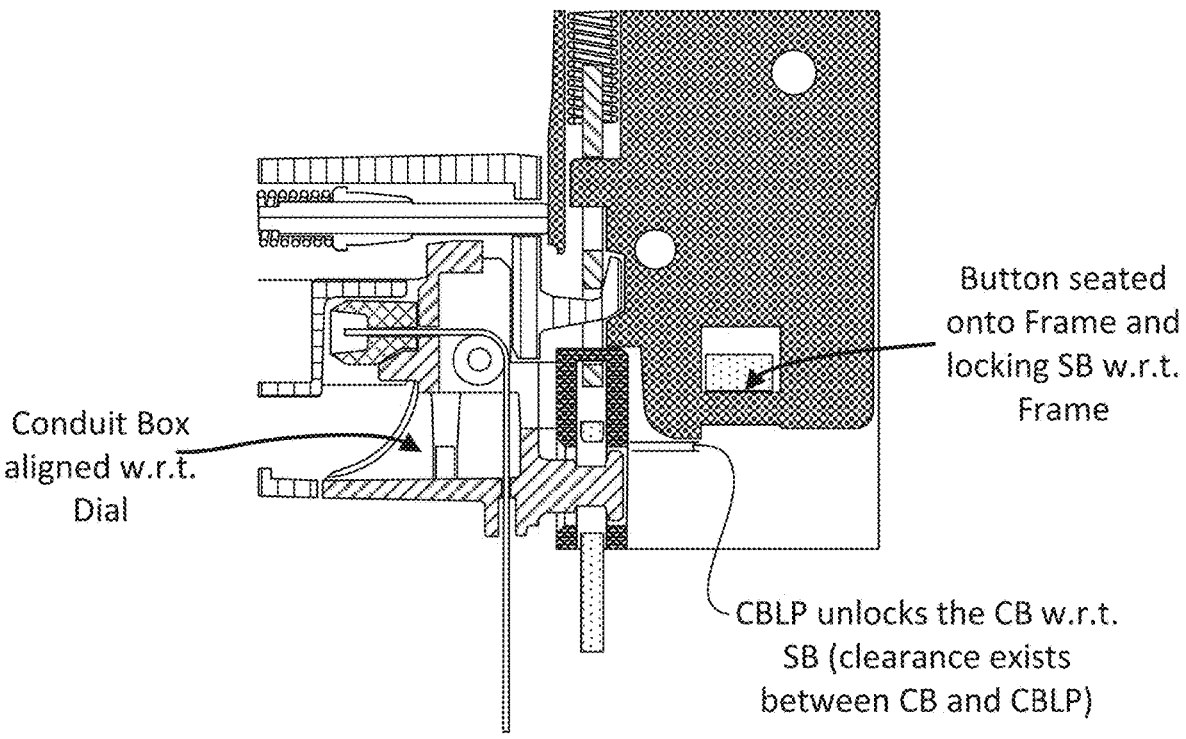
Figure 81:
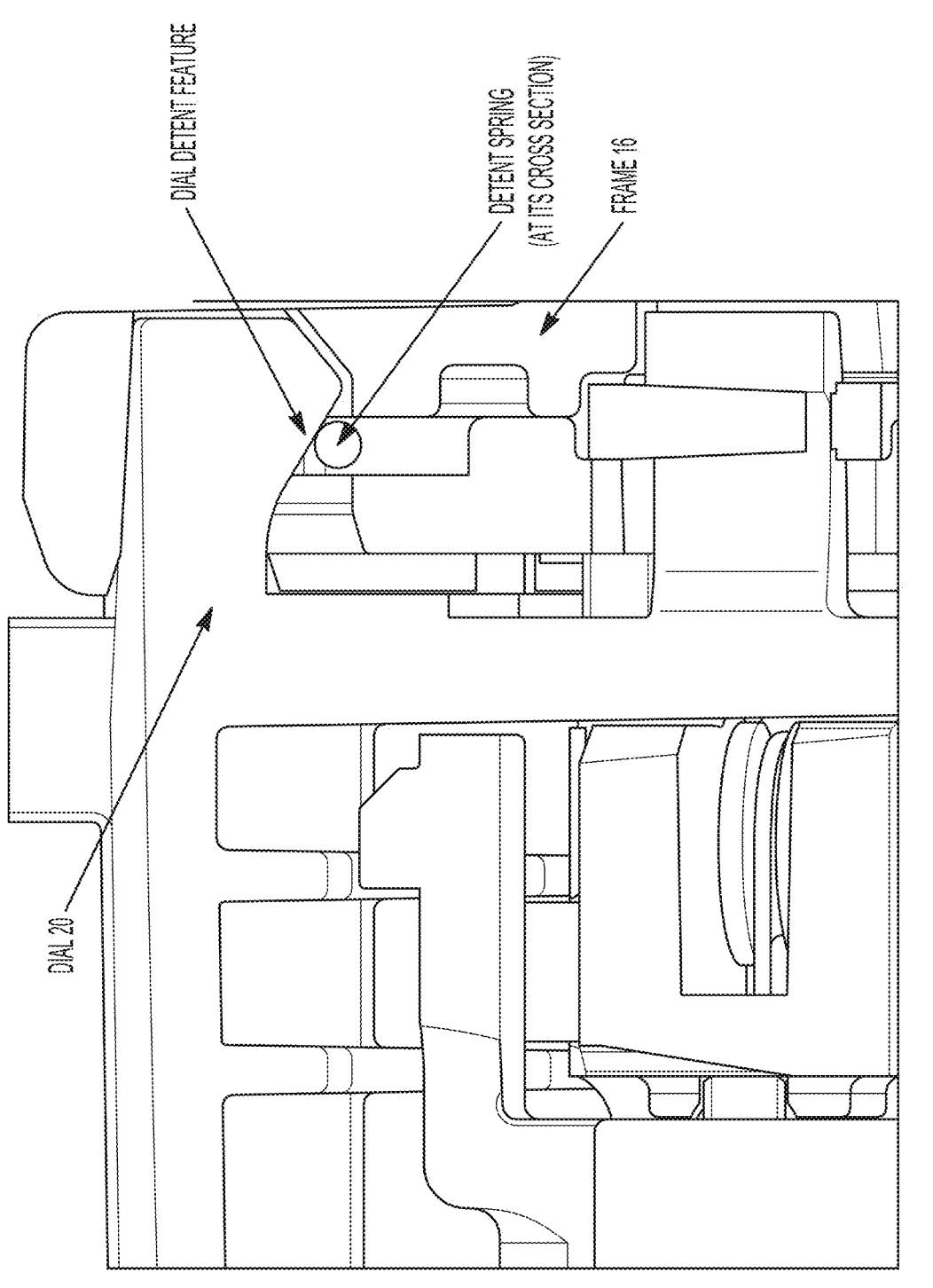
Figure 82:
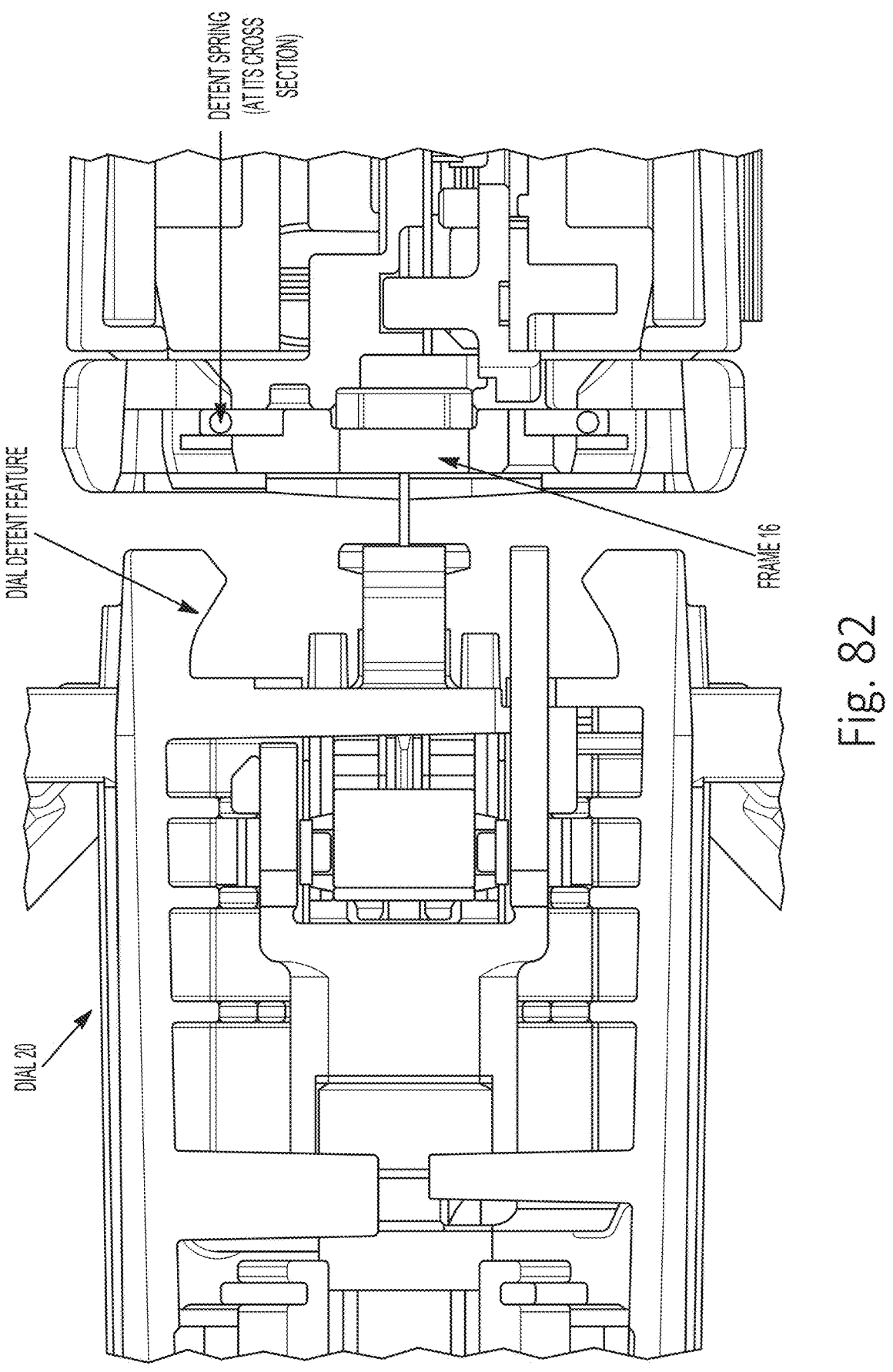
Figure 83:
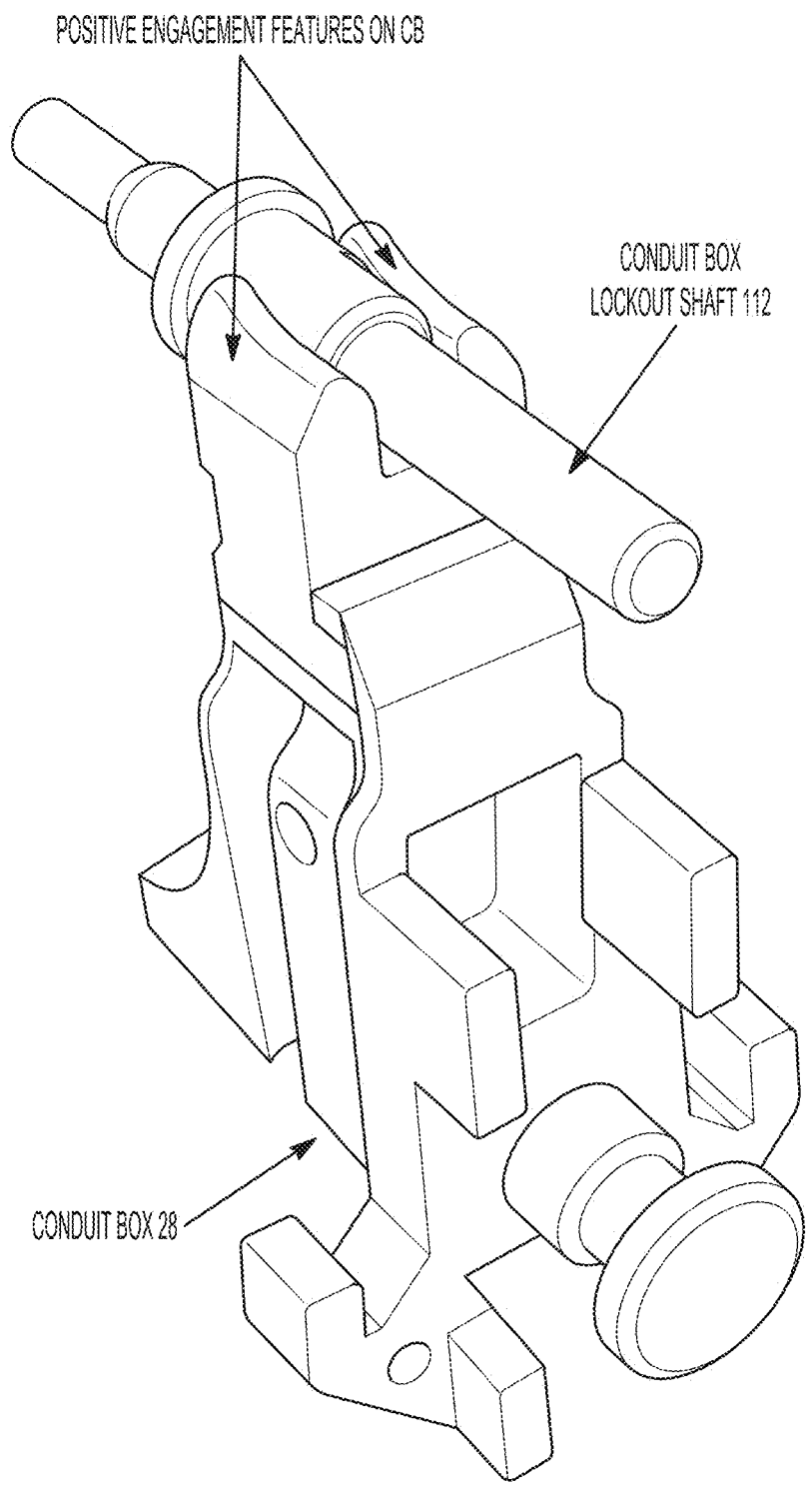
Figure 84:
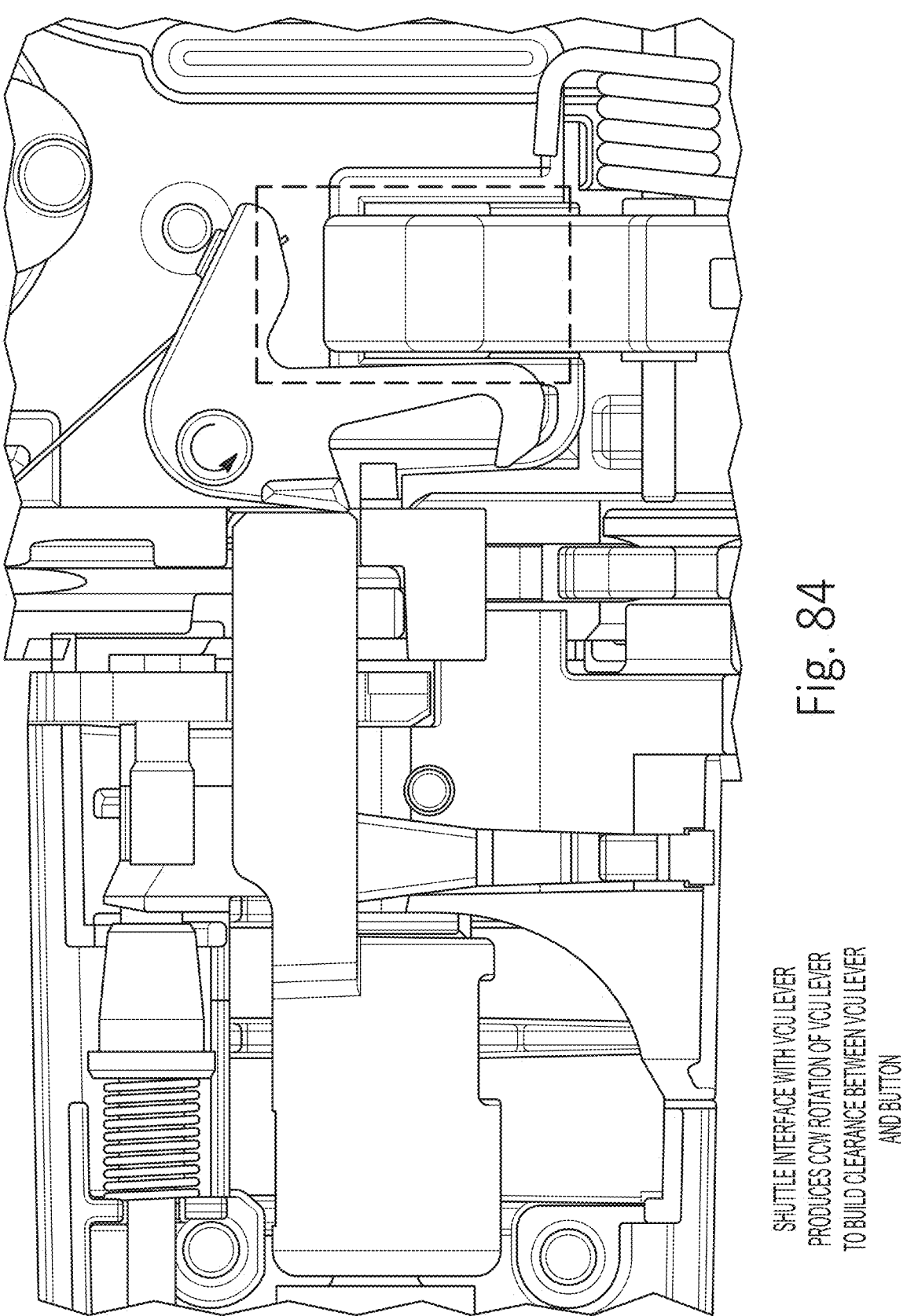
Figure 85:
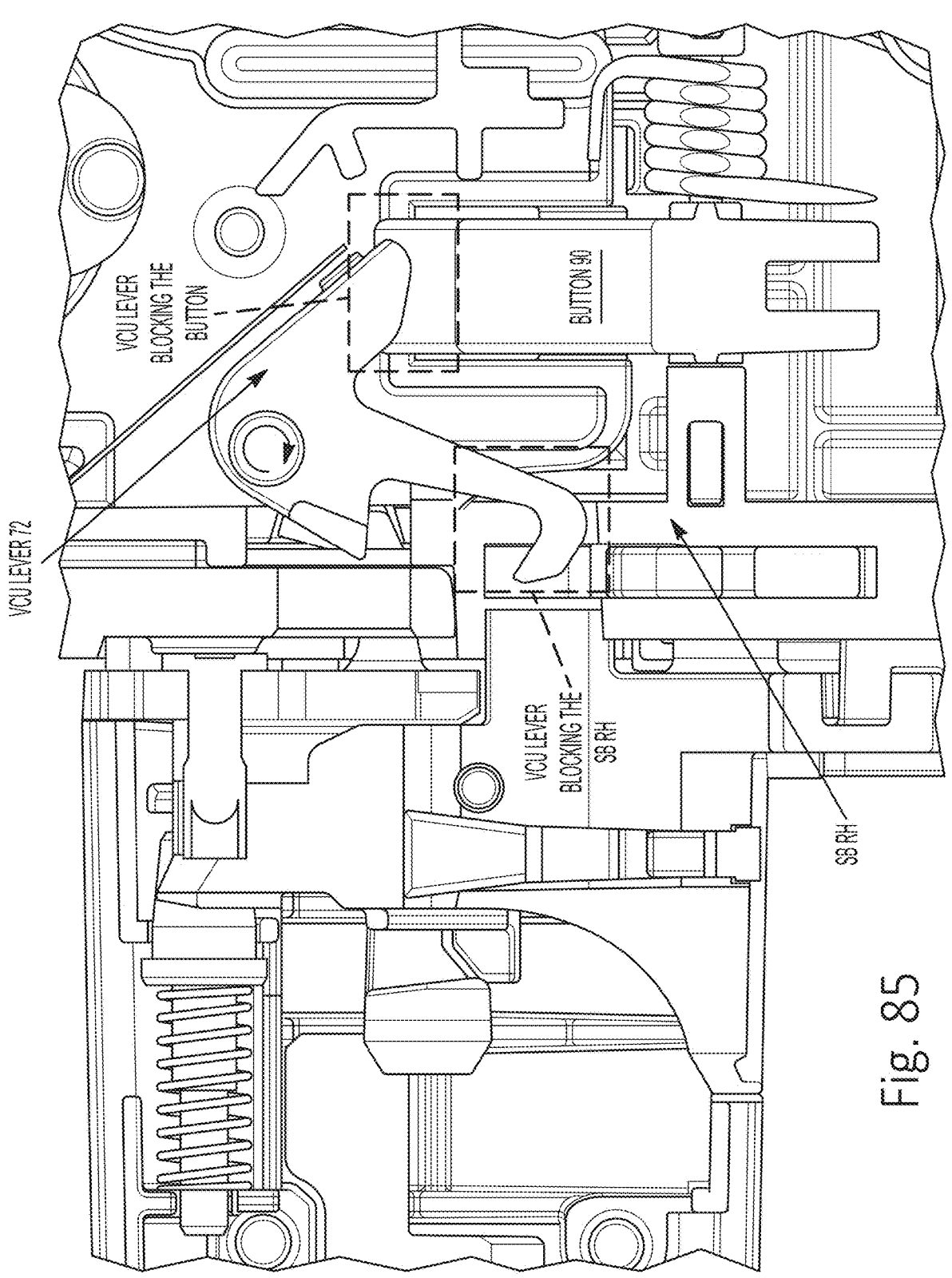
Figure 86:
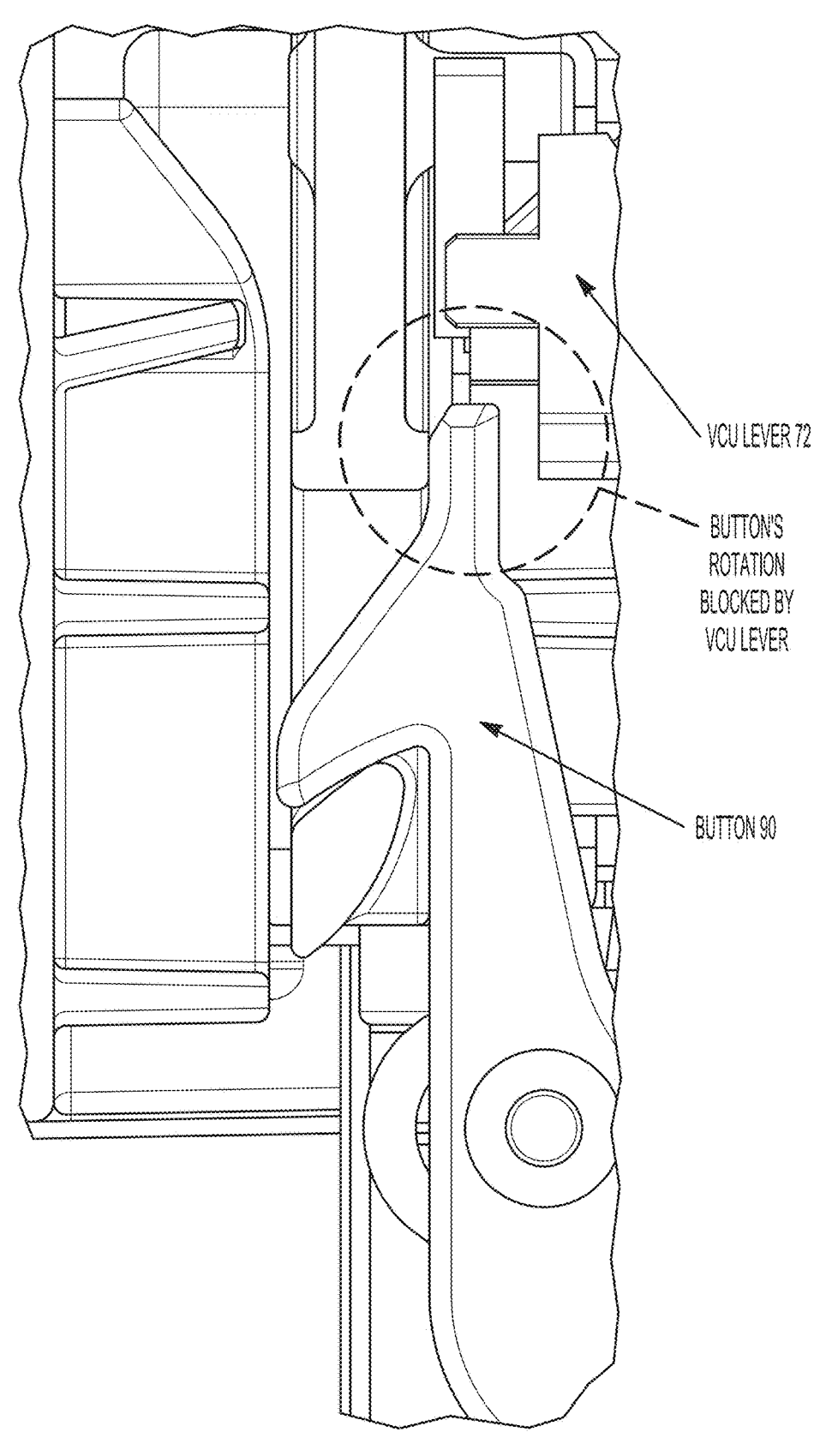
Figure 87:
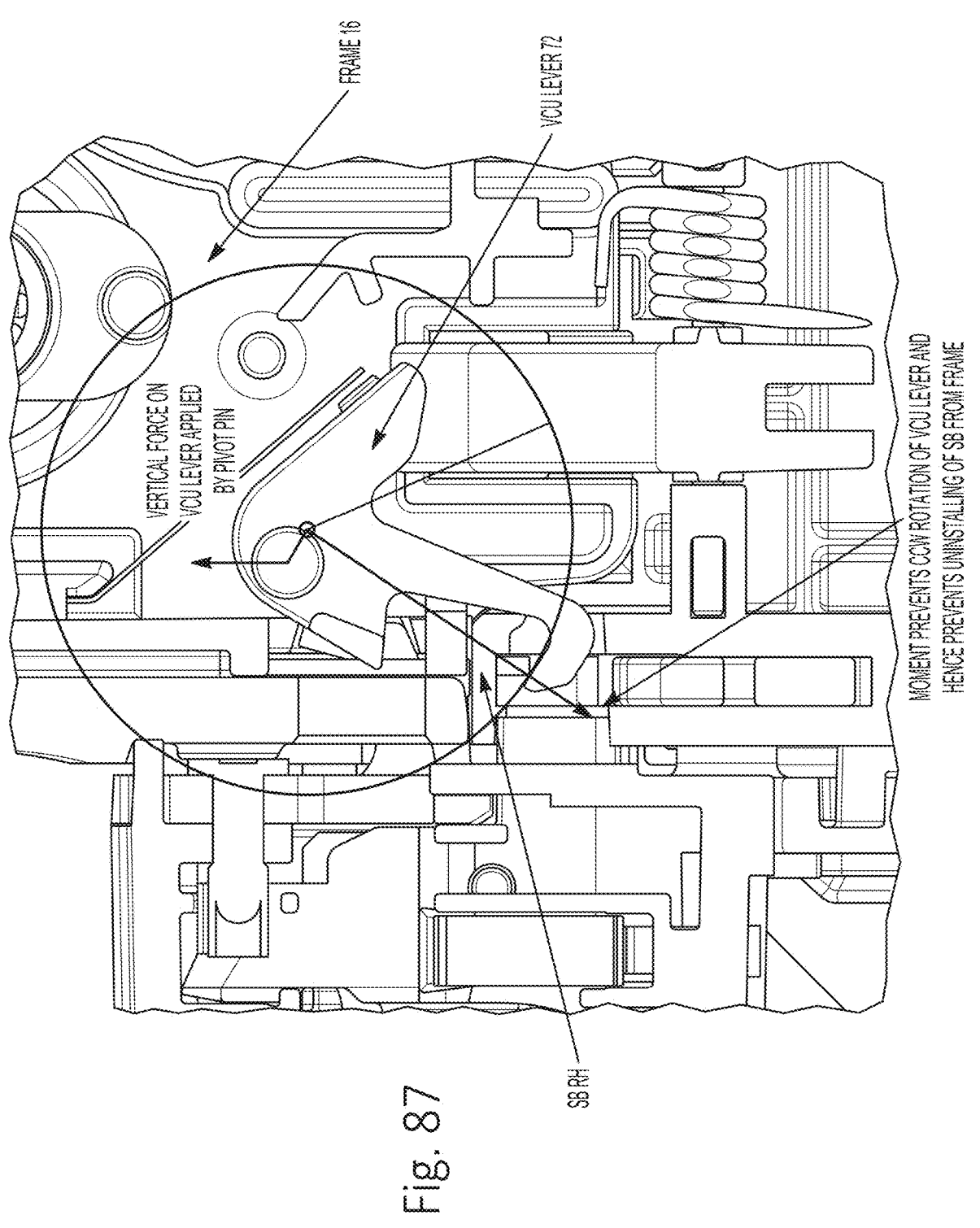
Figure 89:
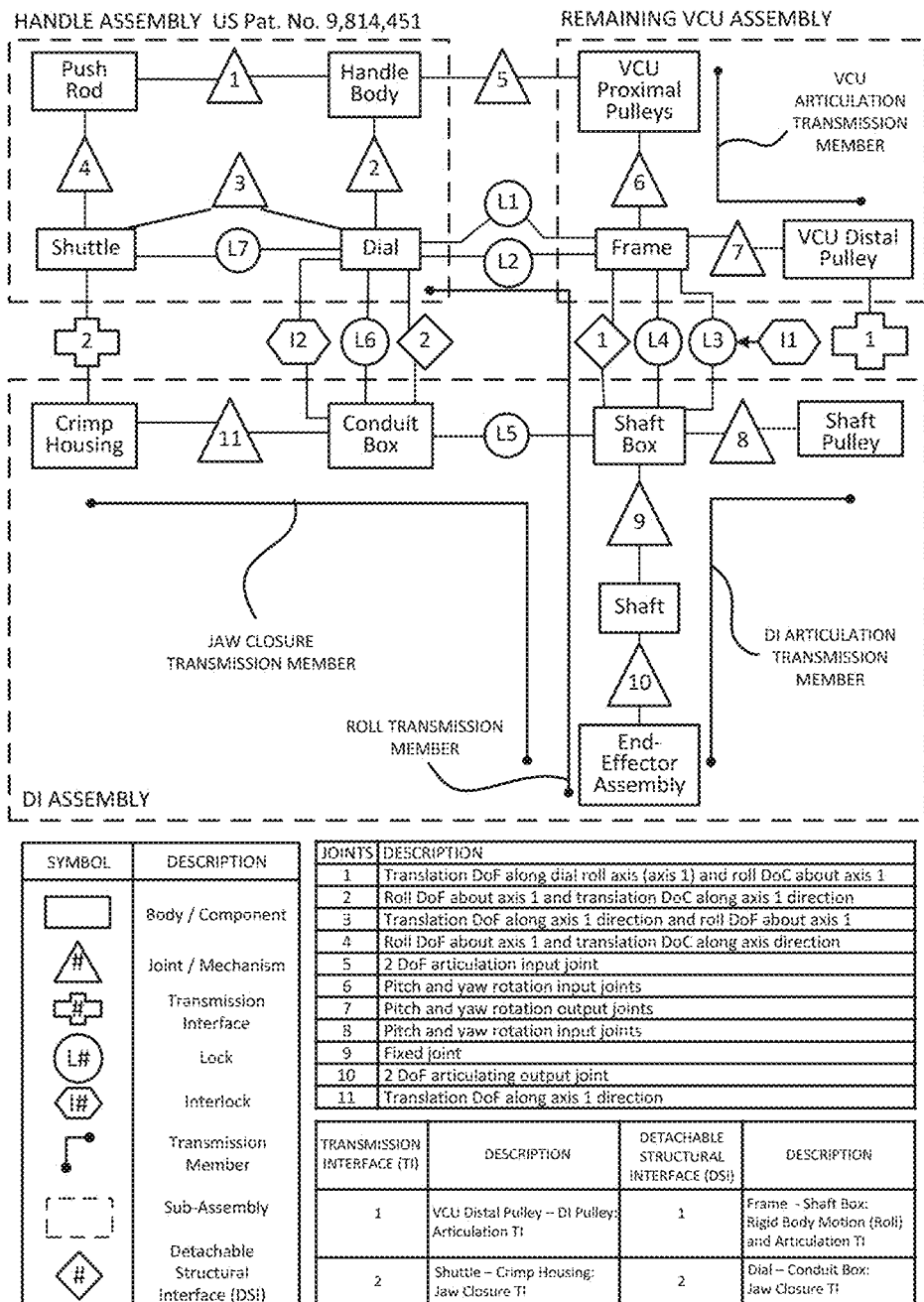
Figure 90:
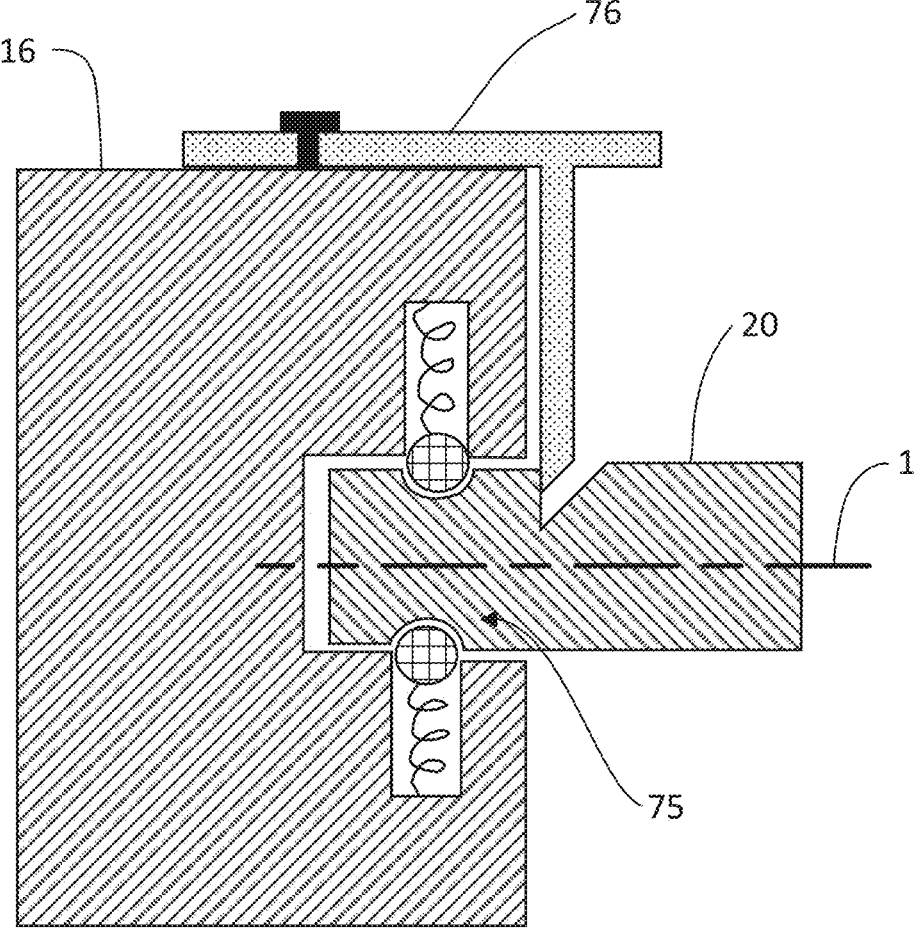
Figure 91:
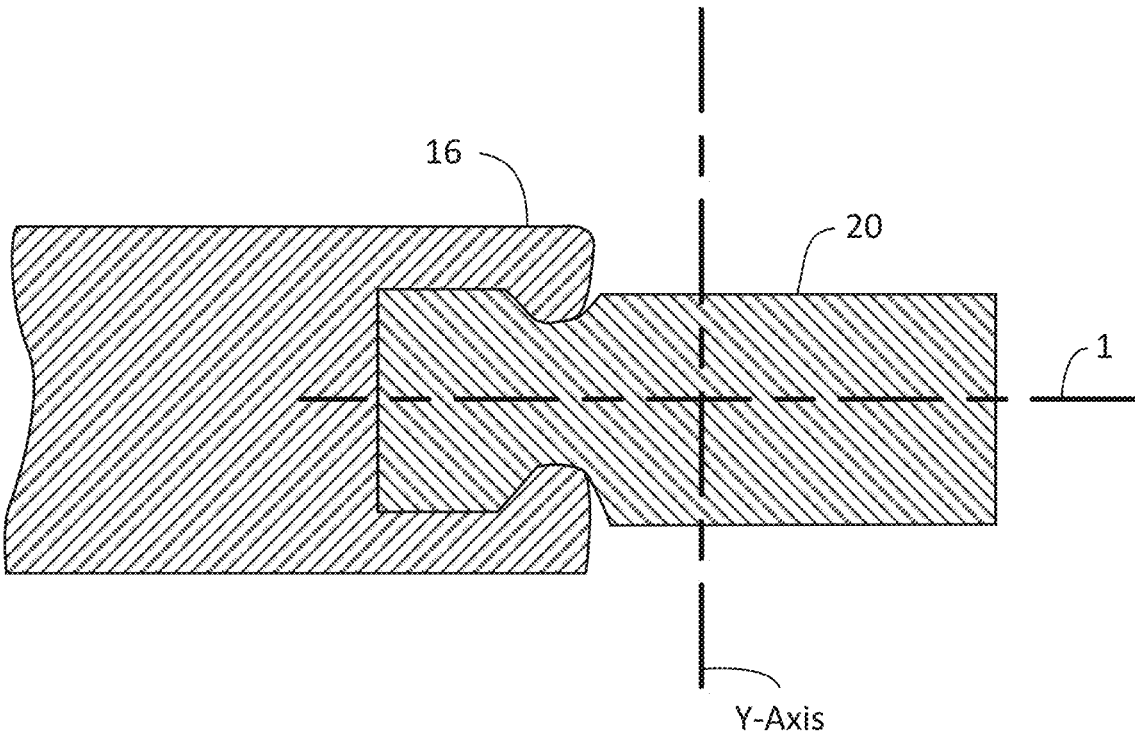
Figure 92:
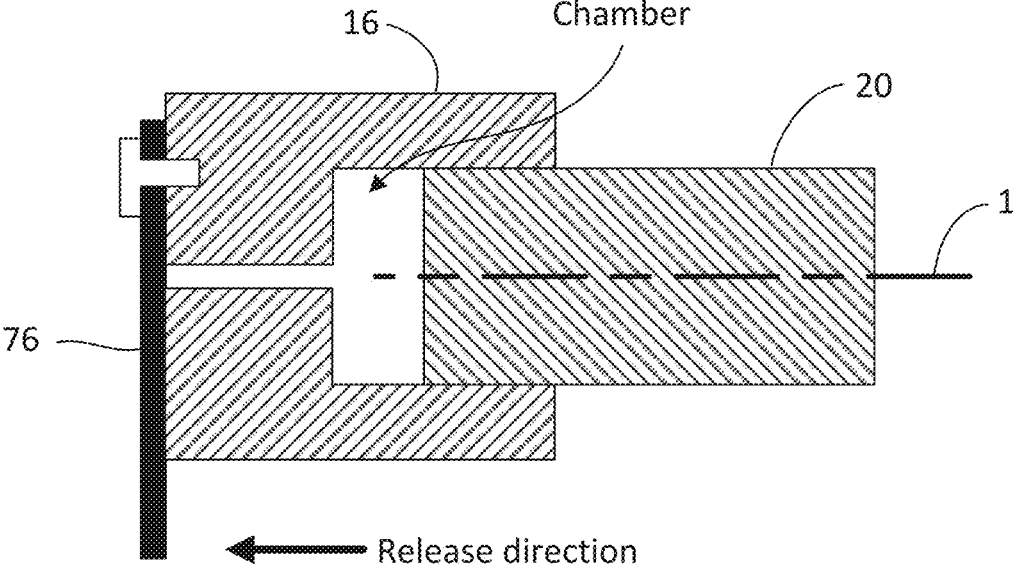
Figure 93:
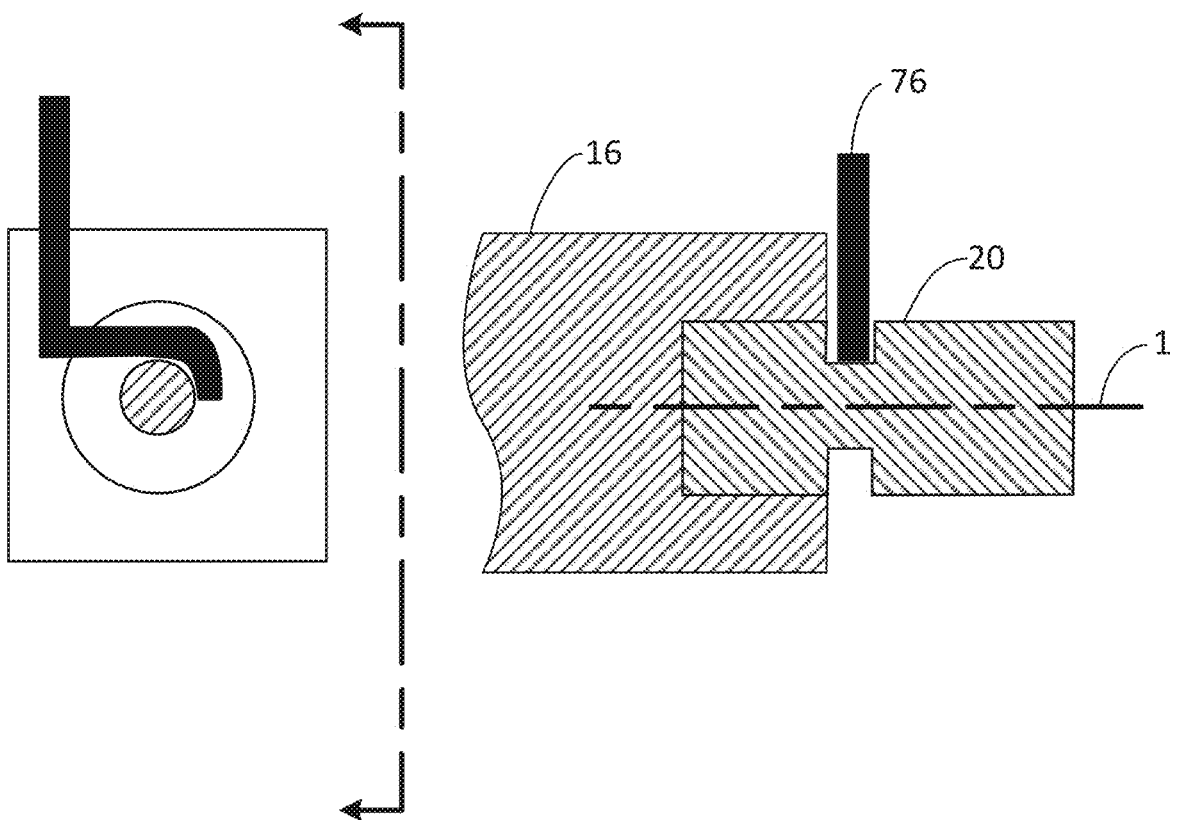
Figure 94:
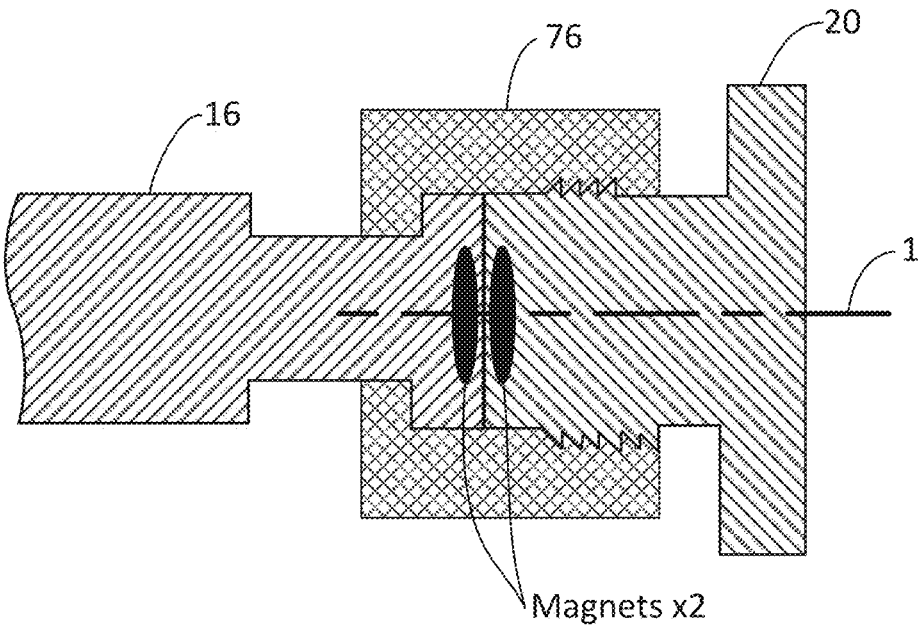
Figure 95A:
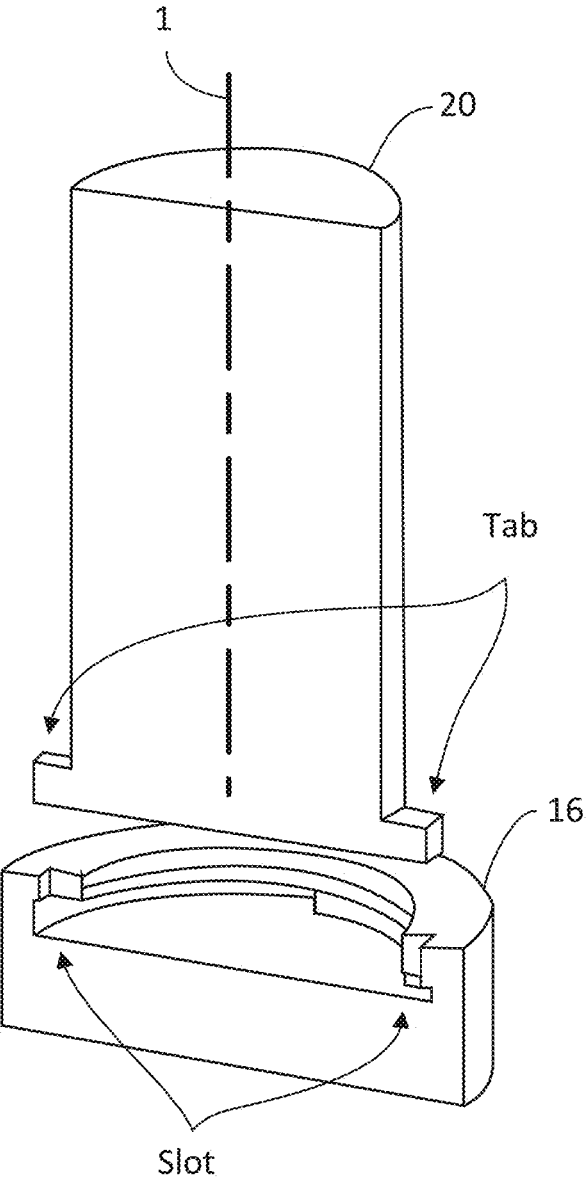
Figure 95B:
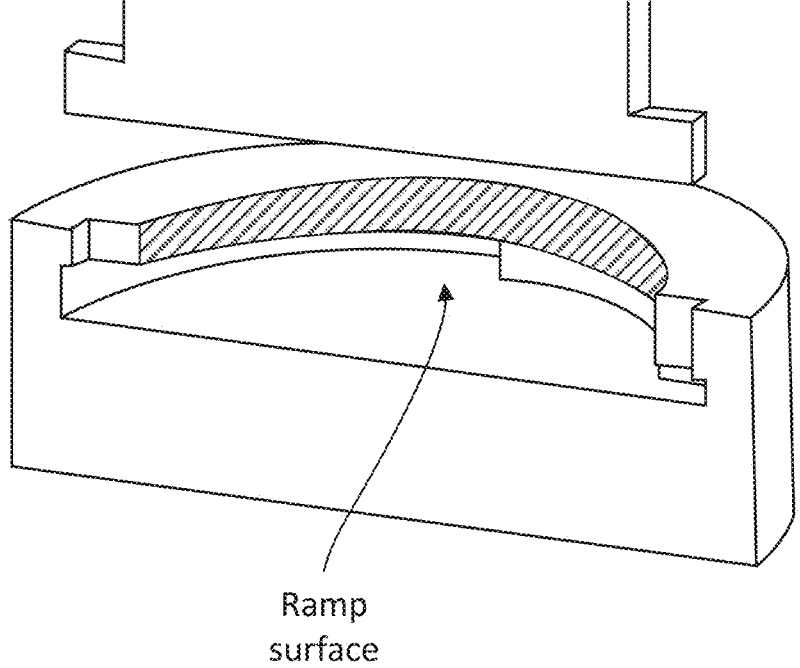
Figure 96:
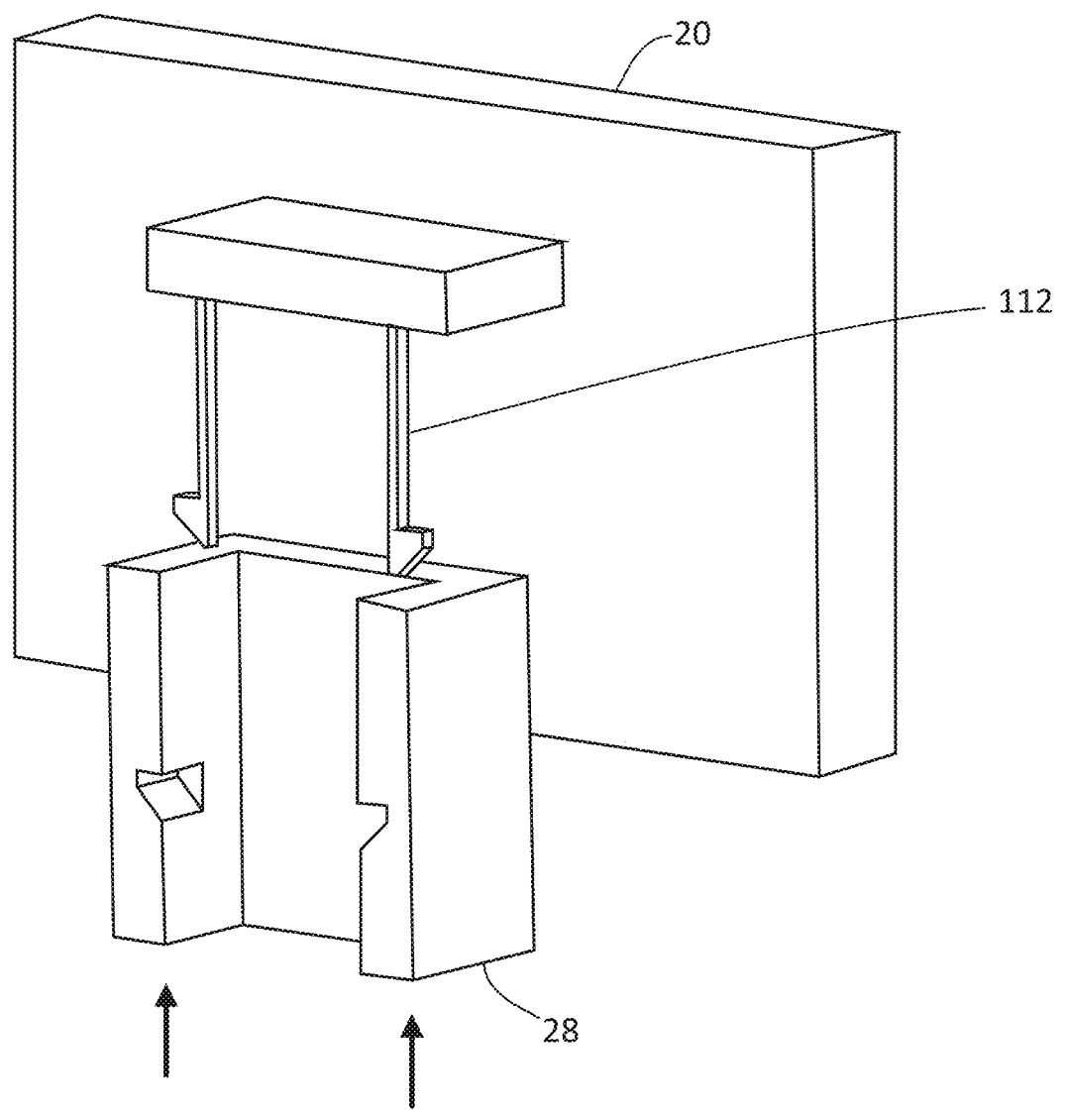
Figure 97:
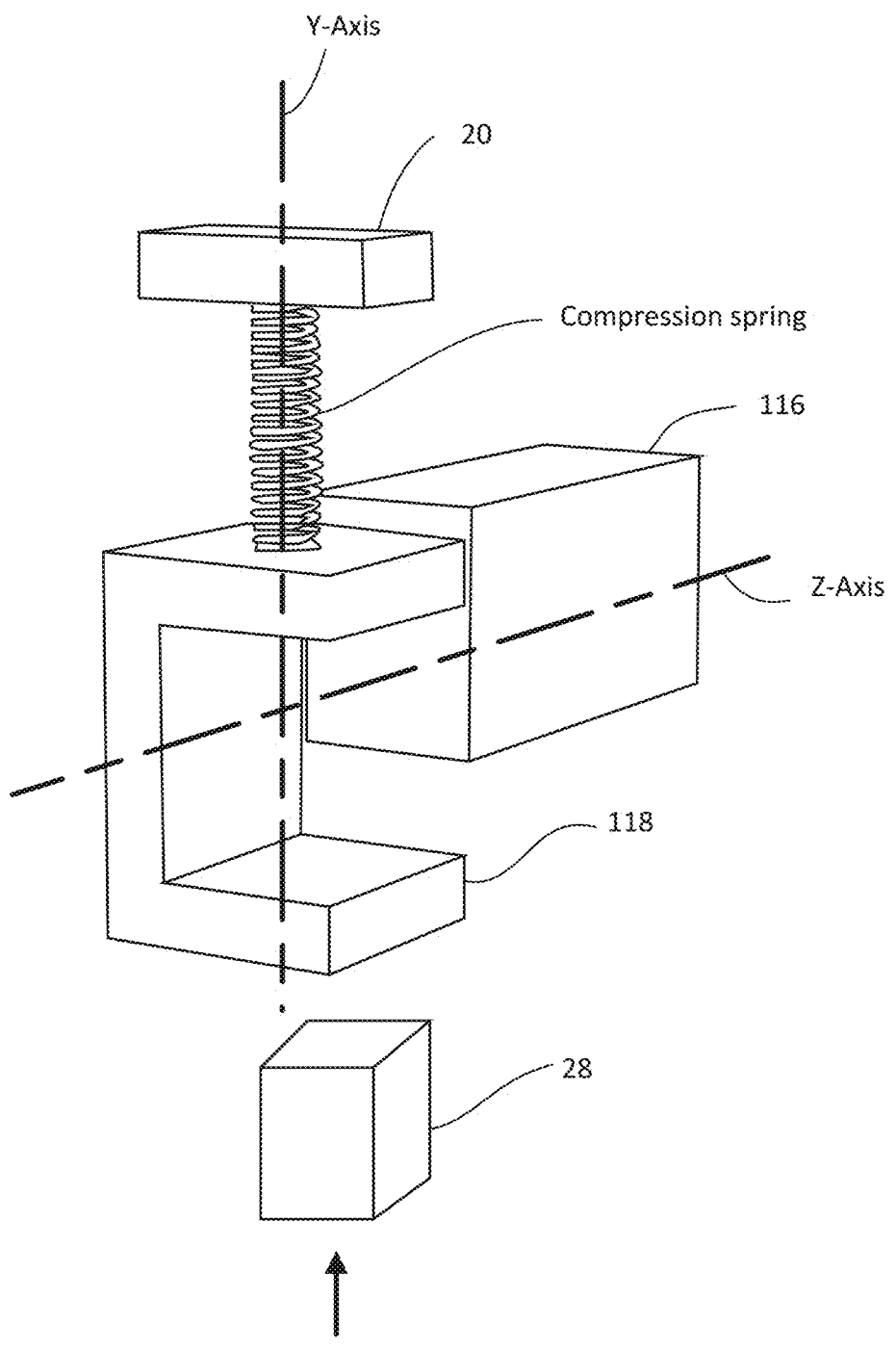
Figure 98A:
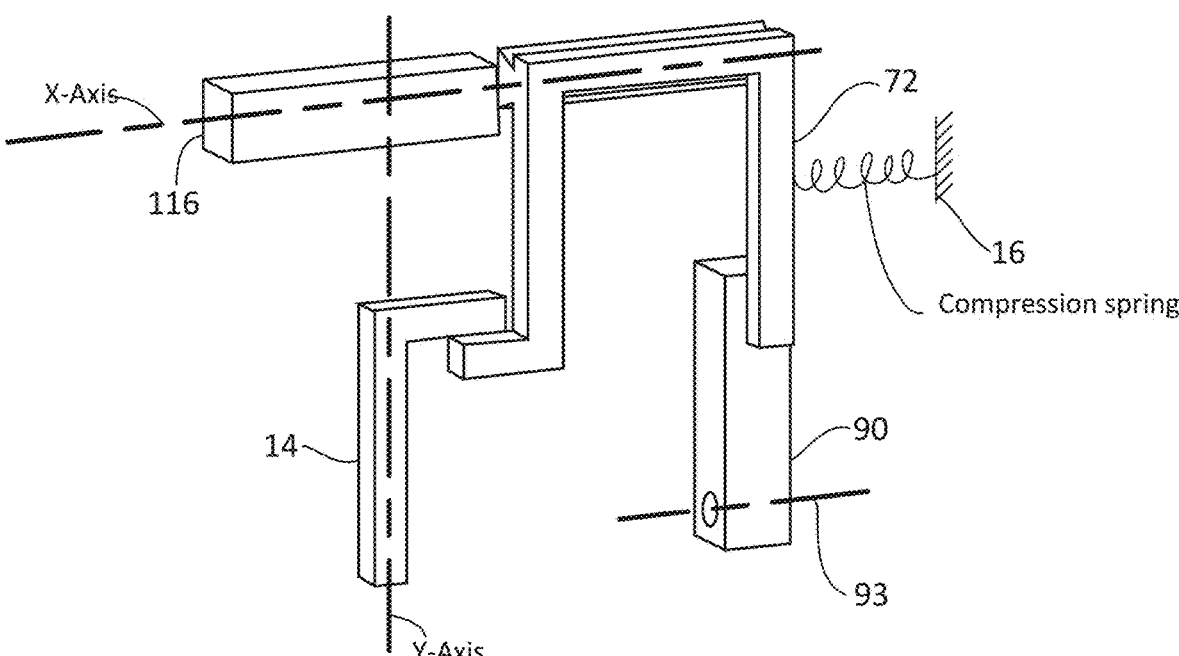
Figure 98B:
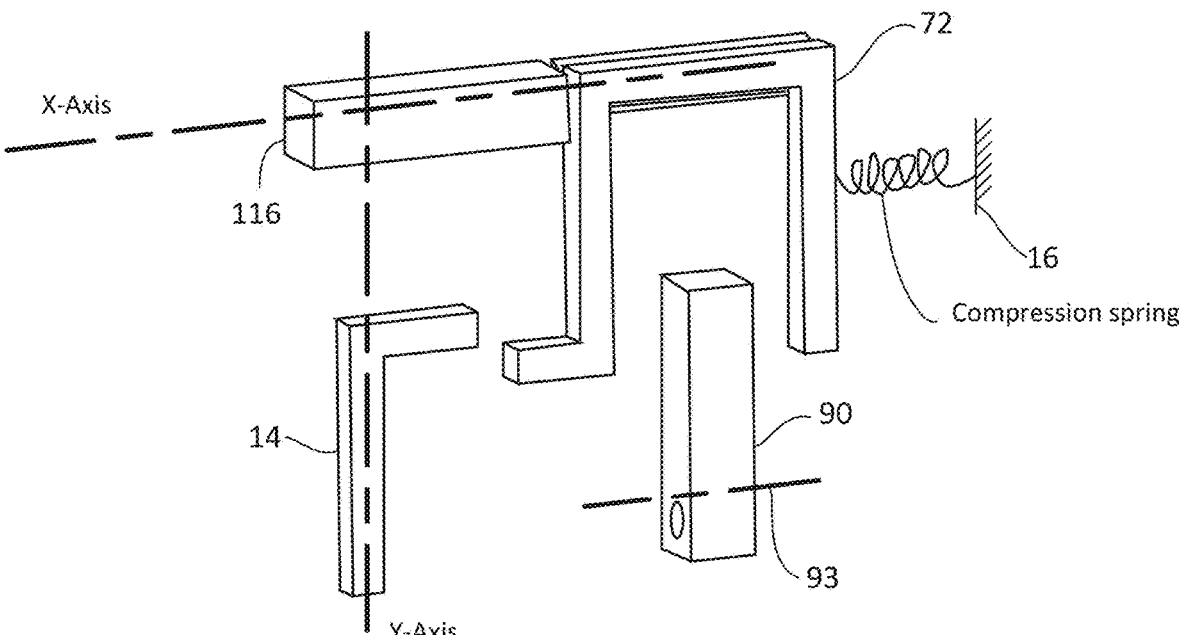
Figure 99:
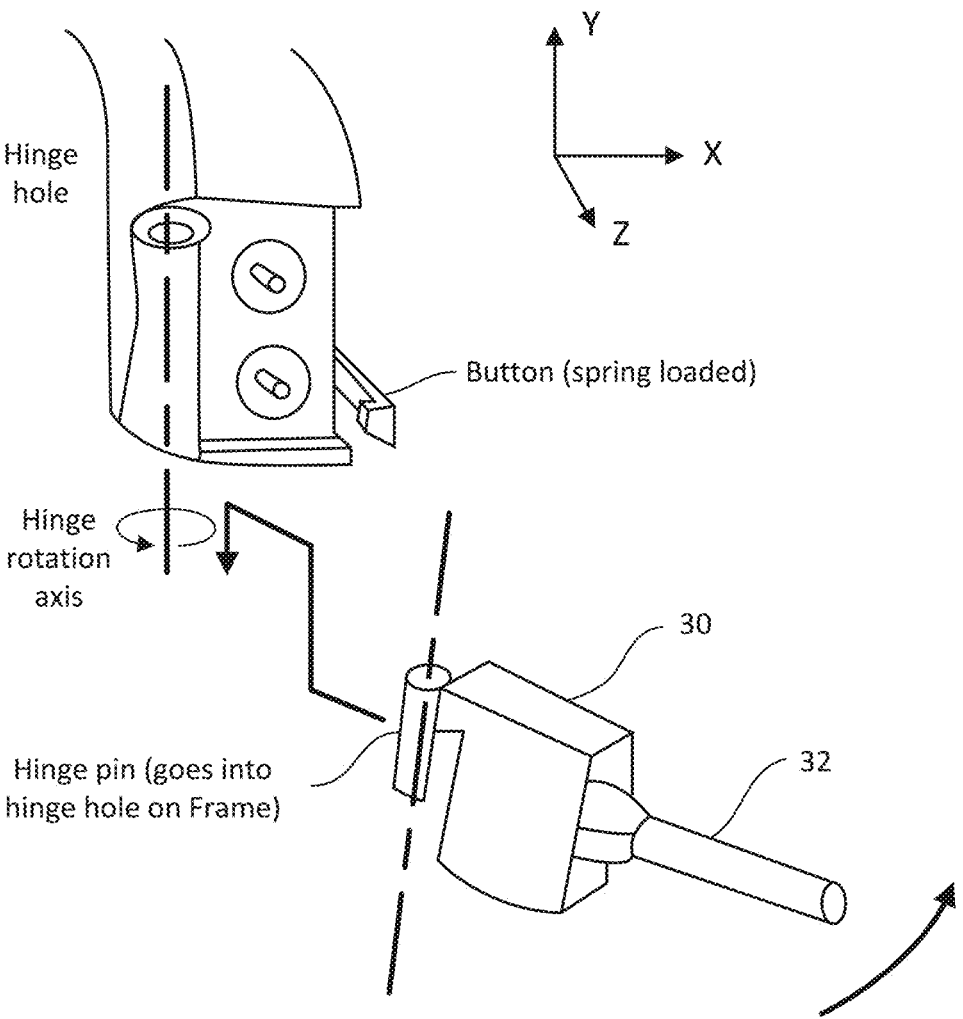
Figure 100A:
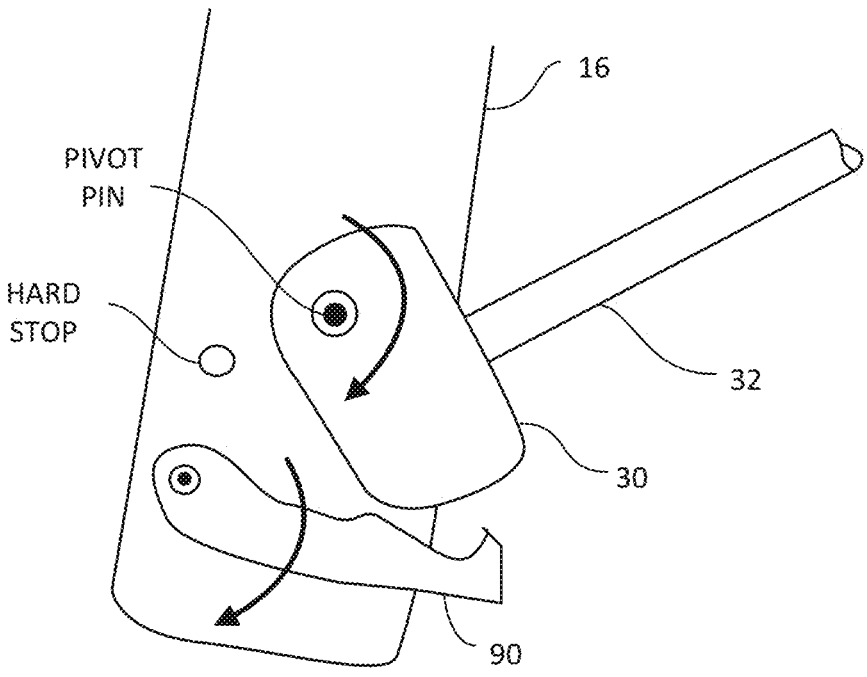
Figure 101:
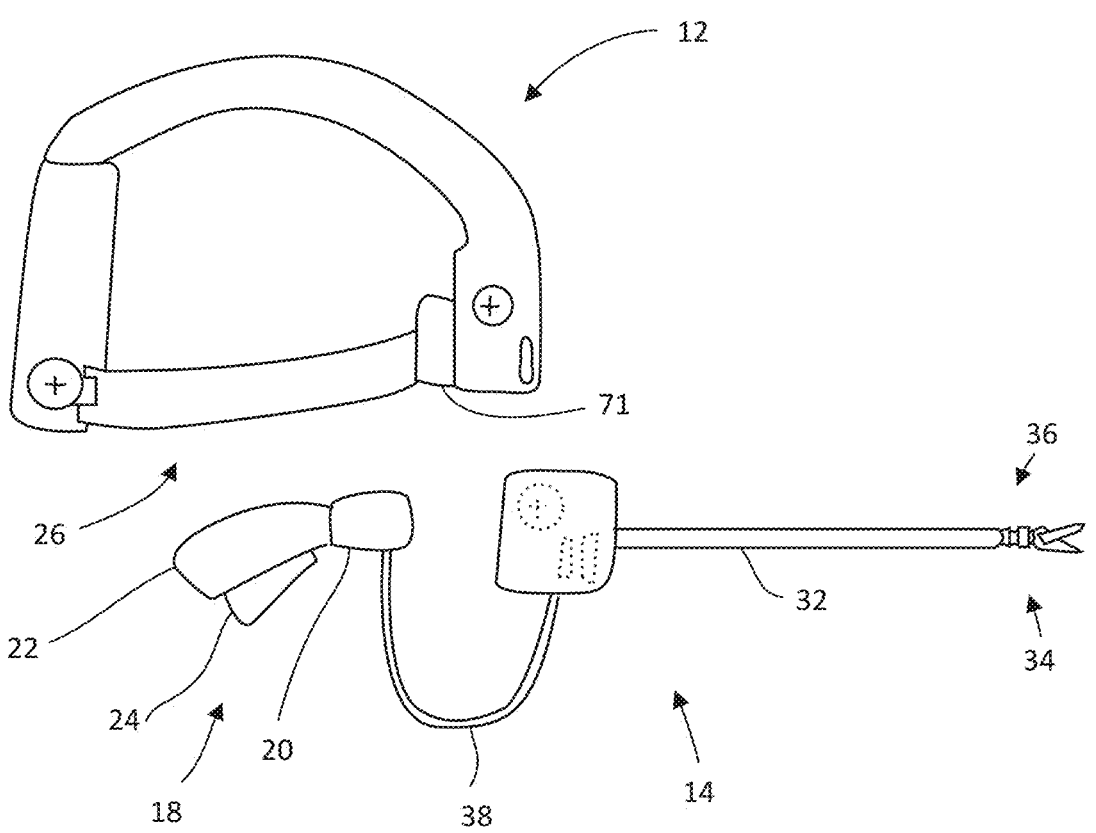
Figure 103A:
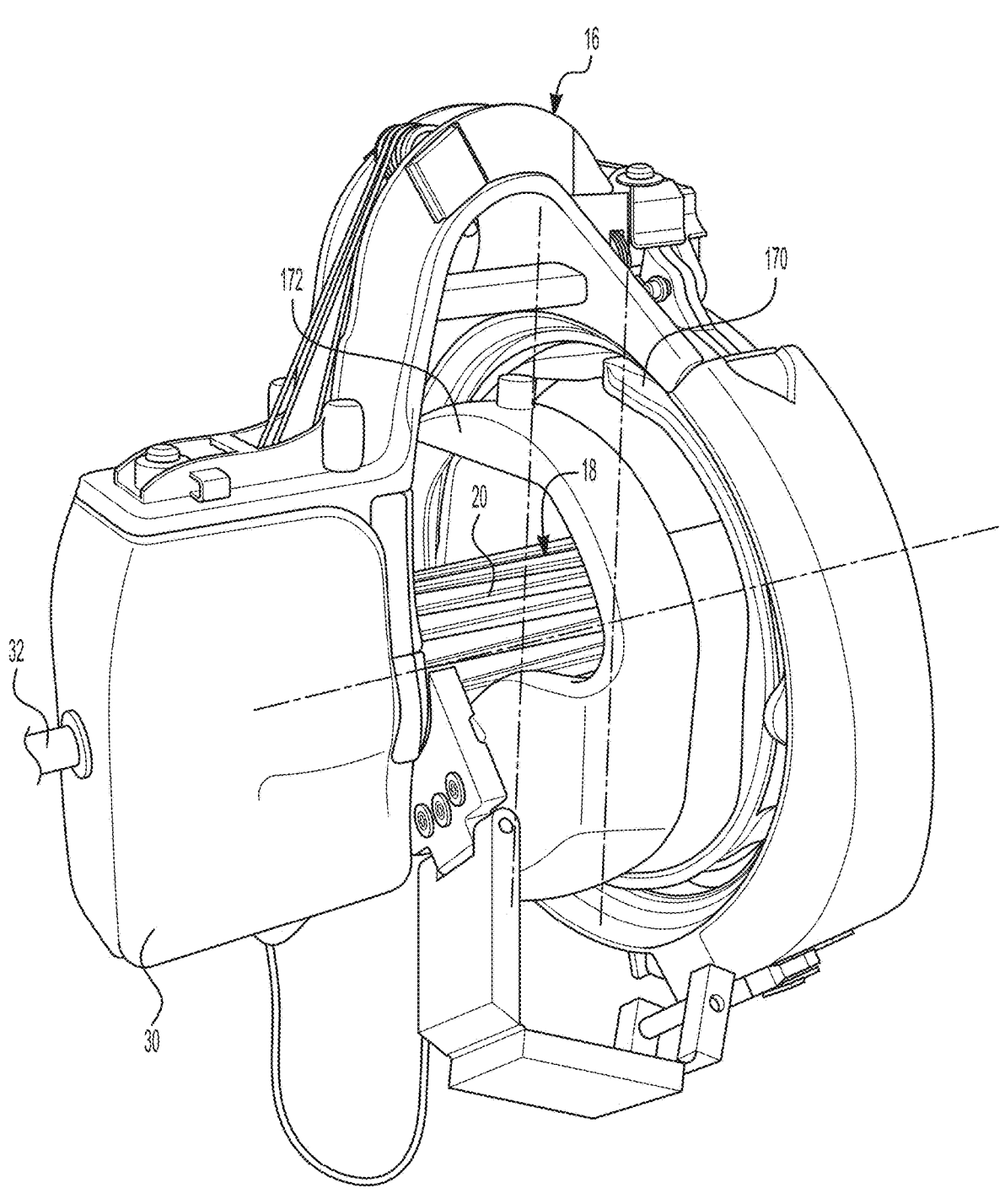
Figure 103B:
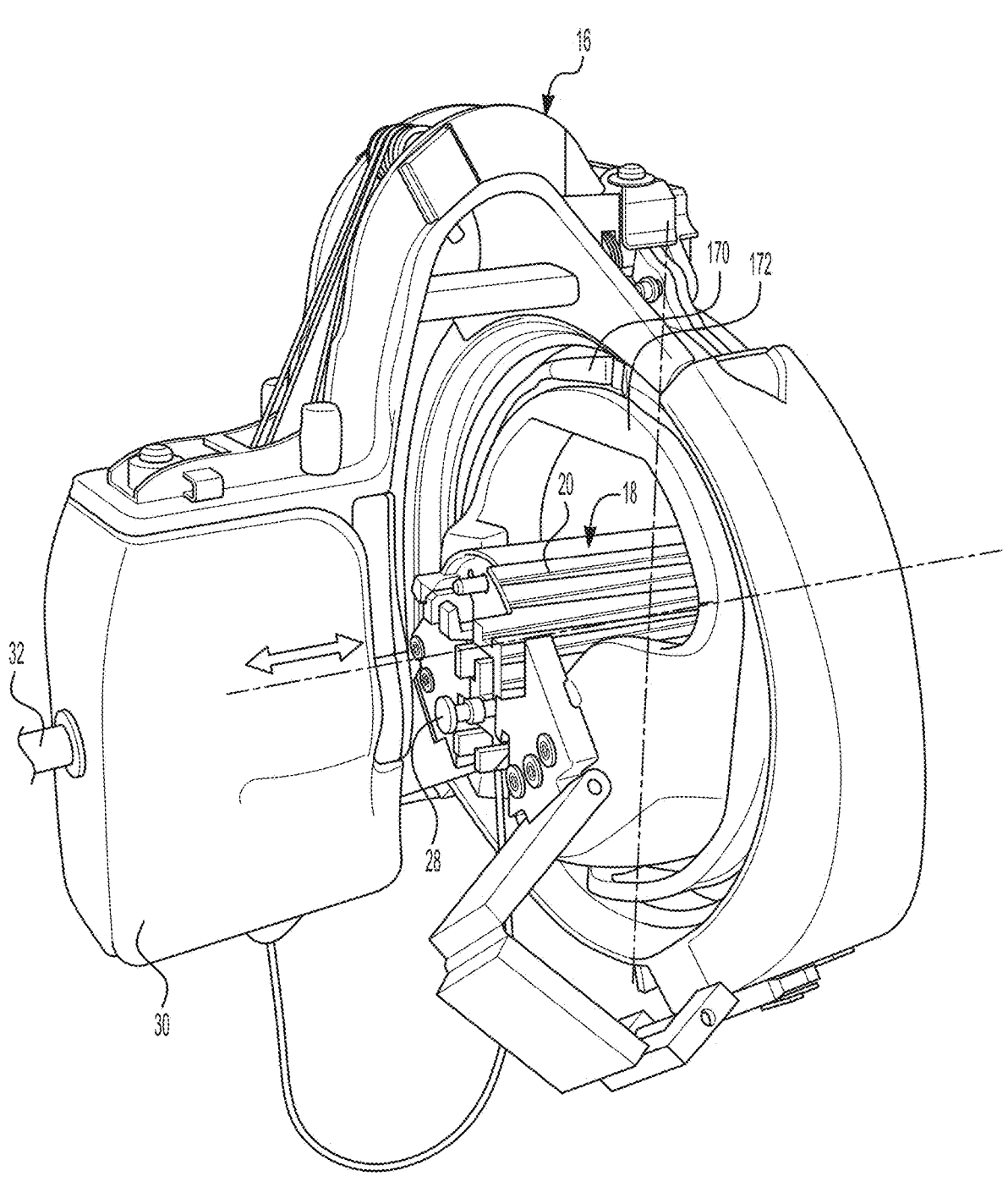

FIG. 70 depicts CB guide channel and dial guide post alignment;

FIG. 71 depicts Button locking interface with respect to (w.r.t.) frame;

FIG. 72 depicts Button drive-in profile;

FIG. 73 is a section view showing shuttle, CB, and crimp housing;

FIGS. 74A-B depict Shuttle-crimp housing interface; A—section showing shuttle-crimp housing interface; B—section showing shuttle-crimp housing non-back drive-able angle specifications;

FIG. 75 depicts crimp housing-shuttle interface with pre-built interference along normal to the contact surface;

FIG. 76A-B depict shuttle lockout spring's interaction as conduit box moves along +Y axis direction;

FIG. 77 depicts DLP and dial interface;

FIG. 78 depicts CB unlocked w.r.t. frame when SB is installed onto the frame;

FIG. 79 depicts clearances between VCU distal articulation pulley and SB articulation pulley;

FIG. 80 is a Transition 1 timing plot;

FIG. 81 depicts Dial locked w.r.t. frame via dial detent spring;

FIG. 82 depicts Dial unlocked w.r.t. frame and not locked via dial detent spring;

FIG. 83 depicts positive engagement feature on conduit box used to interface with CBLS;

FIG. 84 depicts clearance between VCU lever and button built-in by interface between shuttle and VCU lever;

FIG. 85 depicts VCU lever blocking button and locking SB RH;

FIG. 86 is a side view showing VCU lever blocking button;

FIG. 87 is a free body diagram of VCU lever when it interacts with SB RH;

FIG. 88 is a Transition 2 timing plot;

FIG. 89 is a tool apparatus device map;

FIG. 90 depicts another embodiment showing Dial, Frame, Dial Lockout Plate, and Detent Spring;

FIG. 91 depicts another embodiment showing Dial and Frame;

FIG. 92 depicts another embodiment showing Dial, Frame, and Dial Lockout Plate;

FIG. 93 depicts another embodiment showing Dial, Frame, and Dial Lockout Plate;

FIG. 94 depicts another embodiment showing Dial, Frame, and Dial Lockout Plate;

FIGS. 95A-B depict depicts another embodiment showing Dial and Frame;

FIG. 96 depicts an embodiment for dial-conduit box retention interface;

FIG. 97 depicts another embodiment showing Dial, Shuttle, and Conduit Box;

FIGS. 98A-B depict an embodiment for VCU Lever;

FIG. 99 depicts SB and Frame Interface-Hinge Joint embodiment;

FIGS. 100A-B depict SB and Frame Interface-Pivot Pin embodiment (where, (A) shows transition from Storage to Assembled State and (B) shows the Assembled State);

FIG. 101 depicts an embodiment of a tool apparatus where handle assembly is part of DI assembly;

FIGS. 102A-D depict Side zoomed (A) and Side (B) views of a tool apparatus;

FIG. 103A depicts another embodiment of a surgical tool presented in a homed state, this embodiment lacking a wrist grounding component; and FIG. 103B depicts the surgical tool of FIG. 103A presented in an un-homed state.

DETAILED DESCRIPTION

Multiple embodiments of surgical tools are depicted in the figures and detailed in this description. In general, the surgical tools can be employed for use in minimally invasive surgical (MIS) procedures and remote access surgical procedures. Embodiments of the surgical tools can be handheld instruments. The surgical tool may also be referred to as a tool apparatus. Definitions of certain terms are presented prior to particular figure references in this description:

1.1 Body—Body is a discrete continuous component that can be used as structural components to form an assembly or sub-assembly. The displacement/motion state of a body can be completely defined with respect to a reference ground by six degrees of freedom (DoF). A body can be part of an assembly, wherein the assembly may comprise multiple bodies that are inter-connected by joints. Generally, a body is rigid (i.e., with no compliance). One or more discrete bodies may be connected together via a rigid joint. These bodies together are still termed as a body as there are no single or multi degree of freedom joints between these bodies. In certain scenarios, this body may be produced out of a single/monolithic structure and therefore, be only a single body. In certain scenarios, a body may be compliant (i.e., not rigid) but still discrete and continuous. In any case, the body may be monolithic or assembled using rigid joints. The body may be of homogenous material composition or heterogenous material composition. In general, a body may comprise several features including geometric shapes. Specific features of the body that are relevant to the discussion will be specified while describing a body. Wherever there is specific function that a body serves, a qualifier is attached to the term "body." E.g., "body" as an "interlock," etc.

1.2 Mechanisms/Joints—In general, there is a certain equivalence between the terms, "mechanism" and "joint." All of these can be viewed as allowing certain motion(s) along certain degree(s) of freedom between two bodies and constraining the remaining motions. A mechanism generally comprises multiple joints and bodies. Typically, a joint is of simpler construction, while a mechanism is more complex as it can comprise multiple joints. But what is simple and what is complex depends on the context. A mechanism under consideration may appear simple or small in the context of a much bigger mechanism or machine, in which case the particular mechanism under consideration may be called a joint. Thus, what was viewed as a mechanism may also be viewed as a joint. Also note that "joint" here refers to a mechanical connection that allows some motions as opposed to a fixed joint (such as welded, bolted, screwed, or glued jointly). In the latter case, the two bodies are fused with each other and are considered one and the same in the kinematic sense (because there is no relative motion allowed or there are no relative degrees of freedom between the two). The term "fixed joint" will be specifically used herein to refer to this kind of joint between two bodies. When reference to the term "joint" is made, it means a connection that allows at least some motions or degrees of freedom, e.g., a pin joint, a pivot joint, a universal joint, a ball and socket joint, etc.

1.3 Degree of Freedom (DoF)—As noted already, a joint or mechanism allow certain motions between two bodies and constrains the rest. "Degrees of freedom" is a technical term to capture or convey these "motions." In all, there are six independent motions and therefore degrees of freedom possible between two rigid bodies when there is no joint between them: three translations and three rotations. A joint will allow anywhere between zero and 6 DoFs between the two bodies. For the case when the joint allows zero DoFs, this effectively becomes a "fixed joint," as described above, where the two bodies are rigidly fused or connected to each other. In this case, from a kinematic sense, the two bodies are one and the same. For the case when the joint allows 6 DoFs, this effectively means that there is no joint, or that the joint does not constrain any motions between the two bodies. In other words, the motions of the two bodies is entirely independent of each other. Any practical joint for the purpose this application allows 1, or 2, or 3, or 4, or 5 DoF between two rigid bodies. If it allows 1 DoF, then the remaining 5 possible motions are constrained by the joint. If it allows 2 DoF, then the remaining 4 possible motions are constrained by the joint, and so on.

1.4 Degree of Constraint (DoC)—Degree of constraint refers to directions along which relative motion is constrained between two bodies. Since relative motion is constrained, these are directions along which motion and loads (i.e., forces or moments) can be transmitted from one body to the other body. Since the joint does not allow relative motion between the two bodies in the DoC direction, if one body moves in the DoC direction, it drives along with it the other body as well along that direction. In other words, motions are transmitted from one rigid body to another in the DoC directions. Consequently, loads are also transmitted from one rigid body to another in the DoC directions, which are sometimes also referred to as the load bearing directions or simply bearing directions. The term "retention" may also be used in the context of a DoC direction. For example, one body may be constrained or equivalently retained with respect to a second body along a certain DoC. This means that relative motion is not allowed between the two bodies in the DoC direction, or equivalently the direction of constraint, or equivalently the direction of retention.

1.5 Reference Ground—In the context of an assembly of bodies inter-connected by joints (e.g., a multi-body system, a mechanism), one or more bodies may be referred to as the "reference" or "ground" or "reference ground." The body referred to as the reference ground is not necessarily an absolute ground (i.e., attached or bolted to the actual ground). Rather, the body that is selected as a reference ground simply serves as a mechanical reference with respect to which the motions of all other bodies are described or investigated. Also, selecting a specific body in an assembly of bodies as the reference ground does not, in general, limit the functionality of the assembly.

1.6 Axis and Direction—Axis refers to a specific line in space. A body may rotate with respect to (w.r.t.) another body about a certain axis. Alternatively, a body may translate w.r.t. another body in a certain direction. A direction is not defined by a particular axis and is instead commonly defined by multiple parallel axes. Thus, X-axis is a specific axis defined in space, while X direction refers to the direction of the X-axis or any other axis that is parallel to the X-axis. Multiple different but parallel axes can have the same X direction. Direction only has an orientation and not a location in space. A direction may be specified to be positive or negative.

1.7 Structural Interface—A structural interface is an interface between two bodies that provides structural continuity from one body to another. In other words, this means rigid body motion of a body can be transmitted to another body as rigid body motion of one body is retained w.r.t. the rigid body motion of another body. A structural interface requires retention of all 6 DoFs and may or may not require alignment of all 6 DoFs. Retention of all 6 DoFs means the same thing as having 6 DoCs between two bodies. In that sense, a structural interface is like a "fixed joint" defined above. A structural interface may be permanent or non-detachable (once created), or may be detachable for service or disassembly, or may be detachable as part of an intended functionality. That latter case is referred to as a detachable structural interface in this patent application. In general, a structural interface between two bodies allows for the transmission of rigid body motions (i.e., all 6 DoF motions) from one body to the other by means of the structural interface. If any of these six directions is inadequately retained/constrained (e.g., the interface is not structurally rigid), then the transmission of motion along this particular direction is compromised.

Once a structural interface is established between two bodies, the two bodies are one and the same in a kinematic sense and these two bodies can now serve as a common ground or reference upon which a transmission system can be built. For example, one can establish a cable transmission system comprising various pulleys, where some pulley axles can be mounted on the first body while other pulley axles can be mounted on the second body. Since the two bodies have been retained or constrained in all 6 DoF directions, the two bodies are structurally continuous or an extension of the other. Therefore, these various pulleys—some on the first body and some on the second body—can remain fixed in location with respect to the other, thereby comprising an effective common transmission system that spans both the bodies. If the two bodies did not have a structural interface, then a cable transmission that spans the two bodies would be impractical because any relative motion between the two bodies would lead to motion between the locations of pulleys on one body with respect to the location of pulleys on the second body. This would lead to variation in cable path length or an inability to maintain cable tension to achieve proper cable-based transmission.

1.8 Transmission Interface—A transmission interface between two bodies refers to the interface between these bodies that provides a direct load transmission path. These bodies that interface relative to each other may be housed in separate sub-assemblies or within the same sub-assembly. These bodies shall be mounted to respective housing bodies in each sub-assembly via a joint or mechanism. For proper transmission, these housing bodies (to which the two bodies involved in the transmission interface are mounted) shall have a structural interface established between them (defined above). This transmission of motion takes place via transmission of force, torque, etc. The effectiveness of the transmission of load through a transmission interface is influenced by the coefficient of friction between bodies involved in the transmission. A transmission interface can be permanent or detachable. Interfaces between components related to lock or interlocks are not considered as transmission interfaces.

1.9 User Interface—A user interface acts as an input interface that a user interacts with to provide input to a machine or instrument or mechanism with the objective of producing some change or outcome in the machine or instrument or mechanism. User interface is often an ergonomic feature on a body, which is part of an instrument, that is triggered or actuated by the user, e.g., a knob on a car dashboard can be rotated by a user to increase/decrease speakers' sound volume. Here, the knob, specifically the knurled outer circumference (feature) of the knob, is the user interface.

1.10 Finite State Machine (FSM)—For the purpose of this patent application, a finite-state machine (FSM) or simply a state machine or FSM system, is a system of multiple bodies that can exist in a finite number of configurations or states but may only assume one configuration or state at a time. Each state is governed by existence of alignment and/or retention features/bodies between two or more bodies. Each state of the FSM either holds a functional purpose or is non-functional. An FSM can be incorporated into a tool apparatus (e.g., a surgical tool apparatus) and be used to drive user experience with the tool by changes in states.

1.11 State—A state is a configuration of an FSM that describes the structural and functional state of the FSM. A state describes how the bodies within the FSM are configured (i.e., aligned and/or retained) w.r.t. each other. A particular state can be either functional or non-functional. A state can be "allowed" or "disallowed". An allowed state is a configuration that is designed to be possible only through intended use. A disallowed state is a configuration that can only be achieved through unintended use, mis-handling, or misuse, and may also be referred to as a "misuse" state herein. A disallowed state can be "recoverable" or "non-recoverable". A disallowed state is recoverable if the FSM can be brought back to a functional state after some finite number of transitions that may involve going through other allowed or disallowed intermediate states (these transitions may or may not be reversible). A disallowed state is non-recoverable when it is not possible to transition to a functional state, such as when bodies or interactions elements of the FSM are physically broken.

1.12 Action—An action includes all the inputs applied to an FSM to change its state from an initial state to a different state by producing a transition between those states. An action may either be a user input or an action that is triggered by a certain mechanism internal to the FSM (e.g., an internal clock).

1.13 Transition—A transition is referred to the phenomenon representing change in state of a system from initial to final state. A transition in a computer or electronic system occurs within a short span of time. The change from one state to another takes place with actuation of a digital or physical switch. In a physical or mechanical system, there is some finite amount of time associated with a transition from one state to another. In the FSM described herein, a transition can be "reversible" or "non-reversible". A reversible transition is one where upon reversal of the action that brought the FSM from an initial state to a final state, the FSM can transition back to the initial state. Transitions are reversible between any two functional states and/or any two allowed, non-functional states. This means that while exactly reversing the transition and its associated transition steps, state reversal can be achieved. Transitions may not be reversible between allowed and disallowed states.

1.14 Transmission Member—A transmission member is a rigid or compliant body that transmits motions from the input body, that produces input motion that needs to be transmitted, to the output body, that produces the output motion. The path that a transmission member takes, starting at the input body to the output body, largely impacts the feasibility and efficiency of a transmission system.

1.15 Alignment Feature—An alignment feature is a geometric feature on a body. An alignment feature could be a positive cylindrical surface (like a peg or post or pin), or a negative cylindrical surface (like a hole), or a flat surface, or spherical surface, or a wedge, or a ramp, etc. An alignment feature helps locate one body w.r.t. another body along one or more directions or DoFs. There can be 6 potential directions of alignment (corresponding to 6 DoFs) that exist between two bodies. One alignment feature may provide alignment in one or more of the 6 potential directions. Also, alignment features may provide unidirectional or bidirectional alignment (i.e., the same alignment feature may provide alignment along positive X direction only, or negative X direction only, or both). When a body is said to be aligned along a certain direction, this means it is limited to move along that specific direction. For examples, if body A is only aligned with body B along the positive X direction, body A cannot translate past a certain point w.r.t. body B, but may translate in the negative X direction or in any direction normal to the X direction (i.e., positive and negative Y direction and positive and negative Z direction). A second body is aligned w.r.t. a first body along a certain direction with the goal to achieve certain determinism in the location of the second body w.r.t. the first body, based on the functional requirement of the system that includes these two bodies. One such functional requirement could be to create a structural interface, between the two bodies, that enables a transmission interface.

Also, while alignment features provide location between two bodies, they do not necessarily provide retention between the two bodies. For example, placing a sphere on a flat plate aligns (or locates) the sphere along the direction normal to the plate surface. Here, the outer surface of the sphere and the flat surface of the plate are alignment features. What these features do not do is retain the sphere to the plate. The sphere can still be lifted off the plate by merely applying the force equal to the weight of the sphere. Retention, which is discussed next, provides the necessary normal force or pressure between the sphere and the plate to keep the two together.

1.16 Retention Feature or Lock—Two or more bodies can be attached to each other along certain directions via "retention features" (also referred to as "locking features") on the two or more bodies that are retained together. Two or more bodies may also be retained via a third body, referred to as a "lock". In general, a "retention feature", "locking feature", or "lock" is a feature on a body. A body with retention/locking features whose main purpose is to retain two other bodies together may be termed as a lock (as mentioned, the term "lock" may also be used to refer to a retention feature/locking feature on a body). A retention feature may be subject to contact pressure between two bodies that are retained together. A retention feature may be part of respective bodies that are being retained. For example, a detent on body 1 mating to a divot (retention feature) on body 2 provides retention between the two bodies along specific directions w.r.t. the bodies. These features are part of each respective body and are both examples of retention features. In other scenarios, there may be an external body that mates to a body and another body to provide retainment between the two bodies. E.g., a door lock latch retains a door (one body) to a wall (another body). Here the door lock latch is the lock.

A retention feature or lock can be classified based on whether it provides positive engagement or non-positive engagement. A non-positive engagement lock refers to a feature that uses friction, or magnetic field (but not physically blocking/locking features) between two bodies to provide retention between the two bodies. A positive engagement lock refers to a mechanical retention between two bodies that is located between the two bodies and is physically blocking the motion of one body w.r.t. the other body along the direction that is retained. Bodies that provide this retention arrangement are called positive engagement locks. For example, hook-loop (Velcro) assembly, cable ties, key in a key slot, etc.

A lock has either an "on"/"1" status or "off"/"0" status. Furthermore, positive engagement locks can be designed to be back-drivable or non-back drivable. A back-drivable lock can be undone by pulling the two retained bodies apart from each other. A non-back drivable lock cannot be turned "off" by applying separation force on the two bodies that are retained. Therefore, to undo a non-back drivable lock, either the non-back drivable lock needs to be actively unlocked or needs to be broken/dis-mantled by application of significantly high separation forces on the two bodies that are retained.

1.17 Interlock—An interlock is a body or a feature that acts to prevent certain actions that may lead to dis-enabling the locking or unlocking of a lock (either positive engagement lock or a non-positive engagement lock). In the door, door lock, and wall example, once the door is locked, if the user is unable to actuate a handle to retract the door latch from the wall, and thereby unlock the door from the wall, that means that the door lock is interlocked by an interlock body. This interlock body is either external or internal to the overall door lock mechanism. As mentioned in this example, an interlock acts on a lock (e.g., door latch). An interlock interfaces with an "interlock feature" that is present on the lock. This "interlock feature" on the lock may be different from the feature that is involved in locking the two or more bodies. This interlock should not be confused with a secondary lock that may act between the two bodies that are retained (here, the door and the wall). There may exist a secondary lock that needs to be triggered separately (as an additional step) to unlock the door from the wall. This secondary lock is just a lock and not an interlock. An interlock can be found in elevators where interlocks prevent the moving elevator from opening its doors and prevents the stationary elevator (with open doors) from moving. Although both of the mentioned scenarios in case on the elevator example are idiot-proof strategies, an interlock should not be confused with a simple safety switch. For example, in a typical household microwave oven, the switch that disables the magnetron if the door is opened is not an interlock. This is simply a lock/switch that triggers the turn off mode of magnetron when door is opened. Rather, it would be considered an interlock if the door were locked while the magnetron is on, and the magnetron were prevented from operating while the door is open. In this case, there would exist an interlock acting onto the door latch preventing it from un-latching while the magnetron is on.

1.18 Interaction Element—Within a finite-state machine (FSM), there may exist several bodies and interactions between them. Here, interaction is used as a common term to describe an alignment, retention, interface, or joints/mechanisms between bodies. These interactions are produced via one or more of the following interaction elements: i) alignment features (A); ii) retention features/bodies (R); iii) locks (L); iv) interlocks (I); v) transmission interfaces (TI); vi) transmission members (TM); and vii) mechanisms/joints (M/J).

2. Finite State Machine (FSM)

2.1 Architecture of Tool Apparatus Under Consideration

Figure 1:
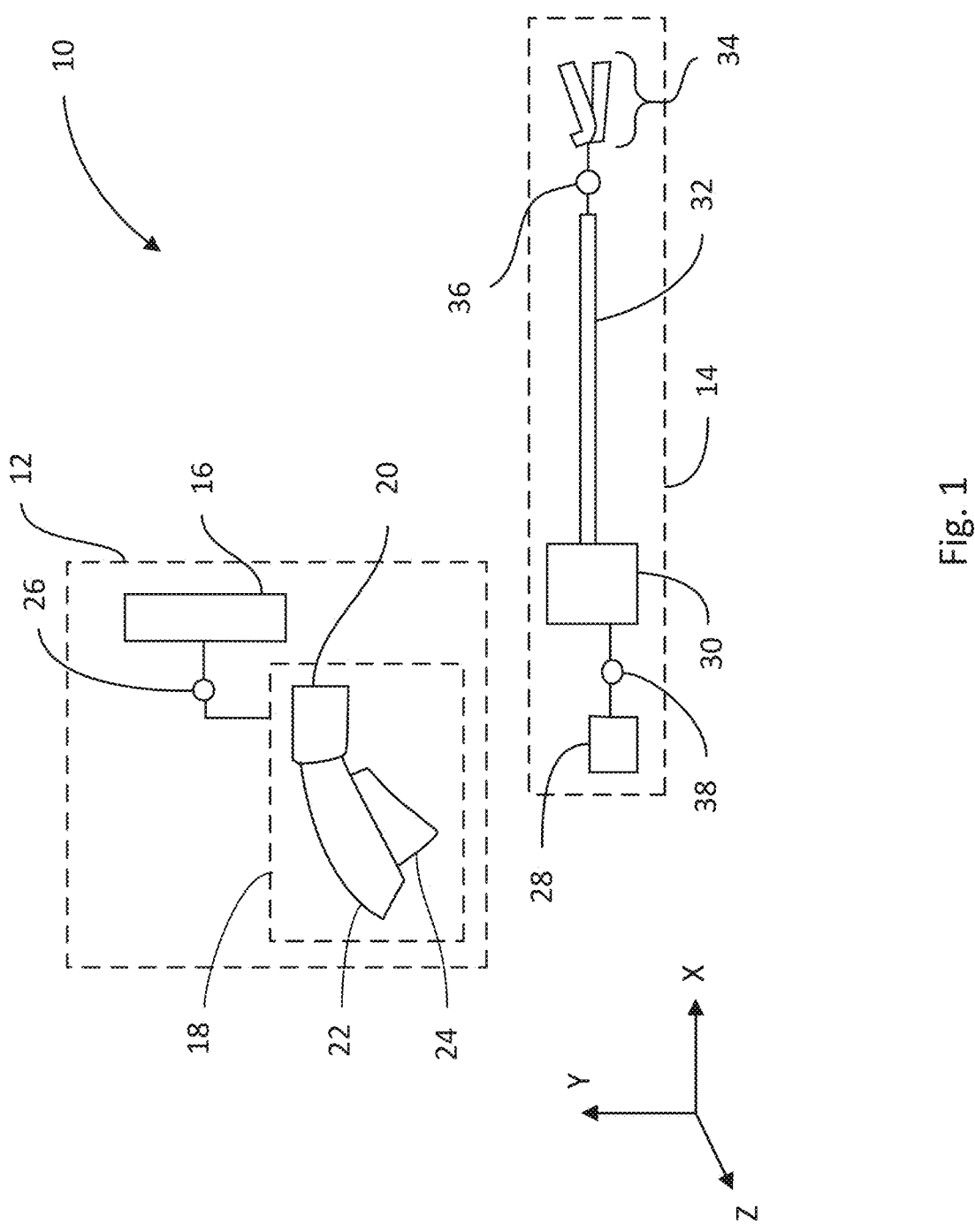
FIG. 1 is a schematic diagram of an embodiment of a tool apparatus architecture.

The finite state machine (FSM) described herein is part of a larger assembly which comprises a surgical tool apparatus 10. This tool apparatus 10 contains various bodies that are inter-connected by joints and mechanisms to perform certain functions. These functions will be described in detail in the next section. FIG. 1 shows an architecture for the tool apparatus 10 that consists of two major sub-assemblies namely, master instrument (MI) 12 and detachable instrument (DI) 14. Master instrument 12 is the instrument that a user operates and therefore exists in proximity to the user. Detachable instrument 14 attaches to the master instrument 12 to form a structural interface thereby producing a fully assembled tool apparatus 10 that can perform specific functions.

MI 12 consists of bodies and sub-assemblies namely, frame (F) 16 and handle assembly 18. Handle assembly 18 further consists of bodies namely, dial (D) 20, handle body 22, and closure input 24. Frame 16 may (1) house bodies that may have one or more DoFs relative to frame 16, and (2) have a structural interface w.r.t. the bodies. These two categories of bodies may exist based on the functional requirements of the system. These bodies can either be rigidly mounted to frame 16, hence forming a structural interface with frame 16. Any other component that has any of the six degree of freedoms relative to the frame may be "housed," or "packaged," or "placed," or "enclosed" within frame 16 but may not be rigidly mounted to frame 16. When tool apparatus 10 has end-effector (EE) articulation functionality, an input articulation joint 26 exists between handle assembly 18 and frame 16. DI 14 consists of bodies and sub-assemblies namely, conduit box (CB) 28, shaft box (SB) 30, shaft 32, and end-effector assembly 34. Details on each of the bodies mentioned here is described in further sections. For an articulating tool apparatus, there exists an output articulating joint 36 between shaft 32 and end-effector assembly 34. Also, there exists an interface between conduit box and shaft box that helps transmit end-effector jaw actuation motion. This interface is called closure actuation interface 38.

Figure 2:
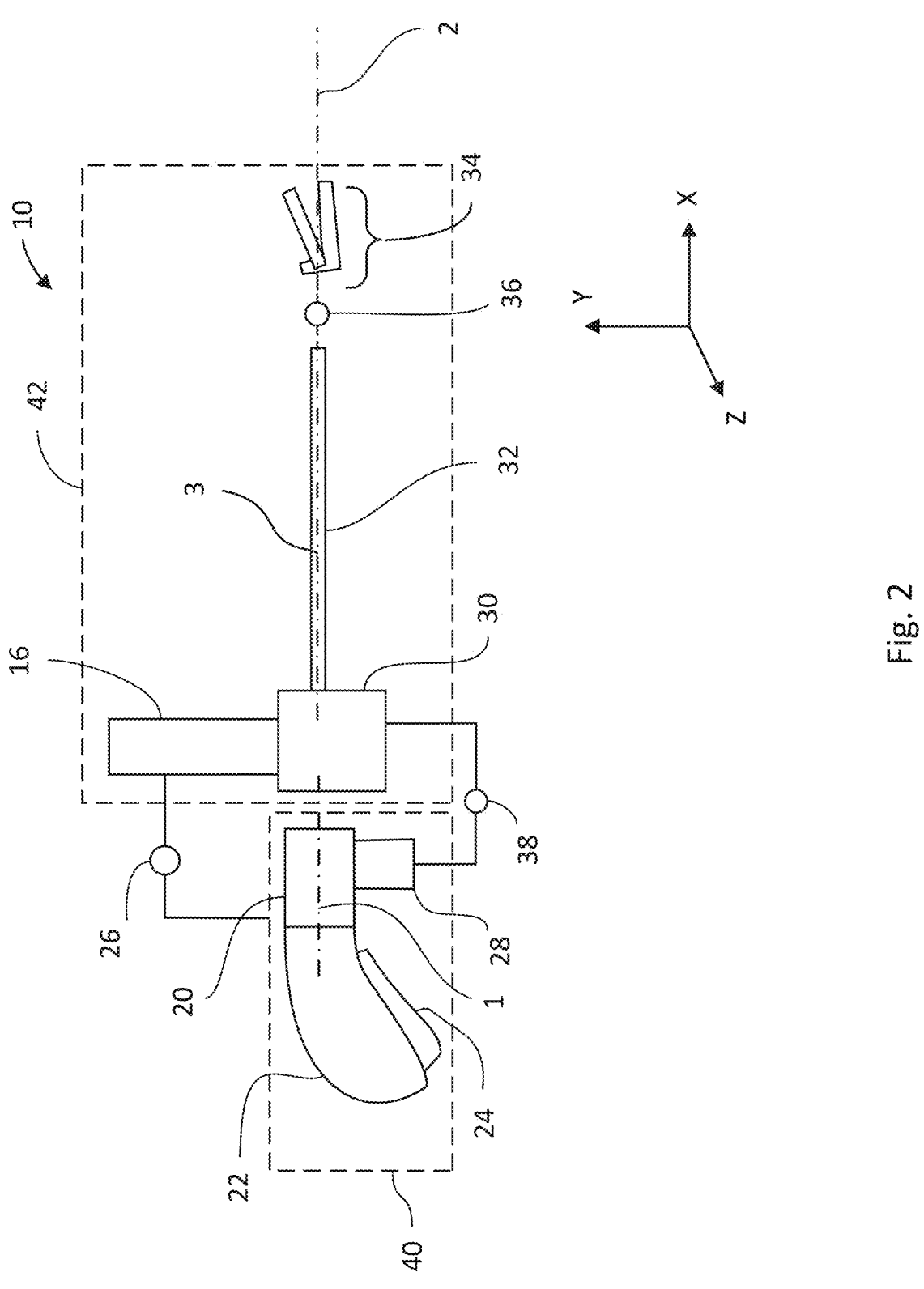
FIG. 2 is a schematic diagram of the tool apparatus shown in use.

When tool apparatus 10 is in use, conduit box 28 has a structural interface with respect to dial 20 and shaft box 30 has a structural interface with respect to frame 16. These structural interfaces enable the creation of transmission interfaces. Together, the structural interfaces and the transmission interfaces help in performing various functions that are described in the next section. This in-use configuration of the instrument has sub-assemblies, namely proximal hand-held assembly 40 and secondary assembly 42. FIG. 2 shows a schematic diagram of tool apparatus 10 in the in-use configuration. As shown, the coordinate system for the tool apparatus 10 is represented as a cartesian coordinate system. X-axis is parallel to tool shaft axis (axis 1). Y-axis lies in the front view plane. Z-axis is normal to the front view plane. This coordinate system is used to describe various tool apparatus architectures and specific tools throughout the description. There also exists axis 1 (dial roll axis) and axis 2 (end-effector roll axis) that are shown in FIG. 2. While the proximal hand-held assembly 40 is not articulated w.r.t. frame 16, axis 1, axis 2, and axis 3 are parallel to each other.

2.2 Apparatus Functions 2.2.1 Articulation Function

Figure 3:
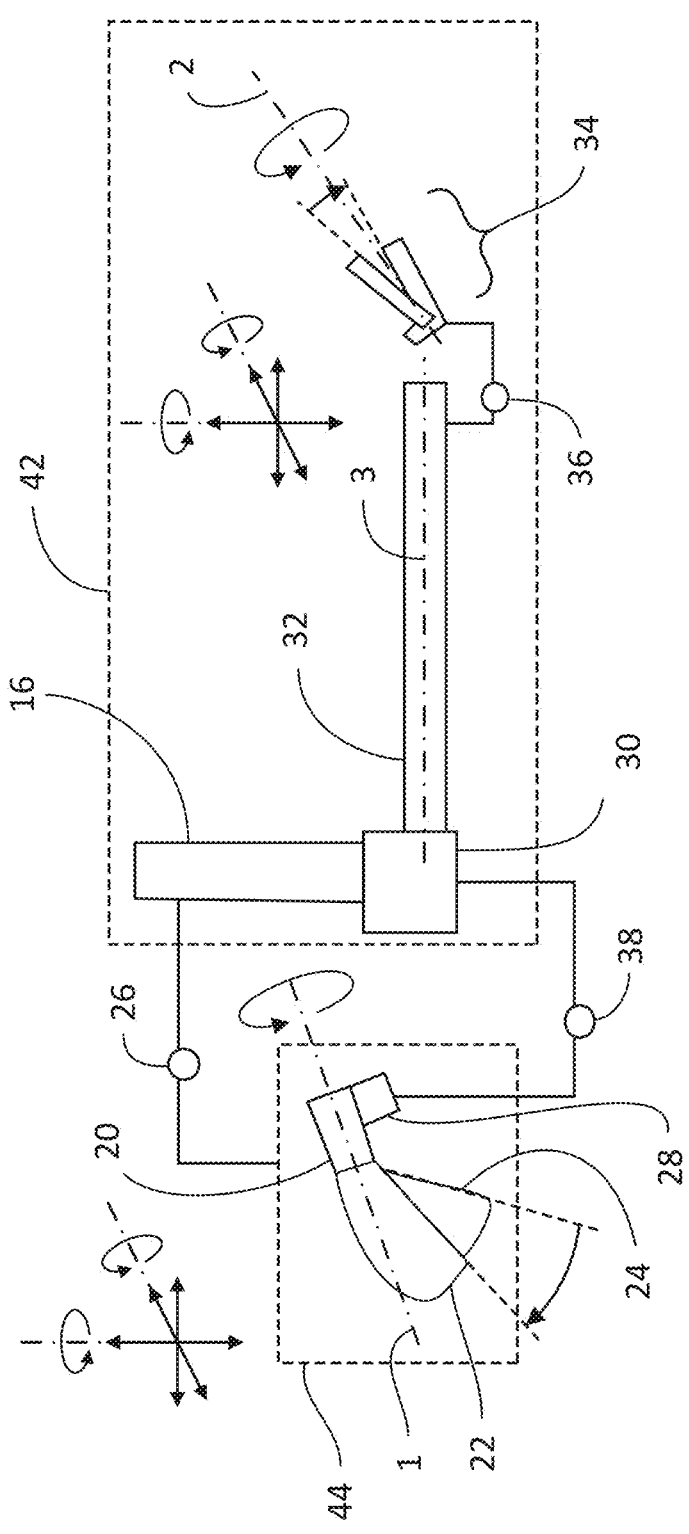
FIG. 3 is a schematic diagram of the tool apparatus shown articulated.

Articulation of the tool apparatus 10 is a key function where pitch and yaw output motion are produced at the distal end of the shaft 32 (at the end-effector assembly 34) based on pitch and yaw input motion of the handle assembly 18. FIG. 3 shows a tool architecture that includes an articulated proximal hand-held assembly 44 (specifically pitch rotation about the Z-axis direction). Axis 1 is no longer parallel to axis 3. Also, axis 2 is no longer parallel to axis 3 (tool shaft axis). Proximal hand-held assembly 44 can be articulated about pitch axis (axis parallel to Z axis) and about yaw axis (axis parallel to Y axis). This articulation is possible due to the presence of a 2 DoF input articulation joint 26 that exists between handle assembly 18 and frame 16. This input articulation motion leads to the end-effector articulation (pitch and yaw rotation about its respective pitch and yaw rotation axis). To produce articulation, frame 16 and/or shaft 32 can be grounded w.r.t. the user or a ground external to the tool apparatus 10.

Figure 4A:
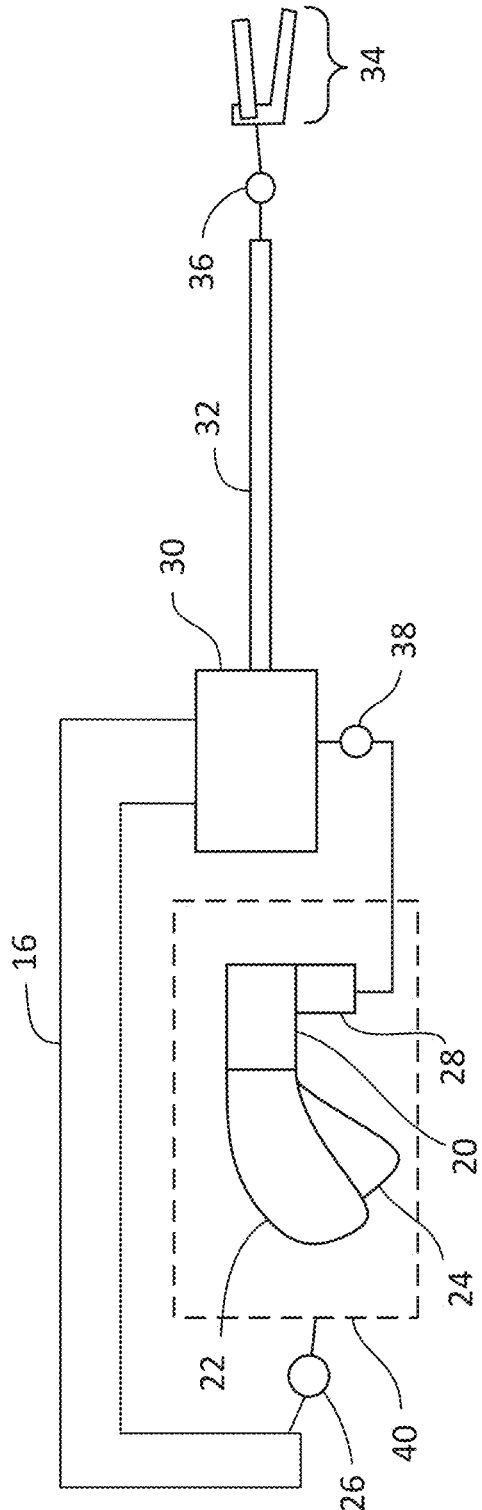
FIGS. 4A-B depict proximal (A) and distal (B) input articulation joint tool apparatus architectures.
Figure 4B:
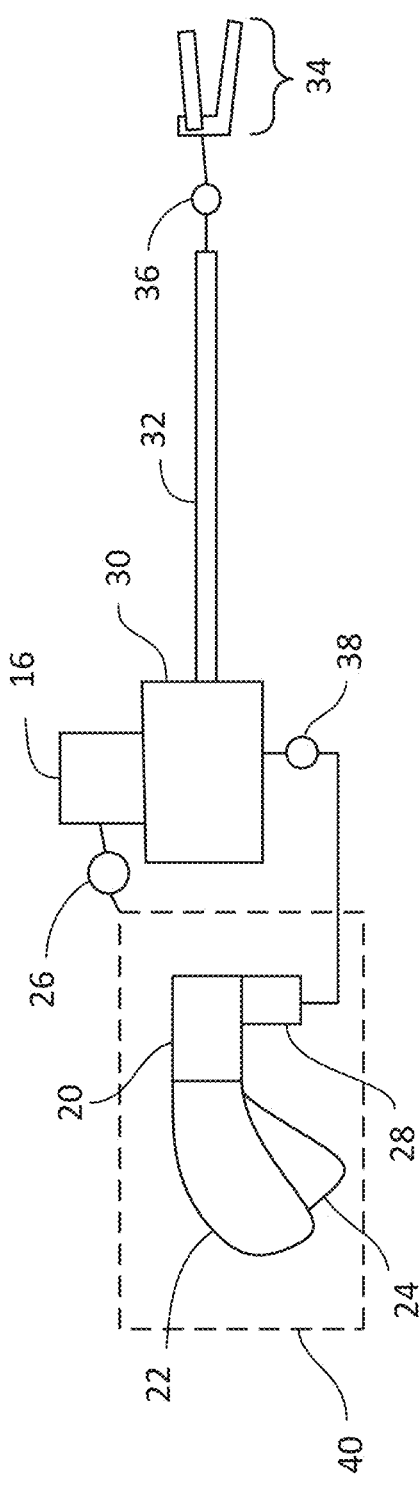

There may exist at least two types of architectures for tool apparatus 10 based on the location of input articulation joint 26 w.r.t. handle assembly 18. FIG. 4A and FIG. 4B show two architectures where the input articulation joint 26 exists proximal and distal to handle assembly 18 respectively.

There may exist at least two other types of architectures for tool apparatus 10 based on the body within handle assembly 18 that connects with the input articulation joint 26. The input articulation joint 26 can exist between handle body 22 and frame 16, or the input articulation joint 26 can exist between dial 20 and frame 16. These architectures are presented and discussed in further sections.

2.2.2 End Effector Actuation Function

Figure 5:
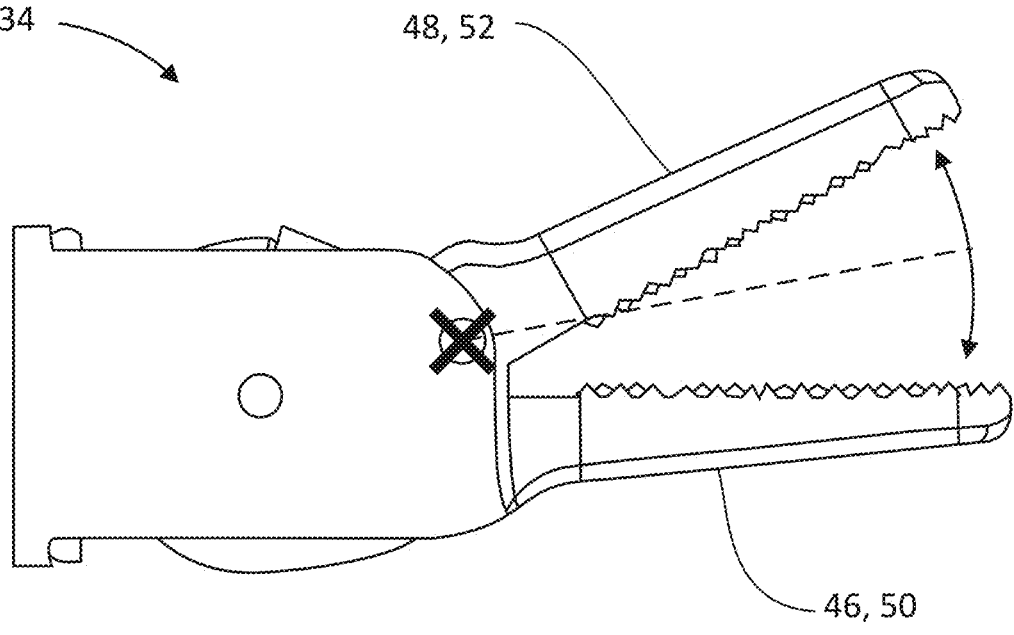
FIG. 5 depicts an end-effector assembly.

End-effector actuation is produced by input motion of closure input 24 w.r.t. handle body 22. Closure input 24 and handle body 22 are part of handle assembly 18. An embodiment of handle body 22 can be found in U.S. Pat. No. 9,814,451. One DoF motion of closure input 24 w.r.t. handle body 22 can produce closure motion at the end-effector assembly 34. FIG. 5 shows an architecture for end-effector assembly 34 which has two portions, a first portion 46 and a second portion 48. Here, second portion 48 rotates w.r.t. the first portion 46 about its closure pivot axis. First portion 46 is also referred to as fixed jaw 50 and second portion 48 is referred to as moving jaw 52.

In other embodiments, there may exist end-effector architectures which may consist of three or more portions, where the second and third portions may move w.r.t. the first portion. One of such end-effector assemblies is termed as "dual (2) action jaws." Also, the term "closure" may be used to denote both closing and opening of the moving jaw 52 w.r.t. fixed jaw 50. Other than motion of the second portion w.r.t. the first portion, "closure" may also refer to a specific motion (e.g., translation, rotation, etc.) that is made by the third or fourth portion relative to the first or second portion. Therefore, motions that lead to end-effector function are termed as "closure." The "end-effector actuation" or "jaw closure" transmission takes places due to various joints, mechanisms and transmission member(s) that exist between handle assembly 18 and end-effector assembly 34. These are discussed in detail in further sections.

2.2.3 Rigid Body Translations and Rotations

As part of the tool apparatus 10 in the in-use configuration as shown in FIG. 2, a structural interface exists between frame 16 and shaft box 30. Motion of frame 16 w.r.t. an external reference ground is transmitted to shaft box 30 and, thereby, to other components and sub-assemblies of the secondary assembly 42 (tool shaft 32 and end-effector assembly 34). Therefore, shaft 32 has three translation DoFs (along X-, Y-, and Z-axis direction) and three rotation DoFs (pitch, yaw, and roll rotation) w.r.t. the external reference ground. FIG. 3 shows tool apparatus 10 in the in-use configuration in which the proximal hand-held assembly 40, frame 16, shaft 32, and end-effector assembly 34 possess these 6 DoFs. The roll DoF is described specifically in next section.

2.2.4 Roll Function (Also Articulated Roll)

Roll DoF of end-effector assembly 34 about its roll axis (axis 2) is one of the six DoFs mentioned in the section above. Rotation of the end-effector assembly 34 requires rotation of dial 20 within handle assembly 18. Rotation of dial 20 w.r.t. handle body 22 about axis 1 leads to rotation of end-effector assembly 34 about axis 2. While handle assembly 18 is not articulated, as shown in FIG. 2, rotation of dial 20 about axis 1 leads to rotation of the end-effector assembly 34 about axis 2, where axis 2 is colinear to axis 3 (i.e., the tool shaft axis). This roll motion is part of the six DoFs (rigid body motion) referred to in section above.

In case handle assembly 18 is articulated, as shown in FIG. 3, rotation of dial 20 about axis 1 leads to rotation of end-effector assembly 34 about axis 2, where axis 2 is no longer colinear to axis 3. This rotation function of the end-effector assembly 34 while being articulated is termed as "articulated roll."

Figure 6A:
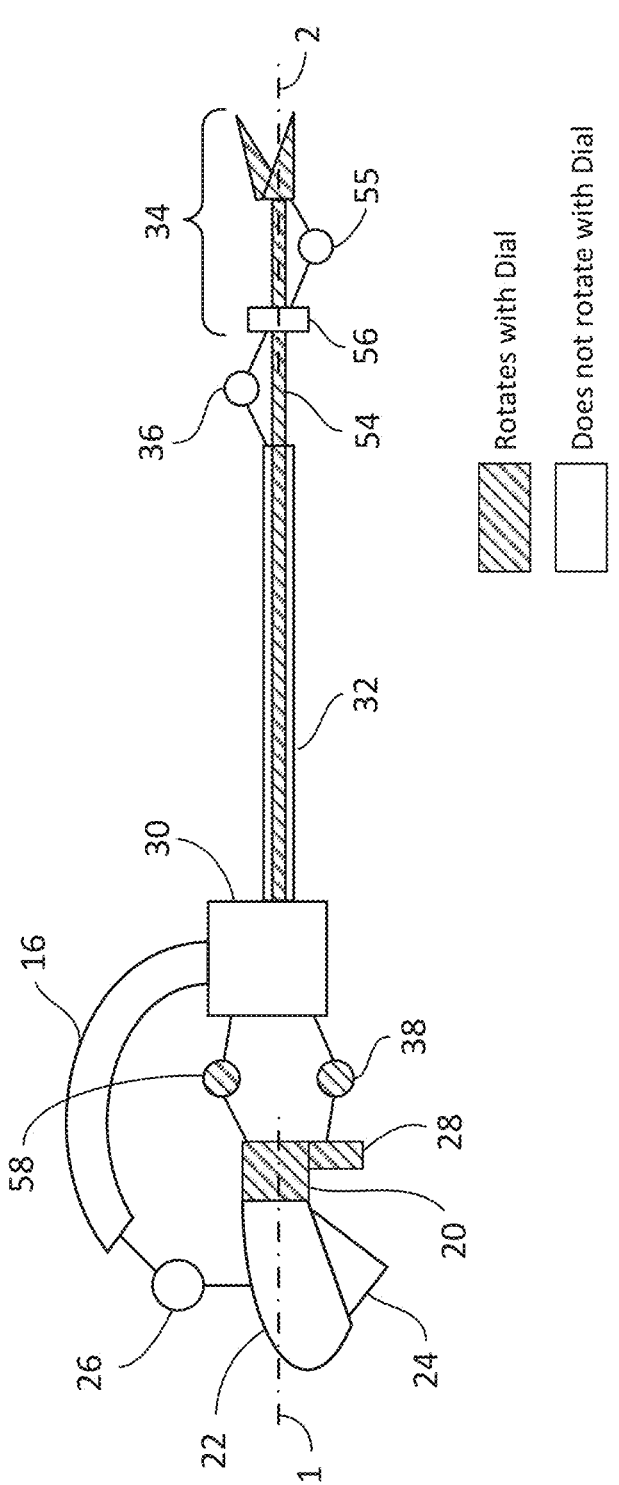
FIGS. 6A-B depict different tool apparatus architectures based on input articulation joint between handle assembly and frame.
Figure 6B:
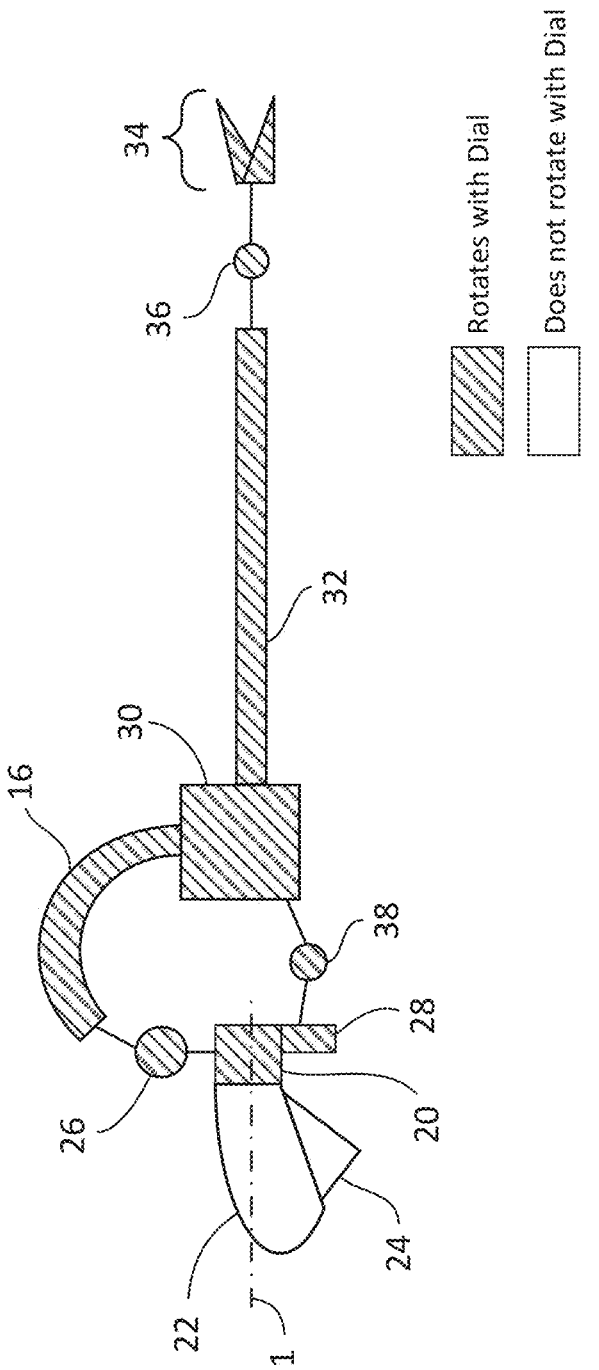

Transmission of roll motion from dial 20 to end-effector assembly 34 may take place in two different ways. As mentioned above while describing articulation function, there may exist at least two different types of architectures for tool apparatus 10 based on which body within handle assembly 18 interfaces to the input articulation joint 26. This differentiation in architecture based on which body connects to the frame 16 via input articulation joint 26 also defines the differentiation in roll motion transmission. FIG. 6A shows a first tool apparatus architecture and FIG. 6B shows a second tool apparatus architecture.

The first architecture is called alpha architecture and is shown in FIG. 6A. In a tool apparatus 10 that includes articulation function, there exists a 2 DoF (pitch and yaw) input articulation joint 26 between handle body 22 and frame 16. In this architecture, roll is transmitted via a roll transmission member 54 that runs internal to shaft 32 and interfaces with end-effector assembly 34. In this configuration, dial 20 rotates and thereby rotates a torsionally stiff roll transmission member 54. But frame 16 and shaft 32 lack rotation.

There exists a roll DoF about tool shaft axis between shaft 32 and end-effector assembly 34. There may exist a body within end-effector assembly 34 called end-effector (EE) base 56 (third portion) that does not rotate upon rotation of dial 20 (about axis 1) but does articulate w.r.t. tool shaft 32. There exists a roll DoF about axis 2 between EE base 56 and fixed jaw 50 via joint 55.

In the first architecture, there exist a roll actuation interface 58 and closure actuation interface 38 between shaft box 30, conduit box 28, and dial 20. These joints may be different or the same. For example, this joint may be formed by a flexible wire like Nitinol wire, or a tube in a tube assembly where an inner tube thereof transmits closure actuation and an outer tube thereof transmits roll actuation, or vice versa. The roll transmission member 54 rotates along with dial 20 w.r.t. shaft box 30.

The second architecture is called beta architecture and is shown in FIG. 6B. In a tool apparatus 10 that includes articulation function, there exists a 2 DoF (pitch and yaw) input joint 26 between dial 20 and frame 16. In this architecture, roll is transmitted via the rigid body arrangement that exists within tool apparatus 10. Rotation of dial 20 leads to rotation of tool shaft 32. Dial 20 and tool shaft 32 are either connected via a fixed joint or an articulation input joint (2 DoF pitch and yaw motion joint). Rotation of tool shaft 32 is further transmitted to end-effector assembly 34. Tool shaft 32 and end-effector assembly 34 are either connected via a fixed joint or an articulation output joint 36 (2 DoF pitch and yaw motion joint), depending on whether the apparatus 10 has articulation function.

2.2.5 Electric Energy Transfer Function

Electrocautery, also known as thermal cautery, refers to a process in which an alternating current is passed through a conducting metal wire electrode (termed as electricity transmission member 60), the electrical current transferred to end-effector assembly 34 leads to heating of the tissue present between the portions of end-effector assembly 34. There is a need to transfer electrical current from an apparatus termed as "electricity box" or "electrocautery box" 62 to tool apparatus 10. This box serves as an input to tool apparatus 10 and provides voltage and/or current input. This input is provided to a conductive metal wire electrode which is termed as a "electricity transmission member" 60 that terminates at end-effector assembly 34. In case of electrocautery, one (mono-polar) or two (bi-polar) portions of end-effector assembly 34 are connected to one or more electricity transmission member 60 respectively to form a closed circuit by passing current through the tissues between the two portions of end-effector assembly 34. This leads to heating of the tissue which is either coagulated or cut depending on the properties of voltage/current supplied by electricity box 62. Another way of utilizing the electricity is by generating ultrasonic vibrations. In this case, the electricity transmission member 60 may be a transducer (e.g., piezoelectric) that converts electricity to ultrasonic vibrations. These vibrations then can be used to excite the tissues between the end-effector portions to cut and cauterize them at the same time.

Figure 7A:
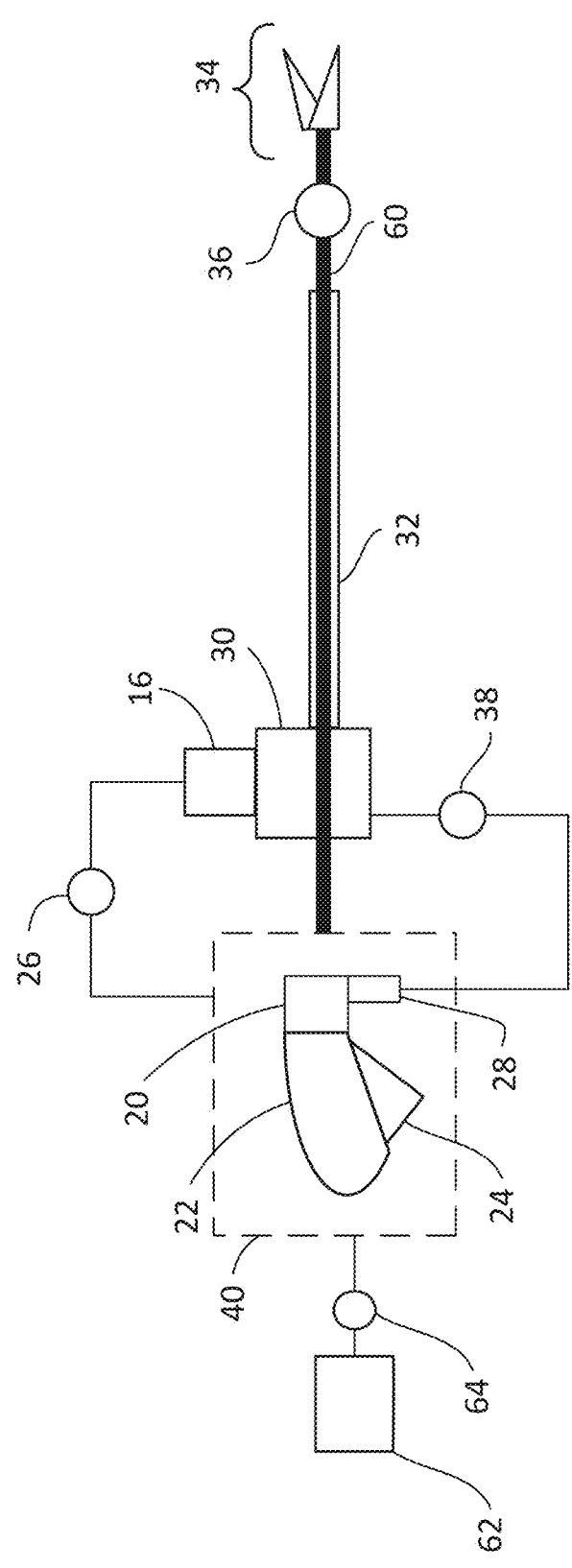
FIGS. 7A-B depict different tool apparatus architectures based on point of attachment of electricity box.
Figure 7B:
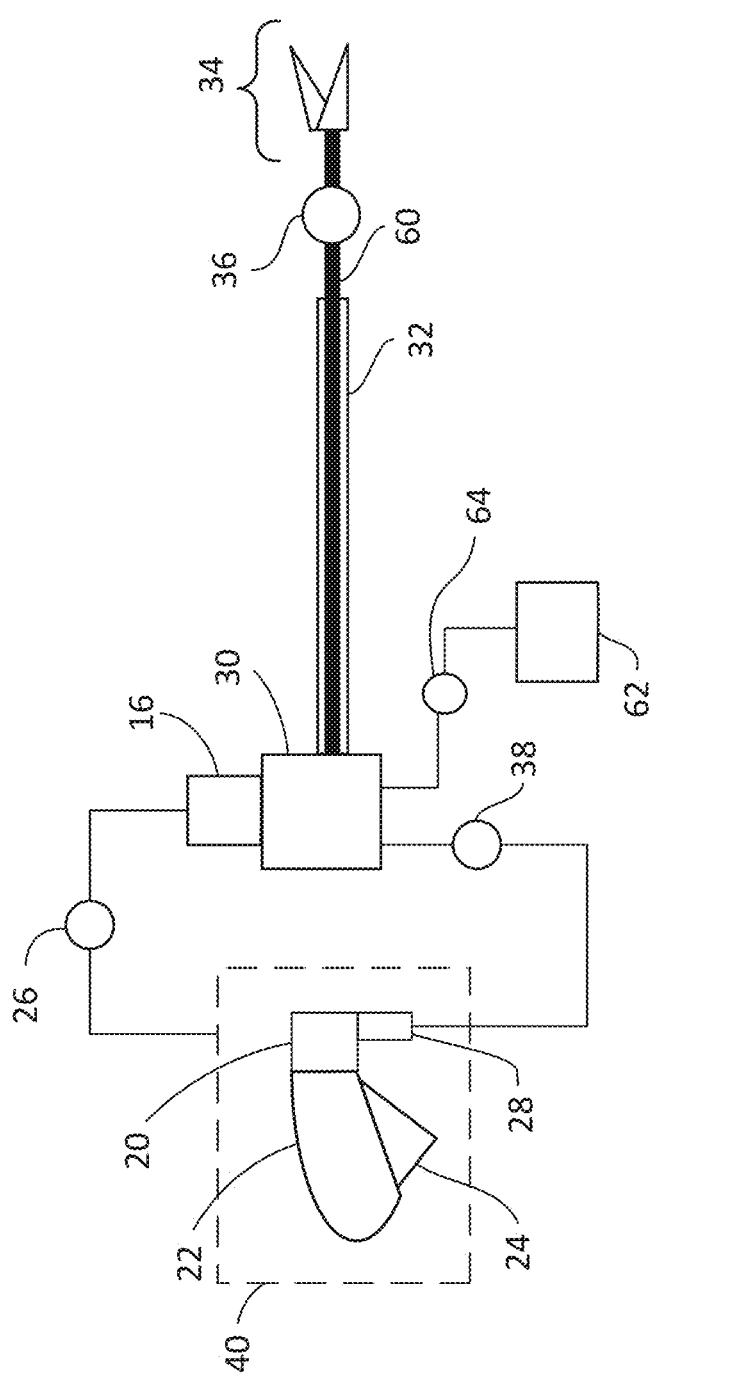

FIG. 7A and FIG. 7B show two different tool apparatus 10 embodiments and architectures based on the location where electricity box 62 body attaches to tool apparatus 10. FIG. 7A shows attachment between electricity box 62 and handle assembly 18 (either of handle body/closure input/dial) via a current (and/or voltage) input joint 64. There exists an electricity transmission member 60 that starts at handle assembly 18 where it receives the current (and/or voltage) input. It travels to and terminates at end-effector assembly 34. FIG. 7B shows the attachment between electricity box 62 and shaft box 30 via a current input interface 64. There may exist an independent electricity transmission member 60 within shaft box 30 or shaft 32 and terminates at end-effector assembly 34. There may exist an electrical connection between jaw closure transmission member 66 and electricity box 62 such that jaw closure transmission member 66 also serves as electricity transmission member 60.

2.3 FSM Configured as a Tool Apparatus

Within a tool apparatus 10 which has any of the architectures described above, there may exist several bodies and interactions between them. Here, interaction is used as a common term to describe an alignment, retention, interface, or joints/mechanisms between two bodies. These interactions are produced via one or more of the following interaction elements: i) alignment features (A); ii) retention features/bodies (R); iii) locks (L); iv) interlocks (I); v) transmission interfaces (TI); vi) transmission members (TM); and vii) mechanisms/joints (M/J). These bodies together constitute a finite state machine (FSM) which has various types of states that are of interest based on the application requirements of tool apparatus 10. These finite states may also contain various states that are of no interest from a given application standpoint and are therefore, prohibited from occurring by one or more of the interaction elements mentioned above.

Here, an FSM is described that consists of at least four bodies namely, frame 16, shaft box (SB) 30, conduit box (CB) 28, and dial 20. As shown above, dial 20 and frame 16 are part of the master instrument (MI) 12 whereas SB 30 and CB 28 are part of the detachable instrument (DI) 14. These bodies interact with each other in certain manners to attain the in-use configuration, shown in FIG. 2, and hence achieve tool apparatus functionality. This configuration is referred as one of the finite states of the FSM and is described and categorized in further sections. For the sake of simplicity, "Frame assembly" is called "Frame," "Shaft Box assembly" is called "Shaft Box," "Conduit Box assembly" is called "Conduit Box," and "Dial assembly" is called "Dial" throughout the description and figures. Each of these assemblies may house certain interaction elements and may contain one or more bodies that have a structural interface with respect to each other (e.g., Shaft Box (SB) assembly has SB LH (left hand) and SB RH (right hand) that have 0 DoF relative to each other and therefore have a structural interface between them). These assemblies are described in detail in further sections.

Figure 8:
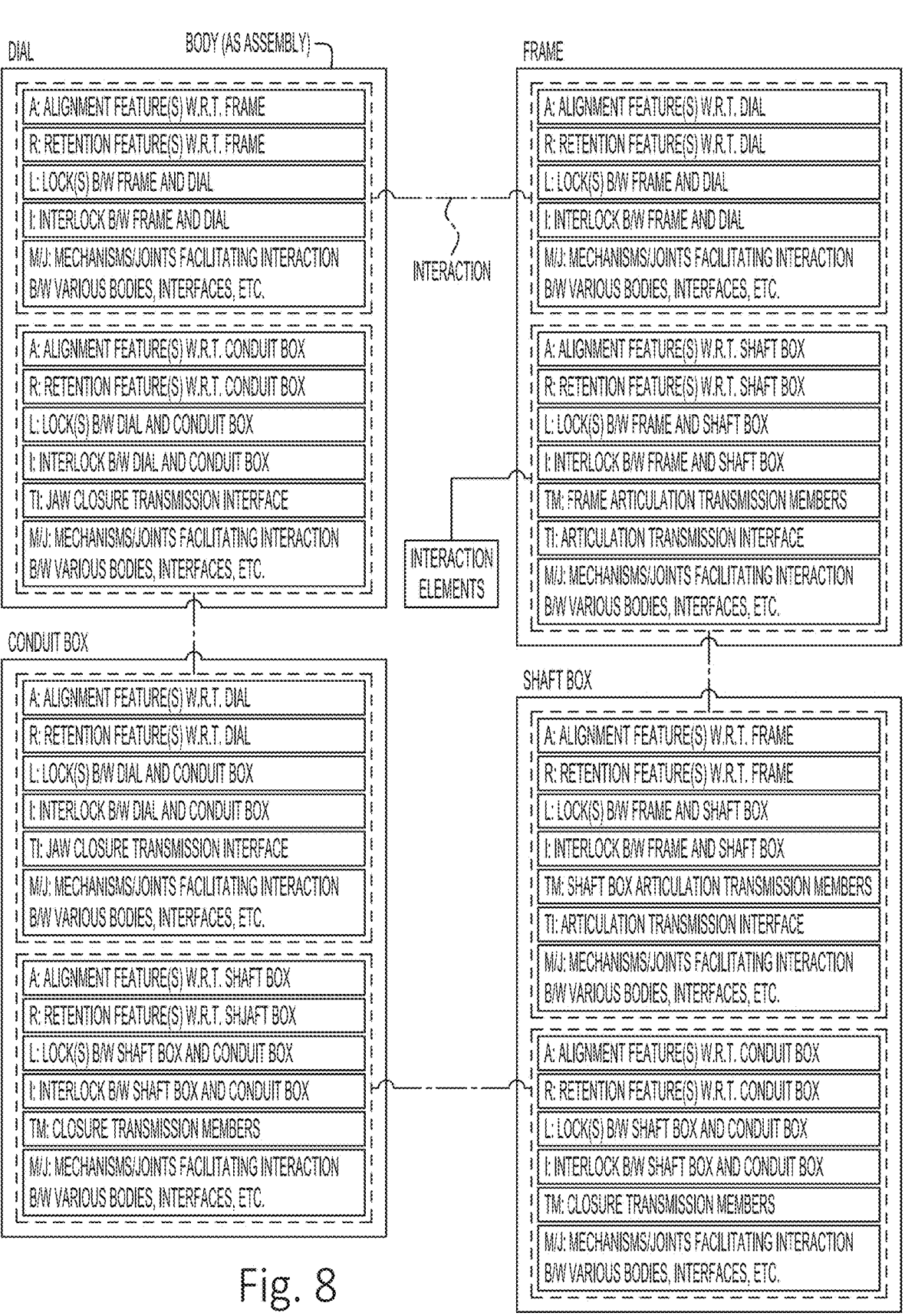
FIG. 8 is a schematic diagram showing finite state machine (FSM), interaction elements and interactions between bodies.

FIG. 8 shows a schematic diagram of an FSM consisting of four bodies and their interaction via seven interaction elements. Each interaction may not involve all the interaction elements. Also, each body is shown to house these interaction elements. This simply means that each body—out of the four bodies mentioned above—may "house" various other bodies and features. For example, frame 16 may house a lock that interacts with frame 16 and shaft box 30. At the same time, frame assembly 16 may not house an interlock that interacts with the lock (that interacts with frame 16 and shaft box 30). This interlock may be housed within shaft box assembly 30. Also, in certain states, some of the pairs of bodies may not have any interaction between their respective interaction elements. These possible forms of states that are of interest are discussed in further sections.

Figure 9:
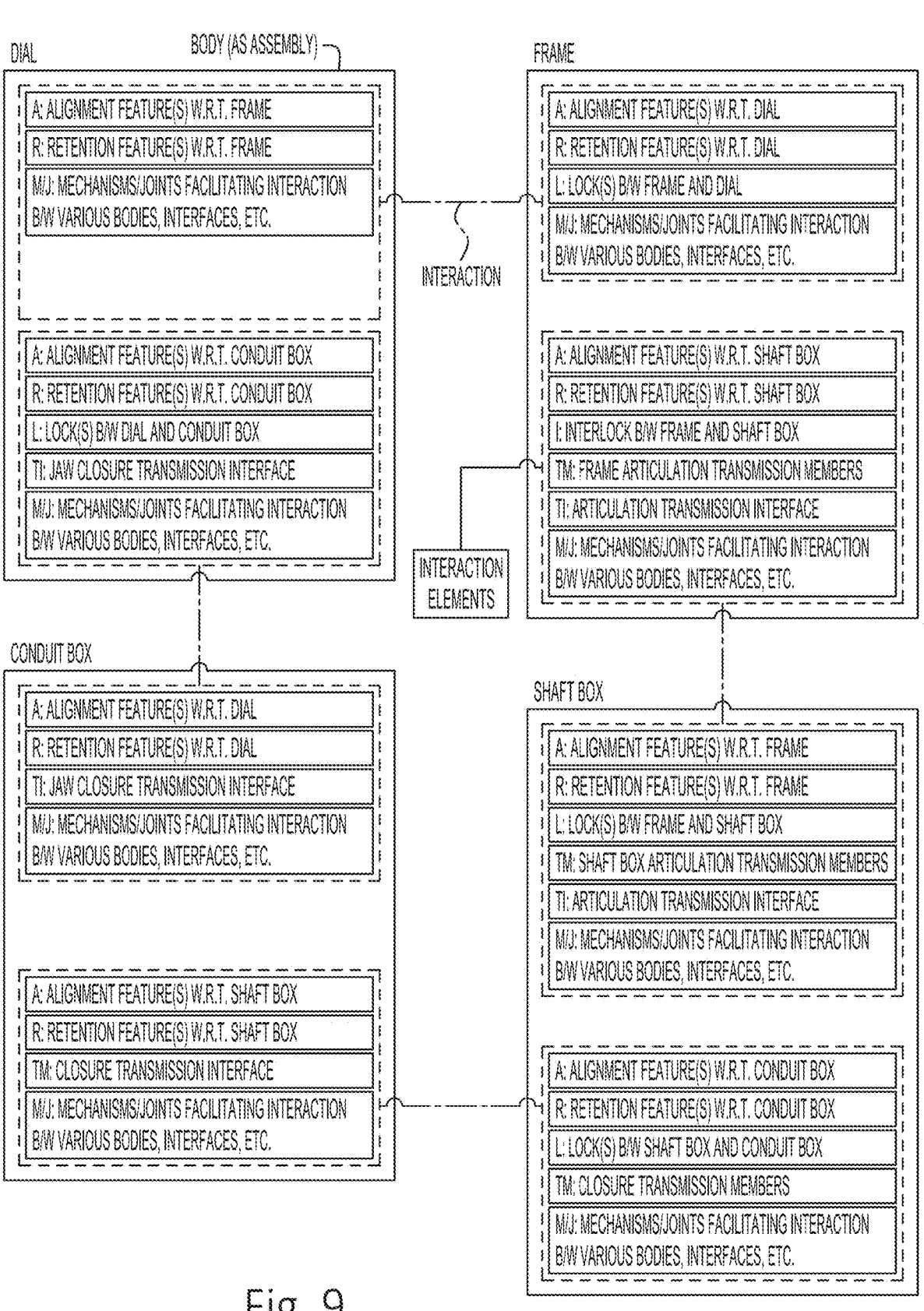
FIG. 9 is a simplified schematic diagram showing FSM, interaction elements and interactions between bodies.

FIG. 9 shows a simplified version of schematic diagram showing FSM consisting of four bodies, interaction elements, and interactions. This schematic diagram is referenced in sections below to map w.r.t. an FSM within a specific embodiment of tool apparatus 10.

2.4 States, Actions, and Transitions

Figure 10:
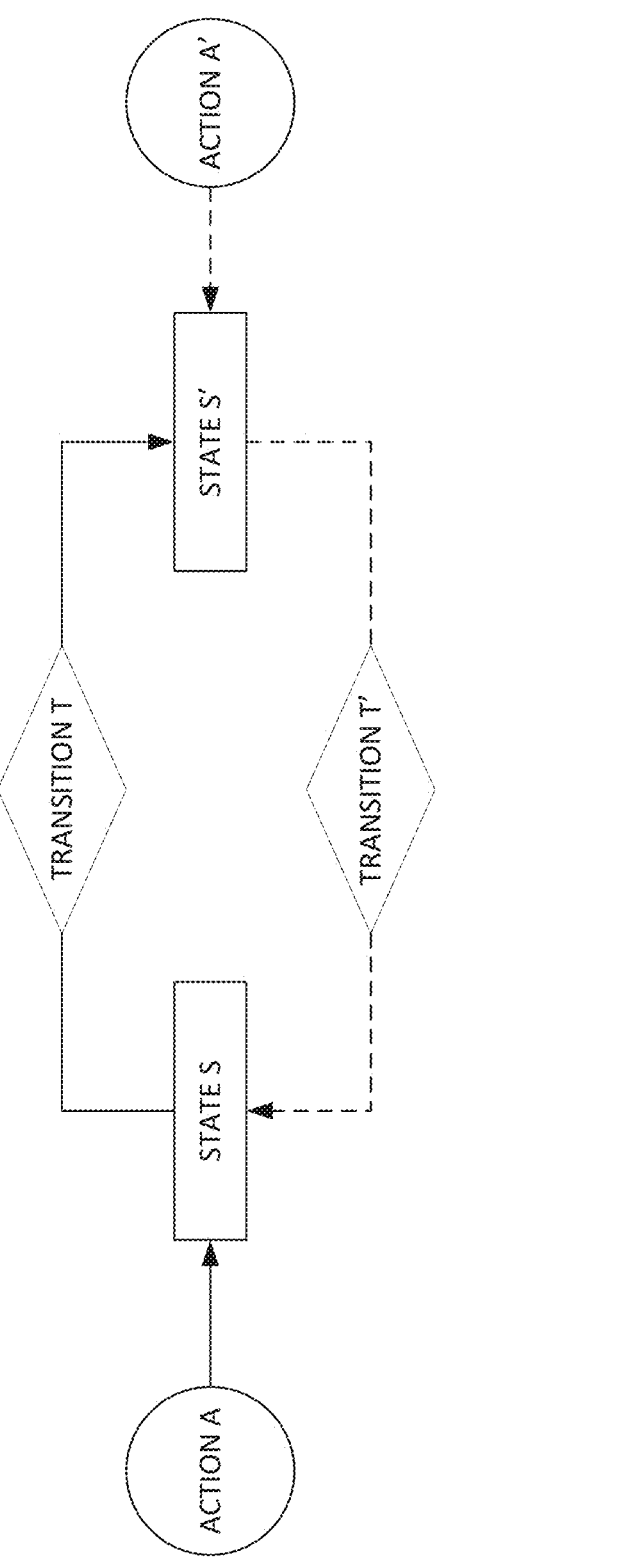
FIG. 10 is a schematic diagram showing relationship between states, actions, and transitions.

There may exist a relationship between any two states; this relationship consists of an action and a transition. An FSM may consist of a state S that transitions to a state S' via transition T. This transition takes place only if there exists an action (action A) that includes inputs/triggers that are provided by the user of tool apparatus 10. This action is applied onto state S. FIG. 10 shows a simple schematic diagram showing the relationship between states, actions, and transitions. Here, action A is applied on a state S. This produces transition T which changes the FSM state to state S'. In certain cases, there exist reversible transitions such that transition T' is reverse of transition T. Which means that transition T' refers to the transition from mentioned state S' to the mentioned state S. There also exist action A' that leads to transition T'. Reversible transitions may or may not exist in certain FSMs.

Another point to note here is that each transition involves the interaction of various interaction elements described in above sections. These interactions take place between bodies and features on certain bodies. Also, these interactions occur in the mechanical domain and, therefore, over a finite amount of time and may not be instantaneous. In contrast, for example, in the electronics domain, a state may transition or switch to another state in a few microseconds, making those transitions practically instantaneous. In the present scenario, each transition can thereby be plotted against time and be fragmented into transition steps that involve interactions between interaction elements. There may exist some transition steps which involve electronic circuitry and may thereby be instantaneous in nature.

2.5 State Types

Each state that an FSM may exist in can be categorized based on the nature of the state. A first category that is relevant in the context of an FSM is whether a state is a functional state or a non-functional state. A functional state of an FSM configures tool apparatus 10 such that it can be used to provide one or more of the functionalities mentioned in above sections. In the case of the tool apparatus 10 presented in FIG. 1, it is shown in a non-use state where MI 12 has no interaction w.r.t. DI 14. Therefore, this is a non-functional state and can be termed as "storage state" or "state 1." In the storage state, MI 12 is not attached to DI 14. This is also termed as "state 1" for the FSM as this is the state in which the system exists before any actions are applied and before any transition has occurred.

FIG. 2 shows the in-use configuration which is a functional state as all the tool apparatus functions are available for use. This state is also termed as "use state." While the FSM is in its use state, all the interactions between four bodies shall occur such that tool apparatus 10 shown in FIG. 2 is able to function as desired. As shown, conduit box 28 shall be aligned and retained along all DoFs w.r.t. dial 20. Also, shaft box 30 shall be aligned and retained along all DoFs w.r.t. frame 16. Also, transmission interfaces for articulation and jaw closure shall be mated together to assist with tool functions.

There may also exist a functional state where one or more, but not all, functions are available. E.g., there may exist a state that is intermediate to storage state and use state. This is the state which is transitioned from storage state. In this state, some functions (e.g., articulation function) may be prohibited from use whereas other functions (e.g., jaw closure function) may still be available. FSM can then either be transitioned to storage state or use state from this state. Being an intermediate state, this can also be termed as "assembled state." At this state, both MI 12 and DI 14 are brought together to produce a structural interface but the tool apparatus 10 may still not be fully functional.

Also, as described, due to the ability for the system to go from assembled state to storage state or to the use state, each of the transitions are reversible in nature. This means that upon reversal of the action that brought the FSM from storage state to assembled state, the transition can be reversed to take the FSM back to storage state. Similarly, upon reversal of the action that brought the FSM from assembled state to use state, the transition can be reversed to take the FSM back to assembled state.

Figure 11:
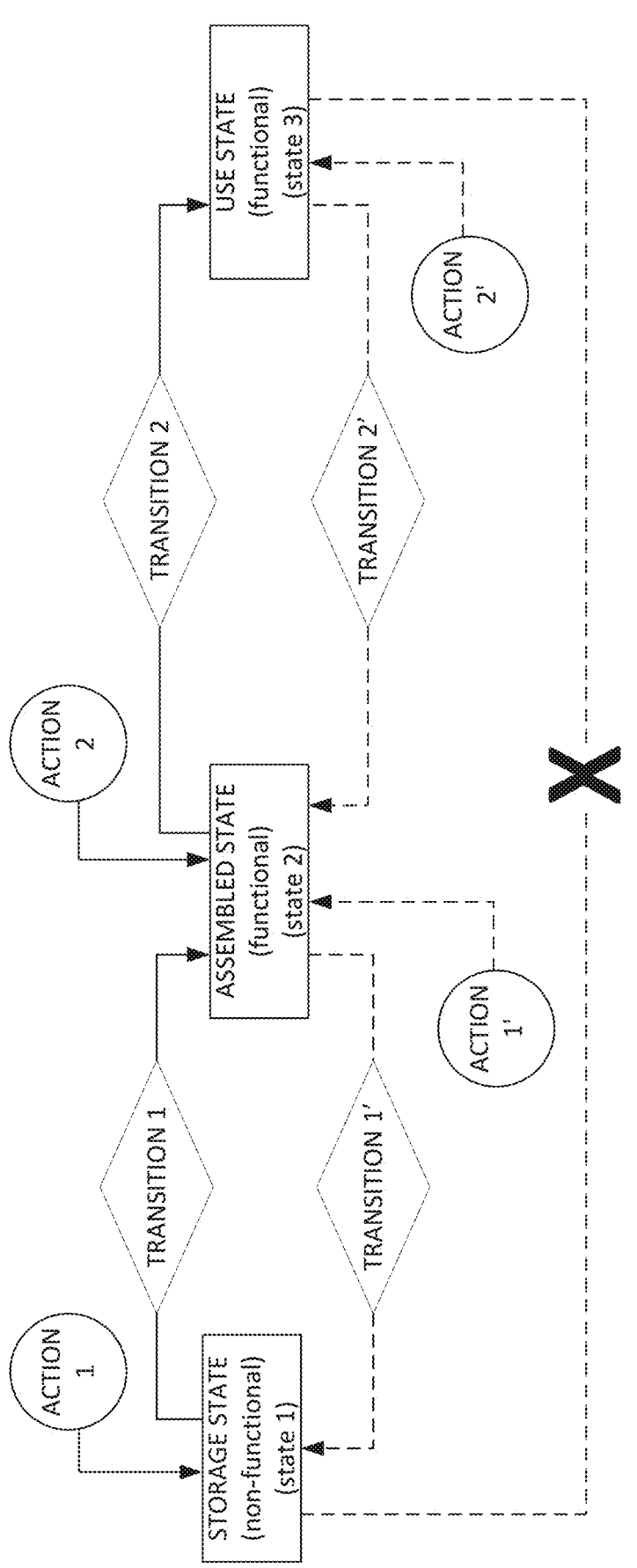
FIG. 11 is a schematic diagram showing actions, transitions, and common states for FSM which includes at least two interlocks in "use state"

Within the FSM, the retention between conduit box 28 and dial 20, and between shaft box 30 and frame 16 may be produced using locks rather than non-positive engagement retention features. Based on the requirement to maintain the FSM in use state, there may also exist interlocks that dis-able the actuation of these locks. Due to the presence of interlocks, the FSM can be prohibited from being transitioned directly to a non-functional state. This means that while the FSM is in use state and consists of interlocks that prevent disabling of locks, there does not exist a single transition or single action that can transition the FSM directly to a non-functional state (e.g., the storage state mentioned above) without changing the state of the FSM to some other intermediate functional state (e.g., the assembled state mentioned above). FIG. 11 shows a schematic diagram that provides a visual representation of possible transitions (transition 1 and 1', and transition 2 and 2') as well as lack of any transition to directly go from use state to a non-functional state (e.g., the storage state mentioned above) for an FSM that consists of aforementioned robust locks and interlocks.

In this example, storage state is a non-functional state that is "allowed." Another example of an allowed non-functional state is "service state." A service state for an FSM is a state at which either the FSM is dis-assembled partially or completely in order to do maintenance of its bodies and interaction elements. The service state specific to tool apparatus 10 is presented in further sections and FIG. 53A-B.

Figure 12:
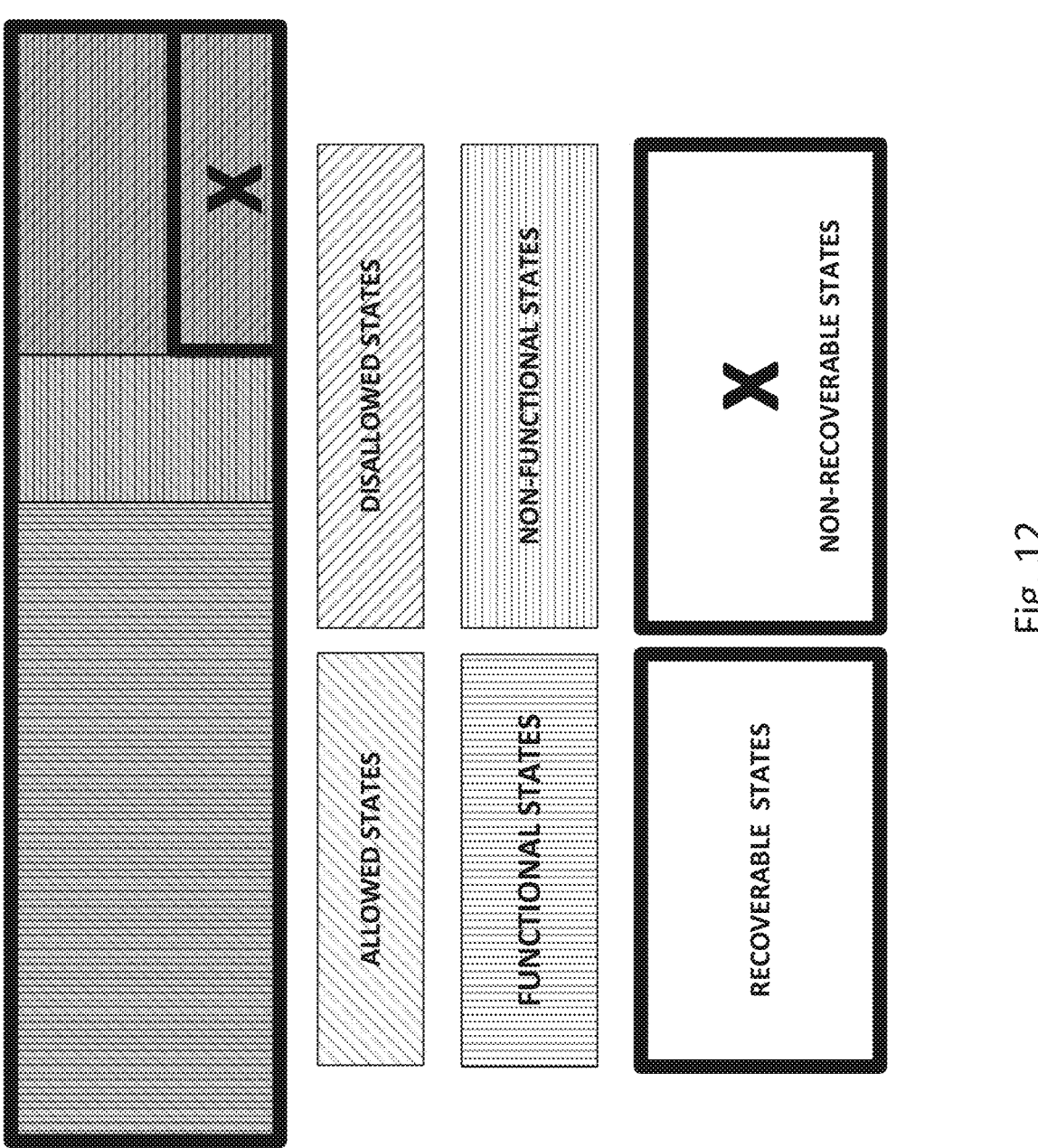
FIG. 12 is a schematic diagram showing relationship between various state categories.

FIG. 12 shows various state categories and relationships between these categories. There may exist some non-functional states that are also disallowed. Every disallowed state is not only non-functional but can also not be reached during handling and use of the FSM which is designed with robust set of locks and interlocks. In scenarios where an FSM consists of robust locks and interlocks, the FSM can only attain a disallowed state if the bodies and interaction elements that are part of the FSM are misused, or are broken, or are manipulated/mis-handled beyond the scope that is intended or instructed for use of tool apparatus 10. One example of mis-handling can be the use of external tools or equipment to undo the interlocks or locks. These external tools may not be prescribed for use as part of tool apparatus 10 or to perform any of the tool apparatus functions. Such manipulation/mis-handling/misuse may put the FSM into a state that is disallowed by design. In some scenarios, a disallowed state may be called as "misuse state." In certain cases, certain external tools may be prescribed to take the tool apparatus 10 from a one state (say, storage state) to another state (say, service state) based on instructions provided for use.

Some of the disallowed states may still be recoverable depending on the design of FSM. A disallowed state is recoverable if the FSM can be brought back to a functional state after some finite number of transitions that may involve going through other allowed or disallowed intermediate states. If the bodies or interaction elements that are part of the FSM are physically broken and it is not possible to recover the FSM back to a functional state, such states are non-recoverable. A non-recoverable state may also be reached by triggering an internal counter or clock within the FSM which leads to malfunctioning or physical damage/breakage of certain components/features/locks within the FSM. This may be a counter of number of uses that FSM goes through or purely a time-based clock.

Another point to note here is that transitions are reversible between any two functional states and/or any two allowed, non-functional states. This means that while exactly reversing the transition and its associated transition steps, state reversal can be achieved. Whereas transitions may not be reversible between allowed and disallowed states. A disallowed state that is reached via a non-reversible transition cannot transition back to the previous state by reversing the actions that resulted in the disallowed state, but may be recoverable by undergoing a different transition.

To summarize, states can be categorized into three broad categories. These categories are as follows: i) functional and non-functional states; ii) allowed or disallowed states; and iii) recoverable or non-recoverable states. These states can be reached from one to the other via transitions that may or may not be reversible. For specific examples of tool apparatus 10 described here, the terms "storage state" (non-functional), "assembled state" (functional), "use state" (functional), "intermediate state" (state between a non-functional and functional state, e.g., assembled state), and "service state" (non-functional).

Relationships among these state categories set forth above are visually presented in FIG. 12.

2.6 Possible Storage States and Functional States

As mentioned in previous sections, an FSM may contain various states that may involve interactions between one or more interaction elements that exist as part of the system. Based on the involvement of these interaction elements, an FSM can exist in various "forms" of state 1 or storage state, and/or assembled state (functional state), and/or use state (functional state). These various possible forms of FSMs described herein are determined by the presence or absence of alignment and retention features. Here, only alignment features and retention features/bodies are considered as variables (i.e., interlocks are not considered unless specifically mentioned). If two bodies are constrained along at least one direction in each of the six DoFs (i.e., either positive or negative direction for all three translation DoFs and all three rotation DoFs), then the two bodies are aligned (also referred to as fully aligned) and alignment is termed as in a "1" condition. Otherwise, if there are DoFs on both the positive and negative directions of translation along any three axes or if there are DoFs on both the positive and negative directions of rotation about any three axes, then the two bodies are not aligned fully and alignment is termed as a "0" condition. If two bodies are fully constrained along each of the 6 DoFs in both directions, the bodies are retained (also referred to as fully retained) and retention is termed as a "1" condition. Otherwise, if there is any DoF between the two bodies, retention is termed as a "0" condition.

While the FSM is in its storage state, dial 20 and frame 16 are part of master instrument 12, and shaft box 30 and conduit box 28 are part of detachable instrument 14 (i.e., each instrument has a pair of bodies). Within each instrument, there may/may not exist an alignment between the pair of bodies. At the same time, there may/may not exist retention between the pair of bodies. Therefore, within each instrument, there are $2^2$ or 4 combinations based on whether alignment and retention exist or not. Hence, there are $4^2$ or 16 forms of FSM possible in a storage state where there may or may not be alignment/retention between respective pairs of bodies in each instrument. FIG. 13A shows a schematic representation showing the possibility of various forms of FSM in storage state for an FSM in which retention, alignment, and/or interlock body/bodies/feature(s) between the pairs of bodies in each instrument may or may not exist (condition 0 or 1 respectively). This type of FSM would have $2^6$ possible forms ($2^3 * 2^3 = 64$).

While the FSM is in its use state, dial 20 and conduit box 28 need to be aligned and retained completely in all six DoFs (to produce a structural interface) in order to facilitate closure function at the end-effector assembly 34. At the same time, frame 16 and shaft box 30 need to be aligned and retained completely in all six DoFs (to produce structural interface) in order to facilitate articulation, rigid body motion, and roll functions. If tool apparatus 10 has articulation function as one of its functional requirements, it is not possible to align or retain dial 20 w.r.t. frame 16 in all six DoFs as dial 20 is required to move relative to frame 16 in order to produce articulation at end-effector assembly 34. Similarly, it is not possible to align or retain shaft box 30 w.r.t. conduit box 28 in all six DoFs as conduit box 28 has a structural interface w.r.t. dial 20 and dial 20 has a two-DoF motion (pitch and yaw) relative to frame 16. Therefore, for an FSM that has articulation and does not have interlocks, there exists only one form of FSM in use state. FIG. 13B shows a schematic representation showing the possibility of various forms of FSM in use state, where there may or may not be interlocks between the pairs of bodies in each instrument and where there may or may not be alignment and/or retention between the two instruments. Furthermore, the number of FSM forms that exist if interlocks are considered is dependent on the number of interlocks that are integrated into the FSM. The lack of complete alignment and retention between respective bodies may lead to poor transmission efficiency while performing these functions.

Figure 13C:
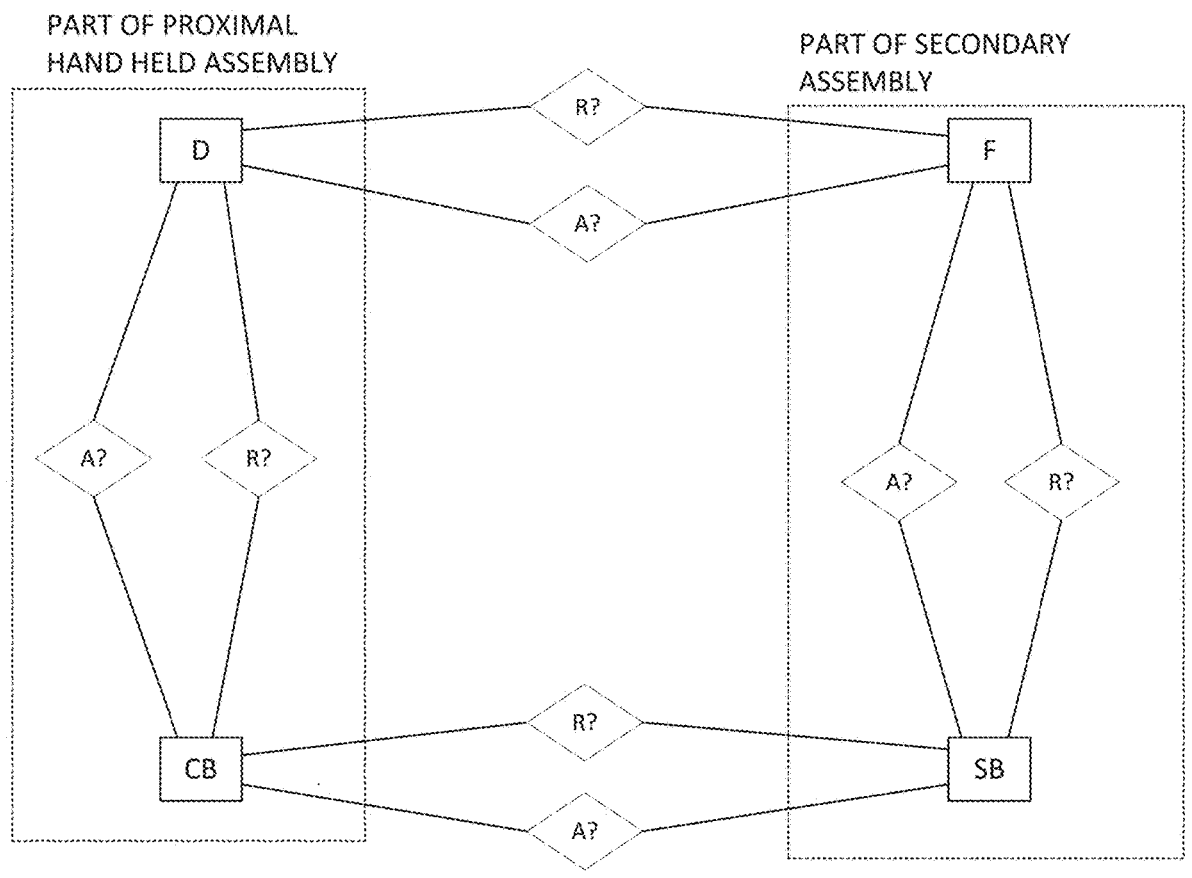

While the FSM is in its assembled state, within each instrument (MI 12 and DI 14) there exist $2^2$ or 4 combinations based on whether complete alignment and retention exist or not between the pair of bodies in each, similar to the storage state without interlocks. As per the definition of retention and alignment and referring to FIG. 13C, there can also exist all 4 combinations in the proximal hand held assembly and secondary assembly based on whether complete (along all 6 DoFs) alignment and retention exist between dial 20 and conduit box 28, and between frame 16 and shaft box 30. Therefore, there exist $4^4$ or 256 possible forms of FSM in the assembled state when considering alignment and retention features only (i.e., without considering interlocks). FIG. 13C shows a schematic representation showing the possibility of various forms of FSM in assembled state.

2.7 Action Categories

In order to transition from one state to another, actions are required as inputs along with knowing the state to which the actions apply. An action is tied up to the state of the FSM to which it is applied. In this section, various forms of actions will be discussed.

2.7.1 Installed/Uninstalled and Attach/Detach

Action 1, i.e., action that is applied on the storage state to transition (via transition 1) to the assembled state, includes assembly of shaft box 30 w.r.t. frame 16. Transition 1 may also include the assembly of conduit box 28 w.r.t. dial 20. In certain scenarios, there may be a separate transition step involving assembly of conduit box 28 w.r.t. dial 20. Assembly and disassembly of the shaft box 30 w.r.t. frame 16 is referred as "installation" and "uninstallation" respectively. Similarly, assembly and disassembly of the conduit box 28 w.r.t. dial 20 is referred as "attachment" and "detachment" respectively. Installation of shaft box 30 w.r.t. frame 16 and attachment of conduit box 28 w.r.t. dial 20 constitute action 1. Similarly, uninstallation of shaft box 30 w.r.t. frame 16 and detachment of conduit box 28 w.r.t. dial 20 constitute action 1'. These actions essentially are produced by bringing the MI 12 close to the DI 14 (in case of Action 1) or taking the MI 12 away from the DI 14 (in case of Action 1').

These actions may contain single or multiple transitions depending on the form that the FSM holds in state 1 (as described in section above). E.g., in case there exists alignment and retention between dial 20 and frame 16, and alignment and retention between conduit box 28 and shaft box 30, only a single transition (Transition 1) is required to take the FSM to the assembled state. In this scenario, Action 1 will include forming structural interface in a single transition between frame 16 and shaft box 30 (installation), and between dial 20 and conduit box 28 (attachment). In case there does not exist any retention between dial 20 and frame 16, and/or between conduit box 28 and shaft box 30, then multiple transitions are required to take the FSM to the assembled state. In this scenario, Action 1 will include forming a structural interface independently between frame 16 and shaft box 30, and between dial 20 and conduit box 28. In the absence of the assembled state, the FSM will be transitioned from storage state to use state.

2.7.2 Un-Homing/Homing

Action 2, i.e., action that is applied on the assembled state to transition (via transition 2) to use state may include the act of breaking the retention and/or alignment between the dial 20 and the frame 16. This act is termed as un-homing of dial 20 w.r.t. frame 16. Upon reversal of transition (i.e., in case of transition 2'), the act gets reversed too and is termed homing of dial 20 w.r.t. frame 16. The act of un-homing may involve translation and/or rotation of dial 20 w.r.t. frame 16 along any of the six DoFs. A simplest version of this action is translating the dial 20 w.r.t. frame 16 along the X-axis direction. FSM involving this simplest version of this action is described in further sections.

2.8 Additional Bodies that are Part of FSM

Other than a four body FSM described here, a five body and a six body FSM is described in sections below. Each body is accompanied by a respective interaction element that exists between that body and an adjacent body.

3. Detailed Description of an FSM 3.1 System Description
3.1.1 Surgical Device—Architecture and Functions In this section, an embodiment of tool apparatus 10 is presented which includes MI 12 and DI 14. Here, MI 12 is termed as virtual center control unit (VCU) 68. Tool apparatus 10 can be categorized by two types of architectures and embodiments, one shown in FIG. 4A (proximal input articulation joint) and another shown in FIG. 6B (beta configuration). Also, in this embodiment, tool apparatus 10 consists of a parallel kinematic input articulation joint 70 which is described in detail in U.S. Pat. Nos. 10,405,936 and 8,668,702.

Figure 14:
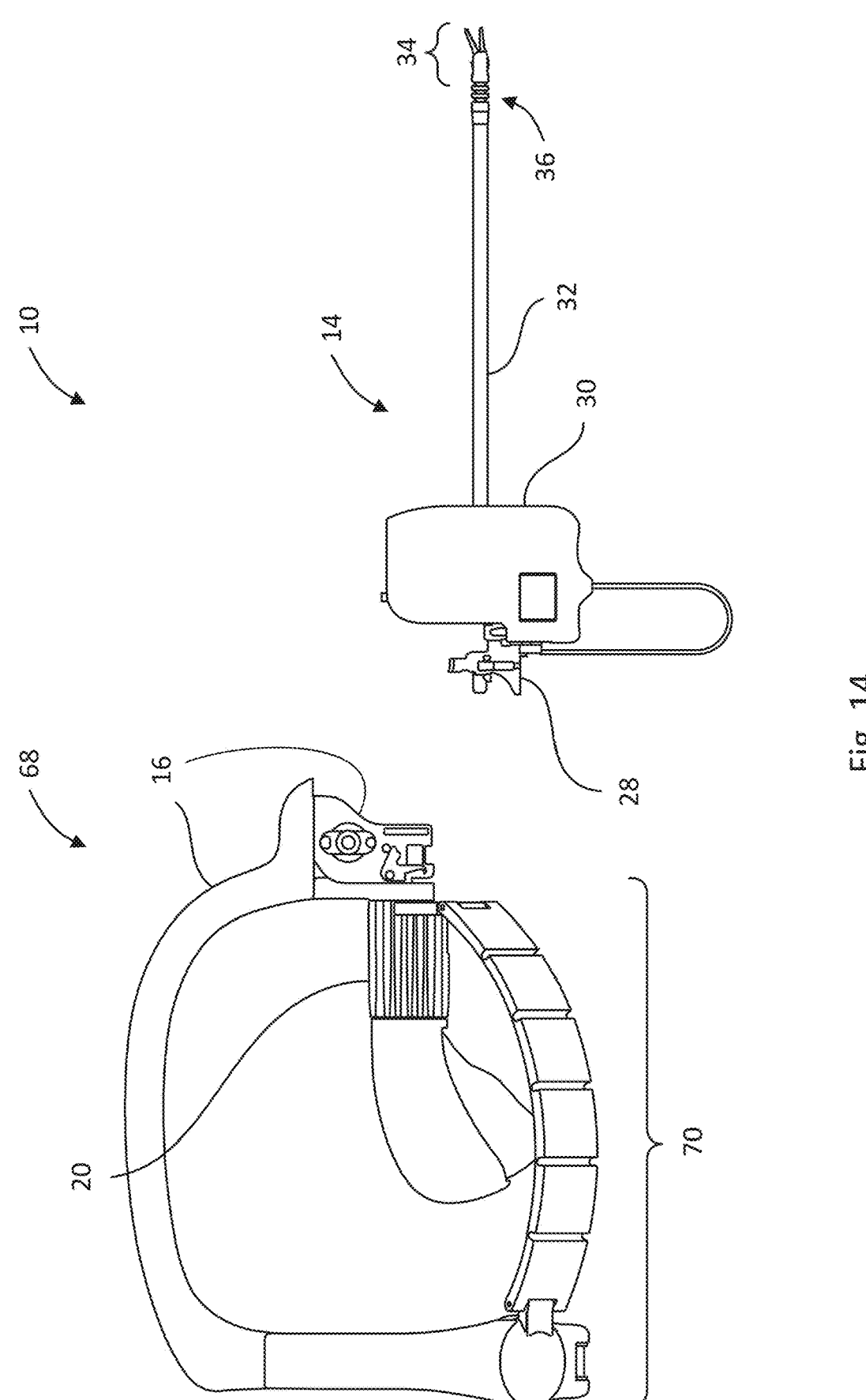
FIG. 14 depicts a tool apparatus including virtual center control unit (VCU) and detachable instrument (DI)

This tool apparatus 10 contains an FSM which may contain four or more bodies. The four bodies are the same as described above. These are namely, frame 16, shaft box 30, conduit box 28, and dial 20. FIG. 14 shows the tool apparatus 10 that consists of these four bodies and maps to tool architectures shown in FIG. 4A (proximal, parallel kinematic input articulation joint) and FIG. 6B (beta configuration). Bodies and their respective interaction elements that are part of the FSM were described in the section above via a schematic representation in FIG. 9. These bodies and respective interaction elements are shown in a physical tool apparatus in further sections.

FIGS. 15A-C show forms of FSM possible in case of the tool apparatus 10 (for various states). This form is one of the many forms that have been covered in the sections above and shown in FIGS. 13A-C. The alignment features and retention features/bodies are presented in detail in sections below.

3.2 Bodies within FSM

Described herein are bodies that are part of the FSM and definitions related to these bodies. These bodies and their respective interaction elements that are part of the FSM were described in the section above via a schematic representation in FIG. 9. These bodies are described as assemblies wherever applicable and respective interaction elements are also described within this section and further in detail in the sections below. While describing the interaction between bodies and interaction elements, the terms "mate," "interact," and "interface" are used interchangeably. A specific case of the interface is a "structural interface" which is defined and described above. Key interaction elements that are covered in this section are as follows: i) alignment features (A), ii) retention features/bodies (R), iii) locks (L), iv) interlocks (I), and v) transmission interfaces (TI).

3.2.1 Frame (F)

FIGS. 16A-D show a frame assembly along with various interaction elements that are housed within the assembly. Frame 16 mates with two other bodies, namely, dial 20 and shaft box 30. It also houses three locks namely, VCU lever 72, dial detent springs 74, and dial lockout plate 76. These locks and their roles are described in the next sections.

Figures 16A, 16B, 16C, 16D:
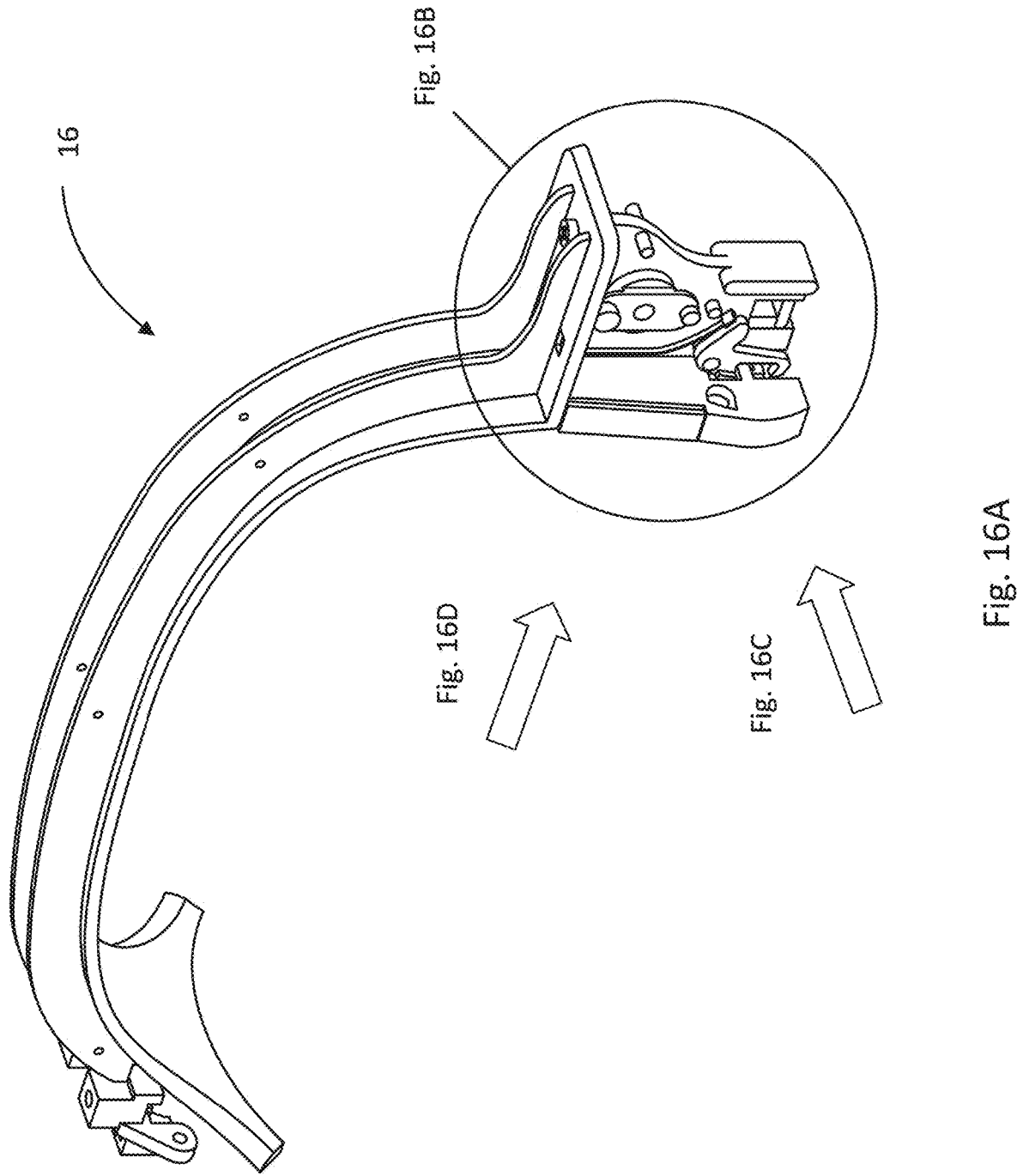
FIGS. 16A-D depict a frame and certain interaction elements.
Figure 16B:
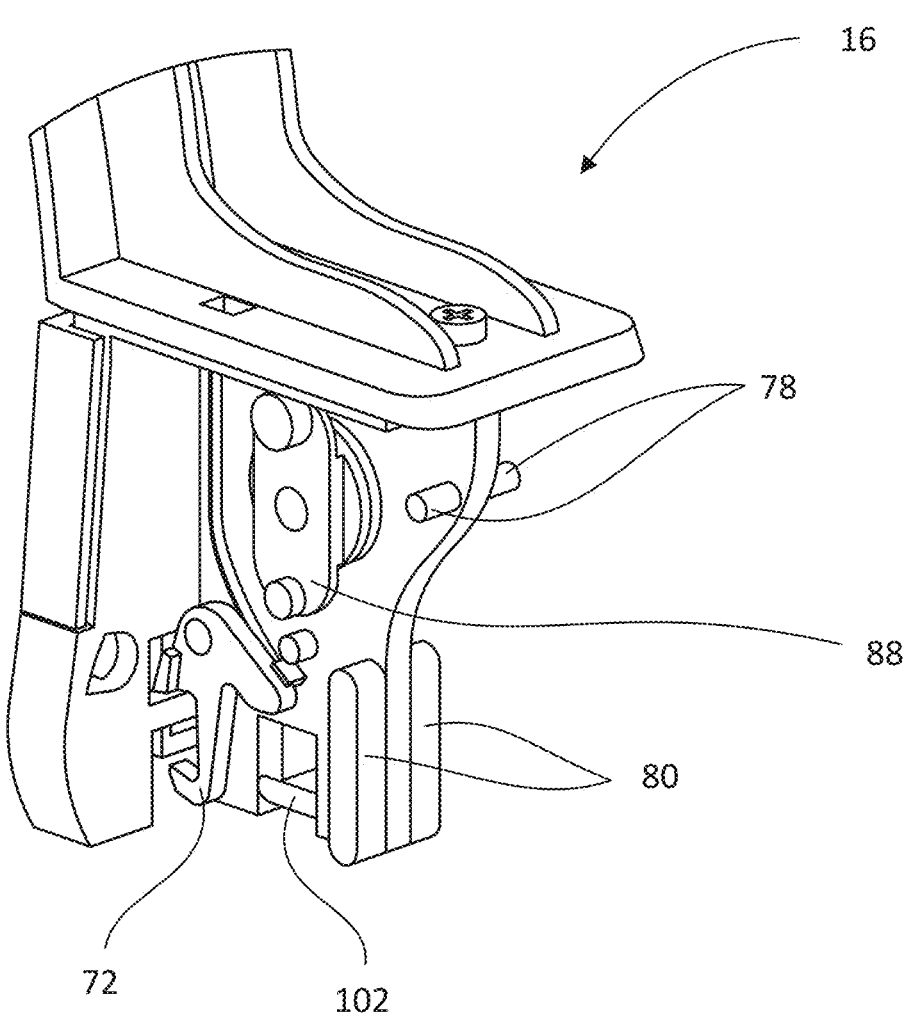
Figure 16C:
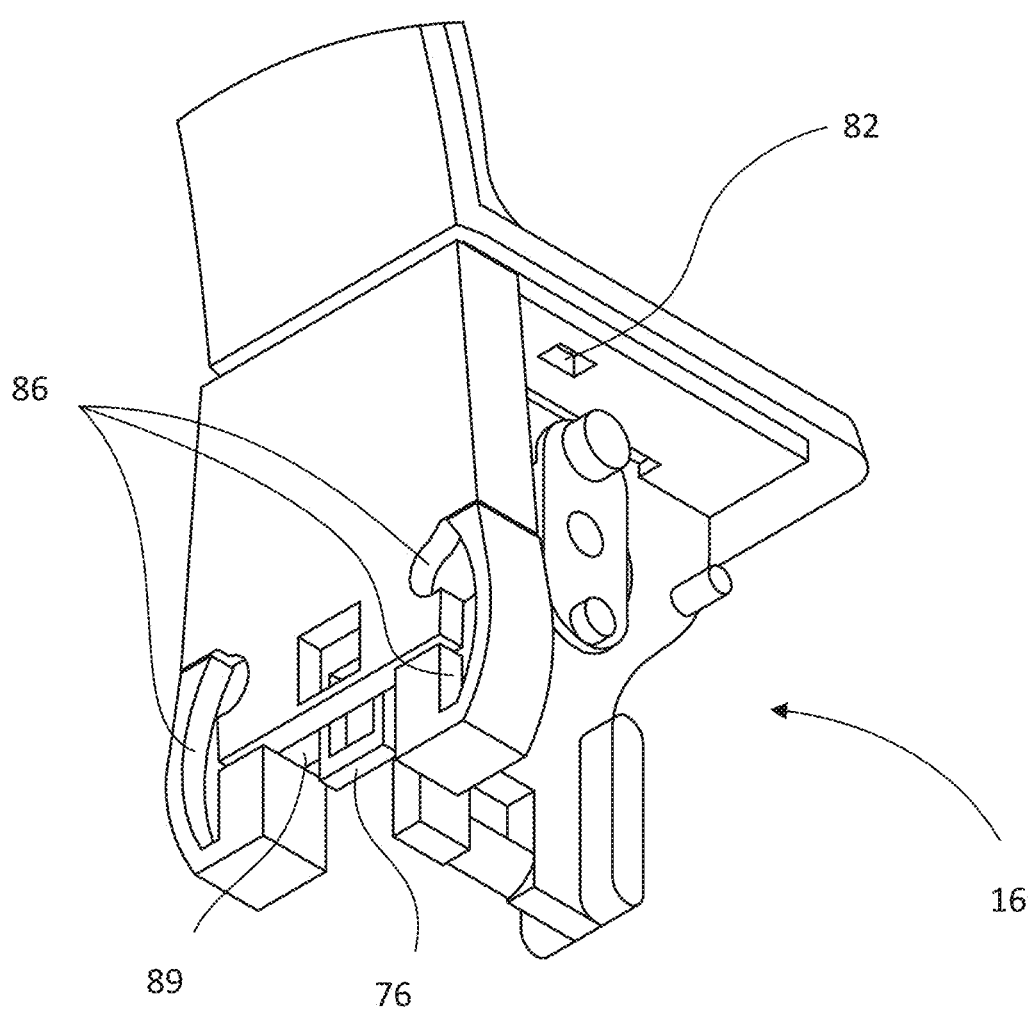
Figure 16D:
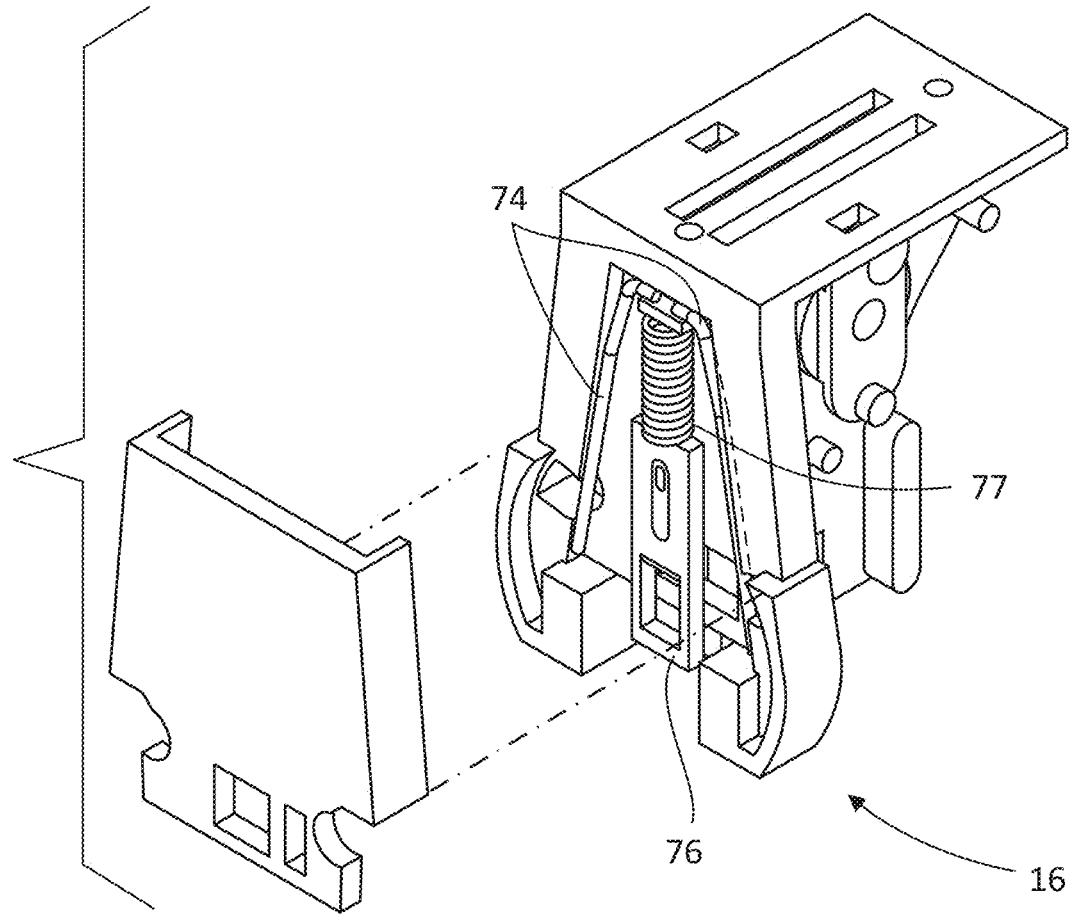

In order for shaft box 30 to install w.r.t. frame 16, frame 16 has alignment features and retention features to hold shaft box 30 relative to frame 16 in a certain state. FIG. 16B shows shaft box guide pins 78 and shaft box guide tabs 80 on frame 16 for aligning shaft box 30 during assembly, and FIG. 16C shows shaft box slots 82 that are used for alignment of shaft box 30 to frame 16 through frame alignment posts 100 on shaft box 30. These alignment features aid with alignment of shaft box 30 along X, +Y, and Z axes directions, and about Θx, Θy, and Θz orientation. In case orientation of axis direction is not specifically mentioned using "+" or "−" signs, both orientations are assumed together. Alignment features on frame 16 that mate w.r.t. shaft box 30 are described in detail in further sections. To retain shaft box 30 along −Y axis as well as to align shaft box 30 along −Y axis direction, frame 16 has a feature termed "button locking face 102" onto which a hook-like feature on shaft box 30 or an independent component housed in the DI assembly sits. To align shaft box 30 w.r.t. frame 16 along +Y axis direction, there is a shaft box hard stop surface 89 on frame 16. In further sections, button 90, which is a lock that is part of the DI assembly, is described to have a hook-like feature which mates with the button locking face 102 on frame 16.

Similarly, dial 20 has alignment and retention features. Dial 20 is aligned w.r.t. frame 16 via dial alignment faces 86 shown in FIG. 16C. These faces interface with mating features on dial 20 and provide alignment along the Y and Z axes directions and about Θx, Θy, and Θz orientations. Dial 20 is retained w.r.t. frame 16 via a lock namely, dial lockout plate (DLP) 76. DLP 76 is a positive engagement, non-back drivable lock. Dial lockout plate 76 locks onto a hook-like feature on dial 20 and is spring loaded by dial lockout plate spring 77 to apply pressure on the hook-like feature on dial 20. This helps retain dial 20 along −X axis direction which is the direction in which dial 20 is pulled during use (as described in further sections). Also, dial detent springs (DDS) 74 are housed within the frame assembly which act as another lock and retain dial 20 along X axis direction. DDS 74 is a positive engagement, back-drivable lock. This is an additional lock that exists between dial 20 and frame 16. This may also be referred as "temporary lock" throughout the description due to the temporary nature of this lock based on how various states are configured. FIG. 16D shows the location of dial detent springs 74 which are housed in frame 16. Frame 16 also houses VCU lever 72, which acts as a lock and an interlock as described in further sections in detail. VCU lever 72 rotates about an axis parallel to Z axis and is spring loaded. The spring which interfaces with VCU lever 72 is also housed in frame 16. Frame 16 also houses VCU distal articulation pulleys 88 that consist of transmission interfaces that mate with corresponding DI articulation pulleys to transmit articulation from the proximal end (input end) to the distal end (output end) of the device.

3.2.2 Shaft Box (SB)

In this section, shaft box 30 and interaction elements associated with shaft box 30 are described. Shaft box 30 has two halves, "Shaft Box LH 31" (left hand) and "Shaft Box RH 33" (right hand). For the sake of simplicity, shaft box LH

31 and shaft box RH 33 are mentioned collectively as shaft box 30. Wherever specific features on shaft box LH 31 or shaft box RH 33 are mentioned, "shaft box LH 31"/"SB LH 31" or "shaft box RH 33"/"SB RH 33" terms will be used respectively. Shaft box LH 31 and RH 33 interface with structural bodies, namely, frame 16 and conduit box 28. Shaft box LH 31 and RH 33 house two locks namely, button (B) 90 and conduit box lockout plate (CBLP) 92. It also houses shaft box articulation pulleys 94 which interfaces with VCU distal articulation pulleys 88 to transmit articulation from the proximal end to the distal end of the apparatus/instrument.

Figure 17A:
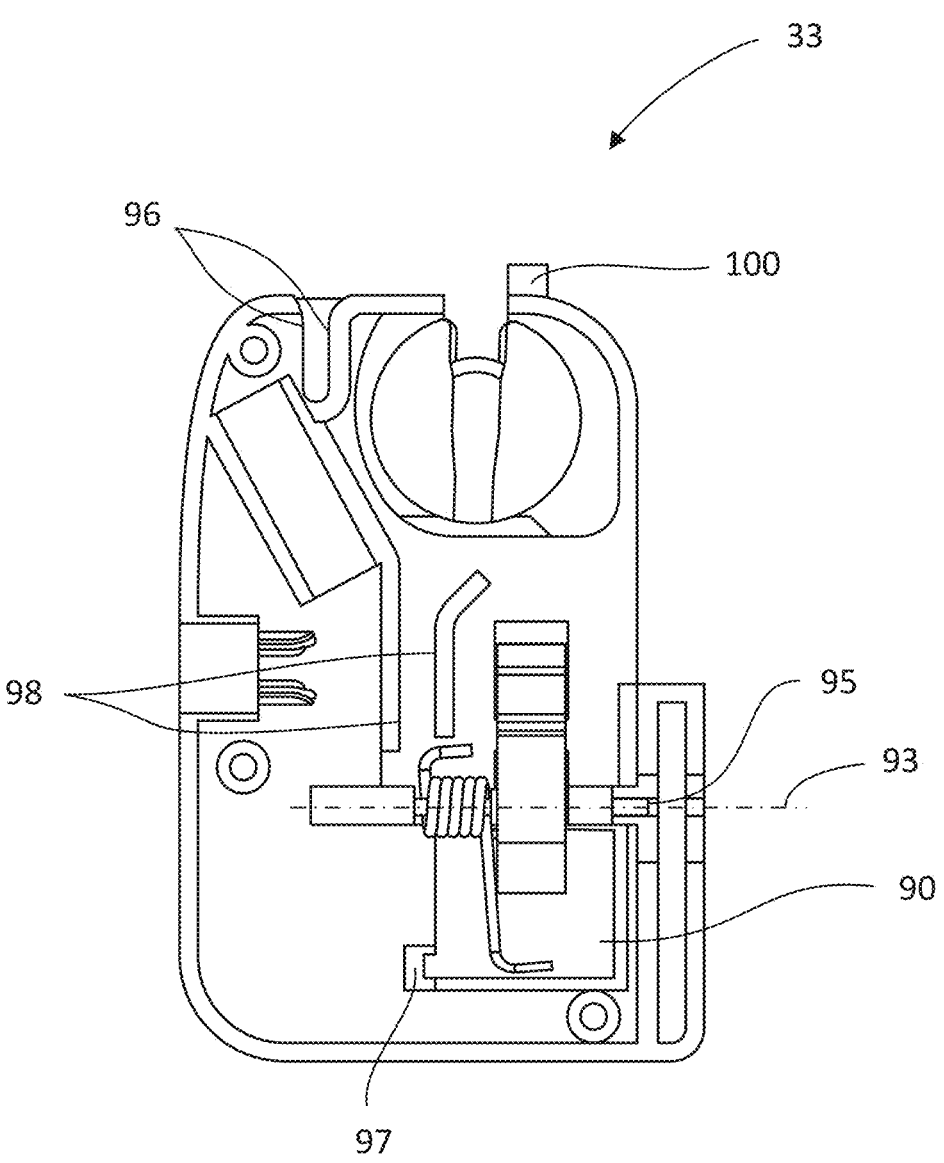
FIGS. 17A-B depict a shaft box (SB) right-hand (RH) side and certain interaction elements.
Figure 17B:
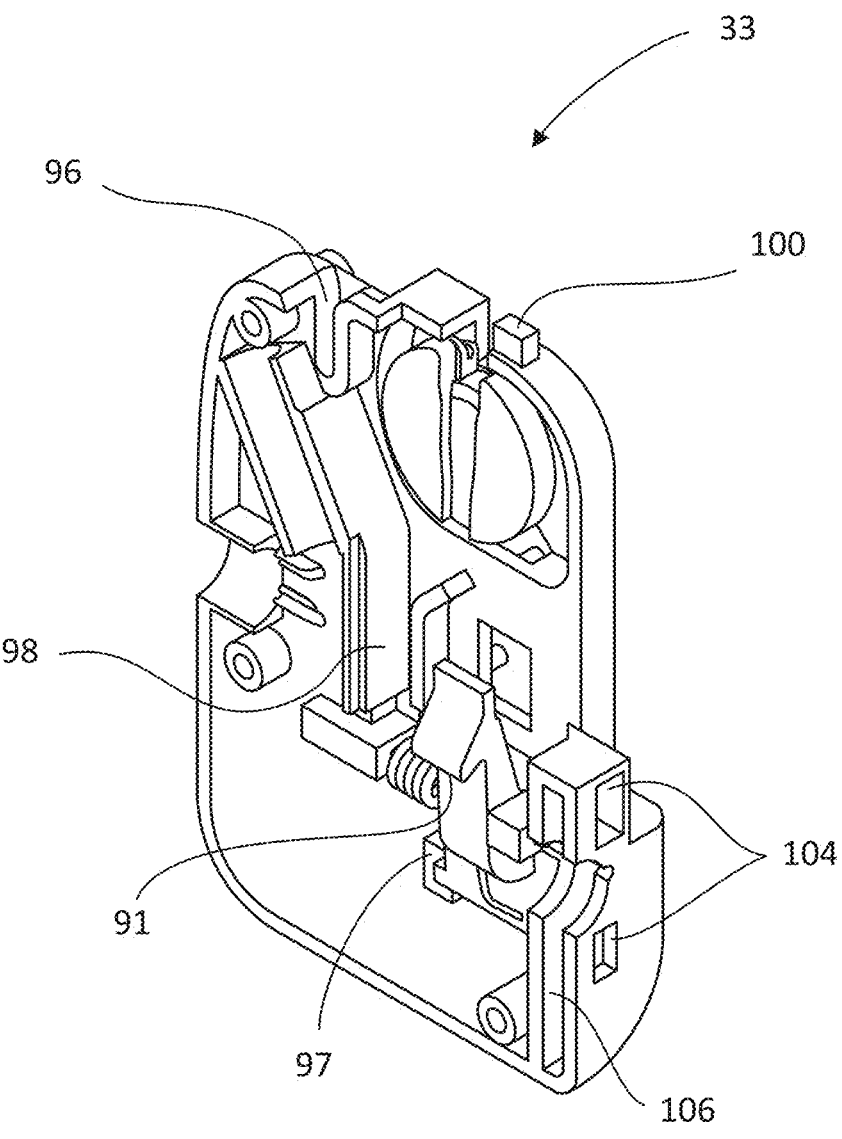
Figure 18:
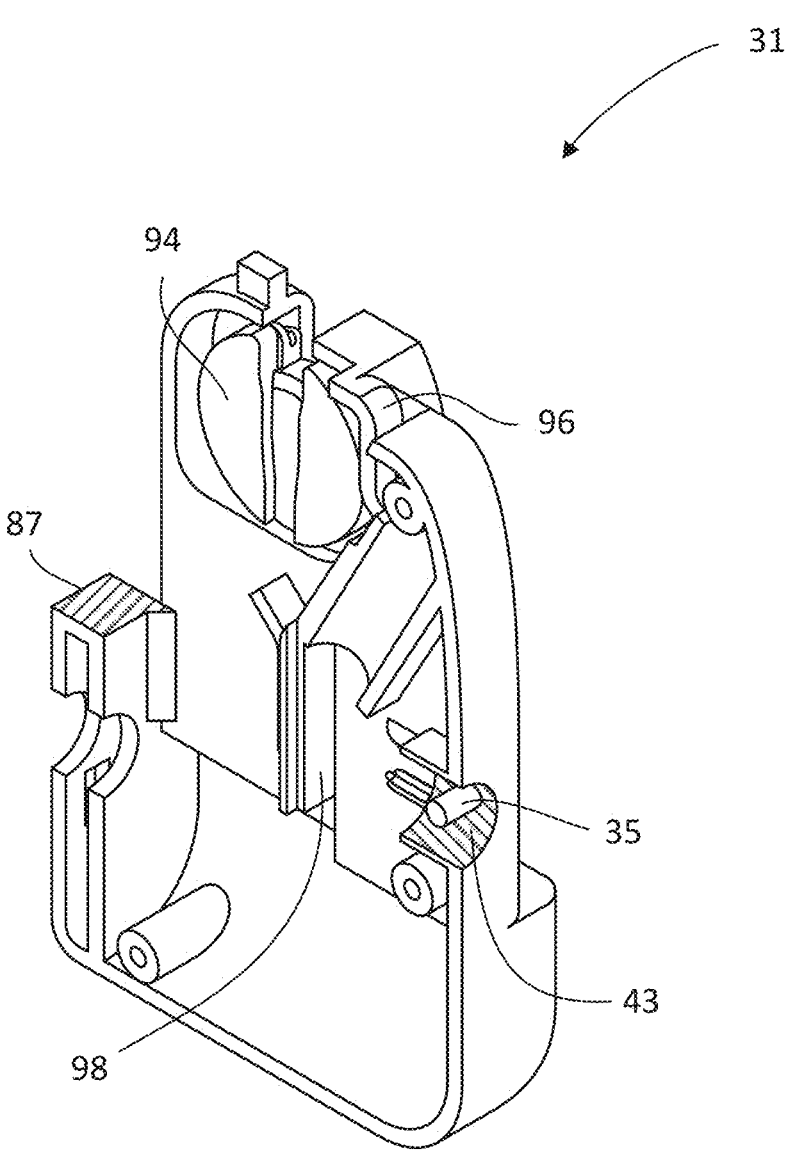
FIG. 18 depicts shaft box left-hand (LH) side and certain interaction elements.

Features on shaft box 30 that mate w.r.t. frame 16 are shown in FIGS. 17A-B (SB RH) and FIG. 18 (SB LH). Upper alignment channels 96, lower alignment channels 98, and frame alignment posts 100 are the alignment features which provide alignment between SB LH/RH and frame 16. These alignment channels exist on both SB LH and SB RH but may exist only on one of the SB LH 31 or SB RH 33 considering the impact of manufacturing, assembly, and part tolerance variation on the effectiveness of positional alignment. There is also a frame 16 Y axis hard stop surface 87 that contacts the corresponding shaft box 30 hard stop surface 89 on frame 16. These features provide alignment along X, +Y, and Z axis direction, and about Θx, Θy, and Θz orientation. SB RH houses the lock named button 90. Button 90 is a lock and aids in the retention of shaft box assembly 30 to frame 16 (distal portion) along −Y axis direction. Button 90 mates w.r.t. the frame 16 by interfacing with button locking face 102 shown in FIG. 16B. Button 90 has a hook-like feature 91 which interfaces with button locking face 102. Button 90 is also spring loaded so that it can interface with the button locking face 102 and help in the retention of SB 30 onto frame 16. Button 90 rotates about button pivot axis 93 and is also aligned and retained within SB RH by button pin 95 and button hard stop surface 97, as shown in FIG. 17A.

SB 30 also interfaces with conduit box 28. Conduit box 28 is aligned w.r.t. SB 30 via conduit box alignment pockets 104 present on both SB LH and SB RH. These pockets align conduit box 28 w.r.t. SB 30 along X, Y, and Z axis direction, and about Θx, Θy, and Θz orientation. The effectiveness of these alignment features is defined based on functional requirement and capability to manufacture alignment features that constrain all 6 DoFs. There exists a lock, namely conduit box lockout plate (CBLP) 92, which is described in a later section in more detail. CBLP 92 helps retain conduit box 28 such that it cannot be pulled along −X axis direction. CBLP 92 is also spring loaded such that it always applies pressure on the mating feature on conduit box 28 and keeps it retained w.r.t. conduit box 28. SB LH and SB RH has conduit box lockout plate alignment pockets 106 which prevent mis-alignment of CBLP 92 which may impact its ability to lock conduit box 28. This way, CBLP 92 remains positioned to lock onto conduit box 28 and retain it w.r.t. SB 30.

Figure 19A:
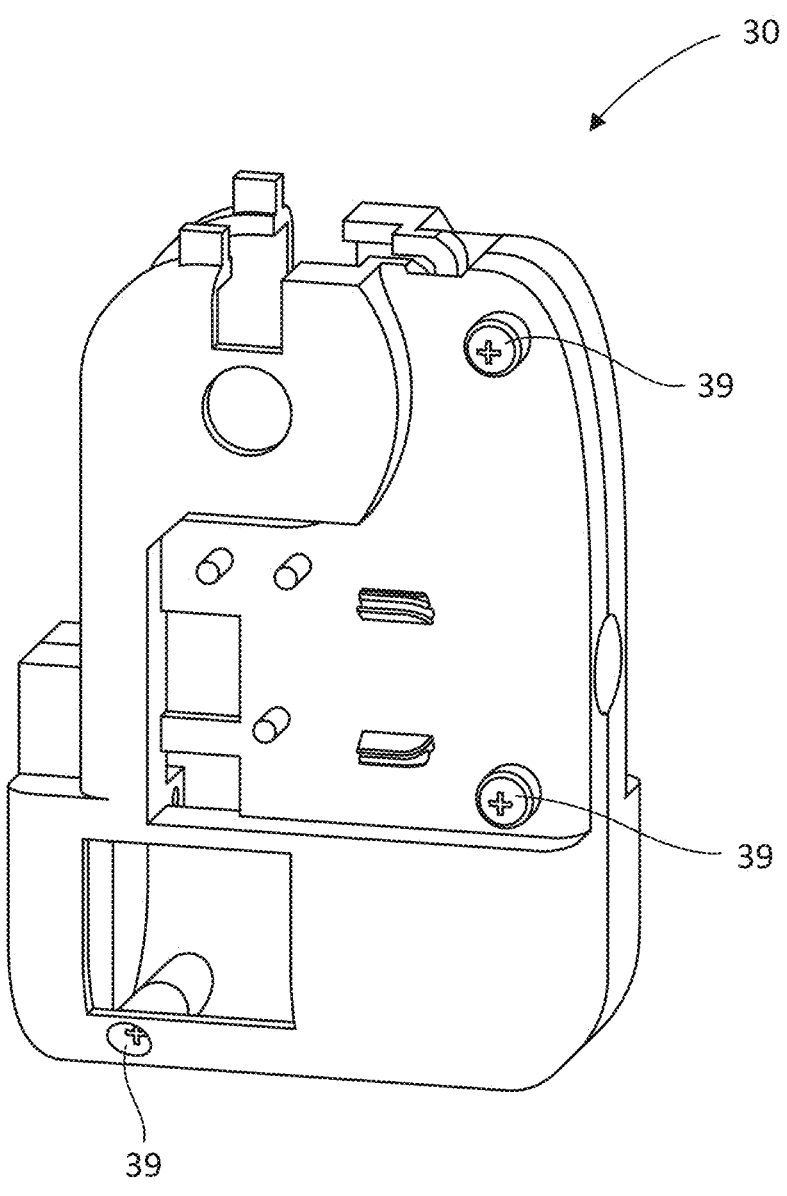
FIGS. 19A-B depict shaft box LH and RH assembly.
Figure 19B:
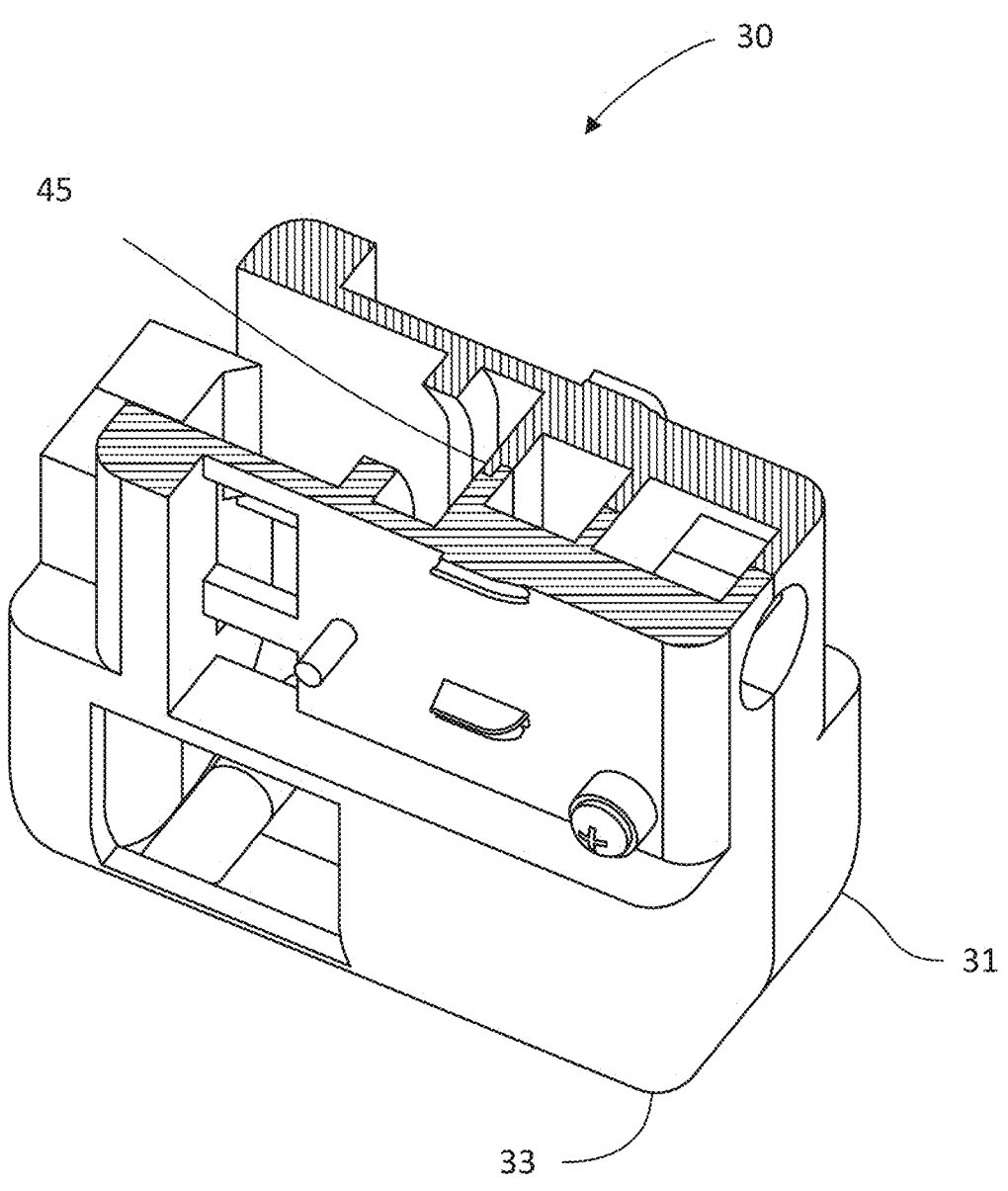

There also exists a shaft 32 alignment surface 43 on SB LH, as shown in FIG. 18. Shaft 32 is aligned by shaft alignment pin 35 and is retained using a clamp that is rigidly attached to SB LH while sandwiching shaft 32 between the clamp and SB LH. FIGS. 19A-B show shaft box assembly 30 consisting of SB LH 31 and SB RH 33 joined together by screws 39, with shaft box lap joint 45 for better alignment.

3.2.3 Conduit Box (CB)

Conduit box 28 is a body which mates/interfaces with shaft box 30 in a certain state (storage state) and mates with dial 20 in another state (assembled and use state). FIGS.

20A-B show alignment and retention features on conduit box 28 that help with the aforementioned mating.

Figure 20A:
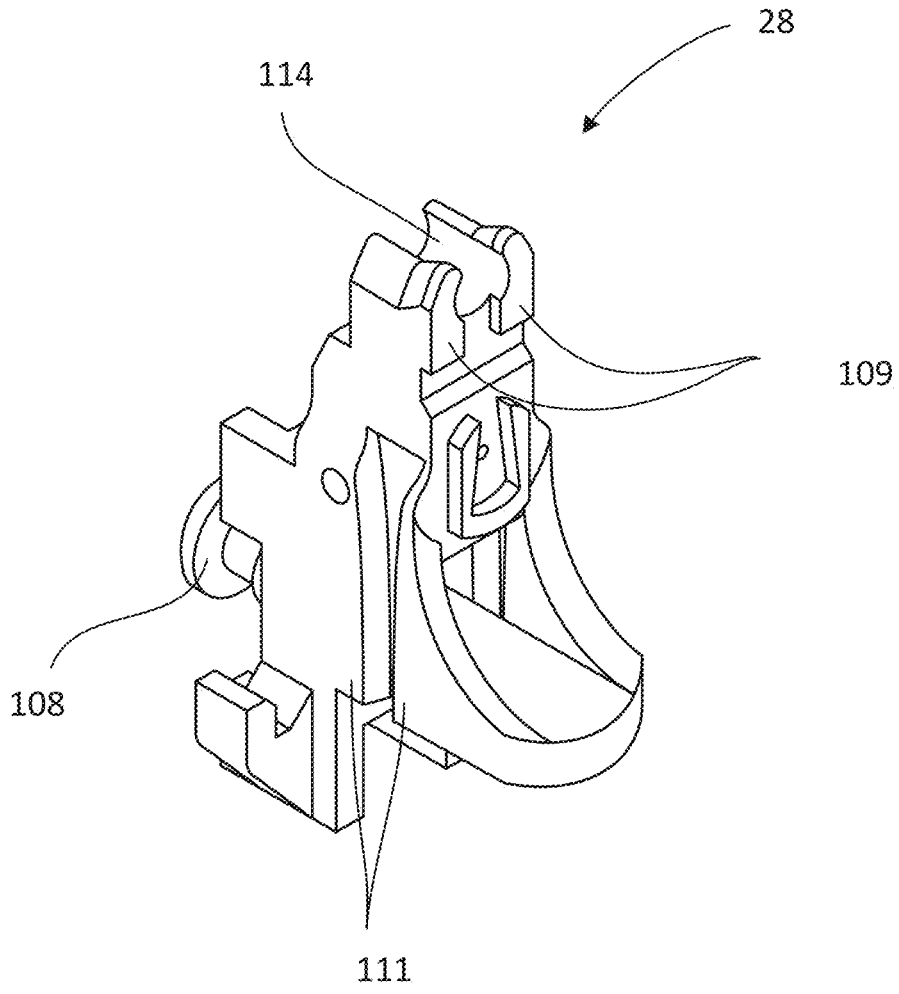
FIGS. 20A-B depict a conduit box (CB) and certain interaction elements.
Figure 20B:
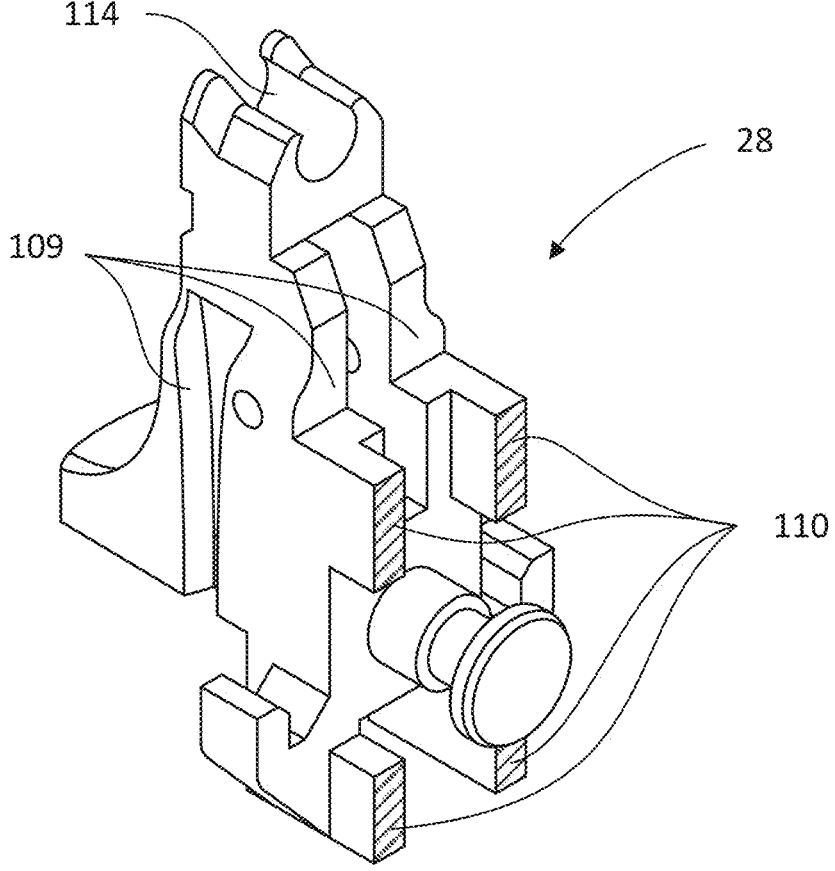

FIG. 20A shows conduit box lockout plate retention and lock interface 108 which is a feature that can be described as a flanged shaft. The inner surface portion of the flange as well as the periphery of flanged shaft interfaces with the CBLP 92 and can lock CBLP 92 in certain configurations. FIG. 20B shows features called alignment tabs 110 that interface with conduit box alignment pockets 104 to align conduit box 28 w.r.t. SB LH 31 and SB RH 33 along +X axis direction.

As mentioned before, CB 28 also aligns with dial 20 in certain system states such that all 6 DoFs are constrained and CB 28 is retained along −Y axis direction. FIGS. 20A-B show alignment features that align CB 28 w.r.t. dial 20 along X, +Y, and Z axis direction and about Θx, Θy, and Θz orientation. CB 28 is aligned and retained w.r.t. dial 20 by conduit box lockout shaft (CBLS) 112 which interfaces with the "lockout shaft interface" 114 shown in FIG. 20B. There are X axis Dial interface alignment faces 109 and Z axis Dial interface alignment faces 111.

A conduit box assembly may house bodies that assist with jaw closure transmission. These bodies will be discussed further in sections below (e.g., crimp housing).

3.2.4 Dial (D)

Dial 20 is a body which interfaces with frame 16, conduit box 28, and shuttle 116. In the above sections about frame 16 and conduit box 28, interfaces of each structural member w.r.t. dial 20 have been described. FIGS. 21A-G show various alignment features, retention features, and two interlocks (that are housed in dial 20) namely, conduit box lockout shaft (CBLS) 112 and shuttle lockout spring (SLS) 118. Like SB LH and SB RH, dial 20 contains two halves namely, "Dial LH 21" and "Dial RH 23." For the sake of simplicity, "Dial LH 21" and "Dial RH 23" will be called as dial. In case specific features on LH and RH portions need to be referenced, "Dial LH 21" and "Dial RH 23" terms are used.

Figure 21A:
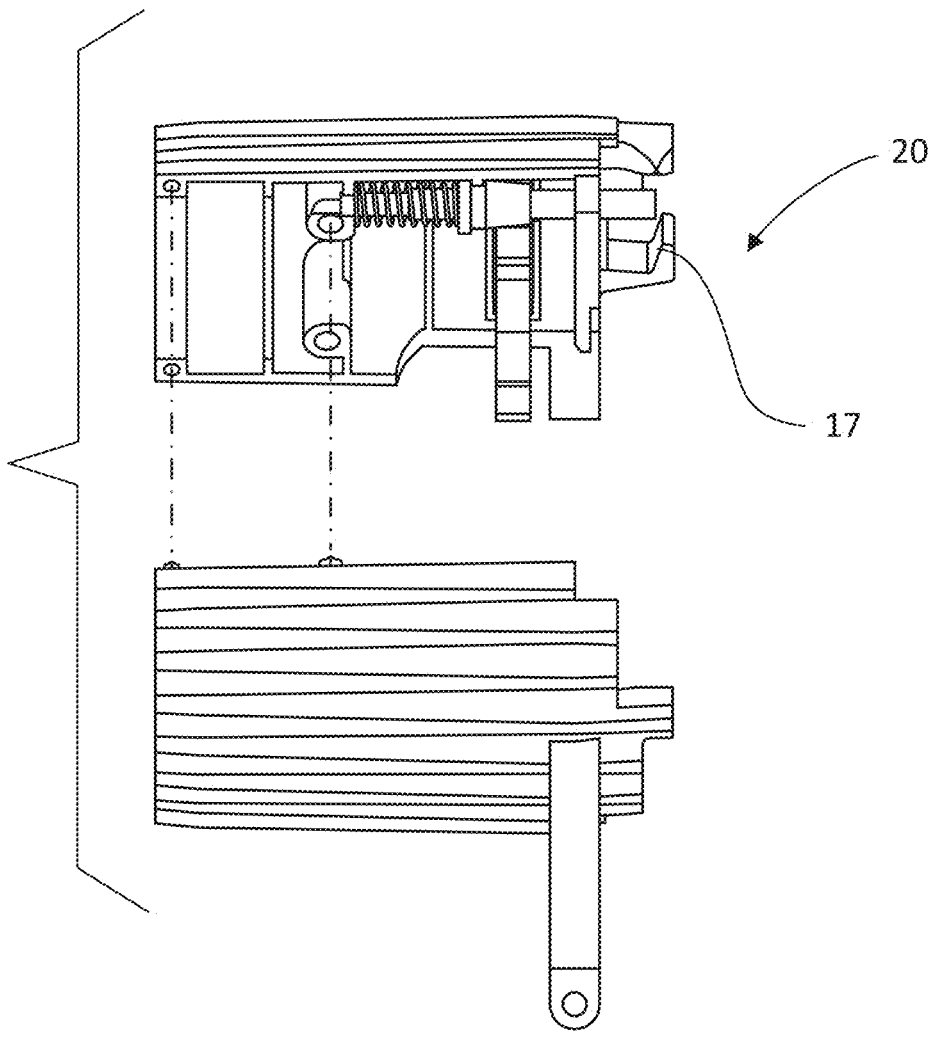
FIGS. 21A-G depict a dial and certain interaction elements.

Dial 20 interfaces with frame 16 such that it aligns to frame 16 and is retained along −X axis direction w.r.t. frame 16 (see "dial lockout plate interface/hook 17" shown in FIG. 21A). FIG. 21C shows dial features named "dial alignment posts 19" that align with corresponding features on frame 16 shown in FIG. 16C. There also exist surfaces named "frame hardstops 25" that act as alignment features along +X direction for dial 20 w.r.t. frame 16. Dial 20 is retained w.r.t. frame 16 along −X axis direction via dial lockout plate interface which mates with dial lockout plate 76 (housed in the frame 16).

Figure 21B:
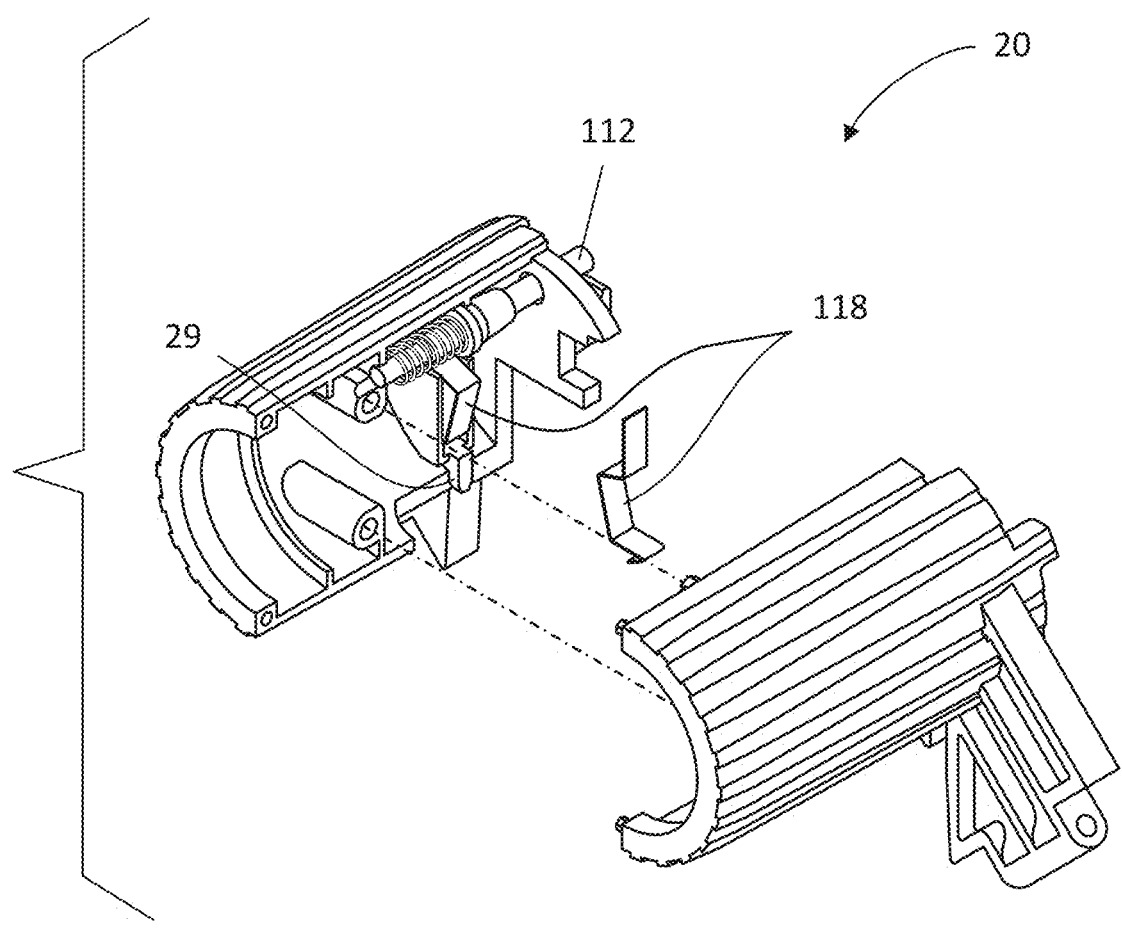
Figure 21C:
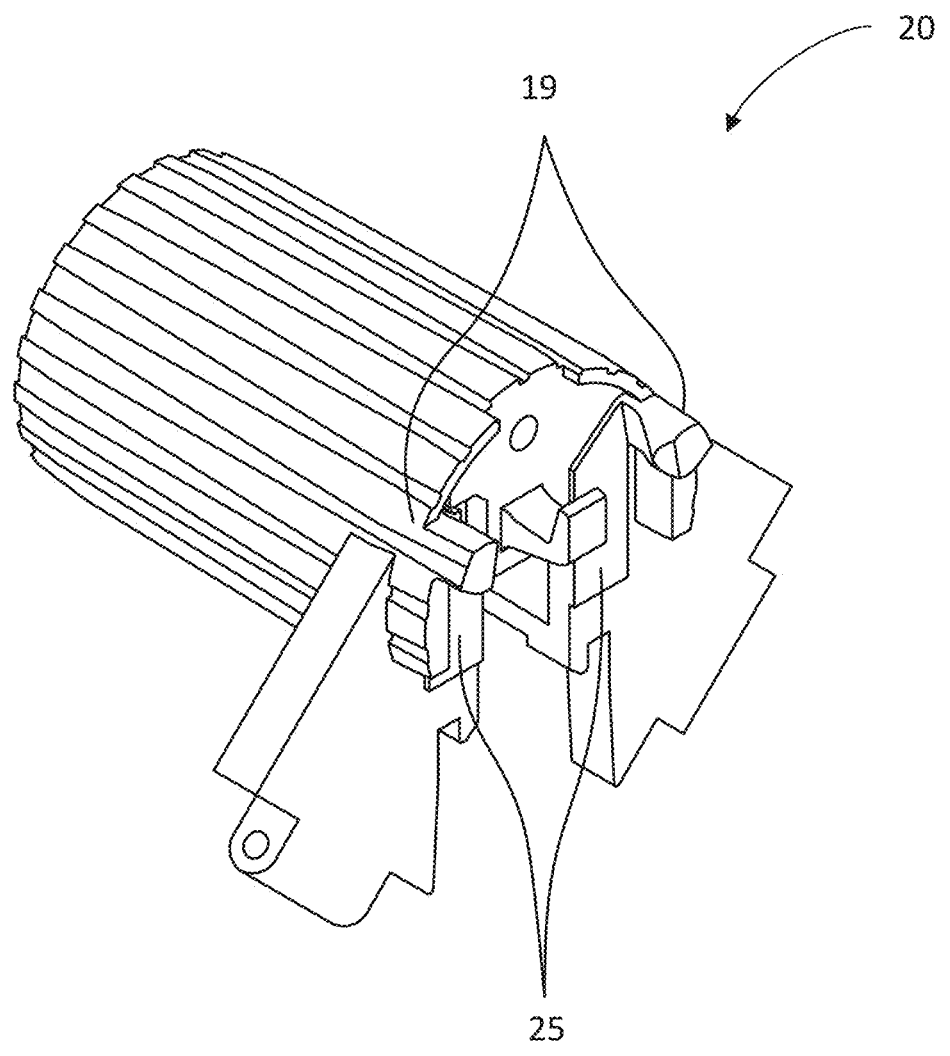

FIG. 21B shows conduit box X axis direction alignment feature 29 present on dial 20 which interface with corresponding "X axis dial interface features 109" on conduit box 28 shown in FIG. 20B. FIG. 21B also shows conduit box lockout shaft (CBLS) 112 which interfaces with a corresponding feature on conduit box 28 shown in FIG. 20A.

Figure 21D:
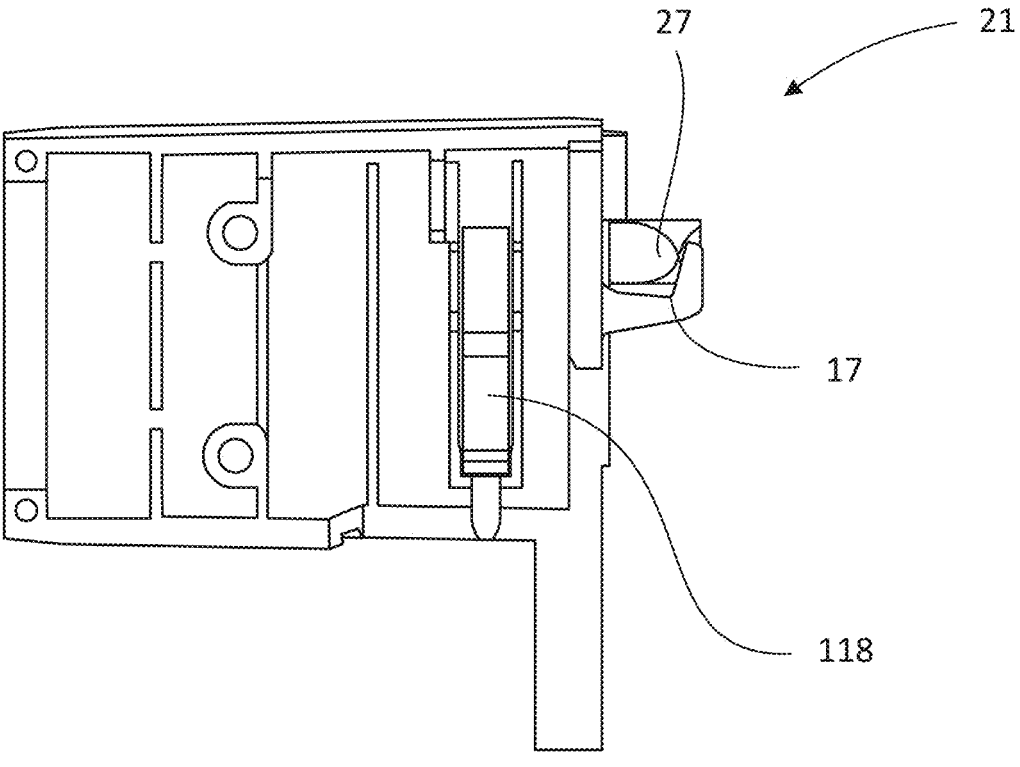
Figure 21E:
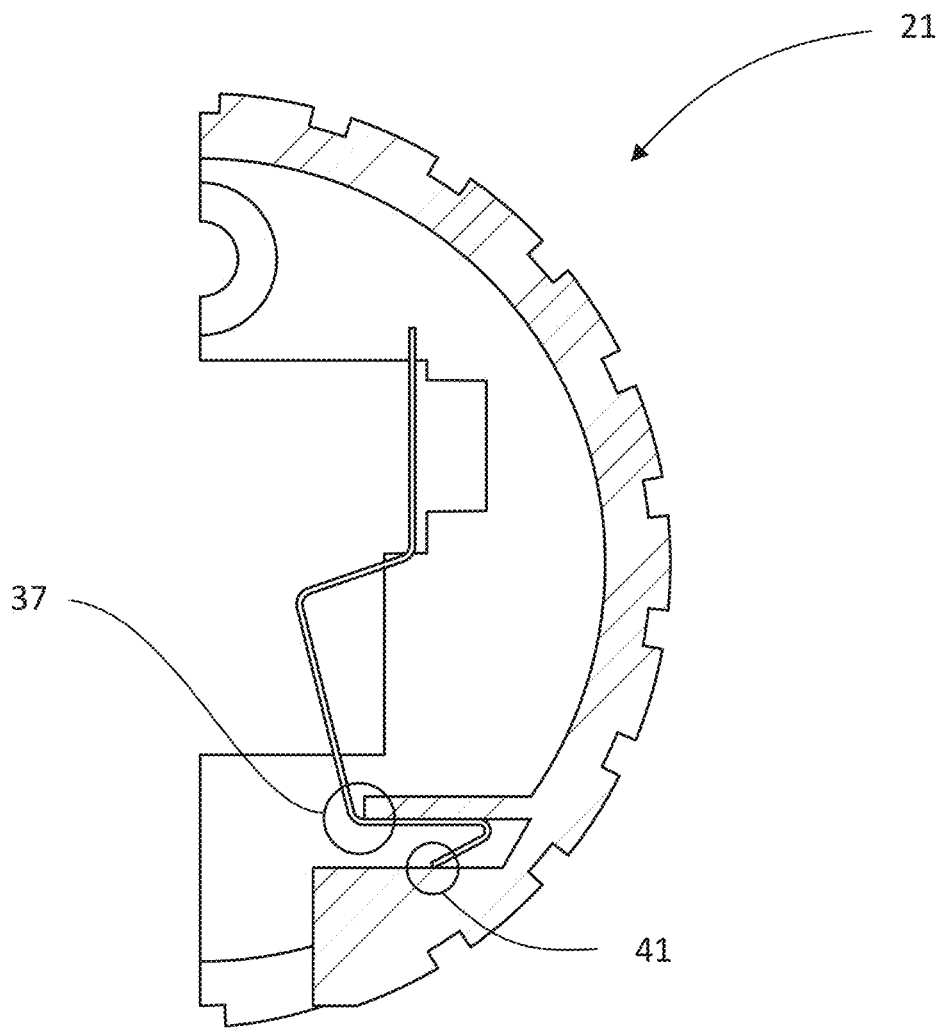
Figure 21F:
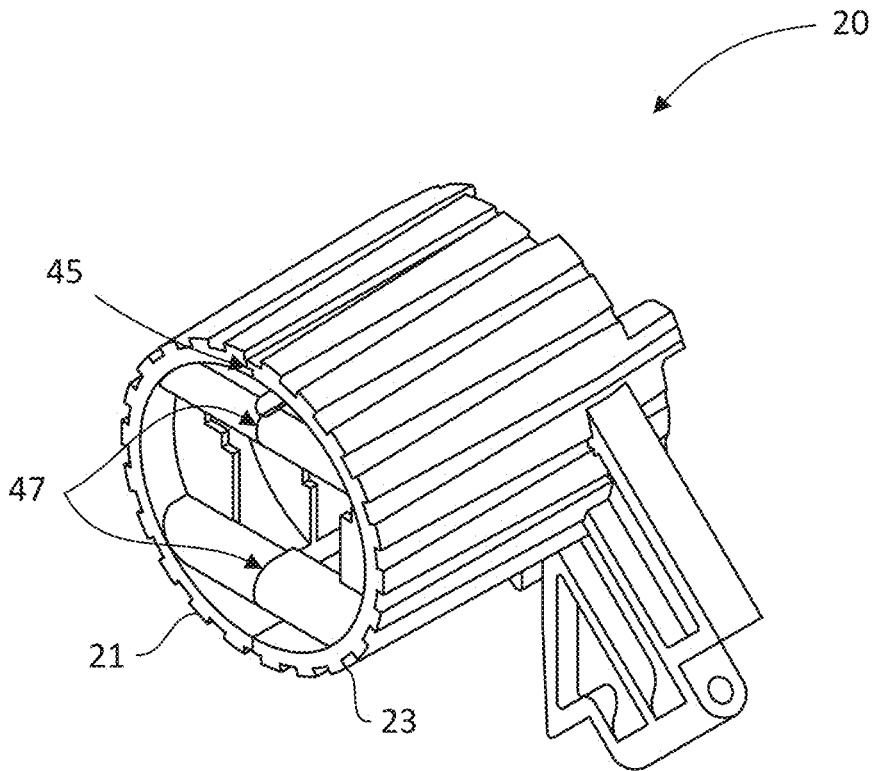
Figure 21G:
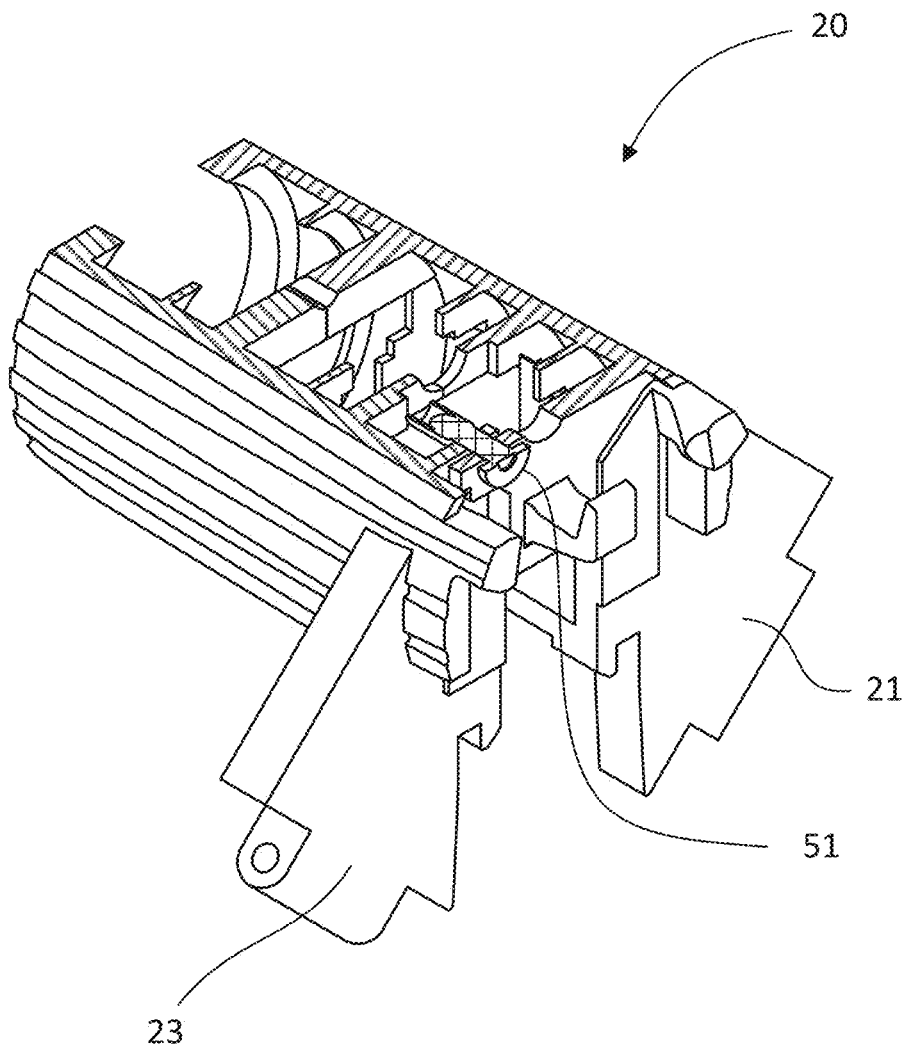

FIG. 21E shows shuttle lockout spring Z alignment feature 37 on dial 20 which helps align shuttle lockout spring (SLS) 118 w.r.t. dial 20. Also shown is shuttle lockout spring 118 retention feature 41 which helps retain shuttle lockout spring 118 in a pocket shown in FIG. 21E. FIGS. 21F-G represents dial assembly 20 in which dial LH 21 and dial RH 23 are shown as part of the dial assembly joined by dial press fit joint 47 and dial lap joint 45 for part alignment, with dial rivet 51 securing the halves together.

3.2.5 Shuttle (SH)

Figure 22A:
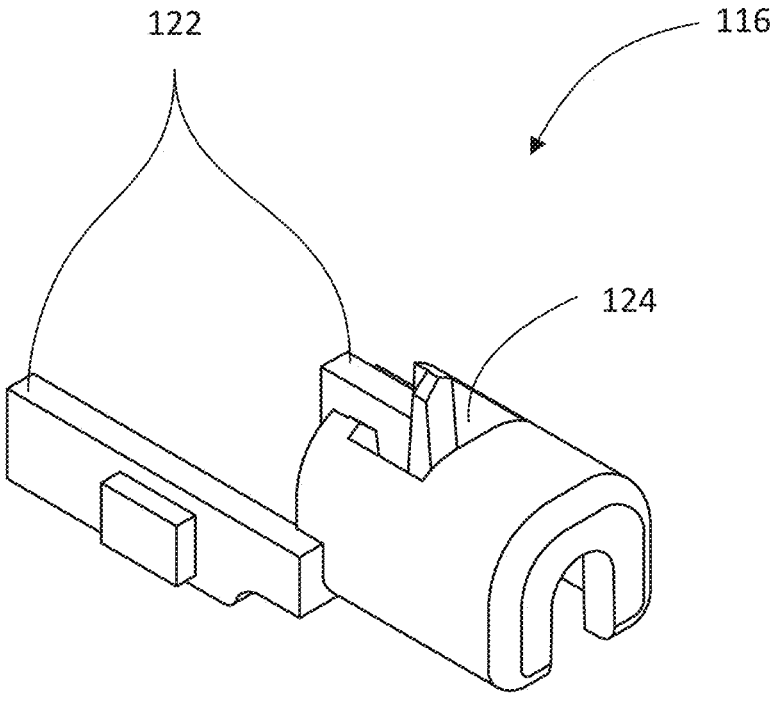
FIGS. 22A-C depict a shuttle and certain interaction elements.
Figure 22B:
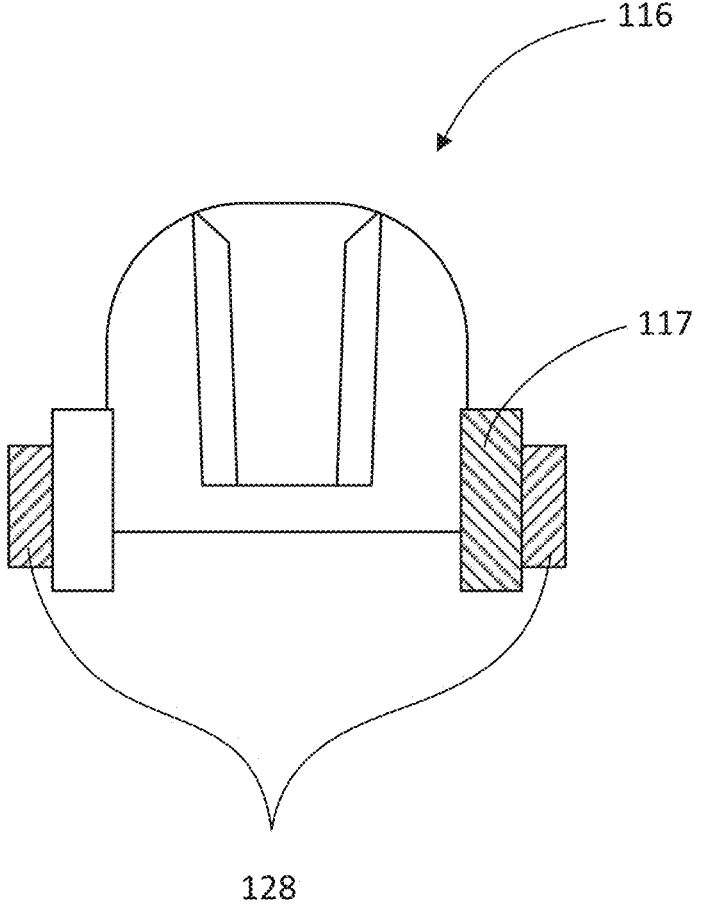
Figure 22C:
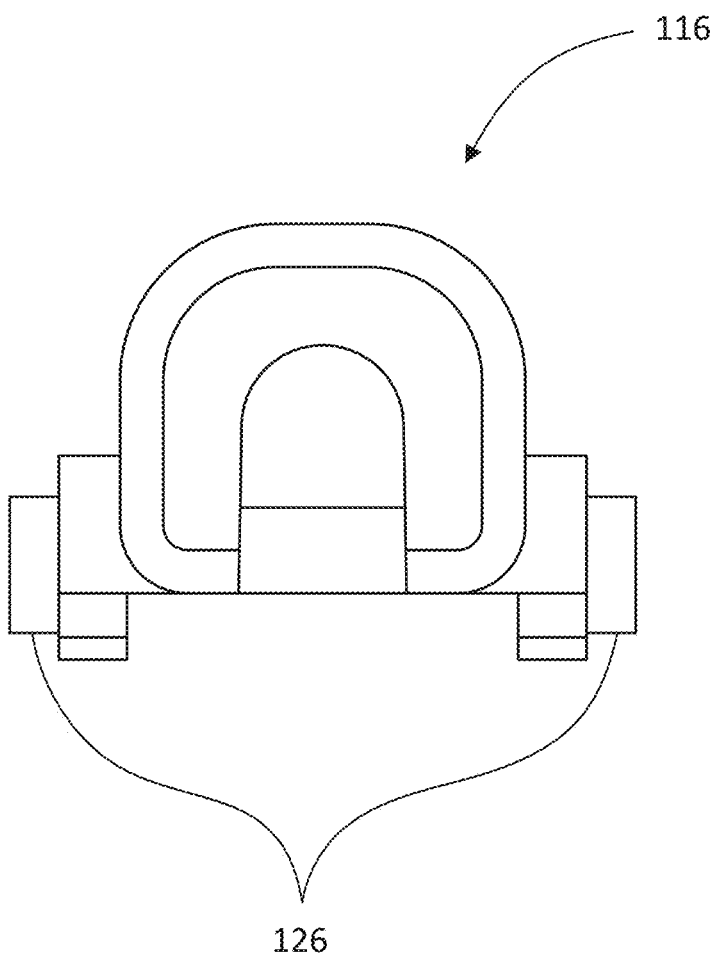

Shuttle 116 is a body that interfaces with other bodies, namely, dial 20 and cable crimp housing 120. Shuttle 116 has a translation DoF w.r.t. dial 20 along the dial roll axis (axis 1) direction and a rotational DoC w.r.t. dial 20 about the dial roll axis (axis 1). Therefore, shuttle 116 can translate back and forth within the dial assembly. Shuttle 116 also interacts with two locks namely, shuttle lockout spring 118 and VCU lever 72. Additionally, VCU Lever 72 is also an interlock and is described in further sections. FIGS. 22A-C show shuttle 116 and interaction elements associated with it.

FIG. 22A shows "guide tabs" alignment features 122 on shuttle 116 that help it align w.r.t. dial 20. Shuttle 116 also interfaces with crimp housing 120 which is described in detail in sections below. FIG. 22A shows a transmission interface pocket 124 where crimp housing 120 sits. Translation of shuttle 116 within dial 20 along negative axis 1 direction is constricted by shuttle lockout springs 118. Shuttle lockout springs 118 interface with two tabs 126 on shuttle 116 shown in FIG. 22C, specifically the alignment "shuttle lockout spring hard stops 128". These springs lock the shuttle 116 and prevent it from moving along negative (−) dial roll axis direction. These springs, as shown in sections below, are switched from locked state to unlocked state by conduit box 28 while it enters the dial 20. FIG. 22B also shows a transmission interface feature 117 on shuttle 116 that interacts with VCU lever 72. This shuttle-VCU lever interface 117 is described in detail in sections below.

3.2.6 Cable Crimp Housing (CH)

Figure 23:
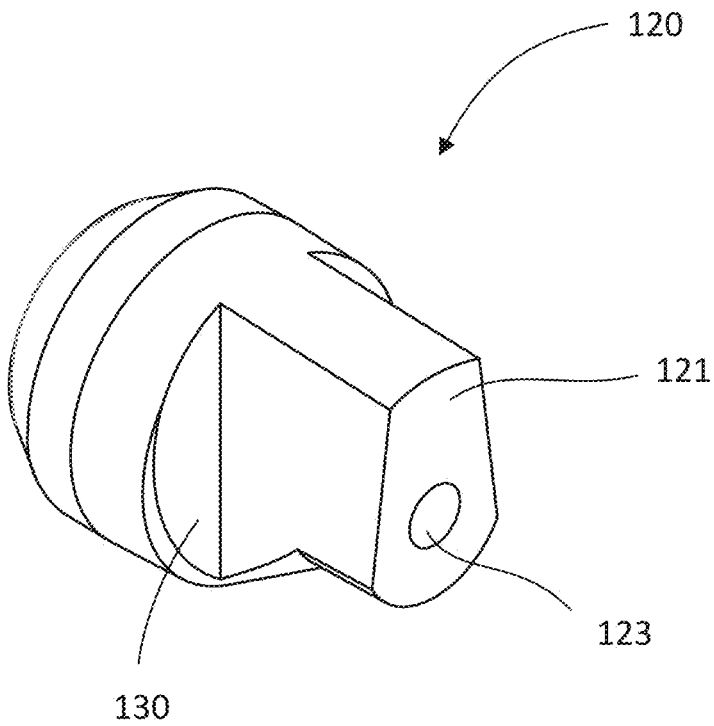
FIG. 23 depicts a cable crimp housing and certain interaction elements.
Figure 24A:
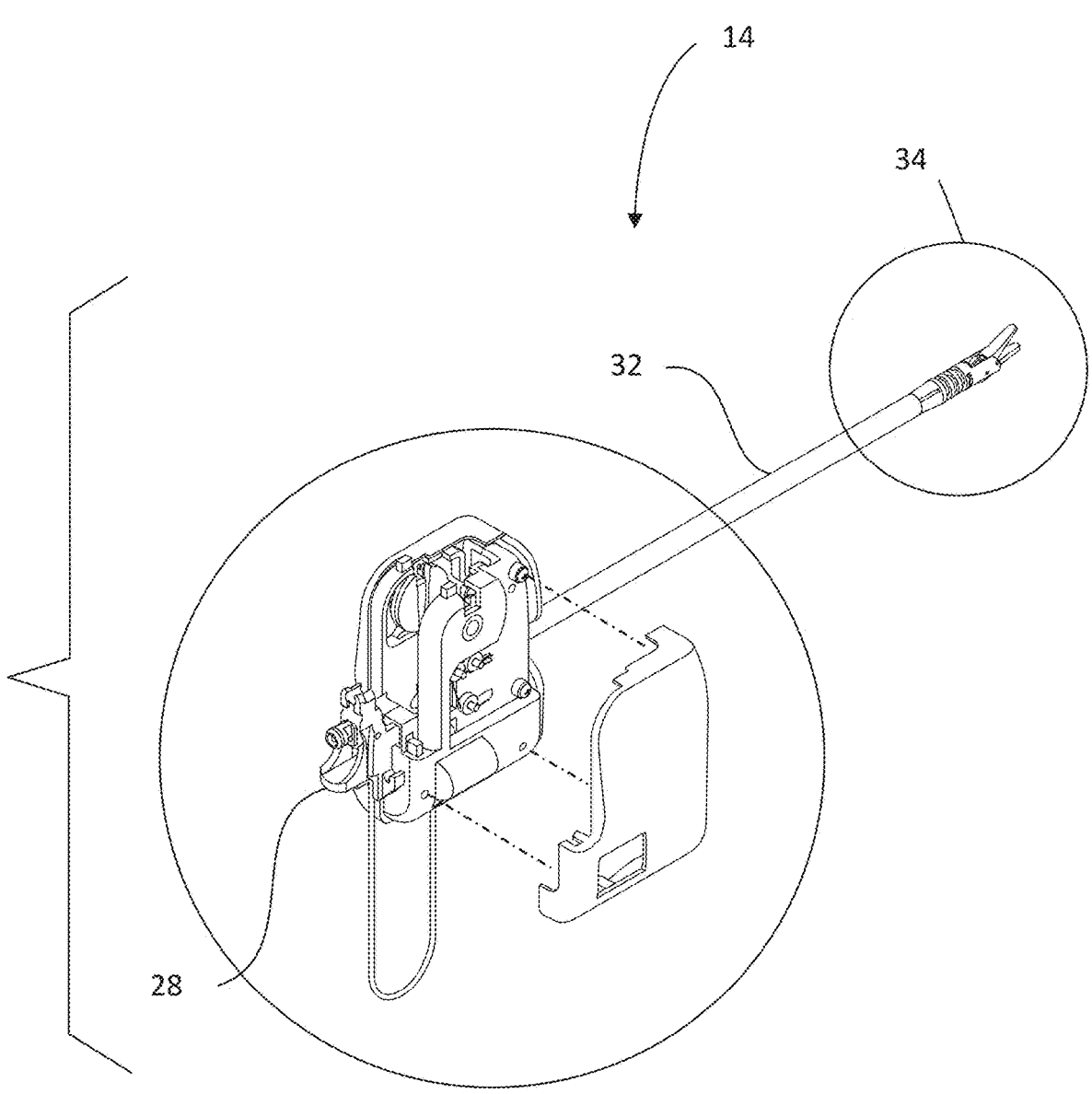
FIGS. 24A-D depict DI consisting of bodies and certain interaction elements.
Figure 24B:
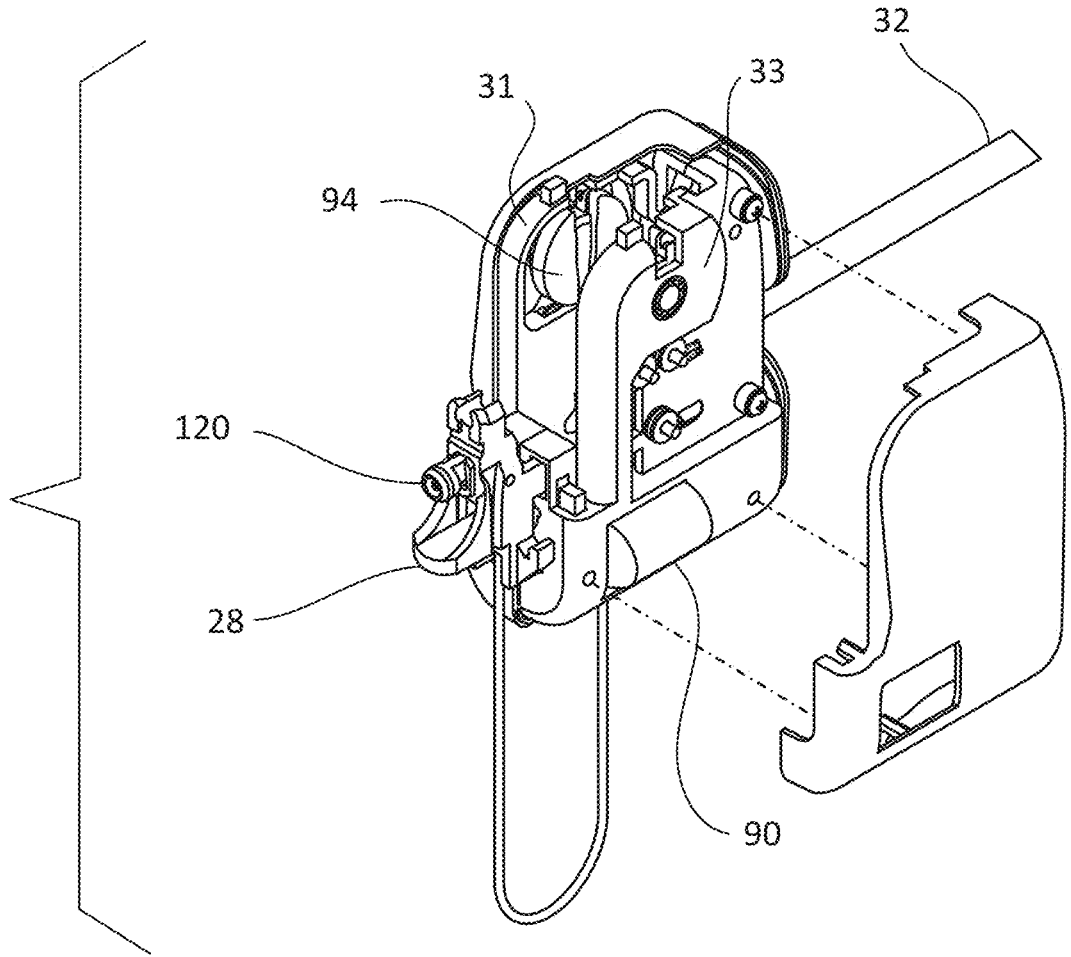
Figure 24C:
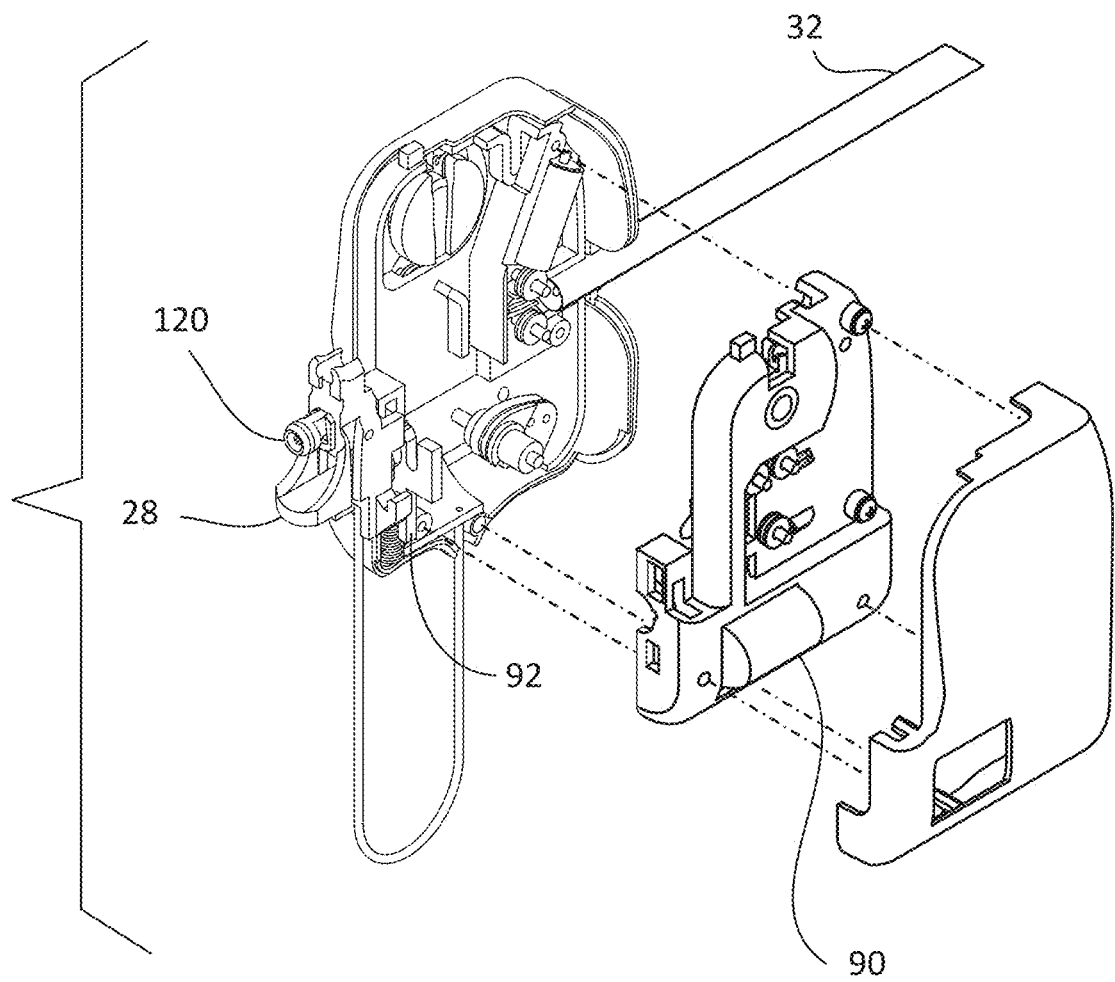
Figure 24D:
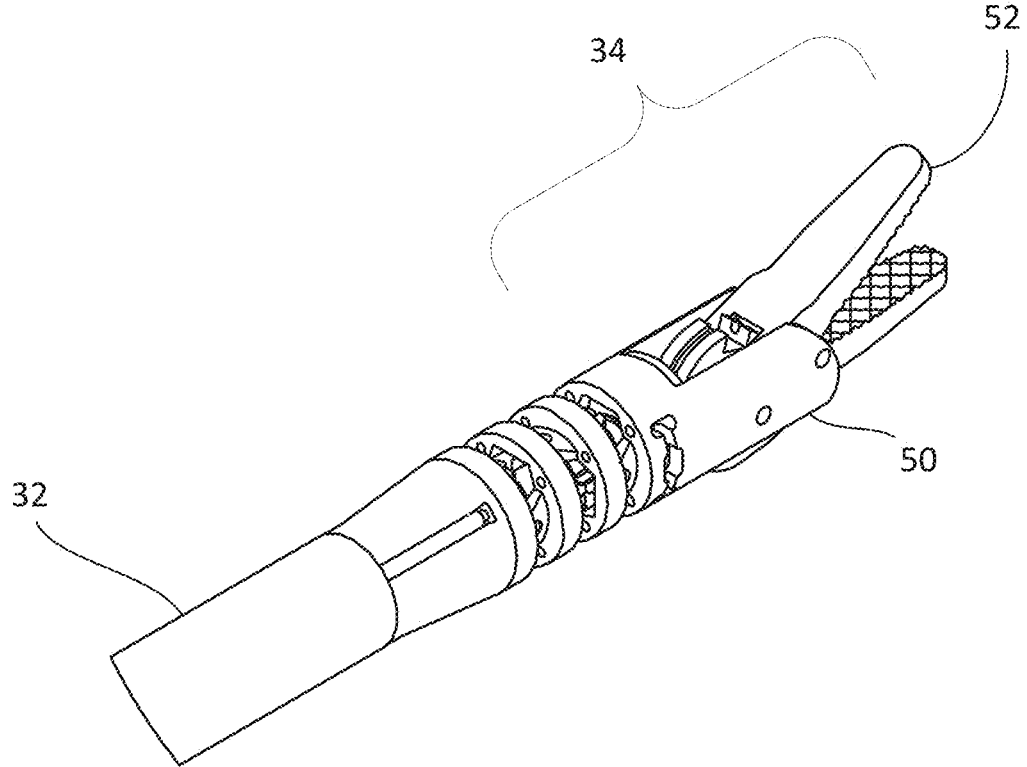

Cable crimp housing 120 or crimp housing (CH) is a member that forms a transmission interface with shuttle 116. FIG. 23 shows a transmission interface feature called "shuttle hard stop 130" that interfaces with shuttle 116 and helps in transmission of force when shuttle 116 translates within the 20. Alignment and retention of crimp housing 120 w.r.t. shuttle 116 leads to translation of crimp housing 120 along with shuttle 116. There is also a CB hard stop surface 121 and a cable path alignment feature 123.

3.2.7 Detachable Instrument (DI)

DI 14 refers to the assembly that consists of, in one embodiment, shaft box LH 31, shaft box RH 33, conduit box 28, crimp housing 120, shaft 32, end-effector assembly 34, conduit box lockout plate 92, button, and shaft box articulation pulleys 94. FIGS. 24A-D show various components that are part of DI assembly 14. There may be other bodies, joints, and mechanisms that are required to fulfill instrument functional requirements but the are not required to describe functions and define the FSM.

3.2.8 Virtual Center Control Unit (VCU)

Figure 25A:
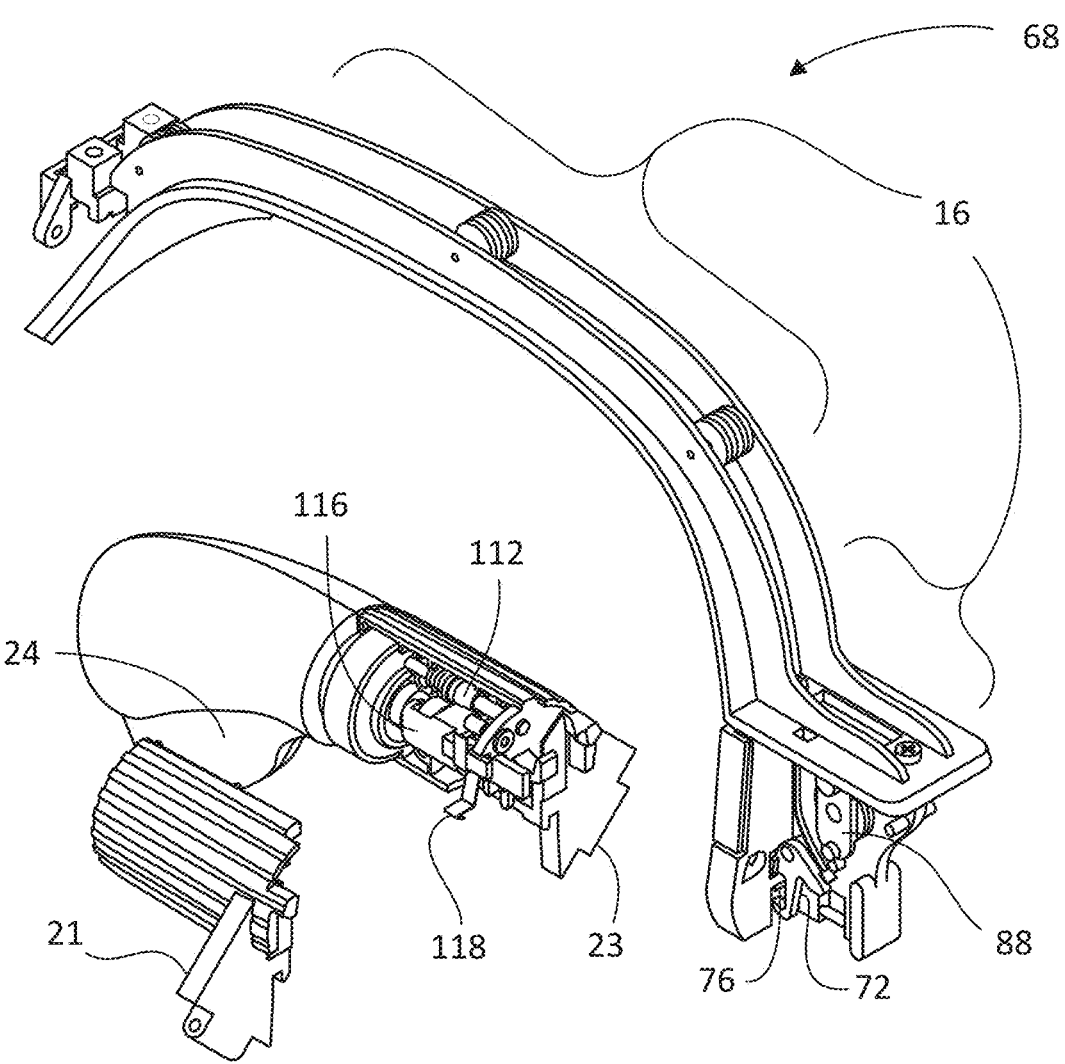
FIGS. 25A-B depict VCU consisting of bodies and certain interaction elements.
Figure 25B:
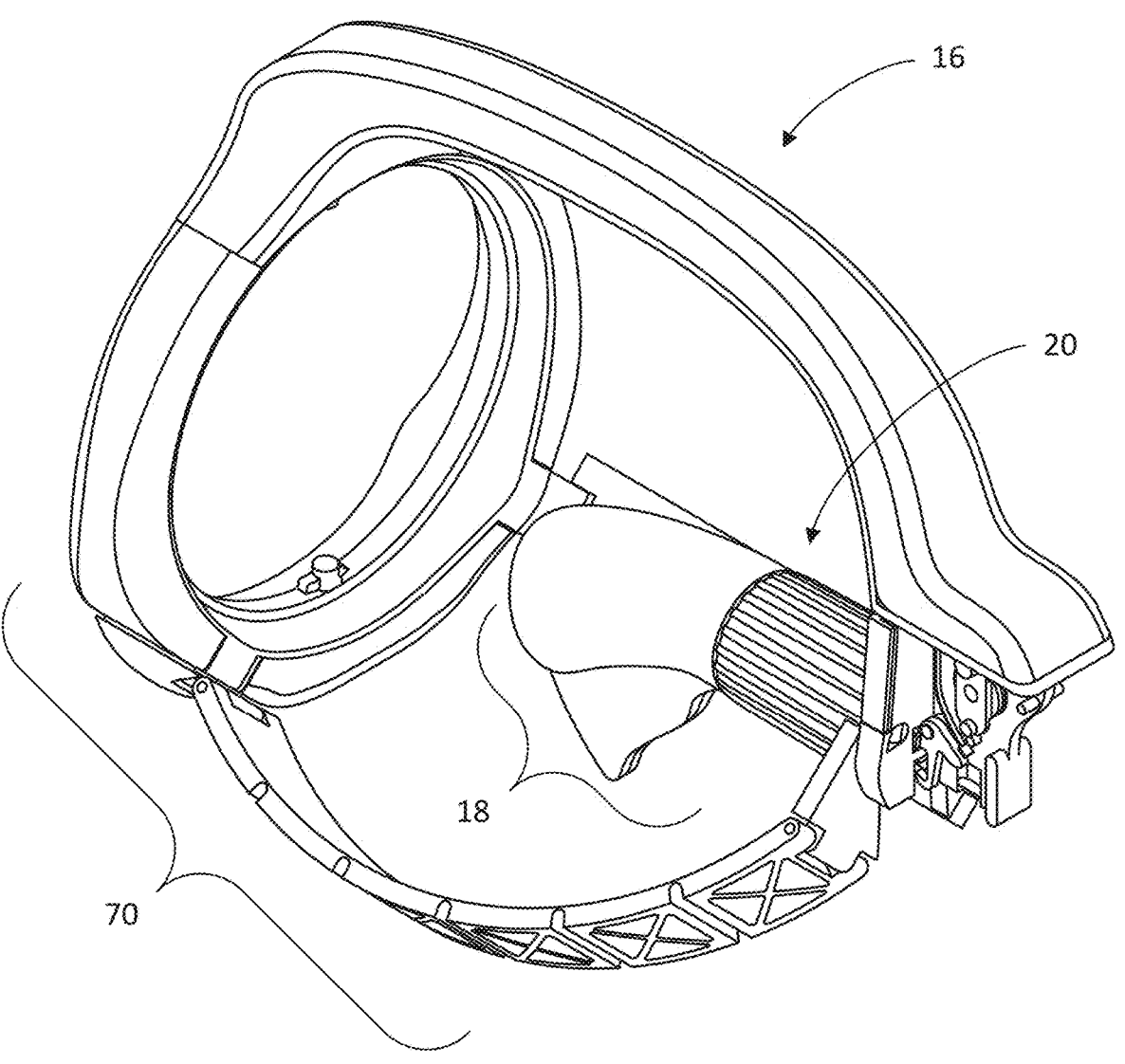

VCU 68 refers to the assembly that consists of, in one embodiment, frame 16, dial 20, shuttle 116, closure input 24, dial lockout plate 76, VCU lever 72, conduit box lockout shaft 112, shuttle lockout springs 118, VCU distal articulation pulleys 88, VCU proximal articulation pulleys, and other bodies within handle assembly 18. This is a specific form of master instrument (MI) 12 which has been described in sections above. FIGS. 25A-B show various components of VCU 68. There may be other bodies, joints, and mechanisms that assist in fulfilling instrument functional requirements but are not required to describe functions and define the FSM.

3.2.9 Tool Shaft

This refers to the elongate member that extends distal to frame 16. It generally has a fixed joint w.r.t. frame 16. Tool shaft 32 may have end-effector assembly 34 at its distal end either joined rigidly or via an output joint. Tool shaft 32 may be referred to as simply shaft 32 herein.

3.2.10 End-Effector (EE) Assembly

Figure 26:
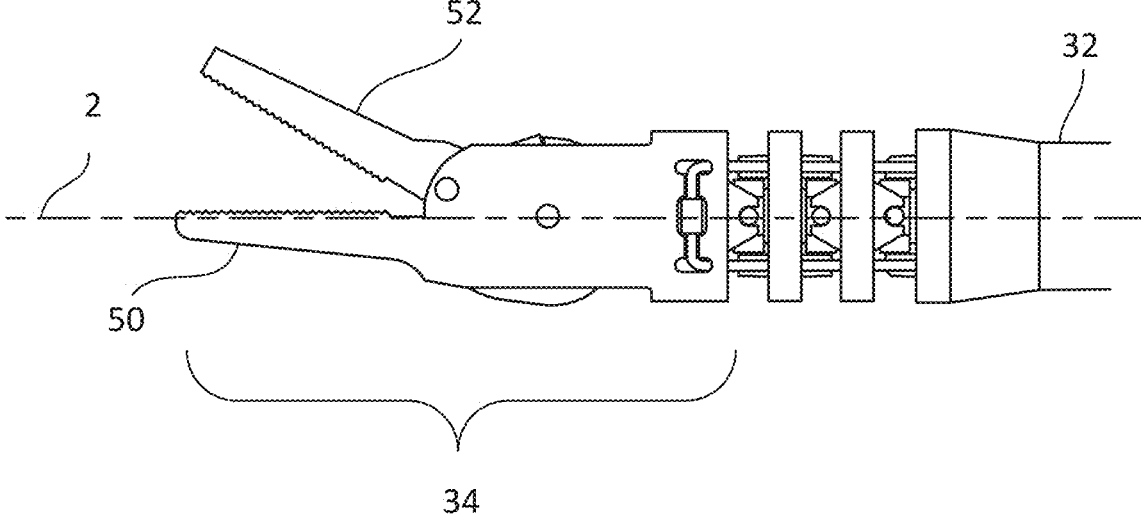
FIG. 26 depicts an end-effector assembly.

End-effector or jaw assembly 34 has been defined in sections above. This description is similar to one presented above and is mentioned here in context of tool apparatus 10. End-effector assembly 34 exists at the distal end of the elongated tool shaft 32, hence the name "end-effector." An end-effector or jaw assembly 34 may consist of a stationary or a moving component. The stationary component may be either connected to tool shaft 32 via a joint/mechanism or may be rigidly attached to tool shaft 32. The moving and stationary components of end-effector assembly 34 can be termed as "moving jaw 52" and "fixed jaw 50" respectively. Here, moving jaw 52 may have one or more joints (revolute, prismatic, cylindrical, etc.) w.r.t. fixed jaw 50 such that moving jaw 52 can rotate w.r.t. fixed jaw 50 about the jaw axis 57. Also, the entire end-effector assembly 34 may rotate about its roll axis termed as "EE roll axis" (axis 2). End-effector assembly 34 may be interchangeably referred as "jaw assembly" or "EE assembly." FIG. 26 shows a magnified view of end-effector assembly 34.

3.2.11 Tool Apparatus Axes of Rotation

Figure 27:
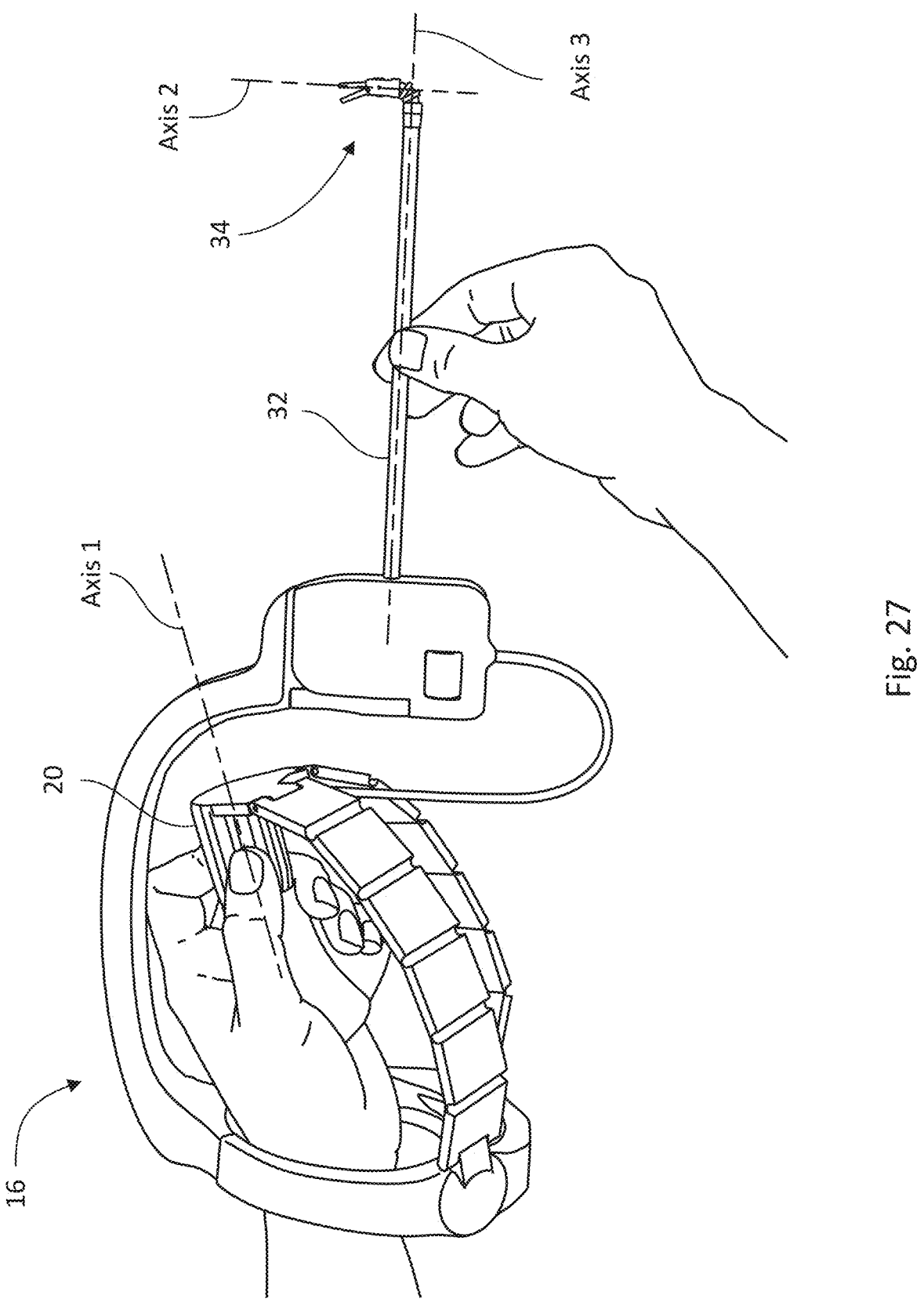
FIG. 27 depicts a tool apparatus axis 1, axis 2, and axis 3.

FIG. 27 shows all three axes of rotation namely, dial roll axis (axis 1), shaft roll axis (axis 3) and end-effector roll axis (axis 2).

3.3 Locks and Interlocks within FSM 3.3.1 CB Lockout Plate (CBLP)

Conduit box lockout plate 92 is a lock (positive engagement, non-back drivable lock) that interfaces with conduit box 28 and is housed within shaft box 30 assembly. FIG. 28A shows various lock interface features on CBLP 92 including conduit box interface 132 and frame interface 134. Additionally, there is a conduit box retention interface 133. FIGS. 28B-C respectively show X and Z alignment features that help align CBLP 92 w.r.t. SB LH 31 and SB RH 33. FIG. 28B shows a conduit box lockout plate spring hard stop 99 and Z-axis alignment faces 101. FIG. 28C shows X-axis alignment face 103.

3.3.2 CB Lockout Shaft (CBLS)

CBLS 112 is a lock (positive engagement, non-back drivable lock) which that interfaces with conduit box 28 and frame 16. It is housed in the dial assembly. FIG. 29A shows the tapered surface which acts as the conduit box locking interface 61 and, thereby, locks and unlocks conduit box 28. CBLS 112 also consists of two shaft portions with CBLS 112 alignment surfaces 63 shown in FIG. 29A that are used to align CBLS 112 w.r.t. dial 20. FIGS. 29B-C further show other alignment features of CBLS 112 that help align CBLS 112 along X axis. FIG. 29B shows a conduit box lockout shaft spring hard stop 113. FIG. 29C shows an interlock interface 115 with respect to frame 16 and an alignment hard stop 119 with respect to dial 20.

3.3.3 Dial Lockout Plate (DLP)

Dial lockout plate 76 is a lock (positive engagement, non-back drivable lock) that interacts with dial 20 and shaft box 30. It is shown in FIGS. 30A-C. It is housed in the frame assembly. FIG. 30A shows dial retention interface 79 which is also a locking interface. FIG. 30A also shows Y-axis alignment hard stop 81 against frame 16 and shaft box lock interface 83. DLP 76 is actuated to unlock the dial 20 when shaft box 30 interfaces with the surface shown in FIG. 30A. It pushes the dial 20 along +Y axis direction and releases the contact between dial retention interface and dial lockout plate interface/hook 17 portion on dial 20 (shown in FIG. 21D). FIG. 30B shows Z-axis alignment faces 85 and handle lockout plate spring hard stop 105. FIG. 30C shows X-axis alignment face 107 with respect to frame 16.

3.3.4 Button (B)

Button 90 is a lock (positive engagement, non-back drivable lock) that interfaces with frame 16 and VCU lever 72. It is housed in SB RH 33. Button 90 interfaces with button locking face 102 on frame 16 shown in FIG. 16B for shaft box 30 retention w.r.t. frame 16 along −Y axis direction. FIG. 31A-C represent various features on button 90 which are used for alignment of button 90 w.r.t. SB RH 33 and locking interfaces w.r.t. VCU lever 72 and frame 16. FIG. 31A shows a rotation hard stop 125. FIG. 31C shows frame retention and lock interface 131 which helps retain shaft box 30 assembly to frame 16 (distal portion of frame 16) as well as acts as a lock interface. There also exists VCU lever interlock interface 136 shown in FIG. 31A which interfaces with VCU lever 72 while the VCU lever 72 blocks the rotation of button 90 about its pivot axis. Button pivot axis 93 helps with alignment along Y and Z axis direction whereas, face marked in FIG. 31B shows button 90 X axis alignment feature 127. FIG. 31A also shows a user input interface trigger 129 on button 90.

3.3.5 VCU Lever

VCU lever 72 is a lock which interfaces with shaft box RH 33. VCU lever 72 also acts as an interlock and interfaces with shaft box RH 33, shuttle 116, and button 90. VCU lever 72 is housed within frame 16 assembly and rotates about VCU lever 72 pivot axis 11 with an alignment rotation hard stop 135. The rotation is forced by a VCU lever leaf spring that fits between alignment rotation hard stop 135 and VCU lever spring guide post 53. VCU lever 72 has three key locking and interlocking interfaces which are shown in FIGS. 32A-C. The locking feature is "shaft box retention interface 138." As shown in FIG. 15B, there exist two retention bodies/features retaining frame 16 and shaft box 30 in the use state, these are namely button 90 and VCU lever 72.

The interlocking interface is "button interface 140." Shaft box retention interface 138 feature helps retain SB 30 w.r.t. frame 16 along the Y axis direction. Z-axis hard stop 139 surface helps align VCU lever 72 with respect to frame 16. There also exists "shuttle interface 142" which is a transmission interface where Shuttle 116 contacts VCU lever 72 and helps with enabling or disabling the interlocking of button 90. Button interface 140 is used to block the rotation of button 90 about button pivot axis 93 as needed in certain states. The functional aspect of these features is described in more detail in sections below.

3.3.6 Shuttle Lockout Spring (SLS)

Shuttle lockout spring 118 is a lock (positive engagement, non-back drivable lock) that interfaces with shuttle 116 and conduit box 28. It is housed within the dial assembly through retention and alignment dial contacts 141. FIGS. 33A-B show various alignment and retention features on shuttle lockout spring 118. FIG. 21E shows SLS 118 housed within dial 20. SLS 118 pivots about Z axis alignment hard stop 137 that contacts the corresponding feature on dial 20 and rotates about it to lock and unlock the shuttle 116. Rotation of SLS 118 is actuated via conduit box 28 as conduit box 28 contacts lock interface "conduit box interface 144" shown in FIGS. 33A-B. Lock interface "shuttle interface 146" shown in FIG. 33B acts w.r.t. shuttle lockout spring tabs 126 shown in FIG. 22C and blocks the motion of shuttle 116 in negative (−) axis 1 direction (proximal to user, away from end-effector).

3.3.7 Dial Detent Spring (DDS)

Dial detent spring (DDS) 74 is a lock (positive engagement, back drivable lock) that locks dial 20 to frame 16. Detent spring tab 27, shown in FIG. 21D, is the feature on dial 20 that interfaces with DDS 74. Also, FIG. 16D shows dial detent spring 74 housed within the frame assembly. A cross section of this interface is shown in FIG. 34. DDS 74 is aligned w.r.t. frame 16 and retained within frame 16 such that translation of dial 20 along +X axis direction deflects the long leg portion of the DDS 74 along Z direction. DDS 74 then sits on detent spring tab 27 and temporarily locks dial 20 w.r.t. frame 16. The transition which describes the locking and unlocking of dial 20 in detail is described in further sections. As shown in FIG. 15A, in the storage state, there exist two retention bodies namely DLP 76 and DDS 74.

3.3.8 Dial Lever

Tool apparatus 10 may have a form which is different from the form presented in FIGS. 15A-C. There may exist another interlock between dial 20 and conduit box 28. The form represented in FIG. 15B shows that there exists an interlock between frame 16 and shaft box 30, i.e., VCU lever 72. This interlock disables unlocking of button 90. But there does not exist an interlock between dial 20 and conduit box 28, termed here as "dial lever 73." The form of FSM represented here does not prevent the FSM to go from use state to storage state because CBLS 112 can be unlocked while the system is in use state. This unlocking of CBLS 112 can lead to detachment of the conduit box 28 w.r.t. the dial 20, thereby placing the FSM in a non-functional state. This is a non-functional allowed state that exists in the presented FSM form shown in FIGS. 15A-C. This can be changed to a non-functional disallowed state, in case when the action involved is unlocking the CBLS 112, by introducing an interlock that disables unlocking of CBLS 112. This interlock (dial lever 73) can be actuated during transition from state 1 to state 2, or from state 2 to state 3. Dial lever 73 can be either housed within the dial assembly or within conduit box 28.

3.4 Different Transmission Systems 3.4.1 Jaw Closure Transmission

This refers to components/bodies, transmission members, joints and/or mechanisms going from input to output that are involved in performing jaw closure and jaw opening.

3.4.2 Articulation Transmission

This refers to components/bodies, transmission members, joints and/or mechanisms going from input to output that are involved in performing articulation of end-effector assembly 34.

3.4.3 Roll Transmission

This refers to components/bodies, transmission members, joints and/or mechanisms going from input to output that are involved in performing rotation of end-effector assembly 34 about EE roll axis (axis 2).

3.5 Transmission Interfaces and Detachable Structural Interfaces 3.5.1 SB Articulation Pulley-Frame Articulation Transmission Interface: For Articulation Transmission Frame articulation pulley 88 and SB articulation pulley 94 constitute an articulation transmission interface. Being part of separate assemblies, the effectiveness of this interface facilitates achieving maximized articulation transmission efficiency. This effectiveness of the interface is governed by the alignment of the SB articulation pulley 94 axis of rotation 13 w.r.t. the frame articulation pulley 88 axis of rotation 15. This alignment may be important, in certain embodiments, in both X and Y axis directions. The alignment of these axes is thereby governed by alignment of SB 30 w.r.t. frame 16. Therefore, the design and tolerance variation based on manufacturing or based on the design of all the aforementioned interaction elements may be important. The transmission interface presented in this description consists of pegs 148 on frame articulation pulley 88 and driving slot 150 on SB articulation pulley 94. These mate w.r.t. each other and provide the needed transmission interface. Also, these are pair of pegs 148 equally spaced from the center of the frame articulation pulley 88 going into a single elongated slot 150 so that forces that are transferred to SB LH and SB RH do not lead to a net force and moment on the shaft box assembly. This interface is shown in FIGS. 35A-B.

There is another embodiment of interface that can be formed which does not require high reliance on alignment of SB 30 w.r.t. frame 16 to get the axes of rotation aligned. FIG. 36 shows an embodiment of frame distal articulation pulley 88 and SB articulation pulley 94 where pulley axes are not aligned. This is the practical configuration which accommodates potential mis-alignment between SB 30 and frame 16 which eventually define the alignment of frame distal articulation pulley 88 and SB articulation pulley 94. While the two pulleys rotate about their respective axis, there exists a prismatic joint between a peg 152 and a slot 154. Here, peg 152 is a rigid feature that exists on SB articulation pulley 94 and slot 154 is a rigid feature that exists on frame distal articulation pulley 88. In order to avoid binding between the peg 152 and slot 154, a low coefficient of friction at the peg-slot interface and clearance at this interface are helpful.

3.5.2 Shuttle-Crimp Housing Transmission Interface: For Jaw Closure Transmission The shuttle-crimp housing interface produces a jaw closure transmission interface between VCU 68 and DI 14. Crimp housing 120 is rigidly attached to jaw closure transmission member 66 and is housed within the conduit box assembly. Shuttle 116 is housed within the dial assembly. Upon attachment of conduit box 28 to the dial 20, the crimp housing interfaces with shuttle 116 such that crimp housing 120 is constrained along axis 1 and, thereby, translates along with shuttle 116. This interface is described further while describing transitions in further sections.

3.5.3 VCU-DI Detachable Structural Interface: For Rigid Body Motion of Device

The VCU-DI interface aims at creating a rigid assembly that consists of VCU 68 and DI 14 assembly by producing structural interface between shaft box assembly and frame assembly. Once the assembly is formed, VCU 68 can be translated in along all 3 axis and rotated about these axes in order to produce 1:1 motion at the end-effector assembly 34. VCU 68 and DI 14 have alignment and retention features in order to constrain all 6 DoFs. Alignment and retention are required to produce a functional state for FSM where the tool apparatus 10 can be functional. This is desired between shaft box 30 and frame 16, and between conduit box 28 and dial 20. As presented in tool apparatus 10 in the section below, alignment between frame 16 and shaft box 30 takes place by translating shaft box 30 along +Y axis direction w.r.t. frame 16. This also aligns and retains conduit box 28 w.r.t dial 20, as shown in sections below. The alignment features and button 90 act to produce structural interface between frame 16 and shaft box 30.

The VCU-DI interface can also be produced by bringing shaft box 30 and frame 16 together by translation and rotation about either of the 6 DoFs. For example, FIGS. 37A-B show using rotation about Z axis to align frame 16 w.r.t. shaft box 30 in order to change the FSM states from state 1 to state 2. This rotation about a pivot pin 156 shall align the conduit box 28 w.r.t. the dial 20. Also, this act of rotating shaft box 30 w.r.t. frame 16 produces two additional transmission interfaces, namely SB articulation pulley-frame distal articulation pulley interface and shuttle-crimp housing interface.

3.5.4. Dial-CB Detachable Structural Interface: For Jaw Closure Transmission

The purpose of the Dial-CB detachable structural interface is to create a rigid assembly between handle assembly 18 and the conduit box 28 assembly to enable the transmission interface between the jaw closure cable crimp housing 120 and shuttle 116 for jaw closure transmission. In the FSM storage state, dial 20 and conduit box 28 are not joined in any way as they are contained within separate assemblies, namely MI 12 and DI 14 respectively. In the FSM assembled state, once conduit box 28 is assembled with dial 20, there is a structural interface between the two bodies by virtue of the alignment features on both bodies and due to retention between bodies to which they were retained in the storage state (dial 20 retained with frame 16 via dial detent springs 74, and conduit box 28 retained with shaft box 30 via conduit box lockout plate 92). In the FSM use state, when handle assembly 18 is un-homed from frame 16, the structural interface between dial 20 and conduit box 28 is maintained and is locked by conduit box lockout shaft 112.

3.6 Transmission Members (TM's)

3.6.1 Jaw Closure Transmission Member

Jaw closure transmission member 66 is presented in FIGS. 38A-C. Jaw closure mechanism leads to an output at the end effector upon receiving input from the user at closure input 24. Within end-effector assembly 34, relative motion of moving jaw 52 w.r.t. fixed jaw 50 is the desired output of the jaw closure mechanism. Shown here is jaw closure transmission member 66 that routes through DI 14 and helps transmit motion from the input end to the output end. At the input end of DI 14, cable crimp housing 120 interfaces with shuttle 116. Here shuttle 116 further interfaces with closure input 24 (which is also part of handle assembly 18) via joints and mechanisms. This is the input motion. Jaw closure TM 66 routes throughout DI 14 (as shown in FIG. 38B) through components namely, cable crimp housing 120, CB 28, unsupported conduit 158, jaw closure cam 160, shaft 32 and finally, to end-effector assembly 34. This transmission member 66 is a flexible cable which is compliant in bending. Also, this transmission member 66 needs to be axially stiff. It may be axially stiff under tension and/or compression. In FIGS. 38A-C, the transmission member 66 is only axially stiff under tension and not under compression. This means that jaw closure TM 66 requires another end at the input (cable crimp housing 120) in order to produce to and fro motion. FIG. 38A shows the cable returning through the shaft 32 into the shaft box assembly and interfacing with jaw open spring 162.

3.6.2 Frame Articulation TM

Frame articulation transmission member 164 is shown in FIGS. 39A-B. Here, input rotation of VCU proximal articulation pulleys 166 leads to rotation of VCU distal articulation pulleys 88. Frame articulation TM 164 is a flexible cable similar to jaw closure TM 66 which goes from the input end (VCU proximal articulation pulley 166), routes through the frame 16, and mates with VCU distal articulation pulley 88 at the output end. The cable then goes back from the output end to the input end because the cable is only axially stiff under tension. Therefore, to capture both clockwise (CW) and counter-clockwise (CCW) rotation of pulleys 166, 88, the cable needs to loop back to the input end. One cable path can transmit CW motion and another cable path can transmit CCW motion. To capture both pitch and yaw motion produced by the user, two cable loops are used. One cable loop transmits CW and CCW pitch motion and another cable loop transmits CW and CCW yaw motion. Each cable is rigidly connected at the input end (VCU proximal articulation pulley 166) and output end (VCU distal articulation pulley 88). FIG. 39B shows the transmission interface on VCU distal articulation pulley 88 (two vertical pegs) that mate with SB articulation pulley 94 transmission interface.

3.6.3 SB Articulation TM

SB articulation transmission member 168 or DI articulation transmission member is shown in FIGS. 40A-D. Here, input rotation of shaft box articulation pulleys 94 leads to articulation of end-effector assembly 34. There exists a 2 DoF output joint (pitch and yaw motion) between shaft 32 and end-effector assembly 34. SB articulation TM 168 is a flexible cable like jaw closure TM 66 which goes from the input end to the output end. The cable is routed starting from SB articulation pulleys 94, through the shaft box assembly (see FIG. 40C), through shaft 32, through output articulation joint 36 (see FIG. 40D), and finally terminates at end-effector assembly 34. The cable is rigidly connected at both the input end (SB articulation pulleys 94) and the output end (end-effector assembly 34). The cable then goes back from the output end to the input end because the cable is only axially stiff under tension. Therefore, to capture both clockwise (CW) and counter-clockwise (CCW) rotation of the pulleys, the cable loops back to the input end. To capture both pitch and yaw motion produced by the user, two cable loops are utilized. One cable loop transmits CW and CCW pitch motion and another cable loop transmits CW and CCW yaw motion.

3.6.4 End-Effector Roll TM

Based on the route roll transmission path takes, there can be two tool apparatus embodiments and architectures. These architectures are shown in FIG. 6A-B. The first configuration is called alpha configuration and is shown in FIG. 6A. In this configuration, roll is transmitted via roll transmission member 54 that runs internal to shaft 32 and interfaces with end-effector assembly 34. In this configuration, dial 20 rotates and thereby rotates a torsionally stiff roll transmission member 54. But frame 16 and shaft 32 do not rotate. There exists a roll DoF about tool shaft axis between shaft 32 and end-effector assembly 34. In case the assembly has articulation function, there exists a 2 DoF (pitch and yaw) input joint between handle body 22 and frame 16.

The second configuration is called beta configuration and is shown in FIG. 6B. In this configuration, roll is transmitted via the rigid body arrangement that exists within the instrument. Rotation of dial 20 leads to rotation of tool shaft 32. Dial 20 and tool shaft 32 are either connected via a fixed joint or an articulation input joint (2 DoF pitch and yaw motion joint). In case there is an articulation input joint between dial 20 and tool shaft 32, the joint is such that it transmits roll motion from dial 20 to tool shaft 32. Therefore, it provides roll DoC about the dial roll axis when dial 20 is rotated w.r.t. handle body 22. Rotation of tool shaft 32 is further transmitted to end-effector assembly 34. Tool shaft 32 and end-effector assembly 34 are either connected via a fixed joint or an articulation output joint (2 DoF pitch and yaw motion joint).

In case there is an articulation output joint 36 between tool shaft 32 and end-effector assembly 34, the joint is such that it transmits roll motion from tool shaft 32 to end-effector assembly 34. Therefore, it provides roll DoC about the tool shaft roll axis between end-effector assembly 34 and tool shaft 32. In case of second configuration, roll transmission takes place in parallel to articulation motion. For example, FIG. 41A shows a device configuration where roll is transmitted while articulation input joint is not in use. FIG. 41B shows a configuration where articulation roll is transmitted while articulation input joint is in-use. In both scenarios, roll transmission takes place via the same path as shown via FIG. 6B.

3.7 User Interfaces

A user interacts with the instrument via user interfaces while changing states of the FSM and/or performing the tool apparatus functions.

3.7.1 Dial and Closure Input

Dial 20 serves as a user interface while the user is operating an instrument. Here, dial interface is the outer circumference of dial 20 which may have features like knurled embossments, ridges, etc., in order to make the use of dial 20 more ergonomic. One function here is homing the 20 to frame 16 and un-homing it. This is done by holding the dial's outer surface and translating it along its roll axis (here, also the X axis). FIG. 42 shows an embodiment where the user interfaces with dial 20. Apart from the four-body system described herein, another input component that the user interacts with is called "closure input 24" or "handle closure input." Closure input 24 is actuated by the user's finger(s) to produce actuation at end-effector assembly 34 between two components namely, moving jaw 52 and fixed jaw 50. For example, in the embodiment shown in FIG. 42, closure input 24 is used to produce actuation of components within end-effector assembly 34 (not shown in the figure) that lies distal to tool shaft 32.

3.7.2 Button

Button 90 serves as a user interface while the user is detaching shaft box 30 from frame 16. A user presses button 90 to detach the shaft box 30 from frame 16. While doing so, the user also interacts with frame 16 and shaft box 30 as the user may pull shaft box 30 away from frame 16 during this operation. FIG. 43 shows this interface.

3.7.3 Shaft Box and Frame

A user interacts with shaft box 30 and frame 16 while attaching and detaching shaft box 30 and frame 16 together and apart. A user holds frame 16 and draws shaft box 30 towards frame 16 in order to attach them. FIG. 44A and FIG. 44B show user interaction with shaft box 30 and frame 16.

3.8 States, Actions, and Transitions Descriptions (User Experience)

A user, while using the tool apparatus 10 which incorporates a four body FSM system, handles the system through various states that are required to use the device functionally. The main four states are storage state, assembled state, use state, and service state. Tool apparatus 10 is in storage state by default. It goes from storage state to assembled state and eventually to use state. Each of the transitions between these three states are initiated by respective actions and are reversible as all these states are either functional or allowed non-functional states. These states are described in more detail in the following sections.

3.8.1 State 1: Storage State (Non-Functional, Allowed State)

FIGS. 45A-B depict state 1 for the system. While the system is in this state, the user either is about to start using the device or is done using the device and the device is stored. The device is dis-assembled (VCU 68 separated from DI 14) and is stored. This involves DI 14 and VCU 68 that are separate assemblies including corresponding interaction elements namely, transmission interfaces, transmission members, locks, interlocks, etc. In the context of the FSM, VCU 68 includes two main bodies, namely, frame 16 and dial 20. DI 14 includes two main bodies, namely, shaft box 30 and conduit box 28. In this state, in VCU 68, frame 16 is locked w.r.t. dial 20 via a lock namely, dial lockout plate 76. Therefore, dial 20 is homed to frame 16 in this state.

There also exist dial detent springs 74 that are used for temporary locking of dial 20 w.r.t. frame 16 while it goes through subsequent states. Also, there exists another user interface called closure input 24 that is shown in FIG. 42. In state 1, the user is not able to actuate closure input 24. This is because closure input 24 interfaces internally within handle assembly 18 to a component called shuttle 116. The cause for restricted motion of closure input 24 at this state is due to the presence of a lock between shuttle 116 and dial 20. Shuttle 116 is housed/located inside dial 20 such that without the lock, it has a translational DoF along dial roll axis direction and a rotational DoC about the dial roll axis. Actuation of closure input 24 leads to translation of shuttle 116 which thereby leads to closure of moving jaw 52 w.r.t. fixed jaw 50. Therefore, the lock between shuttle 116 and dial 20, called "shuttle lockout spring 118" locks the translation of shuttle 116 w.r.t. dial 20 by constraining its translational DoF w.r.t. dial 20. This lock is specifically shown in FIG. 45B.

In this state, in DI 14, conduit box 28 is locked w.r.t. shaft box 30 via the lock called conduit box lockout plate 92. In state 1, the system is ready to move to state 2 which is the fully assembled state where VCU 68 is attached to DI 14. From a function standpoint, three interfaces are ready to be mated in next state. These are: articulation transmission interface between frame distal articulation pulley 88 and shaft box articulation pulley 94; closure transmission interface between shuttle 116 and crimp housing 120; and rigid body detachable structural interface between frame 16 and shaft box 30 as well as between dial 20 and conduit box 28. Therefore, bodies and interface features involved here are aligned to mate w.r.t. each other in the next state.

3.8.2 State 2: Assembled State (Functional, Allowed State)

The user takes VCU 68 and DI 14 shown in FIGS. 45A-B from the state 1 to state 2 by bringing the VCU 68 towards the DI 14 and attaching them together. FIGS. 46A-C show transition from state 1 to state 2. This is termed as "Transition 1." During this transition, shaft box 30 aligns w.r.t. frame 16 and shaft box 30 is installed onto frame 16. Shaft box 30 is retained w.r.t. frame 16 via lock namely, button 90. The locking on shaft box 30 onto the frame 16 also establishes a transmission path for articulation of end-effector assembly 34. Two features (namely, peg feature 148 on VCU distal articulation pulley 88 and slot feature 150 on shaft box articulation pulley 94) engage to form a transmission interface because of this transition and lock between shaft box 30 and frame 16. Also, the rotation axes of these pulleys ideally coincide in terms of their X and Y location so that articulation transmission is efficient. Conduit box 28 is aligned w.r.t. dial 20 and is housed inside dial 20 after the transition. Conduit box 28 is not locked either to dial 20 or shaft box 30 at this state.

Unlike state 1, conduit box 28 is no longer locked w.r.t. shaft box 30 in this state via conduit box lockout plate. Installation of DI onto VCU unlocks the conduit box w.r.t. shaft box by actuating conduit box lockout plate 92. Also, dial 20 is no longer locked to frame 16 in this state via dial lockout plate 76. The only lock which exists between dial 20 and frame 16 is via dial detent springs (DDS) 74 which temporarily lock the dial 20 to the frame 16 at this state. Installation on DI 14 onto VCU 68 unlocks the dial 20 w.r.t. frame 16 by actuating dial lockout plate 76. Also, user can now actuate the closure input 24 as shuttle 116 is no longer locked w.r.t. dial 20. Shuttle lockout spring 118 has been unlocked by conduit box's translation along +Y axis direction. Shuttle 116 can now translate w.r.t. dial 20 along axis 1 direction. This is because entry of conduit box 28 into the dial 20 changes the state of shuttle lockout spring 118 and unlocks the shuttle 116 w.r.t. the dial 20.

The act of the conduit box 28 entering dial 20 also mates crimp housing 120 to shuttle 116. Crimp housing 120 is rigidly attached to jaw closure transmission member 66. Jaw closure transmission member 66 terminates onto crimp housing 120 as it travels from end-effector assembly 34 through DI 14. Due to the transmission interface between crimp housing 120 and shuttle 116, translation of the shuttle 116 leads to translation of crimp housing 120. Crimp housing 120, being rigidly connected to jaw closure transmission member 66, leads to actuation of moving jaw 52 w.r.t. fixed jaw 50 in end-effector assembly 34. Overall, the act of bringing these two components together along Y axis direction is an action required to change from state 1 to state 2.

The action described above in this section will be referred as "Action 1" throughout the description below. At this state, all connected interfaces have interfaced for use in the next state (state 3).

State 2 is termed as functional state because the jaw closure function, roll function, and rigid body motion function can still be performed using tool apparatus 10. Articulation and articulated roll functions require the system to go into use state (state 3) where all the functions are available. FIGS. 47A-C show state 2 for the system.

3.8.3 State 3: Use State (Functional, Allowed State)

State 3 is referred to as "use state" because at this state, the device should be configured such that it is ready for functional use. The functional use comprises of articulation of end-effector assembly 34, actuation of moving jaw 52 in end-effector assembly 34, roll of end-effector assembly 34 (with and without simultaneous articulation) and translation as well as rotation (rigid body motion) of the whole assembly (VCU 68 and DI 14 assembled). FIG. 48 shows the transition from state 2 to state 3. This is termed as "Transition 2." During this transition step, the user pulls dial 20 away from frame 16 along the X axis direction. This act of pulling can be termed as "Action 2" and is also referred to as "un-homing." The user un-homes dial 20 w.r.t. frame 16 and while doing so, unlocks dial 20 w.r.t. frame 16. This step of un-homing also unlocks dial 20 w.r.t. frame 16 by switching the temporary lock produced by lock namely, dial detent springs (DDS) 74.

Once dial 20 is un-homed from frame 16, conduit box 28 locks w.r.t. dial 20 via conduit box lockout shaft (CBLS) 112. Therefore, at state 3, dial 20 and conduit box 28 are locked together, frame 16 and shaft box 30 are locked together. Also, shuttle 116 and crimp housing 120 are interfacing together and VCU distal articulation pulley 88 and DI articulation pulley 94 are interfacing together. Articulation and jaw closure transmission systems are in their functional state. Roll transmission system is also in its functional state. In the embodiment shown in FIGS. 49A-B, there exists an input articulation joint 26 between handle assembly 18 (specifically, dial 20) and frame 16. This 2-DoF articulation input joint 26 (pitch and yaw) interfaces with 2-DoF output articulation joint 36 via articulation transmission members (namely, VCU articulation TM and DI articulation TM).

U.S. Pat. No. 8,668,702 describes this articulation input joint in more detail. Apart from acting as an articulation input joint, this joint also provides a rigid body motion path for roll transmission between handle assembly 18 (specifically, dial 20) and frame 16 that has been described above. FIGS. 49A-C represent state 3 of the FSM system.

Each of the states namely, state 1, state 2, and state 3 are allowed states and therefore, consist of reversible transitions. This means that the system can go from state 1 to state 2 while going through "transition 1." It can also go from state 2 to state 1 due to "action 1," i.e., when steps of "action 1" are done in reverse order. Similarly, the system can go from state 2 to state 3 while going through "transition 2." It can also go from state 3 to state 2 if the "action 2" is reversed, i.e., steps are done in reverse order. FIG. 50 shows transition from state 3 to state 2. FIGS. 51A-C show transition from state 2 to state 1.

3.8.4 State 4: Service State (Non-Functional, Allowed State)

State 4, referred to as a service state, is a non-functional but allowed state which only occurs after state 1. FIGS. 52A-B shows transition from state 1 to state 4. This transition step is termed as "Transition 3." A user unlocks dial 20 from frame 16 by actuating dial lockout plate 76 using some tool or hands. This leads to un-homing of dial 20 from frame 16 and provides exposure to the interface between dial 20 and frame 16. Similarly, a user unlocks conduit box 28 from shaft box 30 by actuating conduit box lockout plate 92 using some tool or hands. This leads to dis-engagement of conduit box 28 from shaft box 30 and provides exposure to the interface between conduit box 28 and shaft box 30. The act of transitioning from state 1 to state 4 is termed as "Action 3." Therefore, user has all four bodies separated from each other in state 4. This provides the ability to service each component individually as well as service the interface between two or more components. For that reason, it is called "Service State." There may be instances in which the user may not disassemble both pairs, namely, frame-dial and shaft box-conduit box, but may just disassemble 1 pair. In that case, the state will still be termed as "Service State" or "State 4." FIGS. 53A-B shows service state of the system.

3.9 Four Body System Part of Tool Apparatus

FIG. 54 shows a schematic diagram of a four body FSM. This diagram figuratively shows the bodies, locks, and interlocks that may exist between a four-body system. Here, dial (D) 20 and frame (F) 16 have the dial lockout plate (DLP) 76 as the lock between them. Dial (D) 20 and frame (F) 16 also have dial detent spring (DDS) 74 as a lock between them. Frame (F) 16 and shaft box (SB) 30 have button 90 as the lock between them. Frame (F) 16 and Shaft box (SB) 30 also have VCU lever 72 as a lock between them. Conduit box (CB) 28 and shaft box (SB) 30 have conduit box lockout plate (CBLP) 92 as the lock between them. Dial (D) 20 and conduit box (CB) 28 have the conduit box lockout shaft (CBLS) 112 as the lock between them. These locks have two statuses namely, locked status and unlocked status. Locked and unlocked state of each interlock can be represented by numbers 1 and 0 respectively. Various combinations of locked and unlocked status of each lock lead to various allowed and not-allowed states. There may also exist interlocks that act on specific locks in specific states. Shown here are two interlocks, namely VCU Lever 72 and Dial Lever 73. VCU Lever 72 acts on button 90 to disable its ability to unlock. Dial lever 73 acts on CBLS 112 to disable its ability to unlock. Specific cases of using additional interlocks will be discussed in sections below. There may exist additional interlocks depending on the functionals need of an FSM.

3.10 Five Body System Part of Tool Apparatus

FIG. 55A shows a modification to schematic diagram shown in FIG. 54. In this embodiment, there exists an additional body named shuttle 116 which has been described above. There exists the lock named shuttle lockout spring (SLS) 118 between shuttle (Sh) 116 and dial (D) 20.

In yet another embodiment, there may exist another body that can be part of the tool apparatus 10 named "electricity box 62." This body is shown in tool architecture and embodiment shown in FIG. 7B. In this scenario, "electricity box 62" interfaces with SB 30 and is locked to it via lock called box lockout plate 65. Also, alike VCU lever 72 and Dial lever 73, there may exist an interlock called electricity box lever 67 that disables the unlocking of box lockout plate 65. Like the other two interlocks, this interlock can go into lock status (1), when the FSM is in use state as in-use state. Unlocking of locks between VCU 68 and DI 14 may be prohibited to avoid inadvertent unlocking of assemblies. This six body FSM is shown in FIG. 55B.

FIG. 56A shows a lock status diagram for a five body FSM representing dependency of different states namely, state 1, state 2, state 3, and state 4 on corresponding actions A1 through A3. These states and actions have been described in the above sections. In order to make a transition, in this embodiment, two inputs that are called for are the initial state and the action applied on that state. Each action produces a transition from one state to another. Each action is represented as a binary input, 0 or 1. When a particular action is applied (1), the remaining actions are considered as 0. An action leads to a binary output at a lock push switch. The lock push switch, when turned on (1), represents retention between two bodies via the lock that exists between the two bodies. These locks related to four-body and five-body FSM are described in this section and the previous section. For example, if connection between D (dial) 20 and CB (conduit box) 28 is complete, it means that the switch is turned on. This means that the binary value of the respective lock, CBLS 112 in this case, is 1. Between the switch and action, in some scenarios, there exists commonly known logic gates namely, NOT gate, AND gate, etc. in order to describe the formation of various states for the five body FSM using a circuit diagram.

Also, when a certain action does not apply on a particular lock, the status value (0 or 1) for this lock that was specific in the initial state is considered as default. For example, when going from state 2 to state 3, action A2 does not act on locking or unlocking button (B) 90. However, because the initial state input here is state 2 where button 90 has a lock (1) status, that is considered as default for state 3. FIG. 56B presents a table that shows the status of various locks and interlocks and reflects the results of the lock status diagram.

Based on the FSM, its states, transitions, and actions described above, relationships between states and actions can be produced. There exist two actions namely, install/uninstall and un-home/home that have been described in detail above. FIG. 57 shows this relationship between state 1 through state 3 and the two associated actions to initiate transition 1 and transition 2. Due to the presence of all the interaction elements, especially locks and interlocks between bodies within the FSM, certain actions are possible/not possible or not applicable. For example, when in state 1, installation (between shaft box 30 and frame 16 and, therefore VCU 68 and DI 14) is a possibility. At the same time, un-homing (between dial 20 and frame 16) is not possible. Similarly, when in state 2, uninstallation is possible and un-homing is possible. In state 3, uninstallation is not possible due to locks and, in certain forms of FSM, not possible due to interlocks. Also, homing is possible in state 3.

3.11 Specific Non-Functional States

Described herein are specific disallowed non-functional states that can be achieved if the FSM is misused/mishandled and is taken through transitions that are not described above.

Certain misuse states that are specifically prohibited in order to maintain user experience are restricted to states 1 through 4. Described below are recoverable misuse states M1, M2.1, and M2.2, and transitions T4 and T5 where T4 leads to M1 and T5 may lead to either M2.1 or M2.2. These states (M1, M2.1, and M2.2) originate at state 2 (assembled state). Since transitions T4 and T5 occur between an allowed functional state (State 2) and disallowed (non-functional) states, these transitions are not reversible.

3.11.1 Misuse State M1

FIGS. 58A-B show transition 4 (T4) that takes place while the system starts at initial state 2 (assembled state). T4 includes rotating dial 20 counter-clockwise (CCW) about Y axis which lies distal to handle assembly 18 and unlocking dial LH 21 off the left dial detent spring 74 (interlock housed within frame 16). The detent tab on dial LH 21 is unlocked w.r.t. the left detent spring 74 while still holding the dial 20 at the deflected angle w.r.t. frame 16. Simultaneously, button 90 is pressed in order to uninstall shaft box 30 w.r.t. frame 16. During this transition, the system may transition to either State 1 or a misuse state (M1) or no change (stay at state 2). As part of the user experience described above, this transition is not an intended transition. This does not clearly lead to either of states 1 through 3 or service state (state 4). This transition, in certain four-body or five-body system may lead to misuse state M1. State M1 is shown in FIG. 59. While operating the device or making functional use of the device, reaching state M1 does not produce a functional state of the system. It leads to a misuse state which is a recoverable state. Via certain actions and transitions, the FSM can be brought back to state 2 via state 4 and/or 1. The FSM can be prevented from being in state M1 due to presence of a redundant lock between shaft box 30 and frame 16. VCU lever 72 is required to act on both SB LH and SB RH (it acts only on SB RH in current FSM design that leads to state M1) in order to also lock the SBLH w.r.t. frame 16 while dial 20 is rotated CCW. Here, VCU lever 72 is the redundant, secondary lock that exists between frame 16 and shaft box 30. The first lock is button 90.

3.11.2 Misuse State M2

FIG. 60 shows transition 5 (T5) that takes place while the system starts at initial state 2 (assembled state). T5 includes pressing button 90 while holding shaft box 30 and frame 16 together (immobilized) and un-homing dial 20 simultaneously. All these steps need to be done at the same time. T5, similar to T4, should not be part of the user experience as it deviates away from transitions T1 and T2 that lead to functional states and transition T3 which leads to a service state. FIG. 61 shows a disallowed, non-functional state (misuse state M2.1) that is a potential outcome of transition 5 (T5). Transition T5 is not reversible as it occurs from an allowed state to a disallowed state. However, the final disallowed non-functional state is recoverable and can be transitioned to state 3 (use state) via a different transition. This transition includes translating shaft box 30 w.r.t. frame 16 and bringing both components together until the gap between the two bodies (as shown in FIG. 61) is minimized and shaft box 30 is retained w.r.t. frame 16 via button 90 as it is in state 2.

Another potential state that could occur based on transition T5 starting from initial state 2 is misuse state M2.2. M2.2, as shown in FIG. 62, is a non-functional and disallowed state where conduit box 28 is locked w.r.t. dial 20 while shaft box 30 is completely uninstalled w.r.t. frame 16. Also, dial 20 is un-homed w.r.t. frame 16. State M2.2 can be prohibited by the presence of a redundant lock between shaft box 30 and frame 16. Here, VCU lever 72 is the redundant, secondary lock that exists between frame 16 and shaft box 30. The first lock is button 90. Misuse state M2.2 is recoverable and can transition to the service state 4 by disconnecting conduit box 28 from shaft box 30.

3.12 Transitions

In this section, transition 1 and transition 2 are described in detail for a specific tool apparatus 10 and FSM.

3.12.1 Transition 1

As shown in FIGS. 46A-C, transition 1 takes place when the system goes from state 1 (storage state) to state 2 (assembled state). During this transition, shaft box 30 is installed onto frame 16. This includes aligning of shaft box 30 w.r.t. frame 16 and retaining of shaft box 30 w.r.t. frame 16 via lock namely, button 90. This transition is described in the following transition steps. At the end of the description of transition 1, a timing plot for transition 1 is shown to present the time-domain dependence of each transition step relative to other steps.

Figure 40A:
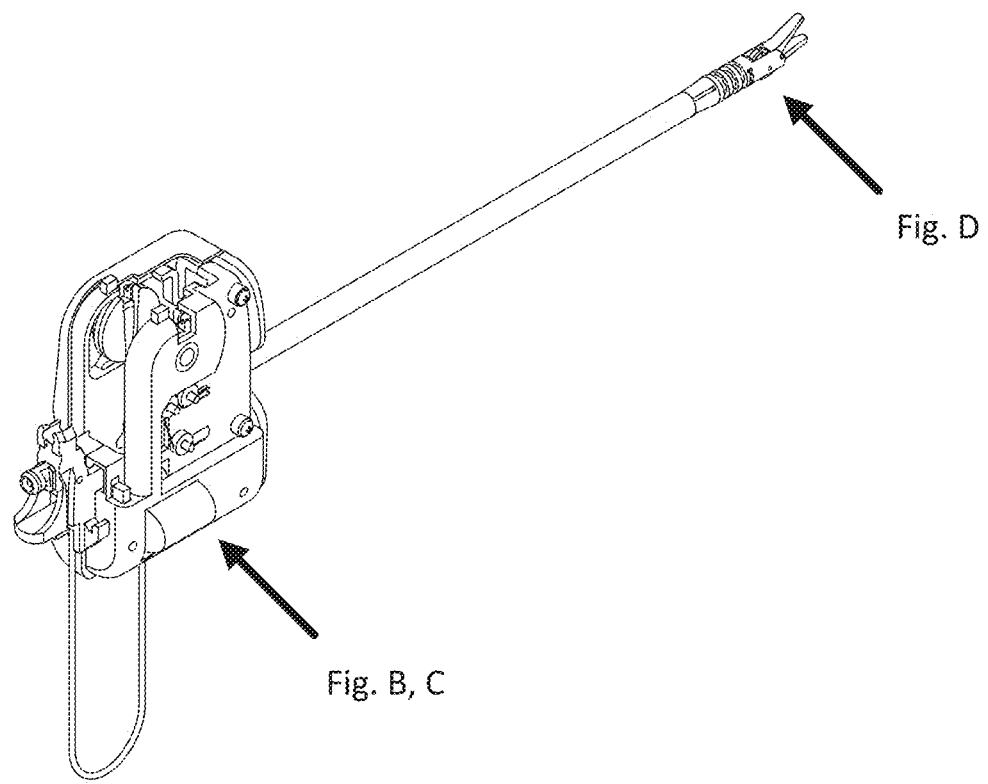
Figure 40B:
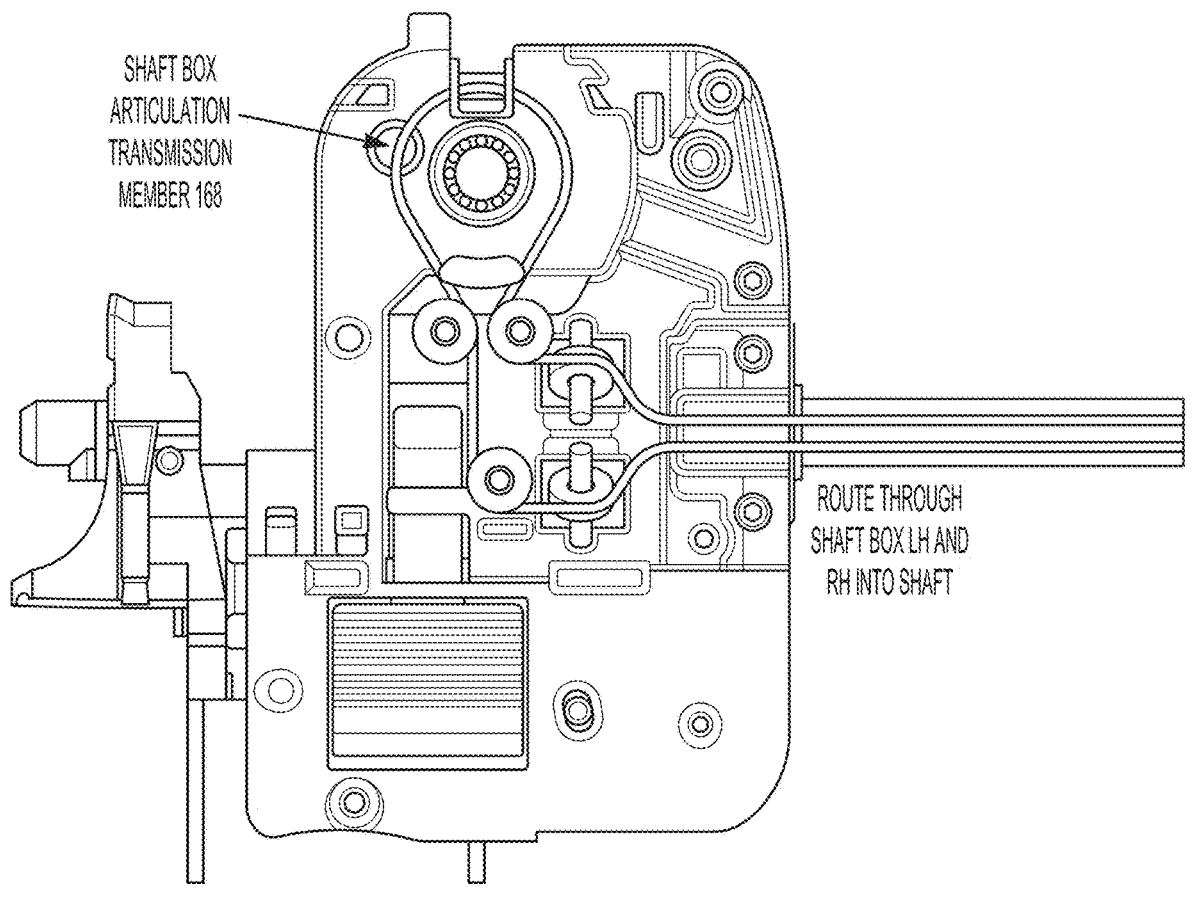
Figure 40C:
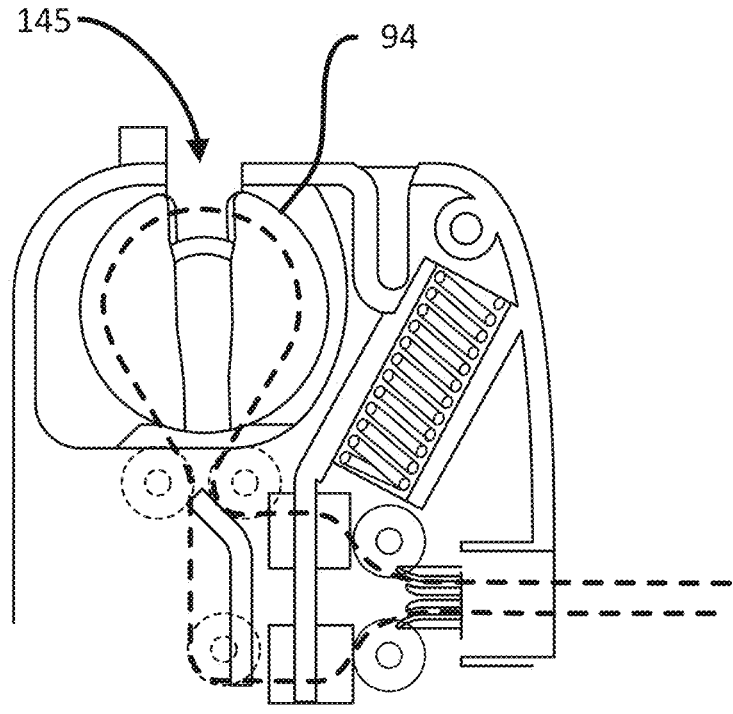
Figure 40D:
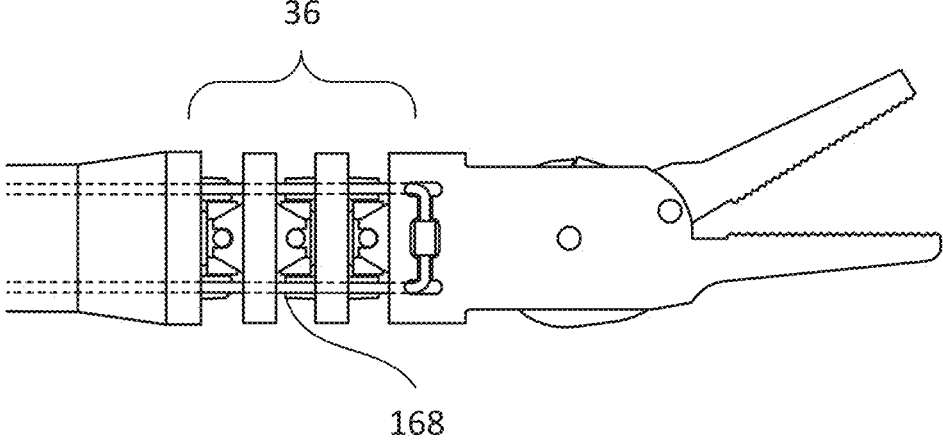

3.12.1.1 T1.1: Shaft Box Alignment to Frame a) Functional Design Intent:

The functional design intent here is to provide precision in alignment between SB 30 assembly and the frame 16 so that rotation axis (which are parallel to Z axis) for VCU distal articulation pulley 88 and shaft box articulation pulley 94 coincide along X and Y axis direction to maximize the transmission efficiency. This interface consists of peg features on VCU distal articulation pulley 88 as shown in FIG. 39B and slot features 145 on shaft box articulation pulley 94 as shown in FIG. 40C.

b) Design Details:

i.) As the SB 30 assembly is aligned w.r.t. frame 16, the bottom guide channel on SB 30 assembly engages with bottom guides on frame 16. These are the first features that act as alignment features between the SB 30 assembly and frame 16. The initial engagement between these two features starts with ample clearance to avoid binding during the installation of SB 30 assembly onto frame 16. FIG. 63 shows these interfaces.

ii.) When the SB 30 assembly is fully installed onto frame 16, a minimal clearance (of 0.0015" on each side of the guide) is maintained between SB RH bottom guide channel to frame 16 bottom guides. This clearance (also shown in FIG. 64) is defined based on the tolerance stack analysis performed to achieve the functional intent described above while still being able to install shaft box 30 onto frame 16 without any issues assembling the components. These alignment features create DoCs along X axis direction and about OY direction for SB assembly w.r.t. frame 16. Ample nominal clearance (of 0.005" on each side of guide) is maintained between SB LH bottom guide channel to frame 16 bottom guide. This clearance is defined to avoid over-constraining the assembly consisting of the SB assembly and frame 16.

iii.) A second alignment feature that comes into play between SB 30 assembly and frame 16 is the top pin channel on shaft box 30 and top pin on frame 16, as shown in the FIG. 65. Ample clearance (of 0.005" on each side of the pin) is maintained between top pin on frame 16 to top pin channel on SB assembly at the entry of the channel to allow for easy installation of SB assembly onto frame 16.

iv.) Frame top pin to SB assembly top pin channel. Minimal clearances are maintained similar to bottom guides (i.e., 0.0015" on each side of the pin) between SB RH and frame 16. Ample clearance (of 0.005" on each side of pin) is maintained between SB LH and frame 16 in order to avoid over-constraining the assembly consisting of SB assembly and frame 16. These clearances were defined based on tolerance stack analysis in order to achieve the design intent described above while still being able to install shaft box 30 onto frame 16 without facing any assembly issues. These alignment features create DoCs along X axis direction and about OY direction for SB assembly w.r.t. frame 16. FIG. 66 shows the interface and alignment clearances between the pin and channel interface.

v.) Third set of features that acts as alignment features between SB assembly and frame 16 are top posts on SB assembly and top pockets on frame 16. These features are shown in FIG. 67 with minimal clearances maintained based on tolerance stack analysis. These features provide DoCs along Z axis, about OX and OY directions for SB assembly w.r.t. frame 16.

vi.) DLP 76 and CBLP 92 are the two spring-loaded locking members, along with button 90 that plays a role in Y direction positioning of SB assembly w.r.t. frame 16. DLP 76 is housed within the frame assembly and CBLP 92 is part of SB assembly. During the installation of SB assembly onto frame 16, CBLP 92 and DLP 76 which are spring loaded will start applying separation forces on frame 16 and SB assembly respectively. CBLP 92 and DLP 76 are considered as soft alignment features in the +Y direction. In case the SB assembly over travels w.r.t. frame 16, surfaces on the SB assembly interface with surfaces on frame 16 to produce hard alignment features in +Y direction. These soft alignment features are also required to allow for over-travel of the SB assembly w.r.t. frame 16 to reach a position in the +Y direction so that button 90 can lock frame 16 and act as a retention feature in the −Y direction amidst tolerance variation in the position of button 90 w.r.t. position of button locking face on frame 16.

3.12.1.2 T1.2: Conduit Box Alignment to Dial a) Functional Design Intent:

The functional intent of aligning conduit box 28 to dial 20 is to constrain CB 28 w.r.t. dial 20 along all 6 DoFs (especially X and ΘZ) while assembling both components to house CB 28 in dial 20 via structural interface. Also, this action is meant to create a transmission interface between crimp housing 120 and shuttle 116 while assembling conduit box 28 and dial 20.

b) Design Details:

i.) Conduit box 28 guide channel and dial 20 guides engage at the entry during initial stages of assembly with ample clearance to allow easy entry of conduit box 28 into dial 20. FIG. 68 shows this interface.

ii.) As conduit box 28 is fully assembled w.r.t. dial 20, the clearance between CB guide channel and dial 20 guides goes to minimal values based on tolerance stack analysis (to 0.0015" on each side). These alignment features act as one of the constraints for conduit box 28 w.r.t. dial 20 in X and ΘZ directions.

iii.) As shown in FIGS. 20A-B, the X axis "dial interface faces" features on conduit box 28 act as constraints in X and ΘZ direction when conduit box 28 is fully assembled w.r.t. dial 20. FIG. 69 specifically highlights these alignment interfaces.

iv.) Conduit box 28 is assembled w.r.t. dial 20 and is house inside dial 20. Conduit box 28 is not locked either to dial 20 or shaft box 30 at this state (state 2). Unlike state 1, conduit box 28 is no longer locked w.r.t. shaft box 30 in this state via conduit box lockout plate 92. Installation of DI 14 onto VCU 68 unlocks the conduit box 28 w.r.t. shaft box 30 by actuating conduit box lockout plate 92. Unlocking of conduit box 28 w.r.t. SB assembly is discussed in a later section.

v.) While going from state 1 to state 2, conduit box 28 aligns w.r.t. dial 20. Alignment of CB 28 w.r.t. dial 20 is needed to provide rigidity for the detachable structural interface between conduit box 28 and dial 20 for the jaw closure transmission. In state 2, CB 28 is aligned to dial 20 to meet the mentioned need and, at the same time, is still housed w.r.t. SB assembly. The alignment features between CB 28 and shaft box (SB) assembly have not changed since state 1. Therefore, to provide the proper alignment w.r.t. dial 20 while accounting for tolerance variation in position of dial 20 w.r.t. conduit box 28, alignment features w.r.t. shaft box assembly need to be soft (more clearance based) alignment features. Therefore, alignment along X, Y, and Z axes directions of CB 28 w.r.t. SB LH and SB RH is maintained with ample clearance such that it accounts for tolerance variation in the position of dial 20 w.r.t. DI 14 (CB 28 and SB assembly) along X, Y, and Z axes directions. FIG. 70 shows CB guide channel and dial bottom guide post alignment.

3.12.1.3 T1.3: Shaft Box Retention to Frame a) Functional Design Intent:

The overall functional intent here is to provide rigid retention between SB assembly and frame 16 so that the SB assembly does not disassemble w.r.t. frame 16 while the system is in state 2 or state 3.

b) Design Details:

i.) SB assembly is retained w.r.t. frame 16 via lock namely, button 90.

ii.) Button 90 provides −Y direction DoC for SB assembly w.r.t. frame 16.

iii.) Button 90 and the "button locking face 102" shown in FIG. 16B (interface on frame 16 that interacts with button 90) are designed to withstand high separation forces between the SB assembly and frame 16.

iv.) The profile of the button's locking feature, as shown in FIG. 71, is engineered such that any reaction force on the surface of the button 90 intersects the button pivot axis 93.

v.) The button's "drive-in profile" (shown in FIG. 72) allows button 90 to rotate clockwise (CW when seen by user along +X axis direction) and provides gradual transition for button 90 to translate along +Y axis direction and seat the locking profile of button 90 on button locking face 102 on frame 16.

3.12.1.4 T1.4: Alignment and Retention of Crimp Housing w.r.t. Shuttle a) Functional Design Intent:

The overall functional intent here is to provide alignment precision and rigid retention between crimp housing (CH) 120 and shuttle 116. FIG. 73 shows shuttle 116, conduit box 28, and crimp housing 120 in a section view. Shuttle 116 and crimp housing 120 are translated together along −X axis direction upon actuation of closure input 24. This further leads to translation of jaw closure transmission member 66 leading to closure of moving jaw 52 w.r.t. fixed jaw 50. The following supported the overall intent per the embodiment above:

i.) Crimp housing 120 is able to transmit force between handle assembly 18 and DI 14;

ii.) Crimp housing 120 does not bind during entry into shuttle 116;

iii.) There lacks a clearance between crimp housing 120 and shuttle 116 after DI 14 installation;

iv.) Crimp housing 120 does not bind (stick) in shuttle 116 during disassembly of DI 14 from VCU 68; and v.) Crimp housing 120 is able to enter shuttle 116 when shuttle 116 is positioned proximal of shuttle hard stop 130.

b) Design Details:

i.) The "shuttle hard stop 130" face on crimp housing 120 is engineered to have a particular angle (specifically, 7 degrees) measured w.r.t. Y axis. Designing the shuttle's X and Y axis alignment and retention feature based on this angled face has the benefit of easy entry and exit of the crimp housing 120 in and out of shuttle 116. This angle value is selected to also avoid relative motion (back-drive) between crimp housing 120 and shuttle 116 during actuation of closure input 24. Therefore, this angle helps prevent back-driving of crimp housing 120 w.r.t. shuttle 116 as it is pulled by certain forces along −X axis direction while experiencing certain friction forces w.r.t. shuttle 116. FIGS. 74A-B demonstrate this interface and the engineering justification for this particular angle. For low value of the angle, crimp housing 120 can be non-back drive-able for a lower coefficient of friction $\mu$. For example, for 7° angle interface between crimp housing 120 and shuttle 116, $\mu$ is required to be greater than or equal to 0.12 in order for the interface to stay non back drive-able.

ii.) Additionally, the angle of the crimp housing mating surface allows to accommodate relative differences in X axis position between crimp housing 120 and shuttle 116. It is designed such that if the X axis position misalignment between the shuttle 116 and crimp housing 120 is less than certain value (say 0.030 inches), the crimp housing 120 will be able to slide vertically into shuttle 116. Crimp housing 120, being connected to jaw closure transmission member 66, moves along X axis to match the ramp 143 of shuttle 116, as shown in FIG. 74A. FIG. 75 shows crimp housing 120 interfering with shuttle 116 by a certain nominal value (here, 0.010 inches) while there still being a larger value (here, 0.022 inches) of ramp remaining. This nominal value (here, 0.010 inches) helps maintain pre-stretch on jaw closure transmission member 66 in case there is existence of certain slack in jaw closure transmission member 66.

iii.) As conduit box 28 continues installing into dial 20, crimp housing 120 will continue being seated and housed into the crimp housing pocket in shuttle 116. Details on this are shared in next section.

3.12.1.5 T1.5: Shuttle Getting Unlocked w.r.t. Dial a) Functional Design Intent:

The overall functional intent here is to unlock shuttle 116 w.r.t. dial 20 after crimp housing 120 is fully seated into the shuttle pocket. Crimp housing 120 is attached to jaw closure transmission member 66. Unlocking shuttle 116 w.r.t. dial 20 after crimp housing 120 seats at its desired location within the shuttle pocket avoids translation of shuttle 116 without capturing crimp housing 120 (initiated by actuation of closure input 24).

b) Design Details:

i.) The lock that locks and unlocks the shuttle 116 w.r.t. dial 20 is called "shuttle lockout spring 118" or "SLS."

ii.) As shown in FIG. 76, shuttle lockout spring 118 interacts with the shuttle lockout spring tab features on shuttle 116. Here, motion of shuttle lockout spring 118 is shown in reference to motion of crimp housing 120. As crimp housing 120 and CB 28 have translation DoC along Y axis direction, motion of crimp housing 120 is representative of the motion of CB 28.

iii.) Shuttle lockout spring 118 locks the translation of shuttle 116 along −X axis direction w.r.t. dial 20 by blocking the shuttle lockout spring tab features on dial 20 by interfering the path of motion along −X direction for shuttle 116. At this state, CB 28 is not yet installed into dial 20.

iv.) Shuttle lockout spring 118 and CB 28 interface is engineered such that, when conduit box 28 along with crimp housing 120 starts entering dial 20, the crimp housing 120 goes into shuttle pocket and the conduit box 28 gradually activates the shuttle lockout leaf spring to unlock the shuttle 116.

v.) As shown in FIG. 76, crimp housing 120 is comfortably seated in the shuttle 116 when shuttle lockout spring 118 begin to unlock the shuttle 116. This ensures that the handle lever can only be fully actuated after the crimp housing 120 has entered the shuttle 116 such that more than half of crimp housing's cross-sectional area interfaces with shuttle 116. This avoids translation of shuttle 116 w.r.t. dial 20 along −X direction without capturing crimp housing 120, once closure input 24 in the handle assembly 18 is actuated by the user.

3.12.1.6 T1.6: Dial Unlocking w.r.t. Frame a) Functional Design Intent:

The overall functional design intent is to unlock dial 20 from frame 16 ideally at the same time when SB assembly retains w.r.t. frame 16 via lock namely button 90. It is undesirable to have dial 20 unlock from frame 16 much before button 90 locks onto frame 16. If this happens, VCU lever 72 can rotate clockwise (when seeing along −Z direction) w.r.t. its pivot pin and this rotation of VCU lever 72 can block button 90 from interfacing w.r.t. frame 16, preventing any locks from engaging between shaft box and frame. Therefore, a lock is used to prevent premature unlocking of dial 20 w.r.t. frame 16.

b) Design Details:

i.) Dial lockout plate (DLP) 76 interfaces with dial 20 by translating along −Y axis direction w.r.t. frame 16. DLP 76 is spring-loaded vertically (along −Y axis direction) and applies pressure on the dial hook surface. Also, the locking angle between dial 20 and dial lockout plate 76 is engineered to accomplish two engineering functions. First is to make sure that dial lockout plate 76 applies majority of the load along +X axis direction on dial 20 to keep it locked and pre-loaded in locked configuration. See FIG. 77 showing the horizontal force applied along +X axis direction.

ii.) Second is to make sure that accounting for tolerance variations, DLP 76 is still able to lock onto the hook on dial 20 ("dial lockout plate interface/hook 17" shown in FIG. 21D) while dial 20 is aligned to the frame 16 and located w.r.t. frame 16. Dial 20 is temporarily locked w.r.t. frame 16 in state 1 and state 2 via dial detent springs 74 that are housed in frame 16. Along X axis, this temporary lock defines −X axis direction and hardstops define +X axis direction position of dial 20 w.r.t. frame 16. Therefore, while the position of dial 20 varies along X axis direction due to variation of the mentioned alignment features, it leads to variation in position of dial lockout plate interface/hook 17 w.r.t. frame 16. Also, position of dial lockout plate (DLP) 76 along X axis direction varies. These variations in position may be caused due to manufacturing tolerances' variation. Therefore, the locking angle that dial lockout plate interface/hook 17 has, locking angle that dial lockout plate 76 has, and the length of dial hook feature along X axis shall still lead to locking and unlocking function considering all these variations.

3.12.1.7 T1.7: Conduit Box Unlocking w.r.t. Shaft Box a) Functional Design Intent:

The overall functional design intent here is to unlock conduit box 28 from the SB assembly ideally at the same time when the SB assembly is retained w.r.t. frame 16 via lock namely, button 90. This timing helps make sure that the lock between conduit box 28 and shaft box 30 shall not constrain conduit box 28 to align and house inside dial 20. At the same time, conduit box 28 shall not get unlocked w.r.t. shaft box 30 too early and not be able to enter dial 20 while shaft box 30 is not fully installed onto the frame 16. Also, when the shaft box 30 is uninstalled w.r.t. frame 16, conduit box 28 should lock w.r.t. shaft box 30 suitably at the same instant when shaft box 30 moves along −Y axis direction w.r.t. frame 16.

b) Design Details:

i.) FIG. 78 shows the instance when the SB assembly is fully installed onto frame 16. At this instance, conduit box 28 is completely aligned w.r.t. dial 20. Also, conduit box 28 is fully unlocked w.r.t. shaft box 30. The amount of travel that shaft box 30 requires to install onto frame 16 is similar to the travel for CBLP 92 to lock conduit box 28. The difference between the two travels considers manufacturing tolerance variation in position of various bodies (namely, SB LH, SB RH, frame 16, and CB 28) and various locks (namely, button 90 and CBLP 92) involved. This is part of transition 1 from state 1 to state 2.

ii.) When the system goes from state 2 to state 1, conduit box 28 locks w.r.t. shaft box 30 via CBLP 92 within minimal travel of shaft box 30 w.r.t. frame 16 along the −Y axis direction. In this embodiment it is preferable to lock CB 28 to shaft box 30 as soon as shaft box 30 starts uninstalling w.r.t. frame 16 so that CB 28 stays retained/locked to SB 30 as the system transitions to state 1.

3.12.1.8 T1.8: Transmission Interface Alignment Between VCU Distal Articulation Pulley Peg and SB Articulation Pulley Channel a) Functional Design Intent:

The overall functional intent here is to make sure that VCU distal articulation pulley 88 and SB articulation pulley 94 can assemble. Also, there should be precision in alignment along X and Y axes directions between rotation axes (parallel to Z axis) of VCU distal articulation pulley 88 and SB articulation pulley 94. This interface consists of peg feature 148 on VCU distal articulation pulley 88 as shown in FIG. 39B and slot feature 150 on shaft box articulation pulley 94 as shown in FIG. 40C.

b) Design Details:

i.) VCU distal articulation pulley 88 and SB articulation pulley 94 are engineered to deliver maximum efficiency.

ii.) Minimal clearance is maintained between the peg feature 148 of VCU distal articulation pulley 88 and slot feature 150 on shaft box articulation pulley 94 along the X axis direction to compensate for manufacturing tolerance variation in alignment features between SB assembly and frame interface.

iii.) As shown in FIG. 79, a minimal clearance (of 0.005") is maintained in both +X and −X direction between peg feature 148 on VCU distal articulation pulley 88 and slot feature 150 on SB articulation pulley 94.

iv.) Here, VCU articulation pulley 88 is the driving pulley and SB articulation pulley 94 is the driven pulley.

v.) As described in FIG. 39A, the input rotation of VCU proximal articulation pulley 166 leads to rotation of VCU distal articulation pulley 88. Rotation of VCU distal articulation pulley 88 rotates SB articulation pulley 94. The rotation of shaft box articulation pulley 94 leads to articulation of end-effector assembly 34.

3.12.1.9 Timing Plot for Transition 1

Transition 1 is described via eight transition steps mentioned in this section. These can be named as transitions namely, T1.1 through T1.8 and presented in FIG. 80. Each transition starts at certain instance and ends at a certain instance in time that it takes to complete overall transition 1. Here, the overall time taken to complete transition 1 can be calculated by subtracting to from tf, where "to" refers to the time transition starts and "tf" refers to the time transition ends. FIG. 80 is a representation of various transitions namely, T1.1 through T1.8, that take place in the time duration tf–to.

3.12.2 Transition 2

As shown in FIG. 48, transition 2 takes place when the system goes from state 2 (assembled state) to state 3 (use state). During this transition, dial 20 is locked temporarily w.r.t. frame 16 via detent springs in state 2 is un-homed from the frame 16. During this operation, conduit box 28 gets locked w.r.t. dial 20 via interlock namely, conduit box lockout shaft or CBLS 112. This transition is described in following transition steps. At the end of the description, a timing plot for transition 1 is shown to present the time-domain dependence of each transition step.

3.12.2.1 T2.1: Dial Un-Homed w.r.t. Frame a) Functional Design Intent:

The overall functional design intent is to be able to unlock dial 20 w.r.t. frame 16 (that is temporarily locked via dial detent springs 74) and be able to put the system in use state. In use state, dial 20 can be rotated to initiate roll transmission or can be articulated to initiate articulation transmission.

b) Design Details:

This transition refers to translating dial 20 along –X axis direction. In state 2, dial lockout plate 76 is no longer locking dial 20 w.r.t. frame 16. But dial 20 is locked w.r.t. frame 16 via temporary lock namely, dial detent spring 74. Translating dial 20 along –X axis direction unlocks dial 20 w.r.t. dial detent springs 74. FIG. 81 shows dial 20 in locked condition where detent spring is seated on the detent spring lock profile. Pulling dial 20 along –X axis direction leads to deflection of detent spring in a plane parallel to YZ plane. Detent spring moves on dial's detent spring lock profile during the locking and unlocking of dial 20. FIG. 82 shows dial 20 in the un-homed condition where detent spring is not seated on the detent spring lock profile.

3.12.2.2 T2.2: Conduit Box Locked w.r.t. Dial a) Functional Design Intent:

The overall functional design intent is to be able to lock conduit box 28 to dial 20 as soon as dial 20 is un-homed from frame 16. In this embodiment, locking conduit box 28 is called for so that it does not fall right after dial 20 is un-homed from frame 16 and while dial 20 is articulated or rotated about dial roll axis during the use of the device.

b) Design Details:

i.) Conduit box 28 is locked w.r.t. dial 20 via interlock namely, conduit box lockout shaft or CBLS 112. CBLS 112 translates along +X axis direction to interface with "lockout shaft interface" feature on conduit box 28 (also shown in FIG. 5A). CBLS 112 provides retention for CB 28 along Y axis direction. There exists a positive engagement between CBLS 112 and CB 28 such that CB 28 has features that wrap around the CBLS 112 such that once the CBLS 112 completes its translation along +X axis direction, CB 28 cannot be unlocked w.r.t. dial 20 due to this positive engagement feature. This feature is shown in FIG. 83.

3.12.2.3 T2.3 & T2.4: Button Blocked by VCU Lever and Shaft Box Locked by VCU Lever a) Functional Design Intent:

The overall functional design intent is to prevent motion of button 90 once dial 20 is un-homed w.r.t frame 16. Once the device is in use state (state 3), a user shall not be able to disengage the DI 14 w.r.t. VCU 68 by pressing the button 90 as the system is in use state and not in assembled state.

b) Design Details:

i.) VCU lever 72 interfaces with shuttle 116 such that in state 1, shuttle 116 keeps VCU lever 72 clocked or rotated CCW to its max rotation about its pivot axis 11 (when seen towards –Z axis). This keeps VCU lever 72 at an angle at which it does not interface with button 90 while the system goes from state 1 to state 2. Therefore, button 90 can interface with frame 16 to lock frame 16 to SB 30 without any interference of VCU lever 72. FIG. 84 shows configuration at which VCU lever 72 is held so that button 90 can interface with frame 16 to lock frame 16 w.r.t. SB 30.

ii.) When dial 20 is un-homed from frame 16, shuttle 116 also moves along –X axis direction during the un-homing operation that is performed as part of transition 2. This eventually disengages shuttle 116 from VCU lever 72, which is no longer held at its maximum CCW rotation configuration. Therefore, VCU lever 72 rotates CW about its pivot axis 11 (when seen towards –Z axis) and hits hard stop on SB 30.

iii.) FIG. 85 shows VCU lever 72 in its maximum CW rotation configuration. In this configuration, VCU lever 72 produces two functional interfaces. First, it blocks button 90 from rotation such that user can no longer rotate button 90 about its pivot axis 93 (parallel to X axis) in order to disengage SB 30 w.r.t. frame 16. FIG. 86 shows the side view (seeing along +X axis direction) showing the block that is created by VCU lever 72 that restricts rotation of button 90.

iv.) The second functional interface is the positive lock that VCU lever 72 creates w.r.t. SB RH. This is a secondary lock which may prevent motion of SB 30 along –Y axis direction in case user is able to press the button 90. FIG. 85 shows the interface between VCU lever 72 and SB RH that can prevent displacement of SB assembly along –Y axis direction.

v.) The profile of VCU lever 72 that interfaces with SB RH is designed to have non back-drive profile such that under separation load applied to separate frame 16 w.r.t. shaft box 30, VCU lever 72 is not driven out of the SB RH pocket. FIG. 87 shows the free body diagram for VCU lever 72 when the separation load on SB RH is applied along –Y axis direction.

3.12.2.4 Timing Plot for Transition 2

Transition 2 is described via four transitions steps set forth in this section. These can be named as transitions namely, T2.1 through T2.4. Each transition starts at certain instance and ends at a certain instance in time that it takes to complete overall transition 2. These transitions are shown in FIG. 88. Here, overall time time taken to complete transition 2 can be calculated by subtracting to from tf, where "to" refers to the time transition starts and "tf" refers to the time transition ends. FIG. 88 is a representation of various transitions namely, T2.1 through T2.4 that take place in the time duration tf–to.

3.13 Device Map

Device map refers to a schematic diagram that represents a tool apparatus 10 which includes the five-body FSM system. It can be described as having three sub-assemblies namely, VCU assembly containing handle assembly 18 and the remaining VCU assembly, and the DI assembly. There exist bodies, locks, and interlocks that are part of these assemblies that interface via joints/mechanisms and/or via transmission interfaces. There also exists members called transmission members that help transmit motions that produce functional outputs. FIG. 89 shows these sub-assemblies, respective bodies, interlocks, joints/mechanisms, transmission interfaces, and transmission members. Handle assembly 18 presented in this embodiment can be mapped to the handle assembly presented in U.S. Pat. No. 9,814,451.

4. Embodiments

4.1 Various Embodiments of Interlocks, Bodies, and their Respective Interactions This section contains various embodiments of interlocks, bodies, and respective interactions between a pair of bodies.

4.1.1 Embodiments of Dial, Frame, and DLP

FIG. 90 represents an assembly with dial 20 and frame 16 bodies. The assembly also has two locks: dial lockout plate 76 and spring detent 75. Dial lockout plate 76 provides a positive lock between dial 20 and frame 16. It can also be actuated by the user in the release direction to unlock the interface. Detent springs provide a temporary lock between the two bodies.

FIG. 91 represents an assembly with dial 20 and frame 16 bodies. The frame 16 body material is compliant and will deform to allow dial 20 insertion. The compliant member could also be the dial 20 body. Further insertion will create a temporary lock between the two bodies, restricting motion along the X axis direction via detent features. These detent features may also be used for alignment of dial 20 w.r.t. frame 16 along Y direction.

FIG. 92 represents an assembly with dial 20 and frame 16 bodies. The dial lockout plate 76 is a flap and serves as a lock. The interface between dial 20 and frame 16 is air-tight. Dial 20 insertion creates high pressure air in the chamber. This air exits past dial lockout plate 76, thus returning the chamber to (or near) atmospheric pressure. Withdrawing dial 20 from frame 16 creates a negative/low pressure in the chamber. This prevents un-homing of dial 20. If dial lockout plate 76 is moved in the release direction, air may flow back into the chamber, un-homing dial 20.

FIG. 93 represents an assembly with dial 20 and frame 16 bodies. The dial lockout plate 76 is a lock that rotates about an axis parallel to the dial axis to capture dial 20 and prevent un-homing. Moving dial lockout plate 76 in the release direction allows un-homing of dial 20.

FIG. 94 represents an assembly with dial 20 and frame 16 bodies. The dial lockout plate 76 is a lock. Dial 20 and frame 16 bodies have magnets near their mating surface. The magnet's poles are aligned such that they are attracted to one another, creating a detent action. There exists a screw mechanism between dial lockout plate 76 and dial 20. This prevents un-homing when engaged. To un-home dial 20, dial lockout plate 76 must be unscrewed from dial 20. Dial 20 may then be un-homed.

FIGS. 95A-B represent an assembly with dial 20 and frame 16 bodies. The interface between them serves as an interlock via rotation. Dial 20 is rotated to align tabs with slots in the frame 16. After insertion, dial 20 is rotated along its axis until the tabs are captured. This sequence shall be reversed to disengage and un-home dial 20.

4.1.2 Embodiments of Dial, Conduit Box, and CBLS

FIG. 96 represents an assembly with conduit box 28 and dial 20 bodies. The leaf spring(s)/conduit box lockout shaft 112 will deflect upon contact with conduit box 28. When conduit box 28 is inserted far enough, the leaf spring will mate with a pocket on conduit box 28 and lock it in place. Leaf springs shall be deflected inward to release conduit box 28.

4.1.3 Embodiments of Shuttle, Dial, and SLS

FIG. 97 represents an assembly with shuttle 116 and conduit box 28 bodies. The dial leaf spring blocks shuttle 116 travel in the Z axis direction. Conduit box 28 insertion moves the dial leaf spring in the Y axis, compressing the compression spring, and allows the shuttle 116 to travel in the Z axis.

4.1.4 Embodiments of VCU Lever

FIGS. 98A-B represents an assembly with bodies, namely shuttle 116, button 90, DI 14, and VCU lever 72, where reference ground is frame 16. VCU lever 72 serves as an interlock. Shuttle 116 and VCU lever 72 move only in the X axis direction. Button 90 rotates about a pin about an axis parallel to X axis. DI 14 moves in the Y axis direction. When shuttle 116 translates along the +X axis direction, it contacts VCU lever 72, compressing the spring attached to VCU lever 72 on one end and frame 16 on the other end. This lets DI 14 translate downwards (−Y axis direction) and allows rotation of button 90 about its pivot axis 93. This state is shown in FIG. 98B as "DI Unlocked Configuration." When shuttle 116 is retracted, i.e., moved along negative X axis direction, the assembly returns to the "DI Locked" configuration. In this configuration, button 90 is not allowed to rotate and is blocked by a feature on VCU lever 72. Also, another feature shown in FIG. 98A prevents translation of shaft box 30 in −Y axis direction by hooking VCU lever feature onto the shaft box 30.

4.1.5 Embodiments for Frame-SB Structural Interface

FIG. 99 shows an embodiment for Frame-SB structural interface where SB 30 contains a hinge (pin) which sits in a hinge hole present on frame 16. Hinge on SB 30 has a hinge axis which is parallel to Y axis. Upon seating the hinge into the hinge hole, SB 30 rotates about the hinge axis (Y axis) in order to mate the transmission interface between distal articulation pulleys on frame 16 and SB articulation pulleys 94 (not shown in figure). SB 30 is retained w.r.t. frame 16 by button 90 which snaps onto the outer surface of the SB 30.

FIGS. 100A-B show an embodiment for Frame-SB structural interface where SB 30 has a pivot hole which interfaces with the frame 16 by pivoting about a pin (Z axis) which is housed into frame 16. Upon rotation about the pin about Z axis, SB 30 is retained by the button 90 that constrains it from moving in +X axis direction. There also exists a hard stop pin which constrains motion of SB 30 in −X direction and about OZ direction.

4.1.6 Alternate Embodiment for Tool Apparatus

FIG. 101 shows an alternate embodiment for tool apparatus 10 where handle assembly 18 is part of DI assembly. In this embodiment of tool apparatus 10, there is no CB 28 as dial 20 interfaces with SB 30 via closure actuation interface 38 and is part of DI assembly. FIG. 101 shows the state 1 or storage state for the FSM. As the FSM goes to assembled state (state 2), dial 20 interfaces with a dial plate 71 to produce a structural interface, and SB 30 interfaces with frame 16 to produce a structural interface. Un-homing of dial plate 71 relative to frame 16 results in the use state where there still exist structural interfaces between dial 20 and dial plate 71, and between SB 30 and frame 16.

4.2 Various Views of Instrument that Links to Device Map

Figure 102A:
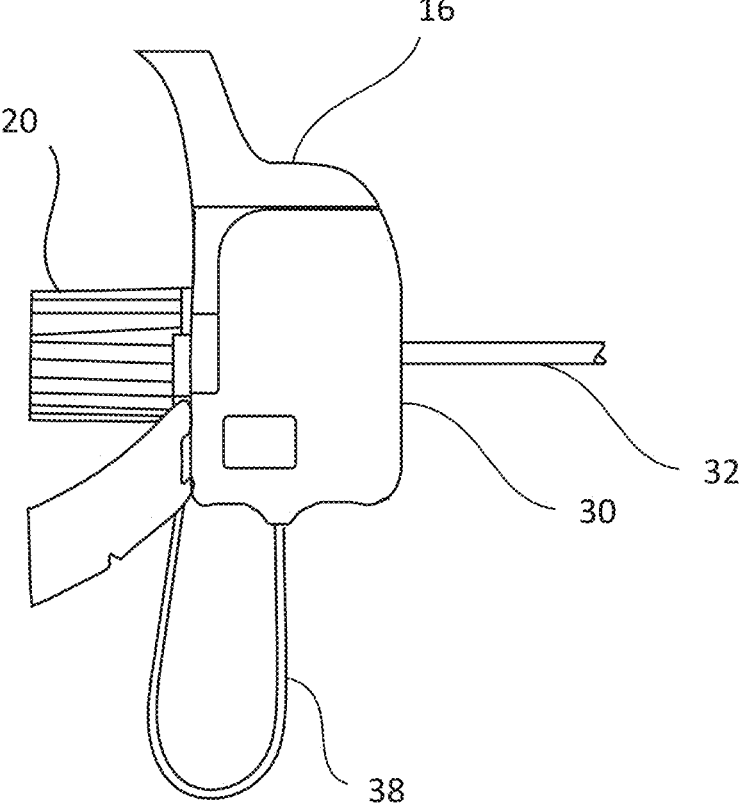
Figure 102B:
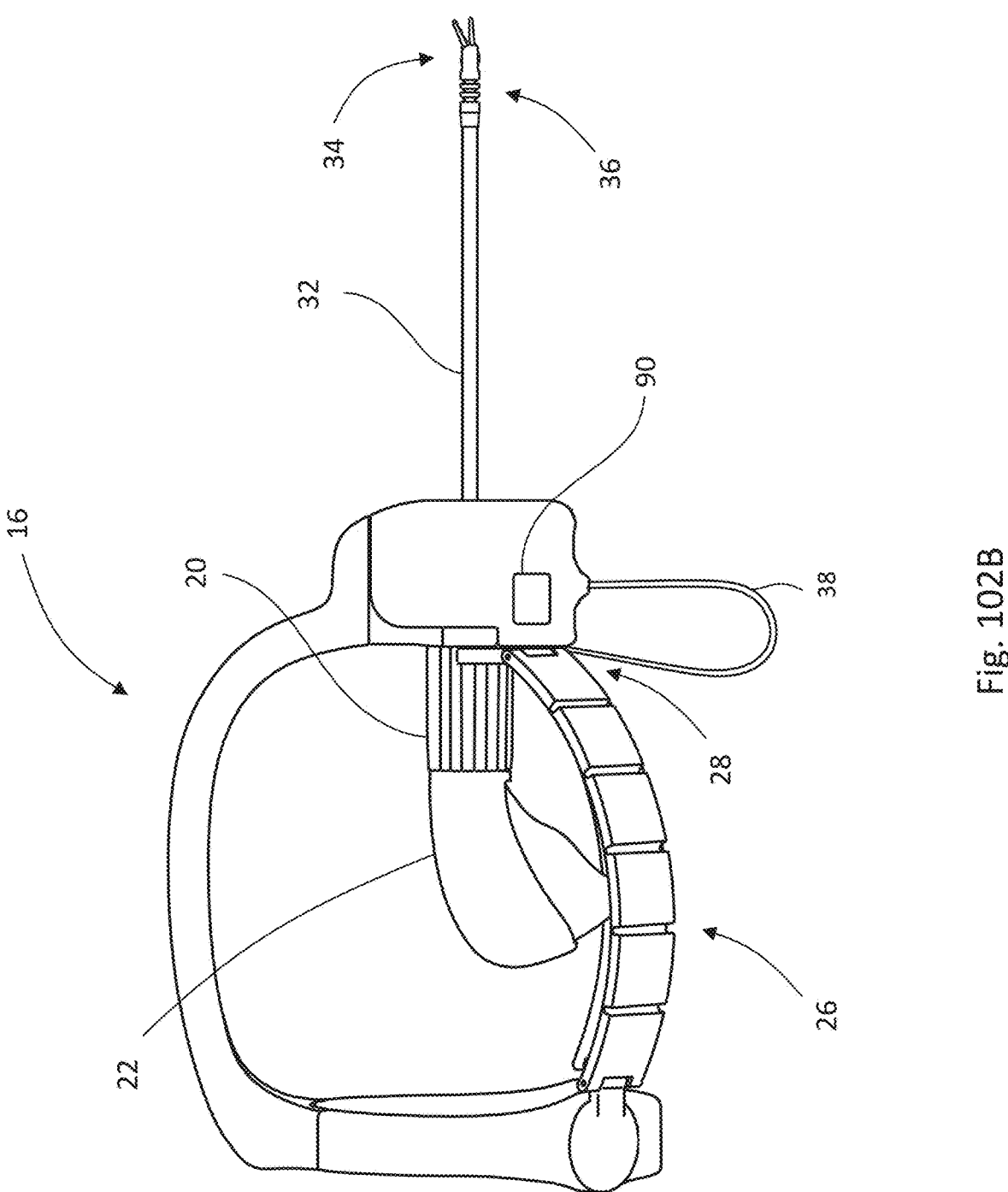

FIGS. 102A-B show various views of a tool apparatus 10 that is configured as an FSM. Tool apparatus 10 is shown to be in state 2.

FIGS. 103A and 103B depict yet another embodiment of tool apparatus 10. This embodiment demonstrates tool apparatus 10 in a design and construction that lacks a wrist grounding component. Frame 16 and handle assembly 18 are arranged in an architecture in which one or more of the following relationships may be satisfied: a first virtual center of the associated articulation input joint and a second virtual center of a grounding joint exhibit a generally coincident arrangement, and/or the shaft axis exhibits a generally intersecting arrangement with the first and second virtual centers. The articulation input joint, in this embodiment, is established between frame 16 and handle assembly 18, and is established by an intermediate body 170 and an intermediate body or deviation ring 172. Further, the articulation input joint can be stablished by additional intermediate bodies and by multiple joints among the intermediate bodies. The grounding joint is established between frame 16 and handle assembly 18. The shaft box 30 and conduit box 28 are depicted in these figures.

Various bodies and interaction elements that are part of FSM have been described using embodiments in sections above. These bodies have been described as discrete components but in certain scenarios, they may have a compliant structure such that two or more bodies, and/or locks, and/or interlocks, act as a single compliant body. This compliance may be built within a uni-body structure or via compliant features made out of materials namely hardened steel, compliant polymers (polypropylene, Delrin, etc.), etc. One example of such joint could be a compliant joint between SB 30 and button 90 where, button 90 is a compliant extension of SB 30 and therefore, they together are part of a single body with compliant member.

Locks and interlocks described herein may not be purely mechanical locks containing springs, pulleys, gears, chains, transmission cables, etc. and may use magnets or electromechanical systems namely transducers (e.g., proximity sensors, rotary sensors, piezoelectric sensors, photoresistors, electromagnetic actuators, etc.), electromagnets, etc.

Overall, the FSM may be a purely mechanical system consisting of mechanical locks and interlocks, interaction elements namely alignment features produced by pins, slots, ball bearings, etc. and like features; transmission members namely transmission cables made out of steel, tungsten, elastic bands, transmission belts, compressed fluids (air, water) etc. There may exist an FSM which includes electromechanical components namely actuators namely servo motors, stepper motors, linear motors, solenoids, electromagnets, etc.; transmission members and interfaces consisting electric cables, maglev bearings, sensors namely proximity sensors, rotary sensors, electromagnets, etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing embodiments only and is not intended to be limiting of the invention. For example, as used herein, the singular forms "a," "an," and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

Although various illustrative embodiments are described above, any of several changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

While embodiments of the invention have been illustrated and described, it is not intended that these embodiments illustrate and describe all possible forms of the invention. It is understood that the features of various implementing embodiments may be combined to form further embodiments of the invention. The words used in the specification are words of description rather than limitation, and it is under stood that various changes may be made without departing from the spirit and scope of the invention.

The examples and illustrations included herein show, by way of illustration and not of limitation, specific embodiments in which the subject matter may be practiced. These embodiments consist of bodies that have various types of joints and/or mechanisms namely, prismatic, revolute, cylindrical, etc. between them. These joints and/or mechanisms may consist of discrete elements/bodies/component or these joint/mechanisms may be created by compliant extensions of other bodies and/or assembles.

It is to be understood that the foregoing description is not a definition of the invention, but is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

The invention claimed is:

1. A surgical tool, comprising:
a first body, a second body, and a third body, wherein said first body is at least a portion of a frame assembly, said second body is at least a portion of a shaft box assembly, and said third body is at least a portion of a handle assembly;
a detachable structural interface establishable between said first body and said second body;
a first lock establishable between said first body and said second body, said first lock being configured, upon its establishment, to maintain engagement between said first body and said second body;
a second lock establishable between said first body and said third body, said second lock being configured, upon its establishment, to retain the pose of said first body and said third body together;
an interlock establishable at said first lock, said interlock being configured, upon its establishment, to prevent disestablishment of said first lock; and
a joint disposed between said first body and said third body, said joint having at least two degrees of freedom;
wherein disestablishment of said second lock for articulating said third body and said joint causes establishment of said interlock for preventing disengagement between said first body and said second body, and said second lock is configured, upon its establishment, to retain the pose of said joint for disenabling the at least two degrees of freedom of said joint.

2. The surgical tool as set forth in claim 1, wherein, in a first state of the surgical tool, said detachable structural interface lacks establishment, said first lock lacks establishment, said second lock is established, and said interlock lacks establishment; and
wherein, in a second state of the surgical tool, said detachable structural interface is established, said first lock is established, said second lock lacks establishment, and said interlock is established.

3. The surgical tool as set forth in claim 2, wherein, in a third state of the surgical tool, said detachable structural interface is established, said first lock is established, and said interlock lacks establishment.

4. The surgical tool as set forth in claim 2, wherein the surgical tool is precluded from transitioning from its first state immediately to its second state via said second lock, and wherein the surgical tool is precluded from transitioning from its second state immediately to its first state via said interlock.

5. The surgical tool as set forth in claim 1, wherein the action of establishing said detachable structural interface prompts disestablish-ability of said second lock, and the action of disestablishing said detachable structural interface prompts establishment of said second lock.

6. The surgical tool as set forth in claim 1, further comprising:
a fourth body;
a second detachable structural interface establishable between said third body and said fourth body; and
a third lock establishable between said third body and said fourth body, upon its establishment said third lock maintains establishment of said second detachable structural interface.

7. The surgical tool as set forth in claim 6, wherein the action of establishing said first detachable structural interface prompts establishment of said third lock.

8. The surgical tool as set forth in claim 6, further comprising a fourth lock establishable between said second body and said fourth body, upon its establishment said fourth lock retains said second body and said fourth body together.

9. The surgical tool as set forth in claim 8, wherein the action of disestablishing said first detachable structural interface prompts establishment of said fourth lock.

10. The surgical tool as set forth in claim 1, wherein the surgical tool is a hand-held surgical tool.

11. The surgical tool as set forth in claim 1, wherein the surgical tool lacks electrical components among said first, second, and third bodies.

12. The surgical tool as set forth in claim 1, further comprising an electrical transmission member for effecting electrocautery via an end effector of the surgical tool.

*   *   *   *   *